(12) United States Patent
King et al.

(10) Patent No.: US 11,771,755 B2
(45) Date of Patent: Oct. 3, 2023

(54) SELF-ASSSEMBLING NANOSTRUCTURE VACCINES

(71) Applicant: UNIVERSITY OF WASHINGTON, Seattle, WA (US)

(72) Inventors: Neil King, Seattle, WA (US); David Baker, Seattle, WA (US); Lance Stewart, Seattle, WA (US); Brooke Fiala, Seattle, WA (US); Daniel Ellis, Seattle, WA (US); Lauren Carter, Seattle, WA (US); Rashmi Ravichandran, Seattle, WA (US); George Ueda, Seattle, WA (US); Jorge Fallas, Seattle, WA (US); Una Nattermann, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/971,278

(22) PCT Filed: Feb. 28, 2019

(86) PCT No.: PCT/US2019/020029
§ 371 (c)(1),
(2) Date: Aug. 19, 2020

(87) PCT Pub. No.: WO2019/169120
PCT Pub. Date: Sep. 6, 2019

(65) Prior Publication Data
US 2020/0397886 A1 Dec. 24, 2020

Related U.S. Application Data

(60) Provisional application No. 62/724,721, filed on Aug. 30, 2018, provisional application No. 62/636,757, filed on Feb. 28, 2018.

(51) Int. Cl.
| | | |
|---|---|---|
| A61K 39/12 | (2006.01) |
| C12N 15/86 | (2006.01) |
| B82Y 5/00 | (2011.01) |
| B82Y 40/00 | (2011.01) |

(52) U.S. Cl.
CPC ............ *A61K 39/12* (2013.01); *C12N 15/86* (2013.01); *B82Y 5/00* (2013.01); *B82Y 40/00* (2013.01); *C12N 2710/16134* (2013.01); *C12N 2710/16234* (2013.01); *C12N 2760/00034* (2013.01)

(58) Field of Classification Search
CPC ............ A61K 39/12; A61K 2039/6031; C12N 15/86; C12N 2710/16134; C12N 2710/16234; C12N 2760/00034; C12N 2760/18534; B82Y 5/00; B82Y 40/00; Y02A 50/30; A61P 31/12; C07K 14/005; C07K 2319/00
See application file for complete search history.

(56) References Cited

U.S. PATENT DOCUMENTS

| | | |
|---|---|---|
| 6,929,933 B1 | 8/2005 | Revuelta Doval et al. |
| 8,563,002 B2 | 10/2013 | Baudoux et al. |
| 8,969,521 B2 | 3/2015 | Baker et al. |
| 9,441,019 B2 | 9/2016 | Nabel et al. |
| 9,487,593 B2 | 11/2016 | Powell et al. |
| 9,630,994 B2 | 4/2017 | Baker et al. |
| 9,738,689 B2 | 8/2017 | Kwong et al. |
| 9,856,313 B2 | 1/2018 | Zheng et al. |
| 9,913,894 B2 | 3/2018 | Tous et al. |
| 9,950,058 B2 | 4/2018 | Che et al. |
| 10,017,543 B2 | 7/2018 | Kwong et al. |
| 10,022,437 B2 | 7/2018 | Pushko et al. |
| 10,040,828 B2 | 8/2018 | Weiner et al. |
| 10,351,603 B2 | 7/2019 | Baker et al. |

(Continued)

FOREIGN PATENT DOCUMENTS

| | | |
|---|---|---|
| CN | 104436202 | 7/2017 |
| CN | 107157933 | 9/2017 |

(Continued)

OTHER PUBLICATIONS

Boyington JC, Joyce MG, Sastry M, Stewart-Jones GB, Chen M, Kong WP, et al. Structure-Based Design of Head-Only Fusion Glycoprotein Immunogens for Respiratory Syncytial Virus. PLoS One. Jul. 27, 2016;11(7):e0159709. (Year: 2016).*

(Continued)

*Primary Examiner* — Rachel B Gill
(74) *Attorney, Agent, or Firm* — McDonnell Boehnen Hulbert & Berghoff

(57) ABSTRACT

Nanostructures and nanostructure-based vaccines that display antigens capable of eliciting immune responses to infectious agents such as bacteria, viruses, and pathogens are provided. Some vaccines are useful for preventing or decreasing the severity of infection with an infectious agent, including, for example and without limitation, lyme disease, pertussis, herpes virus, orthomyxovirus, paramyxovirus, pneumovirus, filovirus, flavivirus, reovirus, retrovirus, meningococcus, or malaria. The antigens may be attached to the core of the nanostructure either non-covalently or covalently, including as a fusion protein or by other means. Multimeric antigens may optionally be displayed along a symmetry axis of the nanostructure. Also provided are proteins and nucleic acid molecules encoding such proteins, vaccine compositions, and methods of administration.

20 Claims, 12 Drawing Sheets

Specification includes a Sequence Listing.

(56) References Cited

U.S. PATENT DOCUMENTS

| | | | |
|---|---|---|---|
| 2011/0200560 A1 | 8/2011 | Zhang | |
| 2012/0213817 A1* | 8/2012 | Haynes | C07K 14/005 424/207.1 |
| 2013/0122032 A1 | 5/2013 | Smith et al. | |
| 2013/0315955 A1* | 11/2013 | Holtz | A61K 47/12 435/23 |
| 2014/0248314 A1 | 9/2014 | Swanson et al. | |
| 2014/0302079 A1* | 10/2014 | Nabel | C12N 7/00 536/23.4 |
| 2015/0110825 A1 | 4/2015 | Sasisekharan et al. | |
| 2015/0356240 A1* | 12/2015 | Baker | C07K 14/00 436/86 |
| 2016/0046675 A1 | 2/2016 | Kwong et al. | |
| 2016/0122392 A1* | 5/2016 | Baker | C07K 14/00 536/23.1 |
| 2016/0324958 A1 | 11/2016 | Burkhard et al. | |
| 2017/0182151 A1 | 6/2017 | Che et al. | |
| 2017/0202948 A1 | 7/2017 | Smith et al. | |
| 2017/0298101 A1 | 10/2017 | Kwong et al. | |
| 2017/0326228 A1 | 11/2017 | Cheminay et al. | |
| 2018/0021258 A1 | 1/2018 | Graham et al. | |
| 2018/0194808 A1 | 7/2018 | Langedijk et al. | |
| 2018/0200360 A1 | 7/2018 | Langedijk et al. | |
| 2018/0237476 A1 | 8/2018 | Swanson et al. | |
| 2018/0256704 A1 | 9/2018 | Nicosia et al. | |
| 2019/0330279 A1 | 10/2019 | Kwong et al. | |

FOREIGN PATENT DOCUMENTS

| | | | |
|---|---|---|---|
| EP | 1 010 760 | 6/2000 | |
| WO | 2006/033679 | 3/2006 | |
| WO | 2010/019725 | 2/2010 | |
| WO | 2010/035009 | 4/2010 | |
| WO | 2011/019585 | 2/2011 | |
| WO | 2013/044203 | 3/2013 | |
| WO | 2013/056122 | 4/2013 | |
| WO | 2014/124301 | 8/2014 | |
| WO | 2015/048149 | 4/2015 | |
| WO | 2015/177312 | 11/2015 | |
| WO | 2016/138525 | 9/2016 | |
| WO | WO-2016138525 A1 * | 9/2016 | C07K 14/00 |
| WO | 2016/160166 | 10/2016 | |
| WO | 2017/005844 | 1/2017 | |
| WO | 2017040387 | 3/2017 | |
| WO | 2017066484 | 4/2017 | |
| WO | 2017/075125 | 5/2017 | |
| WO | 2017/172890 | 10/2017 | |
| WO | 2017/174568 | 10/2017 | |
| WO | 2017/207477 | 12/2017 | |
| WO | 2017/207480 | 12/2017 | |
| WO | 2018/005558 | 1/2018 | |
| WO | 2018/109220 | 6/2018 | |

OTHER PUBLICATIONS

Remota, RouxX, DubuquoyC, Fix J, BouetS, Moudjou M, Eleouet JF, Riffault S, Petit-Camurdan A. Nucleoprotein nanostructures combined with adjuvants adapted to the neonatal immune context: a candidate mucosal RSV vaccine. PLoS One. 2012;7(5):e37722. Epub May 24, 2012. (Year: 2012).*

López-Sagaseta J, Malito E, Rappuoli R, Bottomley MJ. Self-assembling protein nanoparticles in the design of vaccines. Comput Struct Biotechnol J. Nov. 26, 2015;14:58-68. (Year: 2015).*

Tramuto F, et al. Hemagglutinin, partial [Influenza B virus (B/Palermo/Apr. 2013)]. GenBank: AMB72169.1, Dep. May 11, 2016. (Year: 2016).*

Shu B, et al. Hemagglutinin [Influenza A virus (A/California/Jul. 2009(H1N1))]. GenBank: ACP41953.1, Dep. Jun. 1, 2009. (Year: 2009).*

Deng, et al., "Double-layered protein nanoparticles induce broad protection against divergent influenza A viruses," Nature Communications, 359(9):1-12, 2018.

Jones, et al., "A Method for Producing Protein Nanoparticles with Applications in Vaccines," PLoS One, 11(3): e0138761, Mar. 2016.

Kaba, et al., "Self-assembling protein nanoparticles with built-in flagellin domains increases protective efficacy of a Plasmodium falciparum based vaccine," Vaccine, 36(6): 906-914, 2018.

Phippen, et al., "Multivalent Display of Antifreeze Proteins by Fusion to Self-Assembling Protein Cages Enhances Ice-Binding Activities," Biochemistry, 55(49): 6811-6820, Nov. 2016.

Votteler, et al., "Designed proteins induce the formation of nanocage-containing extracellular vesicles," Nature, 540(7632): 292-295, Nov. 2016.

Sun, et al., "Cyclic GMP-AMP synthase is a cytosolic DNA sensor that activates the type 1 interferon pathway," Science, vol. 339, No. 6121, pp. 786-791, 2013.

Thery, et al., "Isolation and Characterization of Exosomes from Cell and Culture Supernatants and Biological Fluids," Current Protocols in Cell Biology, Chapter 3, Unit 3.22, pp. 3.22.1-3 22.19, 2006.

Tobiume, et al., "Nef does not affect the efficiency of human immunodeficiency virus type 1 fusion with target cells," Journal of Virology, vol. 77, No. 19, pp. 10645-10650, 2003.

Tinberg et al. Computational design of ligand-binding proteins with high affinity and selectivity. Nature 501, 212-216 (2013).

Tsai, et al., "Analysis of lattice-translocation disorder in the layered hexagonal structure of carboxysome shell protein CsoS1C," Acta Crystallographica, Section D: Biological Crystallography, vol. 65, Pt 9, pp. 980-988, 2009.

Tsvetkova, et al., "Cutting edge: an NK cell-independent role for Slamf4 in controlling humoral autoimmunity," Protein Cages, Methods in Molecular Biology, 1252:1-15, 2014.

Usami, et al., "SERINC3 and SERINC5 restrict HIV-1 infectivity and are counteracted by Nef," Nature, vol. 526, No. 1572, pp. 218-223, 2015.

Usui et al. Nanoscale elongating control of the self-assembled protein filament with the cysteine-introduced building blocks. Protein Sci. 18, 960-969 (2009).

Van Heel et al., A new generation of the IMAGIC image processing system. J. Struct. Biol. 116, 17-24 (1996).

Van Kooten & Banchereau, CD40-CD40 Ligand, J. Leukoc. Biol. 67:2-17 (Jan. 2000).

Voet et al., Computational design of a self-assembling symmetrical β-propeller protein, Proc. Natl. Acad. Sci. U.S.A. 111:15102-107 (2014).

Votteler, et al., "Virus budding the ESCRT pathway," Cell Host & Microbe, vol. 14, No. 3, pp. 232-241, 2013.

Wang, et al., "Expanding the genetic code of Escherichia coli," Science, vol. 292, No. 5516, pp. 498-500, 2001.

Whitehead, et al., "Optimization of Affinity, Specificity and Function of Designed Influenza Inhibitors Using Deep Sequencing," Nature Biotechnology, vol. 30, No. 6, pp. 543-548, 2012.

Winn, et al., "Macromolecular TLS refinement in REFMAC at moderate resolutions," Methods in Enzymology, vol. 374, pp. 300-321, 2003.

Worsdorfer et al., Directed evolution of a protein container. Science 331, 589-592 (2011).

Worsdorfer et al., Efficient in vitro encapsulation of protein cargo by an engineered protein container. J.Am.Chem.Soc. 134,909-911(2012).

Wu, et al., "Cyclic GMP-AMP is an endogenous second messenger in innate immune signaling by cytosolic DNA," Science, vol. 339, No. 6121, pp. 826-830, 2013.

Yeates et al., "Bacterial microcompailment organelles: protein shell structure and evolution," Annual Review of Biophysics, vol. 39, pp. 185-205, 2010.

Yee et al., "Generation of high-titer pseudotyped retroviral vectors with very broad host range," Methods in Cell Biology, vol. 43, Pt A, pp. 99-112, 1994.

Zaccai, et al., "A de novo peptide hexamer with a mutable channel," Nature Chemical Biology, vol. 7, No. 12, pp. 935-941, 2011.

Zacharias, et al., "Partitioning of lipid-modified GFPs into membrane microdomains in live cells," Science, vol. 296, No. 5569, pp. 913-916, 2002.

(56) References Cited

OTHER PUBLICATIONS

Zakeri et al., Peptide tag forming a rapid covalent bond to a protein, through engineering a bacterial adhesin, Proc. Natl. Acad. Sci U.S.A. 109(12):E690-E697 (Mar. 2012).
Zandi et al., Origin of icosahedral symmetry in viruses, Proc. Natl. Acad. Sci. U.S.A. 101(44):15556-560 (Nov. 2004).
Zhang, "Fabrication of novel biomaterials through molecular self-assembly," Nature Biotechnology, vol. 21, No. 10, pp. 1171-1178, 2003.
Zhao, et al., "A simple guide to biochemical approaches for analyzing lipid-protein interactions," Molecular Biology of the Cell, vol. 23, No. 15, pp. 2823-2830, 2012.
Zheng, et al., "From molecular to macroscopic via the rational design of a self-assembled 3D DNA crystal," Nature, vol. 461, No. 7260, pp. 74-77, 2009.
Zhou et al., Genetically encoded short peptide tags for orthogonal protein labeling by Sfp and AcpS phosphopantetheinyl transferases ACS Chem. Biol. 2, 337-346 (2007).
Zlotnick et al., A Theoretical Model Successfully Identifies Features of Hepatitis B Virus Capsid Assembly, Biochemistry 38:14644-652 (1999).
Zlotnick et al., Mechanism of Capsid Assembly for an Icosahedral Plant Virus, Virology 277:450-56 (2000).
Zschoche & Hilvert, Diffusion-Limited Cargo Loading of an Engineered Protein Container, Am. Chem. Soc. 137:16121-132(2015).
The International Search Report and Written Opinion from International Application No. PCT/US2018/025880; dated Jun. 29, 2018, pp. 1-19.
PCT/US2014/015371 International Search Report and Written Opinion, dated 2014.
PCT/US2016/020090, International Search Report and Written Opinion, 10 pages, dated 2016.
Golovanov, et al., "A Simple Method for Improving Protein Solubility and Long-Term Stability," Journal of the American Chemical Society, vol. 126, No. 29, pp. 8933-8939, 2004.
Gonen et al., Design of ordered two-dimensional arrays mediated by noncovalent protein-protein interfaces, Science 348:1365-68 (2015).
Goodsell & Olson, Structural symmetry and protein function. Annu. Rev. Biophys. Biomol. Struct. 29,105-153 (2000).
Gosser, et al., "Peptide-triggered conformational switch in HIV-1 RRE RNA complexes," Nature Structural Biology, vol. 8, No. 2, pp. 146-150, 2001.
Gray et al., "Cutting Edge: cGAS is Required for Lethal Autoimmune Disease in the Trex1-Deficient Mouse Model of Aicardi-Goutieres Syndrome," Journal of Immunology, vol. 195, No. 5, pp. 1939-1943, 2015.
Gribbon, et al., "MagicWand: a single, designed peptide that assembles to stable, ordered alpha-helical fibers," Biochemistry, vol. 47, No. 39, pp. 10365-10371, 2008.
Griffiths, et al., "Cloning, isolation and characterization of the Thermotoga maritima KDPG aldolase," Bioorganic & Medicinal Chemistry, vol. 10, No. 3, pp. 545-550, 2002.
Grigorieff, "FREALIGN: high-resolution refinement of single particle structures," Journal of Structural Biology, vol. 157, No. pp. 117-125, 2007.
Grigoryan et al. Computational design of virus-like protein assemblies on carbon nanotube surfaces. Science 332, 1071-1076 (2011).
Grueninger et al. Designed protein-protein association. Science 319, 206-209 (2008).
Han et al. DNA gridiron nanostructures based on four-arm junctions. Science 339, 1412-1415 (2013).
Harbury, et al., "High-resolution protein design with backbone freedom," Science, vol. 282, No. 5393, pp. 1462-1467, 1998.
Howorka, Rationally engineering natural protein assemblies in nanobiotechnology. Curr. Opin. Biotechnol. 22, 485-191 (2011).
Hsia et al., Design of a hyperstable 60-subunit protein icosahedron, Nature 535:136-39 (2016).
Huang et al., A de novo designed protein protein interface. Protein Sci. 16, 2770-2774 (2007).
Hurley, et al., "Membrane Budding and Scission by the ESCRT Machinery: It's All in the Neck," Nature Reviews Molecular Cell Biology, vol. 11, No. 8, pp. 556-566, 2010.
Ishikawa, et al., "STING is an endoplasmic reticulum adaptor that facilitates innate immune signalling," Nature, vol. 455, No. 7213, pp. 674-678, 2008.
Jacak, et al., "Computational Protein Design with Explicit Consideration of Surface Hydrophobic Patches," Proteins: Structure, Function, and Bioinformatics, vol. 80, No. 3, pp. 825-838, 2012.
Jackel, et al., "Consensus Protein Design Without Phylogenetic Bias," Journal of Molecular Biology, vol. 399, No. 4, pp. 541-546, 2010.
Jackel et al., Protein design by directed evolution. Annu. Rev. Biophys. 37,153-173 (2008).
Janin et al., Protein-protein interaction and quaternary structure. Q. Rev. Biophys. 41, 133-180 (2008).
Jha et al., Computational design of a PAK1 binding protein. J. Mol. Biol. 400, 257-270 (2010).
Julien, et al., "Crystal structure of a soluble cleaved HIV-1 envelope trimer," Science, vol. 342, No. 6165, pp. 1477-1483, 2013.
Kabsch, Xds. Acta Crystallogr. D Biol. Crystallogr. 66, 125-132 (2010).
Kanekiyo et al., "Self-assembling influenza nanoparticle vaccines elicit broadly neutralizing H1N1 antibodies." Nature. Jul. 4, 2013;499(7456):102-6. doi: 10.1038/nature12202. Epub May 22, 2013. PMID: 23698367.
Karanicolas et al., A de novo protein binding pair by computational design and directed evolution. Mol. Cell 42, 250-260 (2011).
Ke, Three-dimensional structures self-assembled from DNA bricks. Science 338, 1177-1183 (2012).
Khare & Fleishman, Emerging themes in the computational design of novel enzymes and protein-protein interfaces. FEBSLett. 587, 1147-1154(2013).
King & Lai, Practical approaches to designing novel protein assemblies. Curr. Opin. Struct. Biol. 23, 632-638 (2013).
King et al. Computational design of self-assembling protein nanomaterials with atomic level accuracy. Science 336, 1171-1174 (2012).
King et al., "Accurate design of coassembling multi-component protein nanomaterials" Nature 510(7503):103-108 (Jun. 2014). With supplementary data.
Koder, et al., "Design and engineering of an O(2) transport protein," Nature, vol. 458, No. 7236, pp. 305-309, 2009.
Kortemme, et al., "Computational redesign of protein-protein interaction specificity," Nature Structural & Molecular Biology, vol. 11, No. 4, pp. 371-379, 2004.
Kremer, et al., "Computer visualization of three-dimensional image data using IMOD," Journal of Structural Biology, vol. 116. No. 1, pp. 71-76, 1996.
Krissinel & Henrick, Inference of macromolecular assemblies from crystalline state. J. Mol. Biol. 372, 774-797 (2007).
Kuhlman & Baker, Native protein sequences are close to optimal for their structures. Proc. Natl Acad. Sci. USA 97, 10383-10388 (2000).
Kumar, et al., "Crystal structure analysis of icosahedral lumazine synthase from *Salmonella typhimurium*, an antibacterial drug target," Acta Crystallographica, Section D: Biological Crystallography, vol. 67, Pt 2, pp. 131-139, 2011.
Lai et al., Structure of a Designed Protein Cage that Self-Assembles into a Highly Porous Cube, Nat. Chem. 6:1065-71 (2014).
Lai et al., Principles for designing ordered protein assemblies. Trends Cell Biol. 22, 653-661 (2012).
Lai et al., Structure of a 16-nm cage designed by using protein oligomers. Science 336:1129-30 (Jun. 2012).
Lanci et al. Computational design of a protein crystal. Proc. Natl Acad. Sci. USA 109, 7304-7309 (2012).
Laskowski, et al., "PROCHECK: a program to check the stereochemical quality of protein structures," Journal of Applied Crystallography, 26:283-291, 1993.
Lawrence & Colman, Shape complementarity at protein/protein interfaces. J. Mol. Biol. 234, 946-950 (1993).
Lawrence et al., Supercharging Proteins Can Impart Unusual Resilience, J. Am. Chem. Soc. 129, 10110-10112 (2007).

(56) References Cited

OTHER PUBLICATIONS

Leaver-Fay et al., ROSETTA3: an object-oriented software suite for the simulation and design of macromolecules. Methods Enzymol. 487, 545-574 (2011).
Leaver-Fay et al. Scientific benchmarks for guiding macromolecular energy function improvement. Methods Enzymol. 523, 109-143 (2013).
Lemmon, "Membrane recognition by phospholipid-binding domains." Nature Reviews Molecular Cell Biology, vol. 9, No. 2, pp. 99-111, 2008.
Levy, et al., "3D complex: a structural classification of protein complexes," PLoS Computational Biology, vol. 2, No. 11, e155, pp. 1395-1406, 2006.
Lovejoy, et al., "Crystal structure of a synthetic triple-stranded alpha-helical bundle," Science, vol. 259, No. 5099, pp. 1288-1293, 1993.
Lin et al., Structural Fingerprinting: Subgrouping of Comoviruses by Structural Studies of Red Clover Mottle Virus to 2.4—Å Resolution and Comparisons with Other Comoviruses J. Virol. 74, 493-504 (2000).
Website: http://www.genisphere.com/, 1 page retreived on Sep. 12, 2016.
Adams et al., PHENIX: a comprehensive Python-based system for macromolecular structure solution. Acta Crystallogr. D Biol. Crystallogr. 66, 213-221 (2010).
Afosrapan, "Computational design of self- and co-assembling protein nanomaterials with atomic level accuracy" available online at: https://community.apan.org/afosr/w/researchareas/7659.human-performance-and-biosystems.aspx, 2014.
Andersen, et al., "Self-assembly of a nanoscale DNA box with a controllable lid," Nature, vol. 459, No. 7243, pp. 73-76, 2009.
Apolonia, et al., "Promiscuous RNA binding ensures effective encapsidation of APOBEC3 proteins by HIV-1," PLoS Pathogens, vol. 11, No. 1, e1004609, 2015.
Arnold & Volkov, Directed evolution of biocatalysts. Curr. Opin. Chem. Biol. 3, 54-59 (1999).
Bagby, et al., "[2]—Optimization of Protein Solubility and Stability for Protein Nuclear Magnetic Resonance," Methods in Enzymology, vol. 339, pp. 20-41, 2001.
Bale et al., Structure of a designed tetrahedral protein assembly variant engineered to have improved soluble expression, Protein Sci. 24:1695-1701 (2015).
Bale et al., "Accurate design of megadalton-scale two-component icosahedral protein complexes," Science 353 (6297):389-94 (Jul. 2016).
Ballister, et al., "In vitro self-assembly of tailorable nanotubes from a simple protein building block," Proceedings of the National Academy of Sciences USA, vol. 105, No. 10, pp. 3733-3738, 2008.
Bieniasz, "Late budding domains and host proteins in enveloped virus release," Virology, vol. 344, No. 1, pp. 55-63, 2006.
Biswas, et al., "The human immunodeficiency virus type 1 ribosomal frameshifting site is an invariant sequence determinant and an important target for antiviral therapy," Journal of Virology, vol. 78, No. 4, pp. 2082-2087, 2004.
Blanc, et al., "Refinement of severely incomplete structures with maximum likelihood in BUSTER-TNT," Acta Carystallographica, Section D: Biological Crystallography, vol. 60, Pt 12, Pt 1, pp. 2210-2221, 2004.
Bondos, et al., "Detection and Prevention of Protein Aggregation Before, During, and After Purification," Analytical Biochemistry, vol. 316, No. 2, pp. 223-231, 2003.
Boyle et al., Squaring the circle in peptide assembly: from fibers to discrete nanostructures by de novo design. J. Am Chem. Soc. 134, 15457-15467 (2012).
Bradley & Baker, Improved beta-protein structure prediction by multilevel optimization of nonlocal strand pairings and local backbone conformation. Proteins 65, 922-929 (2006).
Bridgeman, et al., "Viruses transfer the antiviral second messenger cGAMP between cells," Science, vol. 349, No. 6253, pp. 1228-1232, 2015.

Brodin et al., et al. Metal-directed, chemically tunable assembly of one-, two- and three-dimensional crystalline protein arrays. Nature Chem. 4, 375-382 (2012).
Burkhard et al., Malaria vaccine based on Self-Assembling Protein Nanoparticles, Expert Rev. Vaccines 14 (12):1525-27 (2015).
Caspar & Klug, The Principles in the Construction of Regular Viruses, Cold Spring Harb. Symp. Quant. Biol. 27, 1-24 (1962).
Cavrois, et al., "A sensitive and specific enzyme-based-assay detecting HIV-1 virion fusion in primary T lymphocytes," Nature Biotechology, vol. 20, No. 11, pp. 1151-1154, 2002.
Chan et al. Structure and function of P19, a high-affinity iron transporter of the human pathogen Campylobacter jejuni. J. Mol. Biol. 401, 590-604 (2010).
Chao, et al., "Isolating and Engineering Human Antibodies Using Yeast Surface Display," Nature Protocols, vol. 1, No. 2, pp. 755-768, 2016.
Chao, et al., "Structural basis for the coevolution of a viral RNA-protein complex," Nature Structural & Molecular Biology, vol. 15, No. 1, pp. 103-105, 2008.
Colovos & Yeates, Verification of protein structures: patterns of nonbonded atomic interactions. Protein Sci. 2, 1511-1519(1993).
Cooper, et al., "Predicting protein structures with a multiplayer online game," Nature, vol. 466, No. 7307, pp. 756-760, 2010.
Correia et al., Proof of principle for epitope-focused vaccine design, Nature 507(7491):201-06 (2014).
Crowley, et al., "Structural insight into the mechanisms of transport across the *Salmonella enterica* Pdu microcompartment shell," Journal of Biological Chemistry, vol. 285, No. 48, pp. 37838-37846, 2010.
Das, et al., "Simultaneous prediction of protein folding and docking at high resolution," Proceedings of the National Academy of Sciences USA, vol. 106, No. 45, pp. 18978-18983, 2009.
Davis et al. MolProbity: all-atom contacts and structure validation for proteins and nucleic acids. Nucleic Acids Res. 35, W375-383 (2007).
De Guzman, et al., "Structure of the HIV-1 nucleocapsid protein bound to the SL3 psi-RNA recognition element," Science, vol. 279, No. 5349, pp. 384-388, 1998.
Dempsey et al., C3d of Complement as a Molecular Adjuvant: Bridging Innate and Acquired Immunity, Science, 271:348-50 (Jan. 1996).
Der et al., Metal-mediated affinity and orientation specificity in a computationally designed protein homodimer. J. Am. Chem. Soc. 134, 375-385 (2012).
DiMaio et al., Modeling symmetric macromolecular structures in Rosetta3. PLoS ONE 6, e20450 (2011).
Douglas & Young, Viruses: making friends with old foes. Science 312, 873-875 (2006).
Dyer et al., High-Throughput SAXS for the Characterization of Biomolecules in Solution: A Practical Approach, Methods Mol. Biol. 1091:245-58 (2014).
Emsley et al., Features and development of Coot. Acta Crystallogr. D Biol. Crystallogr. 66, 486-501 (2010).
Fallas et al., Computational Design of Self-Assembling Cyclic Protein Homo-oligomers, Nat. Chem. 9(4):353-60 (Apr. 2017).
Fleishman, et al., "Hotspot-centric de novo design of protein binders," Journal of Molecular Biology, vol. 413, No. 5, pp. 1047-1062, 2011.
Fleishman et al., Computational design of proteins targeting the conserved stem region of influenza hemagglutinin. Science 332, 816-821 (2011).
Fleishman et al. Community-wide assessment of protein-interface modeling suggests improvements to design methodology. J Mol. Biol. 414, 289-302 (2011).
Fleishman et al. RosettaScripts: a scripting language interface to the Rosetta macromolecular modeling suite. PLoS One 6, e20161 (2011).
Fleishman et al., Restricted sidechain plasticity in the structures of native proteins and complexes. Protein Sci. 20, 753-757 (2011).
Fletcher et al. Self-assembling cages from coiled-coil peptide modules. Science 340, 595-599 (2013).

(56) References Cited

OTHER PUBLICATIONS

Frank et al. SPIDER and WEB: processing and visualization of images in 3D electron microscopy and related fields. J. Struct. Biol. 116, 190-199 (1996).
Freed, et al., "Single amino acid changes in the human immunodeficiency virus type 1 matrix block virus particle production," Journal of Virology, vol. 68, No. 8, pp. 5311-5320, 1994.
Gentili, et al., "Transmission of innate immune signaling by packaging of cGAMP in viral particles," Science, vol. 349, No. 6253, pp. 1232-1236, 2015.
Georgiev et al., "Two-Component Ferritin Nanoparticles for Multimerization of Diverse Trimeric Antigens." ACS Infect Dis. May 11, 2018;4(5):788-796. doi: 10.1021/acsinfecdis.7b00192. Epub Mar. 6, 2018. PMID: 29451984—Abstract provided.
Gibson et al. Enzymatic assembly of DNA molecules up to several hundred kilobases. Nat. Methods 6, 343-345 (2009).
Glen et al., A Randomized, Blinded, Controlled, Dose-Ranging Study of a Respiratory Syncytial Virus Recombinant Fusion, J. Infect. Dis. 213(3):411-22 (2016).
Lin et al., The Refined Crystal Structure of Cowpea Mosaic Virus at 2.8 Å Resolution, Virology 265, 20-34 (1999).
Ludtke et al., EMAN: semiautomated software for high-resolution single-particle reconstructions. J. Struct. Biol. 128, 82-97(1999).
Lüthy et al., Assessment of protein models with three-dimensional profiles. Nature 356, 83-85 (1992).
Lyumkis, et al., "Cryo-EM structure of a fully glycosylated soluble cleaved HIV-1 envelope timer," Science, vol. 342, No. 6165, pp. 1484-1490, 2013.
Mangeot, et al., "Protein transfer into human cells by VSV-G-induced nanovesicles," Molecular Therapy, vol. 19, No. 9, pp. 1656-1666, 2011.
McCoy et al. Phaser crystallographic software. J. Appl. Crystallogr. 40, 658-674 (2007).
McCullough, et al., "Membrane Fission Reactions of the Mammalian ESCRT Pathway," Annual Review of Biochemistry, vol. 82, pp. 663-692, 2013.
McDonald, et al., "No strings attached: the ESCRT machinery in viral budding and cytokinesis," Journal of Cell Science, vol. 122, Pt 13, pp. 2167-2177, 2009.
McLellan et al., "Structure-based Design of a Fusion Glycoprotein Vaccine for Respiratory Syncytial Virus" Science 342(6158):592-98 (Nov. 2013).
Mindell, et al., "Accurate determination of local defocus and specimen tilt in electron microscopy," Journal of Structural Biology, vol. 142, No. 3, pp. 334-347, 2003.
Murshudov, et al., "Refinement of macromolecular structures by the maximum-likelihood method," Acta Crystallographica, Section D: Biological Crystallography, vol. 53, Pt 3, pp. 240-255, 1997.
Nam, et al., "Molecular basis for interaction of let-7 microRNAs with Lin28," Cell, vol. 147, No. 5, pp. 1080-1091, 2011.
Nannenga et al., Overview of electron crystallography of membrane proteins: crystallization and screening strategies using negative stain electron microscopy. Curr. Protoc. Protein Sci. Chapter 17, Unit17.15 (2013).
Ni, et al., "Crystal structure of the MS2 coat protein dimer: implication for RNA binding and virus assembly," Structure, vol. 3, No. 3, pp. 255-263, 1995.
Nivon et al., Automating human intuition for protein design. Proteins (2013). doi: 10.1002/prot.24463.
Ohi, et al., "Negative staining and image classification-powerful tools in modem electron microscopy," Biological Procedures Online, vol. 6, pp. 23-34, 2004.
Olsen, "Gene transfer vectors derived from equine infectious anemia virus," Gene Therapy, vol. 5, No. 11, pp. 1481-1487, 1998.
Otwinowski, et al., "[20] Processing of X-ray diffraction data collected in oscillation mode," Methods in Enzymology, vol. 276, pp. 307-326, 1997.

Oubridge, et al., "Crystal structure at 1.92 A resolution of the RNA-binding domain of the U1A spliceosomal protein complexed with an RNA hairpin," Nature, vol. 372, No. 6505, pp. 432-438, 1994.
Padilla et al., Nanohedra: using symmetry to design self assembling protein cages, layers, crystals, and filaments. Proc. Natl Acad. Sci. USA 98, 2217-2221 (2001).
Pancera, et al., "Structure and immune recognition of trimeric pre-fusion HIV-1 Env.," Nature, vol. 514, No. 7523, pp. 455-461, 2014.
Painter & Merritt, Optimal description of a protein structure in terms of multiple groups undergoing TLS motion. Acta Crystallogr. D Biol. Crystallogr. 62, 439-450 (2006).
Painter, J. & Merritt, TLSMD web server for the generation of multi-group TLS models. Journal of Applied Crystallography 39, 109-111 (2006).
Parent, et al., "Positionally independent and exchangeable late budding functions of the Rous Sarcoma Virus and Human Immunodeficiency Virus Gag proteins," Journal of Virology, vol. 69, No. 9, pp. 5455-5460, 1995.
Patterson, et al., "Characterization of a highly flexible self-assembling protein system designed to form nanocages," Protein Science, vol. 23, No. 2, pp. 190-199, 2014.
Pesarrodona, et al., "Intracellular targeting of CD44+ cells with self-assembling, protein only nanoparticles," International Journal of Pharmaceutics, vol. 473, No. 1-2, pp. 286-295, 2014.
Pettersen et al. UCSF Chimera—a visualization system for exploratory research and analysis. J. Comput. Chem. 25, 1605-1612 (2004).
Prodromou & Pearl, Recursive PCR: a novel technique for total gene synthesis. Protein Eng. 5, 827-829 (1992).
Puglisi, et al., "Solution structure of a bovine immunodeficiency virus Tat-TAR peptide-RNA complex," Science, vol. 270, No. 5239, pp. 1200-1203, 1995.
Raman et al., Design of Peptide Nanoparticles Using Simple Protein Oligomerization Domains, The Open Nanomedicine Journal, 2:15-26 (2009).
Raman et al., Materials Science: Structure-based design of peptides that self-assemble into regular polyhedral nanoparticles, Nanomedicine: Nanotechnology, Biology, and Medicine 2:95-102 (2006).
Resh, "Covalent lipid modifications of proteins," Current Biology, vol. 23, No. 10, pp. R431-R435, 2013.
Resh, "Fatty acylation of proteins: new insights into membrane targeting of myristoylated and palmitoylated proteins," Biochimica et Biophysica Acta, vol. 1451, No. 1, pp. 1-16, 1999.
RINGLER & SCHULZ, Self-Assembly of Proteins into Designed Networks, Science 302:106-09 (2003).
Rosa, et al., "HIV-1 Nef promotes infection by excluding SERINC5 from virion incorporation," Nature, vol. 526, No. 1572, pp. 212-217, 2015.
Rothemund, Folding DNA to create nanoscale shapes and patterns. Nature 440, 297-302 (2006).
Salgado, et al., "Controlling protein-protein interactions through metal coordination: assembly of a 16-helix bundle protein," Journal of the American Chemical Society, vol. 129, No. 44, pp. 13374-13375, 2007.
Salgado et al., Metal-directed protein self-assembly. Acc. Chem. Res. 43, 661-672 (2010).
Schindelin et al. Fiji: an open-source platform for biological-image analysis. Nat. Methods 9, 676-682 (2012).
Schneidman-Duhovny et al., "Accurate SAXS Profile Computation and its Assessment by Contrast Variation Experiements," Biophysical Journal, Aug. 2013, pp. 962-974, vol. 105.
Schneidman-Duhovny et al., "FoXS: a web server for rapid computation and fitting of SAXS profiles," Nucleic Acids Research, 2010, pp. W540-W544, vol. 38.
Schrodinger, LLC, "The PyMOL Molecular Graphics System, Version 1.4," available online at: http://www.pymol.org, 2011.
Schuck, "Size-distribution analysis of macromolecules by sedimentation velocity ultracentrifugation and lamm equation modeling," Biophysical Journal, vol. 78, No. 3, pp. 1606-1619, 2000.
Seeman, Nanomaterials based on DNA. Annu. Rev. Biochem. 79, 65-87 (2010).

(56) References Cited

OTHER PUBLICATIONS

Sheffler & Baker, RosettaHoles2: a volumetric packing measure for protein structure refinement and validation. Protein Sci 19, 1991-1995 (2010).
Sinclair et al., Generation of protein lattices by fusing proteins with matching rotational symmetry. Nature Nanotechnol. 6, 558-562 (2011).
Sinclair, Constructing arrays of proteins. Curr. Opin. Chem. Biol. 17, 946-951 (2013).
Smith, XIMDISP—A visualization tool to aid structure determination from electron microscope images. J. Struct. Biol. 125, 223-228 (1999).
Stahelin, "Lipid binding domains: more than simple lipid effectors," Journal of Lipid Research, vol. 50, Suppl S299-S304, 2009.
Stranges et al., Computational design of a symmetric homodimer using beta-strand assembly. Proc. Natl Acad. Sci. USA 108, 20562-20567 (2011).

* cited by examiner

FIG. 2A
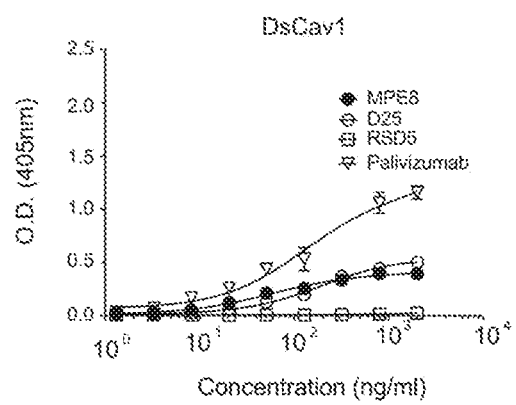
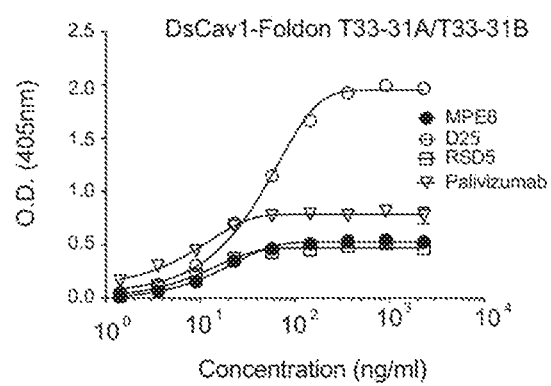
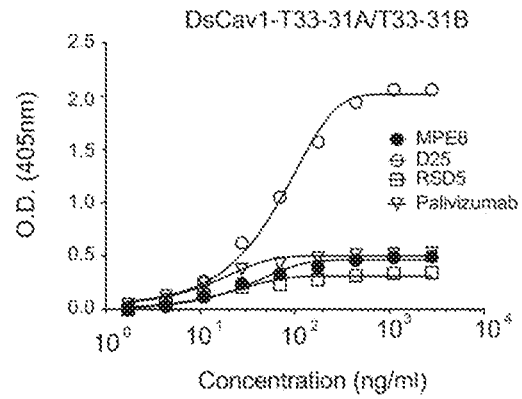
FIG. 2B
FIG. 2C

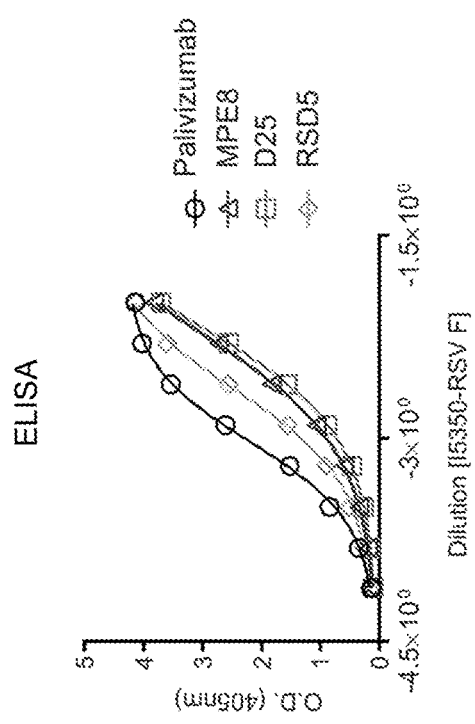
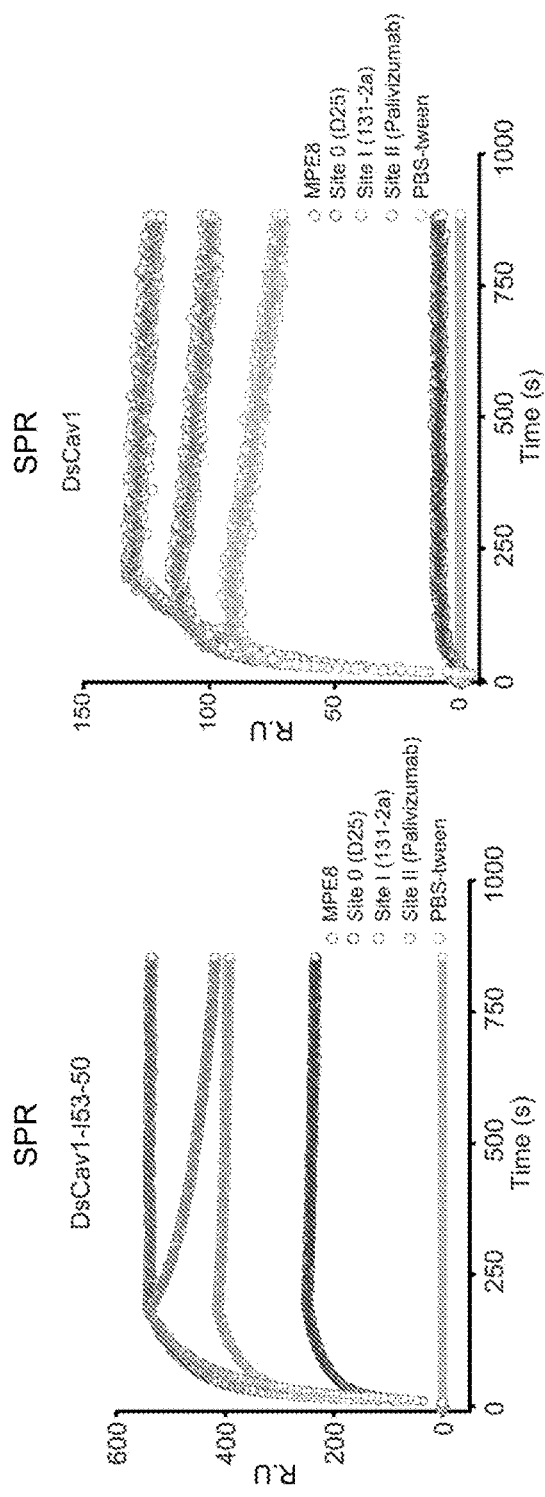
FIG. 6A
FIG. 6B
FIG. 6C

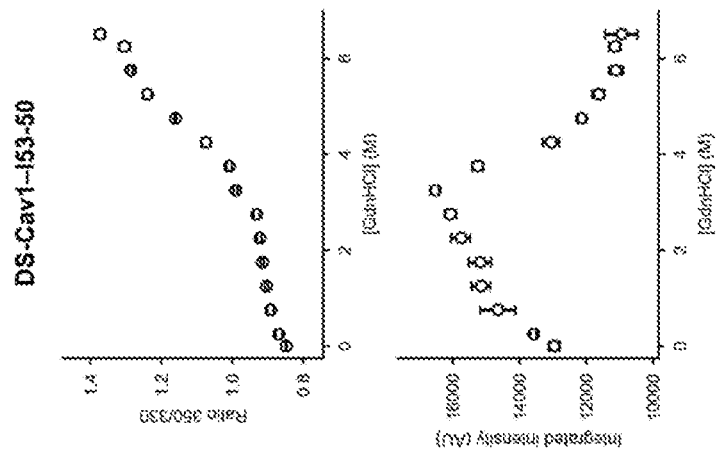
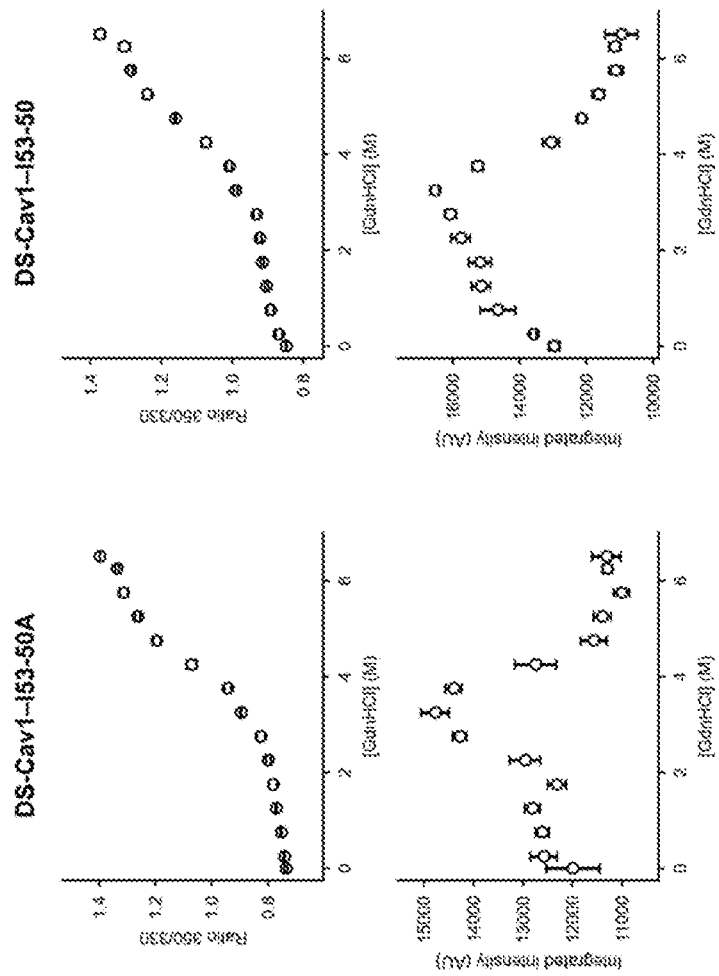
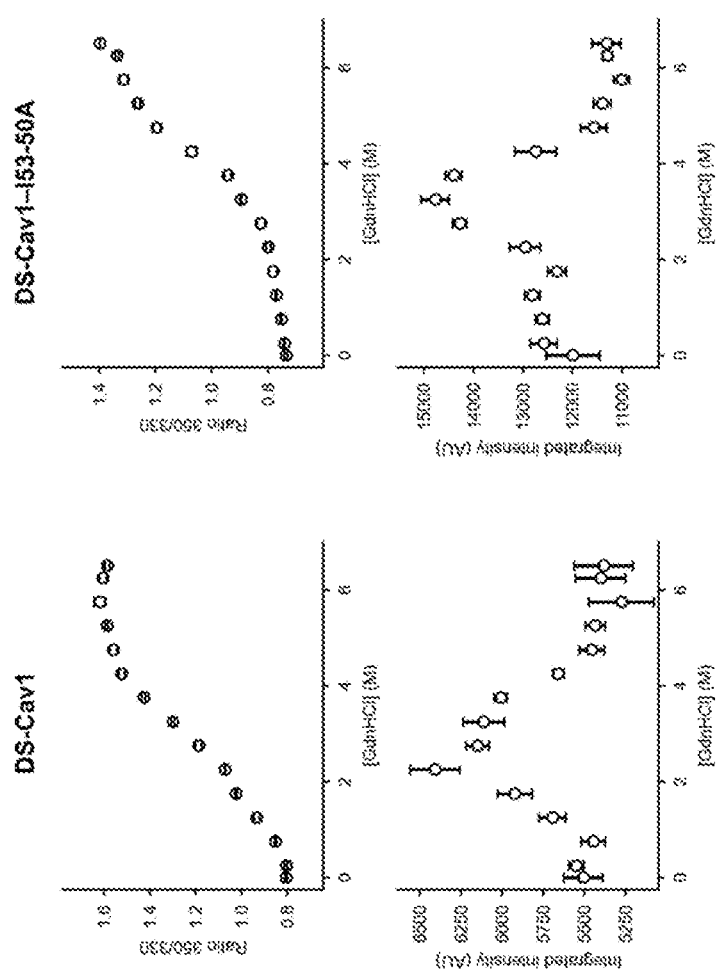

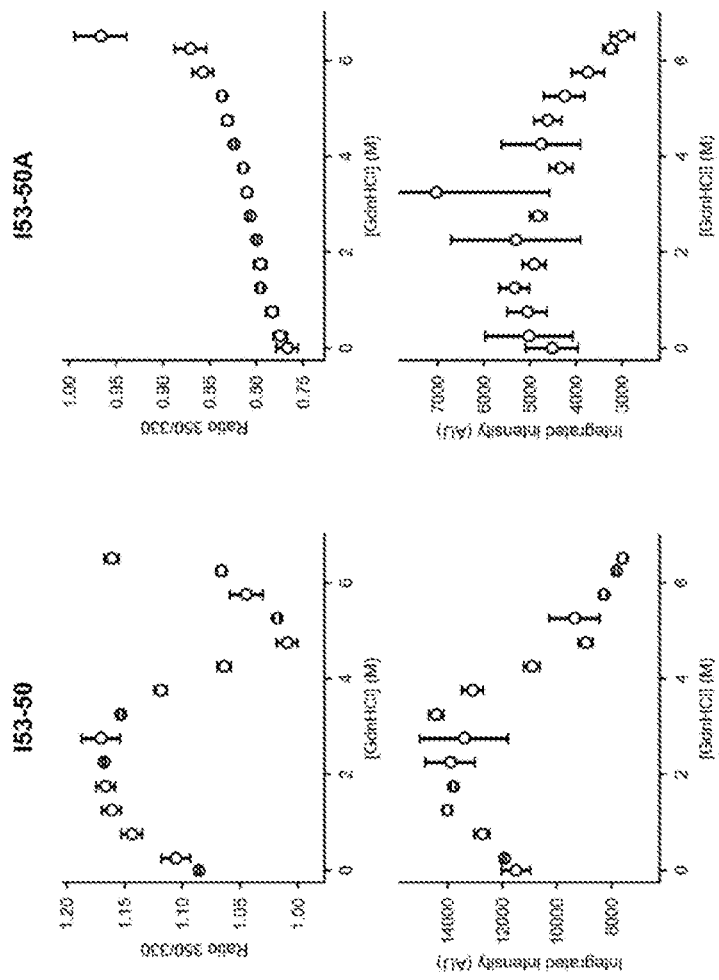

SELF-ASSSEMBLING NANOSTRUCTURE VACCINES

CROSS REFERENCE

This application is a U.S. national phase of International Application No. PCT/US2019/020029, filed on Feb. 28, 2019, which claims priority to U.S. Provisional Application No. 62/724,721, filed Aug. 30, 2018; and U.S. Provisional Application No. 62/636,757, filed Feb. 28, 2018, all of which are incorporated by reference herein in their entirety.

DESCRIPTION OF THE TEXT FILE SUBMITTED ELECTRONICALLY

This application is being filed electronically via EFS-Web and includes an electronically submitted sequence listing in .txt format. The .txt file contains a sequence listing entitled 18-235-PCT-US_SeqList_ST25.txt" created on Nov. 17, 2022 and having a size of 374 kilobytes.

FIELD OF THE INVENTION

The present disclosure relates generally to vaccines and methods of use thereof. Specifically, the disclosure relates to nanostructure-based vaccines capable of eliciting immune responses to antigens, such as antigenic proteins of various infectious agents, including bacteria, viruses, and parasites.

BACKGROUND OF THE INVENTION

Vaccination is a treatment modality used to prevent or decrease the severity of infection with various infectious agents, including bacteria, viruses, and parasites. Development of new vaccines has important commercial and public health implications. In particular, lyme disease, pertussis, herpes virus, orthomyxovirus, paramyxovirus, pneumovirus, filovirus, flavivirus, reovirus, retrovirus, and malaria are infectious agents for which vaccines already exist, are being developed, or would be desirable.

Subunit vaccines are vaccines made from isolated antigens, usually proteins expressed recombinantly in bacterial, insect, or mammalian cell hosts. Typically, the antigenic component of a subunit vaccine is selected from among the proteins of an infectious agent observed to elicit a natural immune response upon infection, although in some cases other components of the infectious agent can be used. Typical antigens for use in subunit vaccines include protein expressed on the surface of the target infectious agent, as such surface-expressed envelope glycoproteins of viruses. Preferably, the antigen is a target for neutralizing antibodies. More preferably, the antigen is a target for broadly neutralizing antibodies, such that the immune response to the antigen covers immunity against multiple strains of the infectious agent. In some cases, glycans that are N-linked or O-linked to the subunit vaccine may also be important in vaccination, either by contributing to the epitope of the antigen or by guiding the immune response to particular epitopes on the antigen by steric hindrance. The immune response that occurs in response to vaccination may be direct to the protein itself, to the glycan, or to both the protein and linked glycans. Subunit vaccines have various advantages including that they contain no live pathogen, which eliminates concerns about infection of the patient by the vaccine; they may be designed using standard genetic engineering techniques; they are more homogenous than other forms of vaccine; and they can be manufactured in standardized recombinant protein expression production systems using well-characterized expression systems. In some cases, the antigen may be genetically engineered to favor generation of desirable antibodies, such as neutralizing or broadly neutralizing antibodies. In particular, structural information about an antigen of interest, obtained by X-ray crystallography, electron microscopy, or nuclear magnetic resonance experiments, can be used to guide rational design of subunit vaccines.

A known limitation of subunit vaccines is that the immune response elicited may sometimes be weaker than the immune response to other types of vaccines, such as whole virus, live, or live attenuated vaccines. The present inventors have recognized and herein disclose that nanostructure-based vaccines have the potential to harness the advantages of subunit vaccines while increasing the potency and breadth of the vaccine-induced immune response through multivalent display of the antigen in symmetrically ordered arrays. Nanostructure-based vaccines are one form of "nanoparticle vaccine." In the present disclosure, nanostructure-based vaccines are distinguished from nanoparticle vaccines, because the term nanoparticle vaccine has been used in the art to refer to protein-based or glycoprotein-based vaccines (see. e.g. U.S. Pat. No. 9,441,019), polymerized liposomes (see, e.g., U.S. Pat. No. 7,285,289), surfactant micelles (see, e.g., US Patent Pub. No. US 2004/0038406 A1), and synthetic biodegradable particles (see, e.g., U.S. Pat. No. 8,323,696). Nanostructure-based vaccination represents a paradigm in vaccination with significant commercial and public health implications. Thus, there exists a need for nanostructure-based vaccines and methods of use thereof for eliciting immune responses to infectious agents, such as bacteria, viruses, and parasites; and for preventing or decreasing the severity of infection with an infectious agent including, for example and without limitation, lyme disease, pertussis, herpes virus, orthomyxovirus, paramyxovirus, pneumovirus, filovirus, flavivirus, reovirus, retrovirus, meningococcus, and malaria.

SUMMARY OF THE INVENTION

Described herein are nanostructures, vaccines, methods of use thereof, and methods of making said nanostructures.

In one aspect, the present disclosure provides nanostructures comprising a first plurality of polypeptides, wherein the first plurality of polypeptides are arranged according to at least one symmetry operator; the nanostructure comprises a first plurality of antigens; each of the first plurality of the antigens has a proximal end and a distal end; and the proximal ends of the antigens are each attached to a member of the first plurality of polypeptides.

In another aspect, the present disclosure provides vaccines comprising any of the nanostructures of the present disclosure, wherein the vaccine is capable of eliciting a neutralizing antibody response to an infectious agent. In an embodiment, the vaccine is provided in a pharmaceutical composition.

In another aspect, the present disclosure provides methods of generating immunity to an infectious agent in a subject, comprising administering any of the vaccines of the present disclosure.

In another aspect, the present disclosure provides methods of making any of the nanostructures of the present disclosure by in vitro assembly of component purified from one or more recombinant expression systems. In another aspect, the present disclosure provides methods of making any of the nanostructures of the present disclosure by co-expression of all components in a recombinant expression system, thereby generating the nanostructure, and purifying the nanostructure.

In an embodiment of the nanostructures of the present disclosure, the nanostructure further comprises a second plurality of polypeptides, wherein the second plurality of polypeptides is attached to the first plurality of polypeptides. In an embodiment, the nanostructure further comprises a second plurality of antigens. In an embodiment, the nanostructure further comprises a second plurality of antigens, each of the second plurality of second antigens has a proximal end and a distal end, and the proximal ends of the second antigens are each attached to a member of the second plurality of polypeptides; and optionally, the proximal ends of the antigens are the N termini of the antigens or the C termini of the antigens.

In an embodiment of the nanostructures of the present disclosure, the plurality of antigens is a plurality of antigenic proteins or antigenic fragments thereof. In an embodiment, the antigenic protein of the nanostructure is selected from SEQ ID NOs: 52-88 and 90-113 or a variant thereof; or the antigenic protein is at least 75, 80, 85, 90, 95, or 99% identical to a polypeptide selected from SEQ ID NOs: 52-88 and 90-97; or the antigenic protein is any of the following: HIV Env, RSV F, Influenza HA, EBV gp350, CMV gB, CMV UL128, CMV UL130, CMV UL131A, CMV gH, CMV gL, Lyme OspA, Pertussis toxin, Dengue E, SARS S, MERS S, Zaire ebolavirus GP, Sudan ebolavirus GP, Marburg virus GP, Hanta virus Gn, Hanta virus Gc, HepB surface antigen, Measles H, Zika envelope domain III, Malaria CSP, Malaria Pfs25, MenB fHbp, MenB NadA, MenB NHBA, Nipah virus F, Nipah virus G, Rotavirus VP4, Rotavirus VP8*, hMPV F, hMPV G, PV F, or PV HN 8.

In an embodiment, the nanostructure is configured to display a target epitope of the antigen; and optionally, the target epitope is accessible to an antibody as defined herein below. In any embodiment where the nanostructure comprises a plurality of antigenic proteins, optionally the nanostructure is configured to elicit an immune response to the first plurality of antigenic proteins, which immune response is preferentially directed to a target epitope of the antigenic protein. In embodiments of the present disclosure, the target epitope is conserved, it is an epitope for neutralizing antibodies, it is an epitope for cross-reactive antibodies, or it is an epitope for a broadly-neutralizing antibody.

In an embodiment of the nanostructures of the present disclosure, the plurality of antigens comprises at least one mutation selected from the group consisting of an interface-stabilizing mutation, complementary cysteine mutations configured to result in a disulfide bond, deletion of a loop, addition of an N-linked glycosylation site, removal of an N-linked glycosylation site, an epitope-destroying mutation, and an epitope-creating mutation. In an embodiment, the plurality of antigens comprises an antigenic oligosaccharide.

In an embodiment of the vaccines of the present disclosure, the neutralizing antibody response is protective against infection by an infectious agent. In an embodiment, the neutralizing antibody response is broadly-neutralizing against diverse strains of an infectious agent. In an embodiment, the infectious agent is any of the following: lyme disease, pertussis, herpesvirus, orthomyxovirus, paramyxovirus, pneumovirus, filovirus, flavivirus, reovirus, retrovirus, meningococcus, or malaria. In an embodiment, the infectious agent is a virus selected from the following: HIV, RSV, Influenza, EBV, CMV, Dengue, Severe Acute Respiratory Syndrome (SARS) virus, Middle East Respiratory Syndrome (MERS) virus, Ebola virus, Marburg virus, Hanta virus, Hepatitis B, HPV, Measles, Nipah virus, Rotavirus, Metapneumo virus, Parainfluenza virus, and Zika. In an embodiment, the infectious agent is lyme disease or pertussis. In an embodiment, the infectious agent is malaria. In an embodiment, the infectious agent is meningococcus.

In an embodiment of the methods of generating immunity of the present disclosure, the method further comprises administering an adjuvant. In an embodiment, the method further comprises administering the vaccine repeatedly. In an embodiment, the method further comprises administering a second vaccine which is selected from following: a nanoparticle-based vaccine, a protein-based vaccine, a live vaccine, a live attenuated vaccine, a whole germ vaccine, a DNA vaccine, or a RNA vaccine; and optionally the first vaccine is a prime and the second vaccine is a boost, or optionally the second vaccine is a prime and the first vaccine is a boost. In an embodiment, the method induces directed affinity maturation. In an embodiment, the method results in a broadly-neutralizing immune response.

In an embodiment of the methods of making any of the nanostructures of the present disclosure, the method achieves in vitro assembly of the nanostructure by sequentially or non-sequentially expressing the first plurality of polypeptides in a first recombinant expression system, expressing the first plurality of antigens in a second recombinant expression system, purifying the first plurality of polypeptides, purifying the first plurality of antigens, provided that expression of each component precedes purification of that component; and then mixing the first plurality of polypeptides and the first plurality of antigens; thereby generating the nanostructure.

In an embodiment of the methods of making a nanostructure, the method achieves in vitro assembly of the nanostructure by sequentially or non-sequentially expressing the first plurality of polypeptides in a first recombinant expression system, expressing the first plurality of antigens in a second recombinant expression system, expressing the second plurality of polypeptides in a third recombinant expression system, purifying the first plurality of polypeptides, purifying the first plurality of antigens, purifying the second plurality of polypeptides, provided that expression of each component precedes purification of that component; and mixing the first plurality of polypeptides, the first plurality of antigens, and the second plurality of polypeptides; thereby generating the nanostructure. Optionally, the first recombinant expression system and the second recombinant expression system are the same, and the first plurality of polypeptides and the first plurality of antigens are purified together.

In an embodiment of the methods of making a nanostructure, the method comprises expressing the first plurality of polypeptides and the first plurality of antigens in a single recombinant expression system, thereby generating the nanostructure, and purifying the nanostructure. In an embodiment, the method comprises expressing the first plurality of polypeptides, the first plurality of antigens, and the second plurality of polypeptides in a single recombinant expression system, thereby generating the nanostructure, and purifying the nanostructure. In an embodiment, optionally, the first plurality of polypeptides and the first plurality of antigens are encoded by a single open reading frame; and optionally, the single open reading frame encodes a fusion protein of the polypeptide and the antigen; and optionally, the single open reading frame encodes a self-cleaving peptide.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE DRAWINGS

FIGS. 2A-2C shows graphs illustrating detection of secreted DS-Cav1 (FIG. 2A), DS-Cav1-foldon-T33-31A (FIG. 2B), and DS-Cav1-T33-31A (FIG. 2C) fusion proteins in tissue culture supernatants. ELISA assays were performed on tissue culture supernatants from cells expressing DS-Cav1 (top), DS-Cav-1-foldon-T33-31A/T33-31B (bottom left), and DS-Cav-1-T33-31A/T33-31B (bottom right). Four different monoclonal antibodies that bind RSV F were used to evaluate the presence of DS-Cav1 or DS-Cav1 fusion proteins in the supernatants. The results confirm the secretion of proteins comprising well-folded RSV F antigen.

FIGS. 6A-6C shows a series of graphs depicting the antigenicity of DS-Cav1-I53-50 nanostructures. Analysis of purified DS-Cav1-I53-50 nanostructures by ELISA (FIG. 6A) using four RSV F-specific monoclonal antibodies, including the prefusion-specific antibodies MPE8, D25, and RSD5, indicated that the DS-Cav1 antigen is correctly folded and maintained in the prefusion state when multivalently displayed on DS-Cav1-I53-50 nanostructures. This finding was confirmed by surface plasmon resonance measurements using multiple RSV F-specific antibodies, which, when compared to trimeric DS-Cav1 (FIG. 6C), further suggested that multivalent display of DS-Cav1 (FIG. 6B) results in an avidity effect that reduces the dissociation rate of the antibodies.

FIGS. 11A-11J are graphs depicting physical stability of the nanostructures. Chemical denaturation in guanidine hydrochloride (GdnHCl), monitored by intrinsic tryptophan fluorescence, was used as a second, antibody-independent technique to evaluate physical stability of trimeric DS-Cav1 (FIG. 1A and FIG. 1B), DS-Cav1-foldon-I53-50A (FIG. 1C and FIG. 1D), DS-Cav1-foldon-I53-50 (FIG. 1E and FIG. 1F), I53-50 (FIG. 1G and FIG. 1H), and I53-50A (FIG. 1I and FIG. 1J). The data indicate superior physical stability of the DS-Cav1 antigen when genetically fused to the I53-50A nanostructure component.

DETAILED DESCRIPTION

Figure 1A:
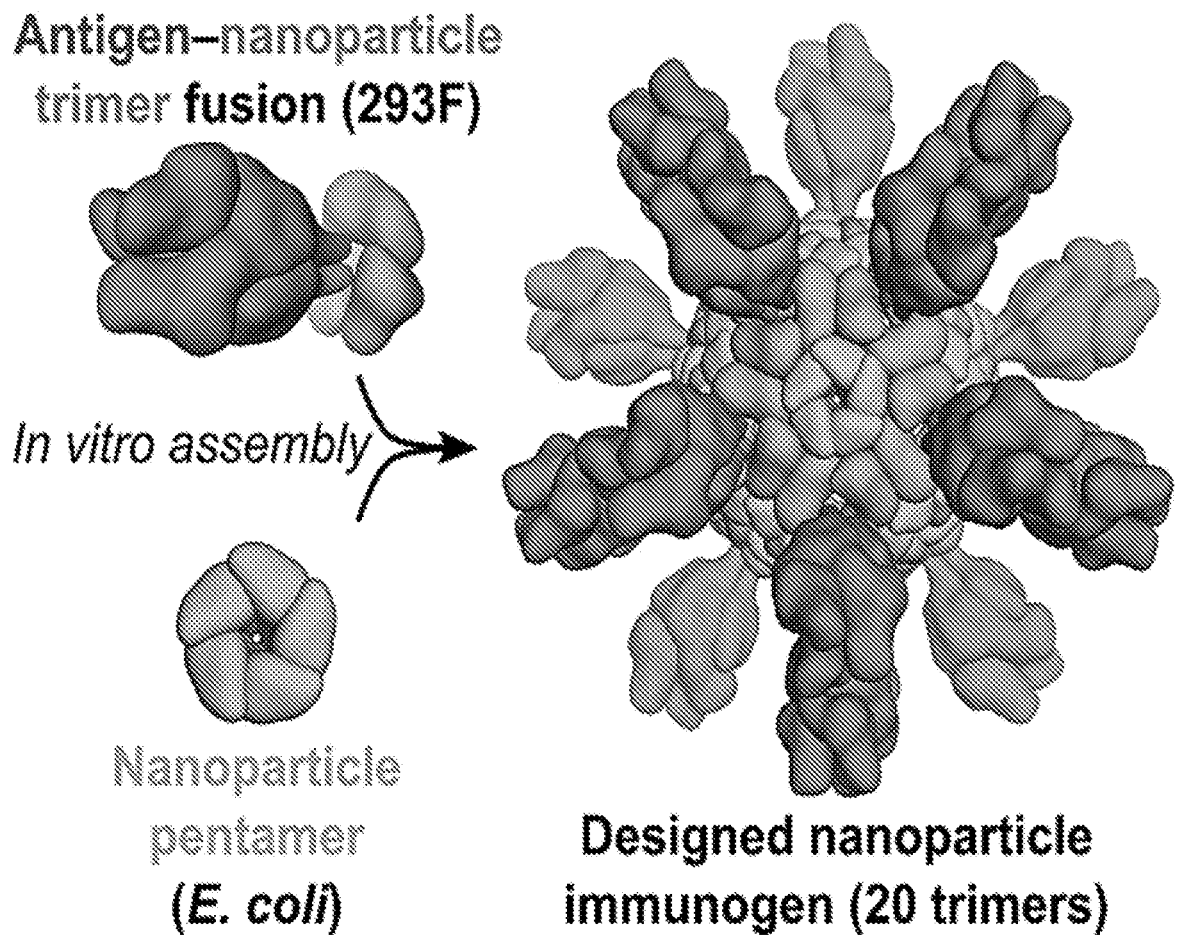
FIG. 1A shows a schematic diagram of the production of antigen-bearing nanostructures by in vitro assembly. The two components or building blocks of a given nanostructure can be expressed and purified individually, which allows assembly of the nanostructure to be initiated by mixing the purified components in vitro, a process referred to as in vitro assembly. In some embodiments, the two components of the nanostructure may be expressed in different expression hosts (e.g., human HEK293F cells or bacterial E. coli cells). The figure schematically depicts assembly of a 120-subunit nanostructure bearing 20 trimeric antigens (60 antigen subunits) via in vitro assembly of an antigen-nanostructure trimer fusion protein produced in HEK293F cells and a nanostructure pentamer protein produced in E. coli.

The present disclosure relates to nanostructures and nanostructure-based vaccines. Some nanostructures of the present disclosure display antigens capable of eliciting immune responses to infectious agents, such as bacteria, viruses, and parasites. Some vaccines of the present disclosure are useful for preventing or decreasing the severity of infection with an infectious agent including, for example and without limitation, lyme disease, pertussis, herpes virus, orthomyxovirus, paramyxovirus, pneumovirus, filovirus, flavivirus, reovirus, retrovirus, meningococcus, and malaria. The antigens may be attached to the core of the nanostructure either non-covalently or covalently, including as a fusion protein or by other means disclosed herein. Multimeric antigens may optionally be displayed along a symmetry axis of the nanostructure. Also provided are proteins and nucleic acid molecules encoding such proteins, formulations, and methods of use.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

1. Overview of Nanostructures

The nanostructures of the present invention may comprise multimeric protein assemblies adapted for display of antigens or antigenic fragments. The nanostructures of the present invention comprise at least a first plurality of polypeptides. The first plurality of polypeptides may be derived from a naturally-occurring protein sequence by substitution of at least one amino acid residue or by additional at the N- or C-terminus of one or more residues. In some cases, the first plurality of polypeptides comprises a gene sequence determined de novo by computational methods. This first plurality of polypeptides may form the entire nanostructure; or the nanostructure may comprise one or more additional polypeptides, such that the nanostructure comprises two, three, four, five, six, seven, or more pluralities of polypeptides. In some cases, the first plurality will form trimers related by 3-fold rotational symmetry and the second plurality will form pentamers related by 5-fold rotational symmetry. Together these one or more pluralities of polypeptides may be arranged such that the members of each plurality of polypeptides are related to one another by symmetry operators. A general computational method for designing self-assembling protein materials, involving symmetrical docking of protein building blocks in a target symmetric architecture, is disclosed in U.S. Patent Pub. No. US 2015/0356240 A1.

The "core" of the nanostructure is used herein to describe the central portion of the nanostructure that links together the antigens or antigenic fragments displayed by the nanostructure. In an embodiment, the core and the displayed antigens are the same polypeptide, meaning that antigens are themselves capable of self-assembly into a nanostructure. An advantage of designing the antigens themselves to self-assemble is that the entire nanostructure then acts as the antigenic component of the vaccine. But in an embodiment, the cores of the nanostructures of the present disclosure are generic platforms adaptable for display of any of various antigens that one might select for inclusion in a vaccine. An advantage of designing a core to be a generic platform is that the one or more pluralities of polypeptides that comprise the core can be designed and optimized in advance and then applied to different antigens. It will be understood that in some cases, the same polypeptide may form a portion of the "core" and then extend outward as either an adaptor for attachment of an antigen and as the antigen itself (i.e., a fusion protein with the antigen). In embodiments of the present disclosure, the antigen is a protein, glycoprotein, or oligosaccharide of an infectious agent.

In some cases, self-assembly may be further promoted by multimerization of the antigen even though the core would, in absence of the antigen, be independently capable of self-assembly. This would be the case for example when a homo-trimeric antigen (such as HIV gp140, influenza HA, or RSV F protein) is the antigen, or one of several antigens, displayed on the particle. In some cases, a trimeric antigen placed along a 3-fold axis of the nanostructure promotes proper folding and conformation stability of the antigen and makes self-assembly of the nanostructure a cooperative process, in that the antigen is trimerized properly in part due to its display on a 3-fold axis of the core of the nanostructure, and the nanostructure is stabilized in its assembled form, at least in part, by non-covalent or covalent interactions amongst the trimer units. In some cases, introduction of mutations to the antigen or to the nanostructure components may optionally further stabilize assembly, in particular if cysteine residues are position to create intramolecular disulfide bonds. In some examples, a dimeric, trimeric, tetrameric, pentameric, or hexameric antigen is displayed upon a core designed to have a matching 2-fold, 3-fold, 4-fold, 5-fold, or 6-fold symmetry axis such that the core accommodates the arrangement of the multimeric antigen with the native symmetry of the antigen.

2. Various Non-Limiting Examples of Nanostructures

A non-limiting example of an embodiment is shown in FIG. 1A, which depicts the RSV F protein genetically fused to a component (a first plurality of polypeptides) of the nanostructure, which is expressed recombinantly in 293F cells; along with a pentameric protein assembly (a second plurality of polypeptides), which is expressed recombinantly in E. coli cells, these two pluralities of polypeptides self-assembling into a nanostructure (a "designed nanoparticle immunogen") displaying 20 F-protein trimers around an icosahedral core. In this embodiment, the core has a generic design. As explained below, in other embodiments, the RSV F protein is replaced with other another antigen protein, such as a trimeric glycoprotein from another virus. In some embodiments, the nanostructure comprises the trimeric glycoproteins of HIV-1, HIV-2, EBV, CMV, RSV, influenza, Ebola, Marburg, Dengue, SARS, MERS, Hantaan, or Zika virus. In some embodiments, the nanostructure comprises the trimeric glycoproteins of viruses that are related evolutionarily or in sequence identity to any of these exemplary virus, including without limitation, a herpes virus, orthomyxovirus, paramyxovirus, pneumovirus, filovirus, flavivirus, reovirus, or retrovirus. In an embodiment, the nanostructure comprises the extracellular domain or domains of a transmembrane protein or glycoprotein, or an antigenic fragment thereof. In some embodiments, the nanostructure comprises the antigen proteins or protein fragments or antigenic oligosaccharides of a bacterial pathogen, including without limitation, *Neisseria meningitides* (also known as "meningococcus"), *Haemophilus influenzae* type B, *Streptococcus pneumonia*, and *Listeria monocytogenes*.

Trimeric antigens that may be used with this or similar nanostructures are in some cases, without limitation. HIV gp140, influenza HA, dengue E protein, or Ebola sGP. When other trimeric antigens are used, they may optionally be placed on the 3-fold symmetry axis of the nanostructure. In some cases, the antigen chosen is monomeric and nevertheless placed on a 3-fold axis. Thus, the nanostructure depicted in FIG. 1A is capable of displaying 20 timeric antigens or 60 monomeric antigens. Additionally or alternatively the pentameric complexes of the nanostructure is used to display a 12 pentameric antigens or 70 monomeric antigens. In an embodiment, the nanostructure comprises 20 copies of a trimeric antigen and 12 copies of a pentameric antigen.

2.1. Nanostructure Cores

Figure 1B:
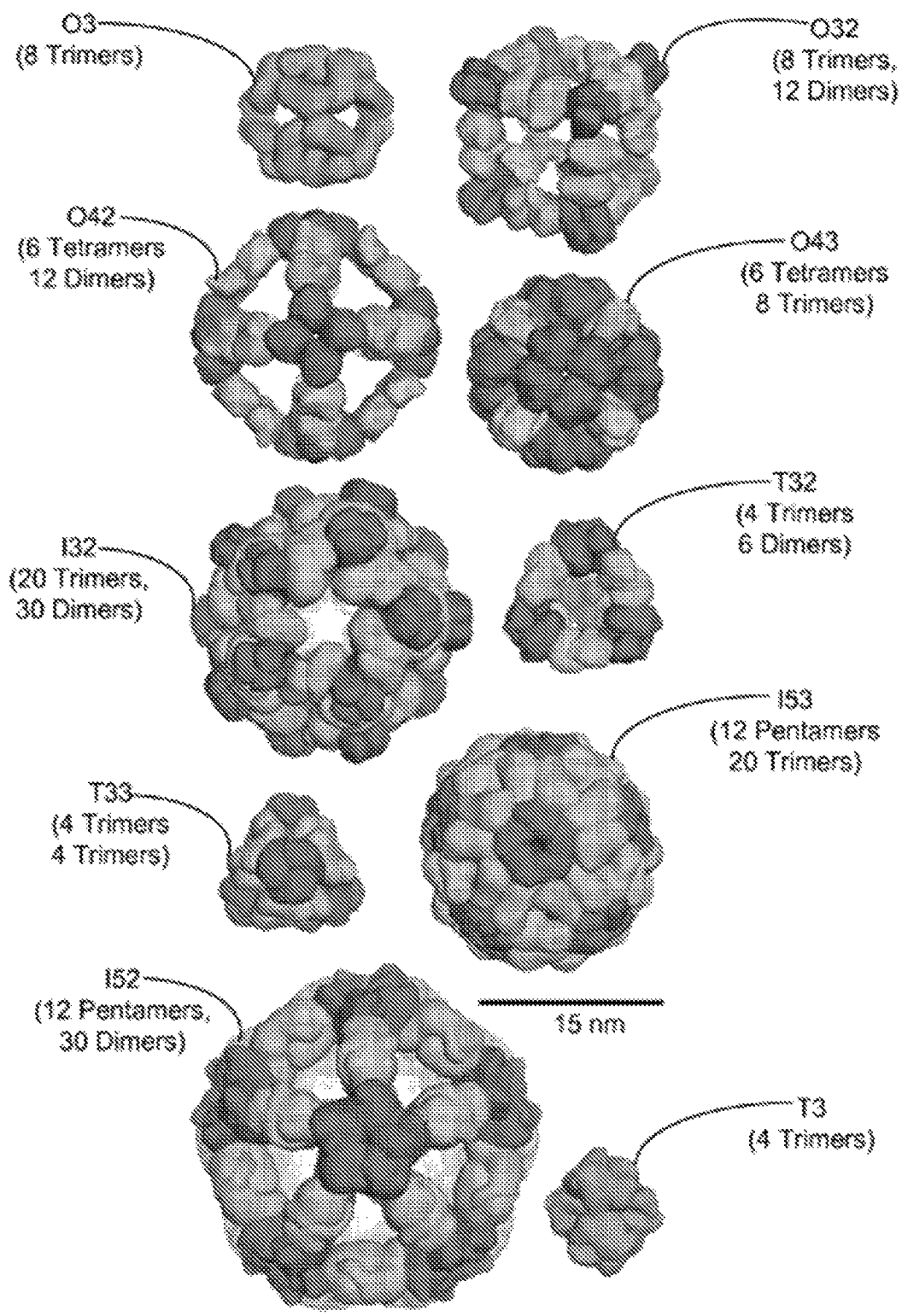
FIG. 1B depicts example nanostructure architectures.

Other potential arrangements of polypeptides of the present disclosure are shown in FIG. 1B. In some embodiments, the nanostructure is adapted for display of up to 8 trimers; 8 timers and 12 dimers; 6 tetramers and 12 dimers; 6 tetramers and 8 trimers; 20 trimers and 30 dimers; 4 trimers and 6 dimers; 4 first trimers and 4 second trimers, or 8 trimers; 12 pentamers and 20 trimers; or 12 pentamers and 30 dimers; or 4 trimers. In some cases, one of the symmetric axes is not used for antigen display, thus, in some embodiments the nanostructure is adapted for display of up to 8 trimers; 12 dimers; 6 tetramers; 20 trimers; 30 dimers; 4 trimers; 6 dimers, 8 trimers; or 12 pentamers. In some cases, monomeric antigens are displayed and thus, the nanostructure is adapted for display of up to 12, 24, 60, or 70 monomeric antigens. In some cases, the nanostructure comprises mixed pluralities of polypeptides such that otherwise identical polypeptides of the core of the nanostructure display different antigens or no antigen. Thus, depending on the ratio of polypeptides, the nanostructure is in some cases adapted for display of between 1 and 130 antigens (e.g., on the 152 particle) where each of the antigens displayed may be the same or may be different members of mixed population in proportion to any ratio chosen. The antigens may be co-expressed in a recombinant expression system and self-assembled before purification. Alternatively, the antigens may be expressed separately and then mixed together, either before or after purification from expression host and associated contaminants. In various embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more antigens are displayed. Non-limiting exemplary nanostructures are provided in Bale et al. *Science* 353:389-94 (2016); Heinze et al. *J. Phys. Chem B*. 120:5945-5952 (2016); King et al. *Nature* 510: 103-108 (2014): and King et al. *Science* 336:1171-71 (2012).

2.2. Mixed Nanostructures

In some embodiments, the nanostructure displays two or more antigens from the same organism, such as without limitation HIV gp140 and HIV gp41; or Ebola virus $GP_1$ and $GP_2$; or Measles H and F proteins; or CMV gB and CMV UL128, UL130. UL131A, gH (UL75) and gL (UL115), on the same nanostructure. In some cases, the nanostructure displays two antigenic proteins or glycoproteins that are generated by post-transcriptional cleavage, such as cleavage of RSV F protein or influenza HA protein by proteases endogenous to the recombinant expression system, or by proteases supplied exogenously.

In some cases, the nanostructure is adapted to display the same antigen from two or more diverse strain of a pathogenic organism. In non-limiting examples, the same nanostructure displays mixed populations of homotrimeric protein antigens or mixed heterotrimers of protein antigens from different strains of the infectious agent. In an embodiment, the nanostructure displays the HA proteins of an H1N1 influenza A and of an H3N2 influenza A proteins. In an embodiment, the nanostructure displays the HA proteins of an influenza A and of an influenza B. In an embodiment, the gp140 proteins from diverse strains of HIV are displayed on a single nanostructure. Two, three, four, five, or six strains of HIV may be displayed by the same nanostructure. Without being bound by theory, an advantage of such a mixed nanostructure is that it promotes the generation of cross-reactive or broadly neutralizing immune responses. In some cases, the nanostructure-based vaccine of the present disclosure is a universal influenza vaccine. In some cases, the nanostructure-based vaccine of the present disclosure is an HIV vaccine. In some case, the nanostructure-based vaccine of the present disclosure provides enduring protection against HIV. In some case, the nanostructure-based vaccine of the present disclosure provides enduring protection against influenza. In an embodiment, the nanostructure is adapted for display of the E proteins of Dengue type 1, type 2, type 3, and type 4. In an embodiment, the nanostructure-based vaccine comprises nanostructures that individually display the protein E from each of Dengue type 1, type 2, type 3, and type 4. In an embodiment, the nanostructure-based vaccine of the present disclosure provides immunity to Dengue virus without increased risk of dengue hemorrhagic fever or dengue shock syndrome.

When mixed nanostructures are made, it may be advantageous to ensure homomerization in a strain-specific manner rather than permit heterodimerization, such that, for example all H1N1 influenza A HA proteins are displayed on one 3-fold axis of a T33 particle whereas all H3N2 influenza A HA proteins are displayed on the other 3-fold axis of the T33 particle. This may be achieved by use a nanostructure comprising two or more pluralities of polypeptides as the core of the nanostructure with each plurality of polypeptides attached to a different antigen. Alternatively, a nanostructure may be engineered with one or more symmetry-breaking mutations, such as knob-in-hole mutations or intramolecular disulfide mutations, which have the effect of preventing trimer formation between the different antigens. In that case, the nanostructure displays multimeric antigens from different strains at symmetrically equivalent positions on the nanostructure, but each position on the nanostructure is occupied by homomers from the same strain, with only an insignificant proportion of inter-strain heteromeric antigens. In some cases, the antigen itself may be genetically engineered to prevent inter-strain heterodimerization. In an embodiment, the nanostructure is engineered to prevent heteromization of two antigenic proteins with conserved structure but divergent antigenicity, such as for example, an HA protein from the 2009 H1N1 California influenza and the HA protein from the 1999 H1N1 New Caledonia influenza. Furthermore, when mixed nanostructures are made and the antigens are displayed as fusion proteins, the nanostructure will comprise three or more different proteins, as the fusion proteins will share identical (or equivalent) domains used to form the core of the nanostructure with different antigenic domains, one for each antigen displayed on the nanostructure.

2.3. Attachment Modalities

The nanostructures of the present disclosure display antigens in various ways including as gene fusion or by other means disclosed herein. As used herein, "attached to" denotes any means known in the art for causing two polypeptides to associate. The association may be direct or indirect, reversible or irreversible, weak or strong, covalent or non-covalent, and selective or nonselective.

In some embodiments, attachment is achieved by genetic engineering to create an N- or C-terminus fusion of an antigen to one of the pluralities of polypeptides composing the nanostructure. Thus, the nanostructure may consist of, or consist essentially of, one, two, three, four, five, six, seven, eight, nine, or ten pluralities of polypeptides displaying one, two, three, four, five, six, seven, eight, nine, or ten pluralities of antigens, where at least one of the pluralities of antigen is genetically fused to at least one of the plurality of polypeptides. In some cases, the nanostructure consists essentially of one plurality of polypeptides capable of self-assembly and comprising the plurality of antigens genetically fused thereto. In some cases, the nanostructure consists essentially of a first plurality of polypeptides comprising the plurality of antigens genetically fused thereto; and a second plurality of polypeptides capable of co-assembling into two-component nanostructure, one plurality of polypeptides linking the antigen to the nanostructure and the other plurality of polypeptides promoting self-assembly of the nanostructure.

In some embodiments, attachment is achieved by post-translational covalent attachment between one or more pluralities of polypeptides and one or more pluralities of antigen. In some cases, chemical cross-linking is used to non-specifically attach the antigen to the nanostructure polypeptide. In some cases, chemical cross-linking is used to specifically attach the antigen to the nanostructure polypeptide. Various specific and non-specific cross-linking chemistries are known in the art, such as Click chemistry and other methods. In general, any cross-linking chemistry used to link two proteins may be adapted for use in the presently disclosed nanostructures. In particular, chemistries used in creation of immunoconjugates or antibody drug conjugates may be used. In some cases, an antigen-nanostructure conjugate (ANC) is created using a cleavable or non-cleavable linker. Processes and methods for conjugation of antigens to carriers are provided by, e.g., U.S. Patent Pub. No. US 2008/0145373 A1. In an embodiment, the antigen is a polysaccharide. In some cases, the antigen is a polysaccharide and the nanostructure acts as a hapten. In an embodiment, the target antigen is a protein and conjugation of the target antigen to a polysaccharide is used to enhance the immune response. Processes for preparing protein-polysaccharide conjugates are provided in, e.g., U.S. Pat. No. 6,248,334. The conjugation of proteins to polysaccharides in some cases converts a polysaccharide from a weakly immunogenic T-cell independent antigen to a T-cell dependent antigen that recruits T-cell help, and thus stimulates heightened immune responses. See J. M. Cruse, et al. (Editors), Conjugate Vaccines, Karger, Basel, (1989); and R. W. Ellis, et al. (Editors), Development and Clinical Uses of Haemophilus B Conjugate Vaccines, Marcel Dekker, New York (1994).

In an embodiment, attachment is achieved by non-covalent attachment between one or more pluralities of polypeptides and one or more pluralities of antigen. In some cases, the antigen is engineered to be negatively charged on at least one surface and the polypeptide is engineered to be positively charged on at least one surface, or positively and negatively charged, respectively. This promotes intermolecular association between the antigen and the polypeptides of the nanostructure by electrostatic force. In some cases, shape complementarity is employed to cause linkage of antigen to nanostructure. Shape complementarity can be pre-existing or rationally designed. In some cases, computational designed of protein-protein interfaces is used to achieve attachment. In an embodiment, the antigen is biotin-labeled and the polypeptide comprises a streptavidin, or vice versa. In an embodiment, streptavidin is displayed by gene fusion or otherwise as a tetramer on a 4-fold axis of the nanostructure and the biotin-labeled antigen is monomeric, dimeric, or tetrameric, permitting association to the nanostructure in a configuration appropriate for native multimerization of the antigen. In some cases, a protein-based adaptor is used to capture the antigen. In some cases, the polypeptide is fused to a protein capable of binding a complementary protein, which is fused to the antigen. In an embodiment, the polypeptide is fused to the rotavirus VP6 protein, which forms a trimer, and the antigen is N-terminally fused to the N-terminal peptide of rotavirus VP7, permitting trimer-to-trimer association of antigen to nanostructure. See Chen et al. Molecular interactions in rotavirus assembly and uncoating seen by high-resolution cryo-EM. PNAS 2009 June, 106 (26) 10644-10648.

In an embodiment, each of the first plurality of the antigenic proteins has a proximal end and a distal end, and the proximal ends of the antigenic proteins are each attached to a member of the first plurality of polypeptides. Thus, the distal end of the antigenic protein is defined as the portion of the antigen furthest from the center of the nanostructure. In an embodiment, the antigenic protein comprises target epitope, and the nanostructure is configured to display the target epitope. In some cases, the antigenic protein may comprise more than one target epitope and the nanostructure is configured to display each of the target epitopes. Epitopes progressively closer to the distal end are (without being bound by theory) in some cases preferentially accessible to the immune system. The distal end of the antigenic protein may be its N terminus, its C terminus, or neither terminus. Thus, depending on how the antigenic protein is attached to the nanostructure, the antigenic protein may be displayed in any orientation. In some cases, the antigenic protein is displayed so that one or more known epitopes are oriented at or towards the distal end of the antigenic protein, such that these epitope(s) are preferentially accessible to the immune system. In some cases, the orientation will recapitulate the orientation of a viral protein with respect to the virus. Thus, in the case of influenza HA, the antigenic protein HA may be oriented so that the receptor binding site is at the distal end of the protein, similar to the orientation of HA in the whole virus; or alternatively, the influenza HA protein may be oriented such that the stem epitope is preferentially accessible to the immune system. The choice of orientation may direct the immune system to one or the other epitope. In this example, the immune response to influenza may be guided to the receptor binding site or to the stem by choice of orientation. Similarly, the orientation of other antigens may influence the immune response. In some embodiments, orientation of the antigen results in an immune response targeted to a preferred epitope. In the case of HIV, the antigenic protein is in some embodiments the Env protein of HIV-1 or HIV-2, or an antigenic fragment thereof. The orientation of the Env or fragment thereof will in some cases recapitulate that the orientation of Env protein with respect to the HIV viron, such that the proximal end is the membrane-proximal end of the Env protein or fragment thereof. In some cases, the preferred epitope is selected from the group consisting of the CD4-binding site (CD4bs); the V2 proteoglycan moiety on the trimer apex of Env; the V3 proteoglycan moiety on the high mannose patch of Env; the membrane proximal external region (MPER) of the Env transmembrane domain; and the gp120-gp41 interface with or without fusion peptide. In some cases, epitope preference is control by other means, such as positioning of glycans on the nanostructure by addition or subtraction of the N-linked glycan sequence motif N-X-[T/S] at predetermined positions in the amino acid sequence of any of the polypeptides of the nanostructure including in the amino acid sequence of the antigen. In some cases, the epitopes found at intermediate distances from the proximal to the distal end will be the preferred over epitopes more distally located depending on various considerations including but not limited to the overall geometry of the nanostructure, surface hydrophobicity, surface charge, and competitive binding of proteins endogenously present in the subject or proteins exogenously provided in the vaccine composition. The present disclosure encompasses all known methods of rational design of protein structure and the foregoing is not intended to be limiting.

2.4. Nanostructure Polypeptide Sequences

The one or more pluralities of polypeptides of the present disclosure may have any of various amino acids sequences. U.S. Patent Pub No. US 2015/0356240 A1 describes various methods for designing nanostructures. As disclosed in US Patent Pub No. US 2016/0122392 A1 and in International Patent Pub. No. WO 2014/124301 A1, the isolated polypeptides of SEQ ID NOS:1-51 were designed for their ability to self-assemble in pairs to form nanostructures, such as icosahedral nanostructures. The design involved design of suitable interface residues for each member of the polypeptide pair that can be assembled to form the nanostructure. The nanostructures so formed include symmetrically repeated, non-natural, non-covalent polypeptide-polypeptide interfaces that orient a first assembly and a second assembly into a nanostructure, such as one with an icosahedral symmetry. Thus, in one embodiment the first and second polypeptides are selected from the group consisting of SEQ ID NOS:1-51. In each case, the N-terminal methionine residue is optional.

TABLE 1

| Name | Amino Acid Sequence | identified interface residues |
|---|---|---|
| I53-34A SEQ ID NO: 1 | MEGMDFLAVLAESRLLPLLTVRGGEDLAGLATVLELMGVGALEITLRTEKGLE ALKALRKSGLLLGAGTVRSPKEAEAALEAGAAFLVSPGLLEEVAALAQARGVP YLPGVLTPTEVERALALGLSALKFFPAEPFQGVRVLRAYAEVFPEVRFLPTGG IKEEHLPHYAALPNLLAVGGSWLLQGDLAAVMKKVKAAKALLSPQAPG | I53-34A 28, 32, 36,37, 186, 188, 191, 192, 195 |
| I53-34B SEQ ID NO: 2 | MTKKVGIVDTTFARVDMAEAAIRTLKALSPNIKIIRKTVTGIKDLPVACKKLL EEEGCDIVMALGMPGKAEKDKVCAHEASLGLMLAQLMTNKHIIEVFVHEDEAK DDDELDILALVRAIEHAANVYYLLFKPEYLTRMAGKGLRQGREDAGPARE | I53-34B: 19, 20, 23, 24, 27, 109, 113, 116, 117, 120, 124, 148 |
| I53-40A SEQ ID NO: 3 | MTKKVGIVDTTFARVDMASAAILTLKMESPNIKIIRKTVPGIKDLPVACKKLL EEEGCDIVMALGMPGKAEKDKVCAHEASLGLMLAQLMTNKHIIEVFVHEDEAK DDAELKILAARRAIEHALNVYYELLFKPEYLTRMAGKGLRQGFEDAGPARE | 153-40A: 20, 23, 24, 27, 8,109, 12, 113, 116, 120, 124 |
| I53-40B SEQ ID NO: 4 | MSTINNQLKALKVIPVIAIDNAEDIIPLGKVLAENGLPAAEITFRSSAAVKAI MLLRSAQPEMLIGAGTILNGVQALAAKEAGATFVVSPGFNPNTVRACQIIGID IVPGVNNPSTVEAALEMGLTTLKFFPAEASGGISMVKSLVGPYGDIRLMPTGG ITPSNIDNYLAIPQVLACGGTWMVDKKLVTNGEWDEIARLTREIVEQVNP | I53-40B: 47, 51, 54, 58, 74, 102 |
| I53-47A SEQ ID NO: 5 | MPIFTLNTNIKATDVPSDFLSLTSRLVGLILSKPGSYVAVHINTDQQLSFGGS TNPAAFGTLMSIGGIEPSKNRDHSAVLEDHLNAMLGIPKNRMYIHFVNLNGDD VGWNGTTF | I53-47A: 22, 25, 29, 72, 79, 86, 87 |
| I53-47B SEQ ID NO: 6 | MNQHSHKDYETVRIAVVRARWHADIVDACVEAFEIAMAAIGGDRFAVDVFDVP GAYEIPLHARTLAETGRYGAVLGTAFVVNGGIYRHEFVASAVIDGMMNVQLST GVPVLSAVLTPHRYRDSAEHHRFFAAHFAVKGVEAARACIEILAAREKIAA | I53-47B: 28, 31, 35, 36, 39, 131, 132, 135, 139, 146 |
| I53-50A SEQ ID NO: 7 | MKMEELFKKHKIVAVLRANSVEEAIEKAVAVFAGGVHLIEITFTVPDADTVIK ALSVLKEKGAIIGAGTVTSVEQCRKAVESGAEFIVSPHLDEEISQFCKEKGVF YMPGVMTPTELVKAMKLGHTILKLFPGEVVGPQFVKAMKGPFPNVKFVPTGGV NLDNVCEWFKAGVLAVGVGSALVKGTPDEVREKAKAFVEKIRGCTE | I53-50A: 25, 29, 33, 54, 57 |
| I53-50B SEQ ID NO: 8 | MNQHSHKDYETVRIAVVRARWHAEIVDACVSAFEAAMADIGGDRFAVDVFDVP GAYEIPLHARTLAETGRYGAVLGTAFVVNGGIYRHEFVASAVIDGMMNVQLST GVPVLSAVLTPHRYRDSDAHTLLFLALFAVKGMEAARACVEILAAREKIAA | I53-50B: 24, 28, 36, 124, 125, 127, 128, 129, 131, 132, 133, 135, 139 |
| I53-51A SEQ ID NO: 9 | MFTKSGDDGNTNVINKPVGKDSPLVNFLGDLDELNSFIGFAISKIPWEDMKKD LERVQVELFEIGEDLSTQSSKKKIDESYVLWLLAATAIYRIESGPVKLFVIPG GSEEASVLHVTRSVARRVERNAVKYTKELPEINREIIVYLNRLSSLLFAMALV ANKRRNQSEKIYEIGKSW | I53-51A: 80, 83, 86, 87, 88, 90, 91, 94, 166, 172, 176 |
| I53-51B SEQ ID NO: 10 | MNQHSHKDYETVRIAVVRARWHADIVDQCVRAFEEAMADAGGDRFAVDVFDVP GAYEIPLHARTLAETGRYGAVLGTAFVVNGGIYRHEFVASAVIDGMMNVQLST GVPVLSAVLTPHRYRSSREHHEFFREHFMVKGVEAAAACITILAAREKIAA | I53-51B: 31, 35, 36, 40, 122, 124, 128, 131, 135, 139, 143, 146, 147 |

TABLE 1-continued

| Name | Amino Acid Sequence | identified interface residues |
|---|---|---|
| I52-03A SEQ ID NO: 11 | MGHTKGPTPQQHDGSALRIGIVHARWNKTIIMPLLIGTIAKLLECGVKASNIV VQSVPGSWELPIAVQRLYSASQLQTPSSGPSLSAGDLLGDSTTDLTALPTTTA SSTGPFDALIAIGVLIKGETMHFEYIADSVSHGLMRVQLDTGVPVIFGVLTVL TDDQAKARAGVIEGSHNHGEDWGLAAVEMGVRRRDWAAGKTE | I52-03A: 28, 32, 36, 39, 44, 49 |
| I52-C3B SEQ ID NO: 12 | MYEVDHADVYDLFYLGRGKDYAAEASDIADLVRSRTPEASSLLDVACGTGTHL EHFTKEFGDTAGLELSEDMLTHARKRLPDATLHQGDMRDFQLGRKFSAVVSMF SSVGYLKTVAELGAAVASFAEHLEPGGVVVVEPWWFPETFADGWVSADVVRRD GRTVARVSHSVREGNATRMEVHFTVADPGKGVRHFSDVHLITLFHQREYEAAF MAAGLRVEYLEGGPSGRGLFVGVPA | I52-03B: 94, 115, 116, 206, 213 |
| I52-32A SEQ ID NO: 13 | MGMKEKFVLIITHGDFGKGLLSGAEVIIGKQENVHTVGLNLGDNIEKVAKEVM RIIIAKLAEDKEIIIVVDLFGGSPFNIALEMMKTFDVKVITGINMPMLVELLT SINVYDTTELLENISKIGKDGIKVIEKSSLKM | I52-32A: 47, 49, 53, 54, 57, 58, 61, 83, 87, 88 |
| I52-32B SEQ ID NO: 14 | MKYDGSKLRIGILHARWNLEIIAALVAGAIKRLQEFGVKAENIIIETVPGSFE LPYGSKLFVEKQKRLGKPLDAIIPIGVLIKGSTMHFEYICDSTTHQLMKLNFE LGIPVIFGVLTCLTDEQAEARAGLIEGKMHNHGEDWGAAAVEMATKFN | I52-32B: 19, 20, 23, 30, 40 |
| I52-33A SEQ ID NO: 15 | MAVKGLGEVDQKYDGSKLRIGILHARWNRKIILALVAGAVLRLLEFGVKAENI IIETVPGSFELPYGSKLFVEKQKRLGKPLDAIIPIGVLIKGSMHFTEYICDST THQLMKLNFELGIPVIFGVLTCLTDEQAEARAGLIEGKMHNHGEDWGAAAVEM ATKFN | I52-33A: 33, 41, 44, 50 |
| I52-33B SEQ ID NO: 16 | MGANWYLDNESSRLSFTSTKNADIAEVHRFLVLHGKVDPKGLAEVEVETESIS TGIPLPDMLLRVLVFQVSKFPVAQINAQLDMRPINNLAPGAQLELRLPLTVSL RGLSHSYNAELLATRLDERRFQVVTLEPLVIHAQDFDMVRAFNALRLVAGLSA VSLSVPVGAVLIFTAR | I52-33B: 61, 63, 66, 67, 72, 147, 148, 154, 155 |
| I32-06A SEQ ID NO: 17 | MTDYIRDGSAIKALSFAIILAEADLRHIPQDLQRLAVRVIHACGMVDVANDLA FSEGAGKAGRNALLAGAPILCDARMVAEGITRSRLPADNRVIYTLSDPSVPEL AKKIGNTRSAAALDLWLPHIEGSIVAIGNAPTALFRLFELLDAGAPKPALIIG MPVGFVGAAESKDELAANSRGVPYVIVRGRRGGSAMTAAAVNALASERE | I32-06A: 9, 12, 13, 14, 20, 30, 33, 34 |
| I32-06B SEQ ID NO: 18 | MITVFGLKSKLAPRREKLAEVIYSSLHLGLDIPKGKHAIRFLCLEKEDFYYPF DRSDDYTVIEINLMACRSEETKMLLIFLLFIALERKLGIRAHDVEITIKEQPA HCWGFRGRTGDSARDLDYDIYV | I32-06B: 24, 71, 73, 76, 77, 80, 81, 84, 85, 83, 114, 118 |
| I32-19A SEQ ID NO: 19 | MGSDLQKLQRFSTCDISDGLLNVYNIPTGGYFPNLTAISPPQNSSIVGTAYTV LFAPIDDPRPAVNYIDSVPPNSILVLALEPHLQSQFHPFIKITQAMYGGLMST RAQYLKSNGTVVFGRIRDVDEHRTLNHPVFAYGVGSCAPKAVVKAVGTNVQLK ILTSDGVTQTICPGDYIAGDNNGIVRIPVQETDISKLVTYIEKSIEVDRLVSE AIKNGLPAKAAQTARRMVLKDY | I32-19A: 208, 213, 218, 222, 225, 226, 229, 233 |
| I32-19B SEQ ID NO: 20 | MSGMRVYLGADHAGYELKQAIIAFLKMTGHEPIDCGALRYDADDDYPAFCIAA ATRTVADPGSLGIVLGGSGNGEQIAANKVPGARCALAWSVQTAALAREHNNAQ LIGIGGRMHTLEEEALRIVKAFVTTPWSKAQRHQRRIDILAEYERTHEAPPVPG APA | I32-19B: 20, 23, 24, 27, 117, 118, 122, 125 |
| I32-28A SEQ ID NO: 21 | MGDDARIAAIGDVDELNSQIGVLLAEPLPDDVRAALSAIQHDLFDLGGELCIP GHAAITEDHLLRLALWLVHYNGQLPPLEEFILPGGARGAALAHVCRTVCRRAE RSIKALGASEPLNIAPAAYVNLLSDLLFVLARVLNRAAGGADVLWDRTRAH | I32-28A: 60, 61, 64, 67, 68, 71, 110, 120, 123, 124, 128 |
| I32-28B SEQ ID NO: 22 | MILSAEQSFTLRRPHGQAAALAFVREPAAALAGVQRLRGLDSDGEQVWGELLV RVPLLGEVDLPFRSEIVRTPQGAELRPLTLTGERAWVAVSGQATAAEGGEMAF AFQFQAHLATPEAEGEGGAAFEVMVQAAAGVTLLLVAMALPQGLAAGLPPA | I32-28B: 35, 36, 54, 122, 129, 137, 140, 141, 144, 148 |
| I53-40A.1 SEQ ID NO: 23 | MTKKVGIVDTTFARVDMASAAILTLKMESPNIKIIRKTVPGIKDLPVACKKLL EEEGCDIVMALGMPGKKEKDKVCAHEASLGLMLAQLMTNKHIIEVFVHEDEAK DDAELKILAARRAIEHALNVYYLLFKPEYLTRMAGKGLRQGFEDAGPARE | I53-40A: 20, 23, 24, 27, 28, 109, 112, 113, 116, 120, 124 |
| I53-40B.1 SEQ ID NO: 24 | MDDINNQLKRLKVIPVIAIDNAEDIIPLGKVLAENGLPAAEITFRSSAAVKAI MLLRSAQPEMLIGAGTILNGVQALAAKEAGADFVVSPGFNPNTVRACQIIGID IVPGVNNPSTVEQALEMGLTTLKFFPAEASGGISMVKSLVGPYGDIRLMPTGG ITPDNIDNYLAIPQVLACGGTWMVDKKLVRNGEWDEIARLTREIVEQVNP | I53-40B: 47, 51, 54, 58, 4, 102 |
| I53-47A.1 SEQ ID NO: 25 | MPIFTLNTNIKADDVPSDFLSLTSRLVGLILSKPGSYAVVHINTDQQLSFGGS TNPAAFGTLMSIGGIEPDKNRDHSAVLFDHLNAMLGIPKNRMYIHFVNLNGDD VGWNGTTF | I53-47A: 22, 25, 29, 72, 79, 86, 87 |
| I53-47A.1NegT2 SEQ ID NO: 26 | MPIFTLNTNIKADDVPSDFLSLTSRLVGLILSEPGSYAVVHINTDQQLSFGGS TNPAAFGTLMSIGGIEPDKNEDHSAVLFDHLNAMLGIPENRKYIHFVDLDGDD VGWNGTTF | I53-47A: 22, 25, 29, 72, 79, 86, 87 |
| I53-47B.1 SEQ ID NO: 27 | MNQHSHKDHETVRIAVVRARWHADIVDACVEAFEIAMAAIGGDRFAVDVFDVP GAYEIPLHARTLAETGRYGAVLGTAFVNGGIYRHEFVASAVIDGMMNVQLDT GVPVLSAVLTPHRYRDSDEHHRFFAAHFAVKGVEAARACIEILNAREKIAA | I53-47B: 28, 31, 35, 36, 39, 131, 132, 135, 139, 146 |

TABLE 1-continued

| Name | Amino Acid Sequence | identified interface residues |
|---|---|---|
| I53-47B.1NegT2<br>SEQ ID NO: 28 | MNQHSHKDHETVRIAVVPARWHADIVDACVEAFEIAMAAIGGDRFAVDVFDVP<br>GAYEIPLHARTLAETGRYGAVLGTAFVVDGGIYDHEFVASAVIDGMMNVQLDT<br>GVPVLSAVLTPHEYEDSDEDHEFFAAHFAVKGVEAARACIEILNAREKIAA | I53-47B:<br>28, 31, 35, 36, 39, 131, 132,<br>135, 139, 146 |
| I53-50A.1<br>SEQ ID NO: 29 | MKMEELFKKHKIVAVLRANSVEEAIEKAVAVFAGGVHLIEITFTVPDADTVIK<br>ALSVLKEKGAIIGAGTVTSVEQCRKAVESGAEFIVSPHLDEEISQFCKEKGVF<br>YMPGVMTPTELVKAMKLGHDILKLFPGEVVGPQFVKAMKGPFPNVKFVPTGGV<br>NLDNVCEWFKAGVLAVGVGDALNKGDPDEVREKAKKFEVEKIRGCTE | I53-50A: 25, 29, 33, 54, 57 |
| I53-50A.1NegT2<br>SEQ ID NO: 30 | MKMEELFKKHKIVAVLRANSVEEAIEKAVAVFAGGVHLIEITFTVPDADTVIK<br>ALSVLKEKGAIIGAGTVTSVEQCRKAVESGAEFIVSPHLDEEISQFCKEKGVF<br>YMPGVMTPTELVKAMKLGHDILKLFPGEVVGPEFVEAMKGPFPNVKFVPTGGV<br>DLDDVCEWFDAGVLAVGVGDALVEGDPDEVREDAKEFVEEIRGCTE | I53-50A: 25, 29, 33, 54, 57 |
| I53-50A.1PosT1<br>SEQ ID NO: 31 | MKMEELFKKHKIVAVLRANSVEEAIEKAVAVFAGGVHLIEITFTVPDADTVIK<br>ALSVLKEKGAIIGAGTVTSVEQCRKAVESGAEFIVSPHLDEEISQFCKEKGVF<br>YMPGVMTPTELVKAMKLGHDILKLFPGEVVGPQFVKAMKGPFPNVKFVPTGGV<br>NLDNVCKWFKAGVLAVGVGKALVKGKPDEVREKAKKFVKKIRGCTE | I53-50A: 25, 29, 33, 54, 57 |
| I53 50B.1<br>SEQ ID NO: 32 | MNQHSHNDHETVRIAVVRAPWHAEIVDACVSAFEAAMRDIGGDRFAVDVFDVP<br>GAYEIPLHARTLAETGRYGAVLGTAFVVNGGIYRHEFVASAVIDGMMNVQLDT<br>GVPVLSAVLTPHRYRDSDAHTLLFLALFAVKGMEAARACVEILAAREKIAA | I53-50B<br>24, 28, 36, 124, 125, 127, 128,<br>129, 131, 132, 133, 135, 139 |
| I53-50B.1NegT2<br>SEQ ID NO: 33 | MNQHSHKDHETVRIAVVRARWHAEIVDACVSAFEAAMRDIGGDRFAVDVFDVP<br>GAYEIPLHARTLAETGRYGAVLGTAFVVDGGIYDHEFVASAVIDGMMNVQLDT<br>GVPVLSAVLTPHEYEDSDADTLLFLALFAVKGMEAARACVEILAAREKIAA | I53-50B:<br>24, 28, 36, 124, 125, 127, 128,<br>129, 131, 132, 133, 135, 139 |
| I53-50B.4PosT1<br>SEQ ID NO: 34 | MNQHSHKDHETVRIAVVRARWHAEIVDACVSAFEAAMRDIGGDRFAVDVFDVP<br>GAYEIPLHARTLAETGRYGAVLGTAFVVNGGIYRHEFVASAVINGMMNVQLNT<br>GVPVLSAVLTPHNYDKSKAHTLLFLALFAVKGMEAARACVEILAAREKIAA | I53-50B:<br>24, 28, 36, 124, 125, 127, 128,<br>129, 131, 132, 133, 135, 139 |
| I53-40 A genus<br>SEQ ID NO: 35 | MTKKVGIVDTTFARVDMASAAILTLKMESPNIKIIRKTVPGIKDLPVACKKLL<br>EEEGGDIVMALGMPGK(A/K)EKDKVCAHEASLGLMLAQLMTNKHIIEVFVHE<br>DEAKDDAELKILAARRAIEHALNVYYLLFKPEYLTRMAGKGLRQGFEDAGPAR<br>E | |
| I53-40 B genus<br>SEQ ID NO: 36 | M(S/D)(T/D)INNQLK(A/R)LKVIPVIAIDNAEDIIPLGKVLAENGLPAAE<br>ITFRSSAAVKAIMLLRSAQPEMLIGAGTILNGVQALAAKEAGA(T/D)FVVSP<br>GFNPNTVRACQIIGIDIVPGVNNPSTVE(A/Q)ALEMGLTTLKFFPAEASGGI<br>SMVKSLVGPYGDIRLMPTGGITP(S/D)NIDNYLAIPQVLACGGTWMVDKKLV<br>(T/R)NGEWDEIARLTREIVEQVNP | |
| I53-47A genus<br>SEQ ID NO: 37 | MPIFTLNTNIKA(T/D)DVPSDFLSLTSRLVGLILS(K/E)PGSYVAVHINTD<br>QQLSFGGSTNPAAFGTLMSIGGIEP(S/D)KN(R/E)DHSAVLFDHLNAMLGI<br>PKNRMYIHFV(N/D)L(N/D)GDDVGWNGTTF | |
| I53-47B genus<br>SEQ ID NO: 38 | MNQHSHKD(Y/H)ETVRIAVVRARWHADIVDACVEAFEIAMAAIGGDRFAVDV<br>FDVPGAYEIPLHARTLAETGRYGAVLGTAFVV(N/D)GGIY(R/D)HEFVASA<br>VIDGMMNVQL(S/D)TGVPVLSAVLTPH(R/E)Y(R/E)DS(A/D)E(H/D)H<br>(R/E)FFAAHFAVKGVEAARACIEIL(A/N)AREKIAA | |
| I53-50A genus<br>SEQ ID NO: 39 | MKMEELFKKHKIVAVLRANSVEEAIEKAVAVFAGGVHLIEITFTVPDADTVIK<br>ALSVLKEKGAIIGAGTVTSVEQCRKAVESGAEFIVSPHLDEEISQFCKEKGVF<br>YMPGVMTPTELVKAMKLGH(T/D)ILKLFPGEVVGP(Q/E)FV(K/E)AMKGP<br>FPNVKFVPTGGV(N/D)LD(N/D)VC(E/K)WF(K/D)AGVLAVGVG(S/K/D)<br>ALV(K/E)G(T/D/K)PDEVRE(K/D)AK(A/E/K)FV(E/K)(K/E)IRGCT<br>E | |
| I53-50B genus<br>SEQ ID NO: 40 | MNQHSHKD(Y/H)ETVRIAVVRARWHAEIVDACVSAFEAAM(A/R)DIGGDRF<br>AVDVFDVPGAYEIPLHARTLAETGRYGAVLGTAFVV(N/D)GGIY(R/D)HEF<br>VASAVI(D/N)GMMNVQL(S/D/N)TGVPVLSAVLTPH(R/E/N)Y(R/D/E)<br>(D/K)S(D/K)A(H/D)TLLFLALFAVKGMEAARACVEILAAREKIAA | |
| T32-28A<br>SEQ ID NO: 41 | MGEVPIGDPKELNGMEIAAVYLQPIEMEPRGIDLAASLADIHLEADIHALKNN<br>PNGFPEGFWMPYLTIAYALANADTGAIKTGTLMPMVADDGPHYGANIAMEKDK<br>KGGFGVGTYALTFLISNPEKQGFGRHVDEETGVGKWFEPPVVTYFFKYTGTPK | |
| T32-28B<br>SEQ ID NO: 42 | MSQAIGILELTSIAKGMELGDAMLKSANVDLLVSKTISPGKFLLMLGGDIGAI<br>QQAIETGTSQAGEMLVDSLVLANIHPSVLPAISGLNSVDKRQAVGIVETWSVA<br>ACISAADLAVKGSNVTLVRVHMAFGIGGKCYMVVAGDVLDVAAAVATASLAAG<br>AKGLLVYASIIPRPHEAMWRQMVEG | |
| T33-09A<br>SEQ ID NO: 43 | MEEVVLITVPSALVAVKIAHALVEERLAACVNIVPGLTSIYRWQGSVVSDHEL<br>LLLVKTTTHAFPKLKERVKALHPYTVPEIVALPIAEGNREYLDWLRENTG | |

TABLE 1-continued

| Name | Amino Acid Sequence | identified interface residues |
|---|---|---|
| T33-09B SEQ ID NO: 44 | MVRGIRGAITVEEDTPAAILAATIELLLKMLEANGIQSYEELAAVIFTVTEDL TSAFPAEAARLIGMHRVPLLSAREVPVPGSLPRVIRVLALWNTDTPQDRVRHV YLNEAVRLRPDLESAQ | |
| T33-15A SEQ ID NO: 45 | MSKAKIGIVTVSDRASAGITADISGLAIILALNLYLTSEWEPIYQVIPDEQDV IETTLIKMADEQDCCLIVTTGGTGPAKRDVTPEATEAVCDRMMPGFGELMRAE SLKEVPTAILSRQTAGLRGDSLIVNLPGDPASISDCLLAVFPAIPYCIDLMEG PYLECNEAMIKPFRPKAK | |
| T33-15B SEQ ID NO: 46 | MVRGIRGAITVNSDTPTSIIATILLLEKMLEANGIQSYEELAAVIFTVTEDL TSAFPAEAARQIGMHRVPLLSAREVPVPGSLPPVIRVLALWNTDTPQDRVRHV YLSEAVRLRPDLESAQ | |
| T33-21A SEQ ID NO: 47 | MRITTKVGDKGSTRLFGGEEVWKDSPIIEANGTLDELTSFIGEAKHYVDEEMK GILEEIQNDIYKIMGEIGSKGKIEGISEERIAWLLKLILRYMEMVNLKSFVLP GGTLESAKLDVCRTIARRALRKVLTVTREFGIGAEAAAYLLALSDLLFLLARV IEIEKNLLKEVRS | |
| T33-21B SEQ ID NO: 48 | MPHLVIEATANLRLETSPGELLEQANKALFASGQFGEADIKSRFVTLEAYRQG TAAVERAYLHACLSILDGRDIATPTLLGASLCAVLAEAVAGGGEEGVQVSVEV REMERLSYAKRVVARQR | |
| T33-28A SEQ ID NO: 49 | MESVNTSFLSPSLVTIRDFDNGQFAVLRIGRTGFPADKGDIDLCLDKMIGVRA AQIFLGDDTEDGFKGPHIRIRCVDIDDKHTYNAMVYVDLIVGTGASEVERETA EEEAKLALRVALQVDIADEHSCVTQFEMKLREELLSSDSFHPDKDEYYKDFL | |
| T33-28B SEQ ID NO: 50 | MPVIQTFVSTPLDHHKRLLLAIIYRIVTRVVLGKPEDLVMMTFHDSTPMHFFG STDPVACVRVEALGGYGPSEPEKVTSIVTAAITAVCGIVADRIFVLYFSPLHC GWNCTNE | |
| T33-31A SEQ ID NO: 51 | MEEVVLITVPSALVAVKIAHALVEERLAACVNIVPGLTSIYREEGSVVSDHEL LLLVKTTTDAFPKLKERVKELHPYEPEIVALPIAEGNREYLDWLRENTG | |

Table 1 provides the amino acid sequence of the first and second polypeptides from embodiments of the present disclosure. In each case, the pairs of sequences together from an I53 icosahedron. The right hand column in Table 1 identifies the residue numbers in each exemplary polypeptide that were identified as present at the interface of resulting assembled nanostructures (i.e.: "identified interface residues"). As can be seen, the number of interface residues for the exemplary polypeptides of SEQ ID NO:1-34 range from 4-13. In various embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given polypeptide), to the amino acid sequence of a polypeptide selected from the group consisting of SEQ ID NOS: 1-34. SEQ ID NOs: 35-51 represent other amino acid sequences of the first and second polypeptides from embodiments of the present disclosure. In other embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a polypeptide selected from the group consisting of SEQ ID NOS:1-51.

As is the case with proteins in general, the polypeptides are expected to tolerate some variation in the designed sequences without disrupting subsequent assembly into nanostructures: particularly when such variation comprises conservative amino acid substitutions. As used here, "conservative amino acid substitution" means that: hydrophobic amino acids (Ala, Cys, Gly, Pro, Met, Val, Ile, Leu) can only be substituted with other hydrophobic amino acids; hydrophobic amino acids with bulky side chains (Phe, Tyr, Trp) can only be substituted with other hydrophobic amino acids with bulky side chains; amino acids with positively charged side chains (Arg, His, Lys) can only be substituted with other amino acids with positively charged side chains; amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

In various embodiments of the nanostructure of the invention, the first polypeptides and the second polypeptides comprise polypeptides with the amino acid sequence selected from the following pairs, or modified versions thereof (i.e.: permissible modifications as disclosed for the polypeptides of the invention: isolated polypeptides comprising an amino acid sequence that is at least 75% identical over its length, and/or identical at least at one identified interface position, to the amino acid sequence indicated by the SEQ ID NO.):

SEQ ID NO:1 and SEQ ID NO:2 (I53-34A and I53-34B);
SEQ ID NO:3 and SEQ ID NO:4 (I53-40A and I53-40B);
SEQ ID NO:3 and SEQ ID NO:24 (I53-40A and I53-40B.1);
SEQ ID NO:23 and SEQ ID NO:4 (I53-40A.1 and I53-40B);
SEQ ID NO:35 and SEQ ID NO:36 (I53-40A genus and I53-40B genus);
SEQ ID NO:5 and SEQ ID NO:6 (I53-47A and I53-47B):
SEQ ID NO:5 and SEQ ID NO:27 (I53-47A and I53-47B.1);

SEQ ID NO:5 and SEQ ID NO:28 (I53-47A and I53-47B.1NegT2):
SEQ ID NO:25 and SEQ ID NO:6 (I53-47A. and I53-47B);
SEQ ID NO:25 and SEQ ID NO:27 (I53-47A.1 and I53-47B.1);
SEQ ID NO:25 and SEQ ID NO:28 (I53-47A.1 and 15347B.1NegT2);
SEQ ID NO:26 and SEQ ID NO:6 (I53-47A.1NegT2 and I53-47B);
SEQ ID NO:26 and SEQ ID NO:27 (I53-47A.1NegT2 and I53-47B.1);
SEQ ID NO:26 and SEQ ID NO:28 (I53-47A.1NegT2 and I53-47B.1NegT2);
SEQ ID NO:37 and SEQ ID NO:38 (I53-47A genus and 15347B genus);
SEQ ID NO:7 and SEQ ID NO:8 (I53-50A and 53-50B);
SEQ ID NO:7 and SEQ ID NO:32 (I53-50A and I53-50B.1);
SEQ ID NO:7 and SEQ ID NO:33 (I53-50A and I53-50B.1NegT2);
SEQ ID NO:7 and SEQ ID NO:34 (I53-50A and I53-50B.4PosT1);
SEQ ID NO:29 and SEQ ID NO:8 (I53-50A.1 and I53-50B);
SEQ ID NO:29 and SEQ ID NO:32 (I53-50A.1 and 53-50B.1);
SEQ ID NO:29 and SEQ ID NO:33 (I53-50A.1 and I53-50B.1NegT2);
SEQ ID NO:29 and SEQ ID NO:34 (I53-50A.1 and I53-50B.4PosT1);
SEQ ID NO:30 and SEQ ID NO:8 (I53-50A.NegT2 and I53-50B);
SEQ ID NO:30 and SEQ ID NO:32 (I53-50A.1NegT2 and I53-50B.1);
SEQ ID NO:30 and SEQ ID NO:33 (I53-50A.NegT2 and 53-50B.1NegT2);
SEQ ID NO:30 and SEQ ID NO:34 (I53-50A.1NegT2 and I53-50B.4PosT1);
SEQ ID NO:31 and SEQ ID NO:8 (I53-50A.1PosT1 and 53-50B);
SEQ ID NO:31 and SEQ ID NO:32 (I53-50A.1PosT1 and I53-50B.1);
SEQ ID NO:31 and SEQ ID NO:33 (I53-50A.1PosT1 and I53-50B.1NegT2);
SEQ ID NO:31 and SEQ ID NO:34 (I53-50A.1PosT1 and I53-50B.4PosT1);
SEQ ID NO:39 and SEQ ID NO:40 (I53-50A genus and I53-50B genus);
SEQ ID NO:9 and SEQ ID NO:10 (I53-51A and I53-51B):
SEQ ID NO:11 and SEQ ID NO:12 (I52-03A and I52-03B);
SEQ ID NO:13 and SEQ ID NO:14 (I52-32A and I52-32B);
SEQ ID NO:15 and SEQ ID NO:16 (I52-33A and I52-33B)
SEQ ID NO:17 and SEQ ID NO:18 (I32-06A and I32-06B);
SEQ ID NO:19 and SEQ ID NO:20 (I32-19A and I32-19B);
SEQ ID NO:21 and SEQ ID NO:22 (I32-28A and I32-28B);
SEQ ID NO:23 and SEQ ID NO:24 (I53-40A.1 and I53-40B.1);
SEQ ID NO:41 and SEQ ID NO:42 (T32-28A and T32-28B):
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and
SEQ ID NO:51 and SEQ ID NO:44 (T33-31A and T33-09B (also referred to as T33-31B))

In one embodiment, the one or more proteins, or antigenic fragments thereof, are expressed as a fusion protein with the first and/or second polypeptides. In these embodiments, one or more proteins, or antigenic fragments thereof are present at the N terminus of the fusion protein, whenever this configuration can facilitate presentation of the one or more proteins, or antigenic fragments thereof on an exterior of the nanostructure. A preference for the presence of the protein at the N terminus of the fusion protein occurs whenever from the location of the C terminus of the proteins is at proximal end of the protein. In these embodiments, one or more proteins, or antigenic fragments thereof are present at the C terminus of the fusion protein, whenever this configuration can facilitate presentation of the one or more proteins, or antigenic fragments thereof on an exterior of the nanostructure. A preference for the presence of the protein at the C terminus of the fusion protein occurs whenever from the location of the M terminus of the fusion protein is at proximal end of the protein.

Non-limiting examples of nanostructures useful in vaccines of the present disclosure include those disclosed in U.S. Pat. No. 9,630,994 and U.S. Provisional Patent Application No. 62/481,331, which are incorporated herein in its entirety.

3. Antigens

The present disclosure provides nanostructure-based vaccines for any of the various known bacteria, viruses, or parasites relevant to human or animal disease. In particular, the present disclosure relates to vaccines for lyme disease, pertussis, herpes virus, orthomyxovirus, paramyxovirus, pneumovirus, filovirus, flavivirus, reovirus, retrovirus, malaria, viral meningitis, fungal meningitis, and bacterial meningitis including *Neisseria meningitides* (also known as "meningococcus"), Haemophilus *influenzae* type B, *Streptococcus pneumonia*, and *Listeria monocytogenes*. For each of these organism, antigens (proteins or polysaccharides) capable of generating protective immune responses are known. The present disclosure relates to incorporation of any of these antigens-particularly antigenic proteins-into nanostructure-based vaccines. Guidance is particularly available from studies of the immune response to infection or vaccination, such as isolation of binding or neutralizing antibodies, genetic analysis of antigen sequence, structural studies of antigenic proteins and antibodies, and most particularly clinical and veterinary experience with subunit vaccines. With few limitations, any known subunit vaccine can be adapted for use with the nanostructures of the present disclosure by employing the display modalities provided above. In some embodiments, the nanostructure-based vaccines of the present disclosure comprise an oligosaccharide (e.g., a meningococcal oligosaccharide) conjugated directly or through an intermediate protein (e.g., diphtheria toxoid, tetanus toxoid, or CRM197) to the nanostructure. In some embodiments, the nanostructure-based vaccines of the present disclosure comprise antigens or antigenic fragments from the list provided in Table 2.

TABLE 2

Non-Limiting List of Antigens

| Infectious Agent | Antigens | Citation |
|---|---|---|
| HIV | gp160, gp140, gp21, MPER | Sok, D., Le, K. M., Vadnais, M., Saye-Francisco, K. L., Jardine, J. G., Torres, J. L., et al. (2017). Rapid elicitation of broadly neutralizing antibodies to HIV by immunization in cows. Nature, 548 (7665), 108-111. |
| RSV | F protein (prefusion) | US20160046675A1, US 2016/0031972 A1, US 2017/0182151 A1, WO 2010/149745 A1, WO 2012/158613 A1, WO 2013/139916 A1, WO 2014/079842 A1, WO 2014/174018 A1, WO 2014/202570 A1, WO 2015/013551 A1, WO 2017/040387 A2, WO2017172890A1 |
| Influenza | HA—Influenza A and B | Nabel et al. Induction of unnatural immunity: prospects for a broadly protective universal influenza vaccine. Nat Med. 2010 December; 16 (12): 1389-91. |
| EBV | glycoprotein 350/220 (L4p350) | Kanekiyo et al. Rational Design of an Epstein-Barr Virus Vaccine Targeting the Receptor-Binding Site. Cell. 2015 August 27; 162 (5): 1090-100. |
| CMV | gB; UL128, UL130, UL131A, gH (UL75) and gL (UL115) | Ciferri et al. Structural and biochemical studies of HCMV gH/gL/gO and Pentamer reveal mutually exclusive cell entry complexes. Proc. Natl. Acad. Sci. U.S.A. 112, 1767-1772 (2015). Chandramouli et al. Structure of HCMV glycoprotein B in the postfusion conformation bound to a neutralizing human antibody. Nat Commun. 2015 Sep. 14; 6:8176, Chandramouli et al. Structural basis for potent antibody-mediated neutralization of human cytomegalovirus Sci. Immunol. 2, eaan1457 (2017). |
| Lyme | Outer Surface Protein A (OspA) | Ma et al, Safety, efficacy, and immunogenicity of a recombinant Osp subunit canine Lyme disease vaccine. Volume 14, Issue 14, October 1996, Pages 1366-1374 |
| Pertussis | Pertussis toxin (PT) | Seubert et al. Genetically detoxified pertussis toxin (PT-91(/129G): implications for immunization and vaccines. Expert Rev Vaccines. 2014 October; 13 (10): 1191-204. doi: 10.1586/14760584.2014.942641. Epub 2014 Sep. 3, |
| Dengue | E protein | Modis, Y., Ogata, S., Clements, D. & Harrison, S. C. (2003) Proc. Natl. Acad. Sci. USA 100, 6986-6991. pmid: 12759475 |
| SARS | Spike (S) glycoprotein | Structure of SARS coronavirus spike receptor-binding domain complexed with receptor. Science. 2005 Sep. 16; 309(5742): 1864-8; WO2006068663A2 |
| MERS | Spike (S) glycoprotein | Immunogenicity and structures of a rationally designed prefusion MERS-CoNT spike antnzen. PNAS 2017 August, 114 (35) E7348-E7357. |
| Ebola | EBOV [$GP_1$ and $GP_2$ subunits | GP or sGP Structures of Ebola virus GP and sGP in complex with therapeutic antibodies. Nat Microbiol. 2016 Aug. 8; 1 (9): 16128. doi: 10.1038/mnicrobiol.2016.128. |
| Marberg | Marbera GP or sGP | Hashiguchi et al. Structural basis for Marburg virus neutralization by a cross-reactive human antibody. Cell. 2015 Feb. 26; 160 (5): 904-912. |
| Hantaan virus | Gn and Gc envelope glycoproteins | Hantavirus Gn and Ge Envelope Glycoproteins: Key Structural Units for Virus Cell Entry and Virus Assembly. Viruses. 2014 April; 6 (4): 1801-1822. |
| Hepatitis B | HepB surface antigen (HBs) | Raldao et al. Virus-like particles in vaccine development. Expert Rev Vaccines. 2010 October; 9 (10): 1149-76. |
| Measles | H and F proteins | Lobanova et al. The recombinant globular head domain of the measles virus hemagglutinin protein as a subunit vaccine against measles. Vaccine. 2012 Apr. 26; 30 (20): 3061-7. |
| Nipah virus | G and F protein | Satterfield et al. Status of vaccine research and development of vaccines for Nipah virus. Vaccine. 34 (26): 2971-2975 (2016). |
| Rotatvirus | VP4 and VP8 | O'Ryan et al. Parenteral protein-based rotavirus vaccine. Lancet Infectious Disease. 17 (8): 786-787 (2017). |
| Human Metapneumo virus | G and F proteins | Aertes et al. Adjuvant effect of the human metapneumovirus (HMPV) matrix protein in HMPV subunit vaccines. J Gen Virol. 2015 April; 96 (Pt 4): 767-74; US 20180008697 A1. |
| Parainfluenza virus | HN and F proteins | Morein et al. Protein subunit vaccines of parainfluenza type 3 virus: immunogenic effect in lambs and mice. J Gen Virol. 1983 July; 64 (Pt 7): 1557-69. |

TABLE 2-continued

Non-Limiting List of Antigens

| Infectious Agent | Antigens | Citation |
|---|---|---|
| Zika | Zika envelope domain III (ZEDIII) | Recurrent Potent Human Neutralizing Antibodies to Zika Virus in Brazil and Mexico. Cell. 2017 May 4;169(4):597-609.e 1 1. doi: 10.1016/j.cell.2017.04.024. |
| Malaria | Pfs25, circumsporozoite protein (CSP) | Lee et al. Assessment of Pfs25 expressed from multiple soluble expression platforms for use as transmission-blockirw, vaccine candidates. Malar J. 2016; 15: 405. Plassmeyer et al. Structure of the Plasmodium falciparum circumsporozoite protein, a leading malaria vaccine candidate. J Biol Chem. 2009 Sep. 25; 284 (39): 26951-63, |
| MenB | fHbp, NadA and N-HBA | Davide et al. The new multicomponent vaccine against meningococcal serogroup B, 4CMenB: immunological, functional and structural characterization of the antigens. Vaccine. 2012 May 30; 30 (0 2): B87-B97. |
| MenA, C. W-135, and Y | oligosaccharide | Tontini et al. Comparison of CRM197, diphtheria toxoid and tetanus toxoid as protein carriers for meningococcal alycoconjugate vaccines. Vaccine. 2013 Oct 1; 31 (42): 4827-33. |

In some embodiments, the antigen is an antigenic protein is selected from a polypeptide of SEQ ID NOs: 52-88 and 90-113 or a variant thereof, as provided in Table 3.

TABLE 3

Non-Limiting List of Antigen Sequences

| Antigen | Amino Acid Sequence (UniPmot) | SEQ ID NO |
|---|---|---|
| Human immunodeficiency virus 1 (HIV-1) gp160 | >tr\|A0A1C9TBY8\|A0A1C9TBY8_9HIV1 Envelope glycoprotein gp160 OS = Human immunodeficiency virus 1 GN = env PE = 3 SV = 1 MRVKGIKKNYQHWWRGGIMLMGMLMICSSAEKLWVTVYYGVPVW KEATTTLFCASDAKAQNPEMHNIWATHACVPTDPNPQEVILKNL TEEFNMWKNNMVEQMHEDIISLWDQSLKPCVKLTPLCVTLNCTN AESLNCTATNGTNNCSASTKPMEEMKNCSFNITTSVQDKKQQEY ALFYKLDIIPIDNNENDLNNTNYTSYRLISCNTSVITQACPKIT FEPIPIHYCAPAGFAILKCKDKRFNGTCPCKNVSTVQCTHGIRF VVSTQLLLNGSLAEEGVVLRSENFTDNAKNIIVQLKDPVNITCT RPNNNTRKSITIGPGRAFYATGQVIGDIRKAHCDLNGTEWDNAL KQIVEELRKQYGNNITIFNSSSGGDPEIVMHSFNCGGEFFYCNT AQLFNSTWLFNSTWNSTERLGNDTERTNDTITLPCKIKQVINMW QTVGKAMYAPPIRGLIRCSSNITGLILTRDGSGNTTGNETFRPG GGNMKDNWRSELYKYKVVKIEPLGVAPTRAKRRVVQREKRAAGL GALFLGFLGMAGSTMGAASLTLTVQARQLLSGIVQQQNNLLRAI EAQQHLLQLTVWGIKQLQARVLAVERYLRDQQLLGIWGCSGKLI CTTTVPWNASWSNKSLDNIWENMTWMQWEKEIDNYTDVIYKLLE ESQNQQEKNEQELLELDKWASLWNWFDITRMLWYIKIFIMIVGG LVGLRIVFAVLSIVNRVRQGYSPLSFQTLFPAPRGPDRPEGTEE GGGERGRDSSDRSAHGFLALIWGDLWSLCLFSYRRLRDLLLIAA RIVELLGRRGWEVLKYWWSLLQYWSQELKKSAVSLLNATAIAVA EGTDRIIEIVQRAGRAIIHIPRRIRQGAERALL | 52 |
| Human immunodeficiency virus 1 (HIV-1) gp120 | gp120>tr\|A0A1C9TBY8\|33-524 LWVTVYYGVPVWKEATTTLFCASDAKAQNPEMHNIWATHACYPT DPNPQEVILKNLTEEFNMWKNNMVEQWHEDIISLWDQSLKPCVK LTPLCVTLNCTNAESLNCTATNGTNNCSASTKPMEEMKNCSFNI TTSVQDKKQQEYALFYKLDIIPIDNNENDLNNTNYTSYRLISCN TSVITQACPKITFEPIPIHYCAPAGFAILKCKDKRFNGTGPCKN VSTVQCTHGIRPVVSTQLLLNGSLAEEGVVLRSENFTDNAKNII VQLKDPVNITCTRPNNNTRKSITIGPGRAFYATGQVIGDIRKAH CDLNGTEWDNALKQIVEELRKQYGNNITIFNSSSGGDPEIVMHS FNCGGEFFYCNTAQLFNSTWLFNSTWNSTERLGNDTERTNDTIT LPCKIKQVINMWQTVGKAMYAPPIRGLIRCSSNITGLILTRDGS GNTTGNETFRPGGGNMKDNWRSELYKYKVVKIEPLGVAPTRAKR RVVQREKR | 53 |

TABLE 3-continued

Non-Limiting List of Antigen Sequences

| Antigen | Amino Acid Sequence (UniPmot) | SEQ ID NO |
|---|---|---|
| Human immunodeficiency virus 1 (HIV-1) gp41 | gp41>tr\|A0A1C9TBY8\|543-733<br>MGAASLTLTVQARQLLSGIVQQQNNLLRAIEAQQHLLQLTVWGI<br>KQLQARVLAVERYLRDQQLLGIWGCSGKLICTTTVPWNASWSNK<br>SLDNIWENMTWMQWEKEIDNYTDVIYKLLEESQNQQEKNEQELL<br>ELDKWASLWNWFDITRWLWYIKIFIMIVGGLVGLRIVFAVLSIV<br>NRVRQGYSPLSFQTL | 54 |
| Human immunodeficiency virus 1 (HIV-1) MPER | >tr\|A0A1C9TBY8\|675-696<br>ELDKWASLWNWFDITRWLWYIK | 55 |
| Respiratory syncytial virus (RSV) type A F protein | >tr\|X4Y973\|X4Y973_9MONO Fusion glycoprotein F0 OS = Respiratory syncytial virus type A GN = F PE = 3 SV = 1<br>MELPILKTNAITTILAAVTLCFASSQNITEEFYQSTCSAVSKGY<br>LSALRTGWYTSVITIELSNIKENKCNGTDAKVKLIKQELDKYKN<br>AVTELQLLMQSTPAANNRARRELPRFMNYTLNNTKNNNVTLSKK<br>RKRRFLGFLLGVGSAIASGIAVSKVLHLEGEVNKIKNALLSTNK<br>AVVSLSNGVSVLTSKVLDLKNYIDKQLLPIVNKQSCSISNIETV<br>IEFQQKNNRLLEITREFSVNAGVTTPVSTYMLTNSELLSLINDM<br>PITNDQKKLMSNNVQIVRQQSYSIMSIIKEEVLAYVVQLPLYGV<br>IDTPCWKLHTSPLCTTNTKEGSNICLTRTDRGWYCDNAGSVSFF<br>PQAETCKVQSNRVFCDTMNSLTLPSEVNLCNIDIFNPKYDCKIM<br>TSKTDVSSSVITSLGAIVSCYGKTKCTASNKNRGIIKTFSNGCD<br>YVSNKGVDTVSVGNTLYYVNIQEGKSLYVKGEPIINFYDPLVFP<br>SDEFDASISQVNEKINQSLAFIRKSDELLHNVNVGKSTTNIMIT<br>TIIIVIIVILLLLIAVGLFLYCKARSTPVTLSKDQLSGINNIAF<br>SN | 56 |
| Influenza A virus HA | >tr\|C3W5X2\|C3W5X2_9INFA Hemagglutinin OS = Influenza A virus (A/Californda/07/2009(H1N1)) GN = HA PE = 1 SV = 1<br>MKAILVVLLYTPATANADTLCIGYHANNSTDTVDTVLEKNVTVT<br>HSVNLLEDKHNGKLCKLRGVAPLHLGKCNIAGWILGNPECESLS<br>TASSWSYIVETPSSDNGTCYPGDFIDYEELREQLSSVSSFERFE<br>IFPKTSSWPNHDSNKGVTAACPRAGAKSFYKNLIWLVKKGNSYP<br>KLSKSYINDKGKEVLVLWGIHHPSTSADQQSLYQNADAYVFVGS<br>SRYSKKFKPEIAIRPKVRDQEGRMNYYWTLVEPGDKITFEATGN<br>LVVPRYAFAMERNAGSGIIISDTPVHDCNTTCQTPKGAINTSLP<br>FQNIHPITIGKCPKYVKSTKLRLATGLRNIPSIQSRGLFGAIAG<br>FIEGGWTGMVDGWYGYHHQNEQGSGYAADLKSTQNAIDEITNKV<br>NSVIEKMNTQFTAVGKEFNHLEKRIENLNKKVDDGFLDIWTYNA<br>ELLVLLENERTLDYHDSNVKNLYEKVRSQLKNNAKEIGNGCFEF<br>YHKCDNTCMESVKNGTYDYPKYSEEAKLNREEIDGVKLESTRIY<br>QILAIYSTVASSLVLVVSLGAISFWMCSNGSLQCRICI | 57 |
| Influensa B virus HA | >tr\|A0A140EM53\|A0A140EM53_9INFB Hemagglutinin OS = Influenza B virus (B/Victoria/809/2012) GN = HA PE = 3 SV = 1<br>MKAIIVLLMVVTSNADRICTGITSSNSPHVVKTATQGEVNVTGV<br>IPLTTTPTKSYFANLKGTKTRGKLCPDCLNCTDLDVALGRPMCV<br>GTTPSAKASILHEVRPVTSGCFPIMHDRTKIRQLANLLRGYENI<br>RLSTQNVIDAEKAPGGPYRLGTSGSCPNATSKSGFFATMAKAVP<br>KDNNKNATNPLTVEVPYICAEGEDQITVWGFHSDNKTQMKNLYG<br>DSNPQKFTSSANGVTTHYVSQIGGFPDQTEDGGLPQSGRIVVDY<br>MMQKPGKTGTIVYQRGVLLPQKVWCASGRSKVIKGSLPLIGEAD<br>CLHEKYGGLNKSKPYYTGEHAKAIGNCPIWVKTPLKLANGTKYR<br>PPAKLLKERGFFGAIAGFLEGGWEGMIAGWHGYTSHGAHGVAVA<br>ADLKSTQEAINKITKNLNSLSELEVKNLQRLSGAMDELHNEILE<br>LDEKVDDLRADTISSQIELAVLLSNEGIINSEDEHLLALERKLK<br>KMLGPSAVDIGNGCFETKHKCNQTCLDRIAAGTFNAGEFSLPTF<br>DSLNITAASLNDDGLDNHTILLYYSTAASSLAVTLMLAIFIVYM<br>VSRDNVECSICL | 58 |
| Epstein-Barr virus (EBV) glycoprotein 350/220 (gp350) | >sp\|P03200\|GP350_EBVB9 Envelope glycoprotein GP350 OS = Epstein-Barr virus (strain B95-8) GN = BLLF1 PE = 1 SV = 1<br>MEALLVCQYTIQSLIHLTGEDPGFFNVEIPEFPFYPTCNVCYTA<br>DVNVTINFDVGGKKHQLDLDFGQLTPHTKAVYQPRGAFGGSENA<br>TNLFLLELLGAGELALTMRSKKLPINVTTGEEQQVSLESVDVYF<br>QDVFGTMWCHHAEMQNPVYLIPETVPYIKWDNCNSTNITAVVRA<br>QGLDVTLPLSLPTSAQDSNFSVKTEMLGNEIDIECIMEDGEISQ<br>VLPGDNKFNITCSGYESHVPSGGILTSTSPVATPIPGTGYAYSL<br>RLTPRPVSRFLGNNSILYVFYSGNGPKASGGDYCIQSNIVFSDE | 59 |

TABLE 3-continued

Non-Limiting List of Antigen Sequences

| Antigen | Amino Acid Sequence (UniPmot) | SEQ ID NO |
|---|---|---|
| | IPASQDMPTNTTDITYVGDNATYSVPMVTSEDANSPNVTVTAFW AWPNNTETEDEKCKWTLTSGTPSGCENISGAFASNRTFDITVSGL GTAPKTLIITRTATNATTTTHKVIFSKAPESTTTSPTLNTTGFA DPNTTTGLPSSTHVPTNLTAPASTGPTVSTADVTSPTPAGTTSG ASPVTPSPSPWDNGTESKAPDMTSSTSPVTTPTPNATSPTPAVT TPTPNATSPTPAVTTPTPNATSPTLGKTSPTSAVTTPTPNATSP TLGKTSPTSAVTTPTPNATSPTLGKTSPTSAVTTPTPNATGPTV GETSPQANATNHTLGGTSPTPVVTSQPKNATSAVTTGQHNITSS STSSMSLRPSSNPETLSPSTSDNSTSHMPLLTSAHPTGGENITQ VTPASISTHHVSTSSPAPRPGTTSQASGPGNSSTSTKPGEVNVT KGTPPQNATSPQAPSGQKTAVPTVTSTGGKANSTTGGKHTTGHG ARTSTEPTTDYGGDSTTPRPRYNATTYLPPSTSSKLRPRWTFTS PPVTTAQATVPVPPTSQPRFSNLSMLVLQWASLAVLTLLLLLVM ADCAFRRNLSTSHTYTTPPYDDAETYV | |
| Human cytomegalovirus gB | >sp\|P06473\|GB_HCMVA Envelope glycoprotein B OS = Human cytomegalovirus (strain AD169) GN = gB PE = 1 SV = 1 MESRIWCLVVCVNLCIVCLGAAVSSSSTSHATSSTHNGSHTSRT TSAQTRSVYSQHVTSSEAVSHRANETIYNTTLKYGDVVGVNTTK YPYRVCSMAQGTDLIRFEPNIICTSMKPINEDLDEGIMVVYKRN IVAHTFKVRVYQKVLTFRRSYAYIYTTYLLGSNTEYVAPPMWEI HHINKFAQCYSSYSRVIGGTVFVAYHRDSYENKTMQLIPDDYSN THSTRYVTVKDQWHSRGSTWLYRETCNLNCMLTITTARSKYPYH FFATSTGDVVYISPFYNGTNRNASYFGENADKFFIFPNYTIVSD FGRPNAAPETHRLVAFLERADSVISWDIQDEKNVTCQLTFWEAS ERTIRSEAEDSYHFSSAKMTATFLSKKQEVNMSDSALDCVRDEA INKLQQIFNTSYNQTYEKYGNVSVFETSGGLVVFWQGIKQKSLV ELERLANRSSLNITHRTRRSTSDNNTTHLSSMESVHNLVYAQLQ FTYDTLRGYINRALAQIAEAWCVDQRRTLEVFKELSKINPSAIL SAIYNKPIAARFMGDVLGLASCVTINQTSVKVLRDMNVKESPGR CYSRPVVIFNFANSSYVQYGQLGEDNEILLGNHRTEECQLPSLK IFIAGNSAYEYVDYLFKRMIDLSSISTVDSMIALDIDPLENTDF RVLELYSQKELRSSNVFDLEEIMREFNSYKORVKYVEDKVVDPL PPYLKGLDDLMSGLGAAGKAVGVAIGAVGGAVASVVEGVATFLK NPEGAFTIILVAIAVVIITYLIYTRQRRLCTQPLQNLFPYLVSA DGTTVTSGSTKDTSLQAPPSYEESVYNSGRKGPGPPSSDASTAA PPYTNEQAYQMLLALARLDAEQRAQQNGTDSLDGQTGTQDKGQK PNLLDRLRHRKNGYRHLKDSDEEENV | 60 |
| Human cytomegalovirus UL128 | >sp\|P16837\|UL128_HCMVA Uncharacterized protein UL128 OS = Human cytomegalovirus (strain AD169) GN = UL128 PE = 1 SV = 2 MSPKDLTPFLTTLWLLLGHSRVPRVRAEECCEFINVNHPPERCY DFKMCNRFTVALRCPDGEVCYSPEKTAEIRGIVTTMTHSLTRQV VHNKLTSCNYNPLYLEADGRIRCGKVNDKAQYLLGAAGSVPYRW INLEYDKITRIVGLDQYLESVKKHKRLDVCRAKMGYMLQ | 61 |
| Human cytomegalovirus UL130 | >sp\|F5HCP3\|UL130_HCMVM Envelope glycoprotein UL130 OS = Human cytomegalovirus (strain Merlin) GN = UL130 PE = 1 SV = 1 MLRLLLRHHFHCLLLCAVWATPCLASPWSTLTANQNPSPPWSKL TYSKPHDAATFYCPFLYPSPPRSPLQFSGFQRVSTGPECRNETL YLLYNREGQTLVERSSTWVKKVIWYLSGRNQTILQRMPRTASKP SDGNVQISVEDAKIFGAHMVPKQTKLLRFVVNDGTRYQMCVMKL ESWAHVFRDYSVSFQVRLTFTEANNQTYTFCTHPNLIV | 62 |
| Human cytomegalovirus UL131A | >sp\|HET4\|U131_HCMVM Protein UL131A OS = Human cytomegalovirus (strain Merlin) GN = UL131A PE = 1 SV = 1 MRLCRVWLSVCLCAVVLGQCQRETAEKNDYYRVPHYWDACSRAL PDQTRYKYVEQLVDLTLNYHYDASHGLDNFDVLKRINVTEVSLL ISDFRRQNRRGGTNKRTTFNAAGSLAPHARSLEFSVRLFAN | 63 |
| Human cytomegalovirus gH (UL75) | >sp\|P12824\|GH_HCMVA Envelope glycoprotein H OS = Human cytomegalovirus (strain AD169) GN = gH PE = 1 SV = 1 MRPGLPPYLTVFTVYLLSHLPSQRYGADAASEALDPHAFHLLLN TYGRPIRFLRENTTQCTYNSSLRNSTVVRENAISFNFFQSYNQY YVFHMPRCLFAGPLAEQFLNQVDLTETLERYQQRLNTYALVSKD LASYRSFSQQLKAQDSLGQQPTTVPPPIDLSIPHVWMPPQTTPH DWKGSHTTSGLHRPHFNQTCILFDGHDLLFSTVTPCLHQGFYLM DELRYVKITLTEDFFVVTVSIDDDTPMLLIFGHLPRVLFKAPYQ RDNFILRQTEKHELLVLVKKAQLNRHSYLKDSDFLDAALDFNYL | 64 |

TABLE 3-continued

Non-Limiting List of Antigen Sequences

| Antigen | Amino Acid Sequence (UniPmot) | SEQ ID NO |
|---|---|---|
| | DLSALLRNSFHRYAVDVLKSGPCQMLDRRTVEMAFAYALALFAA ARQEEAGTEISIPRALDRQAALLQIQEFMITCLSQTPPRTTLLL YPTAVDLAKRALWTPDQITDITSLVRLVYILSKQNQQHLIPQWA LRQIADFALQLHKTHLASFLSAFARQELYLMGSLVHSMLVHTTE RREIFIVETGLCSLAELSHFTQLLAHPHHEYLSDLYTPCSSSGR RDHSLERLTRLFPDATVPATVPAALSILSTMQPSTLETFPDLFC LPLGESFSALTVSEHVSYVVTNQYLIKGISYPVSTTVVGQSLII TQTDSQTKCELTRNMHTTHSITAALNISLENCAFCQSALLEYDD TQGVINIMYMHDSDDVLFALDPYNEVVVSSPRTHYLMLLKNGTV LEVTDVVVDATDSRLLMMSVYALSAIIGIYLLYRMLKTC | |
| Human cytomegalovirus gL (UL115) | >sp\|P16832\|GL_HVMVA Envelope glycoprotein L OS = Human cytomegalovirus (strain AD169) GN = gL PE = 1 SV = 2 MCPRPDCGFSFSPGPVVLLWCCLLLPIVSSVAVSVAPTAAEKVP AECPELTRRCLLGEVFQGDKYESWLRPLVNVTRRDGPLSQLIRY RPVTPEAANSVLLDDAFLDTLALLYNNPDQLRALLTLLSSDTAP RWMTVMRGYSECGDGSPAVYTCVDDLCRGYDLTRLSYGRSIFTE HVLGFELVPPSLFNVVVAIRNEATRTNRAVRLPVSTAAAPEGIT LFYGLYNAVKEFCLRHQLDPPLLRHLDKYYAGLPPELKQTRVNL PAHSRYGPQAVDAR | 65 |
| Lyme Outer Surface Protein A (OspA) | >sp\|Q04968\|OSPA7_BORBG Outer surface protein A OS = *Borreliella burgdorferi* GN = ospA PE = 3 SV = 1 MKKYLLGIGLILALIACKQNVSSLDEKNSVSVDVPGGMKVLVSK EKNKDGKYDLMATVDNVDLKGTSDKNNGSGILEGVKADKSKVKL TVADDLSKTTLEVLKEDGTVVSRKVTSKDKSTTEAKFNEKGELS EKTMTRANGTTLEYSQMTNEDNAAKAVETLKNGIKFEGNLASGK TAVEIKEGTVTLKREIDKNGKVTVSLNDTASGSKKTASWQESTS TLTISANSKKTKDLVFLTNGTITVQNYDSAGTKLEGSAAEIKKL DELKNALR | 66 |
| *Bordetella pertussis* Pertussis toxin (PT) subunits 1-5 | >sp\|P04977\|TOX1_BORPE Pertussis toxin subunit 1 OS = 2 *Bordetella pertussis* (strain Tohama I/ATCC BAA-589/NCTC 13251) GN = ptxa PE = 1 SV = 1 MRCTRAIRQTARTGWLTWLAILAVTAPVTSPAWADDPPATVYRY DSRPPEDVFQNGFTAWGNNDNVLDHLTGRSCQVGSSNSAFVSTS SSRRYTEVYLEHRMQEAVEAERAGRGTGHFIGYIYEVRADNNFY GAASSYFEYVDTYGDNAGRILAGALATYQSEYLAHRRIPPENIR RVTRVYHNGITGETTTTEYSNARYVSQQTRANPNPYTSRRSVAS IVGTLVRMAPVIGACMARQAESSEAMAAWSERAGEAMVLVYYES IAYSF | 67 |
| Dengue virus Envelope protein E | >sp\|P17763\|281-775 MRCVGIGNRDFVEGLSGATWVDVVLEHGSCVTTMAKDKPTLDIE LLKTEVTNPAVLRKLCIEAKISNTTTDSRCPTQGEATLVEEQDT NFVCRRTFVDRGWGNGCGLFGKGSLITCAKFKCVTKLEGKIVQY ENLKYSVIVTVHTGDQHQVGNETTEHGTTATITPQAPTSEIQLT DYGALTLDCSPRTGLDENEMVLLTMEKKSWLVHKQWFLDLPLPW TSGASTSQETWNRQDLLVTFKTAHAKKQEVVVLGSQEGAMHTAL TGATEIQTSGTTTIFAGHLKCRLKMDKLTLKGMSYVMCTGSFKL EKEVAETQHGTVLVQVKYEGTDAPCKIPFSSQDEKGVTQNGRLI TANPIVTDKEKPVNIEAEPPFGESYIVVGAGEKALKLSWFKKGS SIGKMFEATARGARRMAILGDTAWDFGSIGGVFTSVGKLIHQIF GTAYGVLFSGVSWTMKIGIGILLTWLGLNSRSTSLSMTCIAVGM VTLYLGVMVQA | 68 |
| HUMAN SARS coronavirus (SARS) Spike (S) glycoprotein | >sp\|P59594\|SPIKE_CVHSA Spike glycoprotein OS = Human SAPS coronavirus GN = S PE = 1 SV = 1 MFIFLLFLTLTSGSDLDRCTTFDDVQAPNYTQHTSSMRGVYYPD EIFRSDTLYLTQDLFLPFYSNVTGFHTINHTFGNPVIPFKDGIY FAATEKSNVVRGWVFGSTMNNKSQSVIIINNSTNVVIRACNFEL CDNPFFAVSKPMGTQTHTMIFDNAFNCTFEYISDAFSLDVSEKS GNFKHLREFVFKNKDGFLYVYKGYQPIDVVRDLPSGFNTLKPIF KLPLGINITNFRAILTAFSPAQDIWGTSAAAYFVGYLKPTTFML KYDENGTITDAVDCSQNPLAELKCSVKSFEIDKGIYQTSNFRVV PSGDVVRFPNITNLCPFGEVFNATKFPSVYAWERKKISNCVADY SVLYNSTFFSTFKCYGVSATKLNDLCFSNVYADSFVVKGDDVRQ IAPGQTGVIADYNYKLPDDFMGCVLAWNTRNIDATSTGNYNYKY RYLRHGKLRPFERDISNVPFSPDGKPCTPPALNCYWPLNDYGFY TTTGIGYQPYRVVVLSFELLNAPATVCGPKLSTDLIKNQCVNFN FNGLTGTGVLTPSSKRFQPFQQFGRDVSDFTDSVRDPKTSEILD | 69 |

TABLE 3-continued

Non-Limiting List of Antigen Sequences

| Antigen | Amino Acid Sequence (UniPmot) | SEQ ID NO |
|---|---|---|
| | ISPCSFGCVSVITPCTNASSEVAVLYQDVNCTDVSTAIHADQLT PAWRIYSTGNNVFQTQAGCLIGAEHVDTSYECDIPIGAGICASY HTVSLLRSTSQKSIVAYTMSLGADSSIAYSNNTIAIPTNFSISI TTEVMPVSMAKTSVDCNMYICGDSTECANLLLQYGSFCTQLNRA LSGIAAEQDRNTREVFAQVKQMYKTPTLKYFGGFNFSQILPDPL KPTKRSFIEDLLENKVTLADAGFMKQYGECLGDINARDLICAQK FNGLTVLPPLLTDDMIAAYTAALVSGTATAGWTFGAGAALQIPF AMQMAYRFNGIGVTQNVLYENQKQIANQFNKAISQIQESLTTTS TALGKLQDVVKQNAQALNTLVKQLSSNFGAISSVLNDILSRLDK VEAEVQIDRLITGRLQSLQTYVTQQLIRAAEIRASANLAATKMS ECVLGQSKRVDFCGKGYHLMSFPQAAPHGVVFLHVTYVPSQERN FTTAPAICHEGKAYFPREGVFVFNGTSWFITQRNFFSPQIITTD NTFVSGNCDVVIGIINNTVYDPLQPELDSFKEELDKYFKNHTSP DVDLGDISGINASVVNIQKEIDRLNEVAKNLNESLIDLQELGKY EQYIKWPWYVWLGFIAGLIAIVMVTILLCCMTSCCSCLKGACSC GSCCKFDEDDSEPVLKGVKLHYT | |
| Middle East respiratory syndrome-related coronavirus (MERS) Spike (S) glycoprotein | >tr\|R9UCW7\|R9UCW7_9BETC Spike glycoprotein OS = Middle East respiratory syndrome-related coronavirus PE = 4 SV = 1 MIHSVFLLMFLLTPTESYVDVGPDSIKSACIEVDIQQTFFDKTW PRPIDVSKADGIIYPQGRTYSNITITYQGLFPYQGDHGDMYVYS AGHATGTTPQKLFVANYSQDVKQFANGFVVRIGAAANSTGTVII SPSTSATIRKIYPAFMLGSSVGNFSDGKMGRFFNHTLVLLPDGC GTLLRAFYCILEPRSGNHCPAGNSYTSFATYHTPATDCSDGNYN RNASLNSFKEYFNLRNCTFMYTYNITEDEILEWFGITQTAQGVH LFSSRYVDLYGGNMEQFATLPVYDTIKYYSIIPHSIRSIQSDRK AWAAFYVYKLQPLTFLLDFSVDGYIRRAIDCGFNDLSQLHCSYE SFDVESGVYSVSSFEAKPSGSVVEQAEGVECDFSPLISGTPPQV YNFKRLVFTNCNYNLTKLLSLFSVNDFTCSQISPAAIASNCYSS LILDYFSYPLSMKSDLSVSSAGPISQFNYKQSFSNPTCLILATV PHNLTTITKPLKYSYINKCSRLLSDDRTEVPQLVNANQYSPCVS IVPSTVWEDGDYYRKQLSPLEGGGWLVASGSTVAMTEQLQMGFG ITVQYGTDTNSVCPKLEFANDTKIASQLGNCVEYSLIGVSGRGV FQNCTAVGVRQQRFVYDAYQNLVGYYSDDGNYYCLRACVSVPVS VIYDKETKTHATLFGSVACEHISSTMSQYSRSTPSMLKRRDSTY GPLQTPVGCVLGLVNSSLFVEDCKLPLGQSLCALPDTPSTLTPR SVRSVPGEMRLASIAFNHPIQVDQLNSSYFKLSIPTNFSFGVTQ EYIQTTIQKVTVDCKQYVCNGTQKCEQLLREYGQFCSKINQALH GANLRQDDSVRNLFASVKSSQSSPIIPGFGGDFNLTLLEPVSIS TGSRSARSAIEDLLEDKVTIADPGYMQGYDDCMQQGPASARDLI CAQYVAGYKVLPPLMDVNMEAAYTSSLLGSIAGVGWTAGLSSFA AIPFAQSIFYRLNGVGITQQVLSENQKLIANKFNQALGAMQTGF TTTNEAFHKVQDAVNNNAQALSKLASELSNTFGAISASIGDIIQ RLDVLEQDAQIDRLINGRLTTLNAFVAQQLVRSESAALSAQLAK DKVNECVKAQSKRSGFCGQGTHIVSFVVNAPNGLYFMHVGYYPS NHIEVVSAYGLCDAANPTNCIAPVNGYFIKTNNTRIVDEWSYTG SSFYAPEPITSLNTKYVAPQVTYQNISTNLPPPLLGNSTGIDFQ DELDEFFKNVSTSIPNFGSLQINTTLLDLTYEMLSLSQQVVKAL NESYIDLKELGNYTYYNKPWYIWLGFIAGLVALALCVFFILCC TGCGTNCMGKLKCNRCCDRYEEYDLEPHKVHVH | 70 |
| Zaire ebolavirus GP | >sp\|Q05320\|VGP_EBOZM Envelope glycoprotein OS = Zaire ebolavirus (strain Mayinga-76) GN = GP PE = 1 SV = 1 MGVTGILQLPRDRFKRTSFFLWVIILFQRTFSIPLGVIHNSTLQ VSDVDKLVCRDKLSSTNQLRSVGLNLEGNGVATDVPSATKRWGF RSGVPPKVVNYEAGEWAENCYNLEIKKPDGSECLPAAPDGIRGF PRCRYVHKVSGTGPCAGDFAFHKEGAFFLYDRLASTVIYRGTTF AEGVVAFLILPQAKKDFFSSHPLREPVNATEDPSSGYYSTTIRY QATGFGTNETEYLFEVDNLTYVQLESRFTPQFLLQLNETIYTSG KRSNTTGKLIWKVNPEIDTTIGEWAFWETKKNLTRKIPSEELSF TVVSNGAKNISGQSPARTSSDPGTNTTTEDHKIMASENSSAMVQ VHSQGREAAVSHLTTLATISTSPQSLTTKPGPDNSTHNTPVYKL DISEATQVEQHHRRTDNDSTASDTPSATTAAGPPKAENTNTSKS TDFLDPATTTSPQNHSETAGNNNTHHQDTGEESASSGKLGLITN TIAGVAGLITGRRTRREAIVNAQPKCNPNLHYWTTQDEGAAIG LAWIPYFGPAAEGIYIEGLMHNQDGLICGLRQLANETTQALQLF LRATTELRTFSILNRKAIDFLLQRWGGTCHILGPDCCIEPHDWT KNITDKIDQIIHDFVDKTLPDQGDNDNWWTGWRQWIPAGIGVTG VIIAVIALFCICKFVF | 71 |

TABLE 3-continued

Non-Limiting List of Antigen Sequences

| Antigen | Amino Acid Sequence (UniPmot) | SEQ ID NO |
|---|---|---|
| Marburg virus GP | >sp\|P35253\|VGP_MABVM Envelope glycoprotein OS = Lake Victoria marburgvirus (strain Musoke-80) GN = GP PE = 1 SV = 1<br>MKTTCFLISLILIQGTKNLPILEIASNNQPQNVDSVCSGTLQKT EDVHLMGFTLSGQKVADSPLEASKRWAFRTGVPPKNVEYTECEE AKTCYNISVTDPSGKSLLLDPPTNIRDYPKCKTIHHIQGQNPHA QGIALHLWGAFELYDRIASTTMYRGKVFTEGNIAAMIVNKTVHK MIFSRQGQGYRHMNLTSTNKYWTSSNGTQTNDTGCFGALQEYNS TKNQTCAPSKIPPPLPTARPEIKLTSTPTDATKLNTTDPSSDDE DLATSGSGSGEREPHTTSDAVTKQGLSSTMPFTPSPQPSTPQQG GNNTNHSQDAVTELDKNNTTAQPSMPPHNTTTISTNNTSKHNFS TLSAPLQNTTNDNTQSTITENEQTSAPSITTLPPTGNPTTAKST SSKKGPATTAPNTTNEHETSPPPTPSSTAQHLVYFRRKRSILWR EGDMFPPLDGLINAPIDFDPVPNTKTIFDESSSSGASAEEDQHA SPNISLTLSYFPNINENTAYSGENENDCDAELRIWSVQEDDLAA GLSWIPFFGPGIEGLYTAVLIKNQNNLVCRLRRLANQTAKSLEL LLRVTTEERTFSLINRHAIDFLLTRWGGTCKVLGPDCCIGIEDL SKNISEQIDQIKKDEQKEGTGWGLGGKWWTSDWGVLTNLGILLL LSIAVLIALSCICRIFTKYIG | 72 |
| Hanta virus Gn envelope glycoprotein | >sp\|P08668\|19-648<br>LRNVYDMKIECPHTVSFGENSVIGYVELPPVPLADTAQMVPESS CNMDNHQSLNTITKYTQVSWRGKADQSQSSQNSFETVSTEVDLK GTCVLKHKMVEESYRSRKSVTCYDLSCNSTYCKPTLYMIVPIHA CNMMKSCLIALGPYRVQVVYERSYCMTGVLIEGKCFVPDQSVVS IIKHGIFDIASVHIVCFFVAVKGNTYKIFEQVKKSFESTCNDTE NKVQGYYICIVGGNSAPIYVPTLDDFRSMEAFTGIFRSPHGEDH DLAGEEIASYSIVGPANAKVPHSASSDTLSLIAYSGIPSYSSLS ILTSSTEAKHVFSPGLEPKLNHTNCDKSAIPLIWTGMIDLPGYY EAVHPCTVFCVLSGPGASCEAFSEGGIFNITSPMCLVSKQNRFR LTEQQVNFVCQRVDMDIVVYCNGQRKVILTKTLVIGQCIYTITS LFSLLPGVAHSIAVELCVPGFHGWATAALLVTFCFGWVLIPAIT FIILTVLKFIANIFHTSNQENRLKSVLRKIKEEFEKTKGSMVCD VCKYECETYKELKAHGVSCPQSQCPYCFTHCEPTEAAFQAHYKV CQVTHRFRDDLKKTVTPQNFTPGCYRTLNLFRYKSRCYIFTMWI FLLVLESILWAASA | 73 |
| Hanta virus Gc envelope glycoprotein | >sp\|P08668\|649-1135<br>SETPLTPVWNDNAHGVGSVPMHTDLELDFSLTSSSKYTYRRKLT NPLERAQSIDLHIEIEEQTIGVDVHALGHWFDGRLNLKTSFHCY GACTKYEYPWHTAKCHYERDYQYETSWGCNPSDCPGVGTGCTAC GLYLDQLKPVGSAYKIITIRYSRRVCVQFGEENLCKIIDMNDCF VSRHVKVCIIGTVSKFSQGDTLLFFGPLEGGGLIFKHWCTSTCQ FGDPGDIMSPRDKGFLCPEFPGSFRKKCNFATTPICEYDGNMVS GYKKVMATIDSFQSFNTSTMHFTDERIEWKDPDGMLRDHINILV TKDIDFDNLGENPCKIGLQTSSIEGAWGSGVGFTLTCVLSLTEC PTFLTSIKACDKAICYGAESVTLTRGQNTVKVSGKGGHSGSTFP CCHGEDCSQIGLHAAAPHLDKVNGISEIENSKVYDDGAPQCGIK CWTVKSGEWISGIFSGNWIVLIVLCVFLLSLVLLSILCPVRKH KKS | 74 |
| Hepatitis B HepB surface antigen (HBs) | >tr\|Q9DIX1\|Q9DIX1_HBV Surface antigen HBsAg OS = Hepatitis B virus GN = S PE = 4 SV = 1<br>MENITSGFLGPLLVLQAGFFLLTKILTIPQSLNSWWTSLSFLGG NTVCLGQNSQSPTSNHSPTSCPPTCPGYRWMCLRRFIIFLFILL LCLIFLLVLLDYQGMLPVCPLIPGSSTTSTGPCRTCKTPAQGTS MYPSCCCTKPSDGNCTCIPIPSSWAFGKFLWEWASARFSWLSLI VPFVQWFVGLSPTVWLSVIWMMWYWGPSLYSILSPFLPLLPIFF CLWVYI | 75 |
| Measles H protein | >sp\|P08362\|HEMA_MEASE Hemagglutinin glycoprotein OS = Measles virus (strain Edmonston) GN = H PE = 1 SV = 1<br>MSPQRDRINAFYKDNPHPKGSRIVINREHLMIDRPYVLLAVLFV MFLSLIGLLAIAGIRLHRAAIYTAEIHKSLSTNLDVTNSIEHQV KDVLTPLFKIIGDEVGLRTPQRFTDLVKFISDKIKFLNPDREYD FRDLTWCINPFERIKLDYDQYCADVAAEELMNALVNSTLLETRT TNQFLAVSKGNCSGPTTIRGQFSNMSLSLLDLYLGRGYNVSSIV TMTSQGMYGGTYLVEKPNLSSKRSELSQLSMYRVFEVGVIRNPG LGAPVFHMTNYLEQPVSNDLSNCMVALGELKLAALCHGEDSITI PYQGSGKGVSFQLVKLGVWKSPTDMQSWVPLSTDDPVIDRLYLS SHRGVIADNQAKWAVPTTRTDDKLRMETCFQQACKGKIQALCEN PEWAPLEDNRIPSYGVLSVDLSLTVELKIKIASGFGPLITHGSG | 76 |

TABLE 3-continued

Non-Limiting List of Antigen Sequences

| Antigen | Amino Acid Sequence (UniPmot) | SEQ ID NO |
|---|---|---|
| | MDLYKSNHNNVYWLTIPPMKNLALGVINTLEWIPRFKVSPYLFN VPIKEAGEDCHAPTYLPAEVDGDVKLSSNLVILPGQDLQYVLAT YDTSRVEHAVVYYVYSPSRSFSYFYPFRLPIKGVPIELQVECET WDQKLWCRHFCVLADSESGGHITHSGMEGMGVSCTVTREDGTNR R | |
| Measles F protein | >sp\|P69353\|FUS_MEASE Fusion glycoprotein F0 OS = Measles virus (strain Edmonston) GN = F PE = 3 SV = 1 MGLKVNVSAIFMAVLLTLQTPTGQIHWGNLSKIGVVGIGSASYK VMTRSSHQSLVIKLMPNITLLNNCTRVEIAEYRRLLRTVLEPIR DALNAMTQNIRPVQSVASSRRHKRFAGVVLAGAALGVATAAQIT AGIALHQSMLNSQAIDNLRASLETTNQAIEAIRQAGQEMILAVQ GVQDYINNELIPSMNQLSCDLIGQKLGLKLLRYYTEILSLFGPS LRDPISAEISIQALSYALGGDINKVLEKLGYSSGDLLGILESRG IKARITHVDTESYFIVLSIAYPTLSEIKGVIVHRLEGVSYNIGS QEWYTTVPKYVATQGYLISNFDESSCTFMPEGTVCSQNALYPMS PLLQECLRGSTKSCARTLVSGSFGNRFILSQGNLIANCASILCK CYTTGTIINQDPDKILTYIAADHCPVVEVNGVTIQVGSRRYPDA VYLHRIDLGPPISLERLDVGTNLGNAIAKLEDAKELLESSDQIL RSMKGLSSTSIVYILIAVCLGGLIGIPALICCCRGRCNKKGEQV GMSRPGLKPDLTGTSKSYVRSL | 77 |
| Zika Zika envelope domain III (ZEDIII) | >sp\|Q32ZE1\|291-790 IRCIGVSNRDFVEGMSGGTWVDVVLEHGGCVTVMAQDKPTVDIE LVTTTVSNMAEVRSYCYEASISDMASDSRCPTQGEAYLDKQSDT QYVCKRTLVDRGWGNGCGLFGKGSLVTCAKFTCSKKMTGKSIQP ENLEYRIMLSVHGSQHSGMIGYETDEDRAKVEVTPNSPRAEATL GGFGSLGLDCEPRTGLDFSDLYYLTMNNKHWLVHKEWFHDIPLP WHAGADTGTPHWNNKEALVEFKDAHAKRQTVVVLGSQEGAVHTA LAGALEAEMDGAKGRLFSGHLKCRLKMDKLRLKGVSYSLCTAAF TFTKVPAETLHGTVTVEVQYAGTDGPCKIPVQMAVDMQTLTPVG RLITANPVITESTENSKMMLELDPPFGDSYIVIGVGDKKITHHW HRSGSTIGKAFEATVRGAKRMAVLGDTAWDFGSVGGVFNSLGKG IHQIFGAAFKSLFGGMSWFSQILIGTLLVWLGLNTKNGSISLTC LALGGVMIFLSTAVSA | 78 |
| Malaria circumsporozoite protein (CSP) | >sp\|P08677\|CSP_PLAVB Circumsperozoite protein OS = Plasmodium vivax (strain Belem) PE = 3 SV = 2 MKNFILLAVSSILLVDLFPTHCGHNVDLSKAINLNGVNFNNVDA SSLGAAHVGQSASPGRGLGENPDDEEGDAKKKKDGKKAEPKNPR ENKLKQPGDRADGQPAGDRADGQPAGDRADGQPAGDRAAGQPAG DRADGQPAGDRADGQPAGDRADGQPAGDRADGQPAGDRAAGQPA GDRAAGQPAGDRADGQPAGDRAAGQPAGDRADGQPAGDRAAGQP AGDRADGQPAGDRAAGQPAGDRAAGQPAGDRAAGQPAGDRAAGQ PAGNGAGGQAAGGNAGGGQGQNNEGANAPNEKSVKEYLDKVRAT VGTEWTPCSVTCGVGVRVRRRVNAANKKPEDLTLNDLETDVCTM DKCAGIFNVVSNSLGLVILLVALFN | 79 |
| Nipah virus F protein | >sp\|Q9IH63\|FUS_NIPAV Fusion glycoprotein F0 OS = Nipah virus GN = F PE = 1 SV = 1 MVVILDKRCYCNLLILILMISECSVGILHYEKLSKIGLVKGVTR KYKIKSNPLTKDIVIKMIPNVSNMSQCTGSVMENYKTRLNGILT PIKGALEIYKNNTHDLVGDVRLAGVIMAGVAIGIATAAQITAGV ALYEAMKNADNINKLKSSIESTNEAVVKLQETAEKTVYVLTALQ DYINTNLVPTIDKISCKQTELSLDLALSKYLSDLLFVFGPNLQD PVSNSMTIQAISQAFGGNYETLLRTLGYATEDFDDLLESDSITG QIIYVDLSSYYIIVRVYFPILTEIQQAYIQELLPVSFNNDNSEW ISIVPNFILVRNTLISNIEIGFCLITKRSVICNQDYATPMTNNM RECLTGSTEKCPRELVVSSHVPRFALSNGVLFANCISVTCQCQT TGRAISQSGEQTLLMIDNTTCPTAVLGNVIISLGKYLGSVNYNS EGIAIGPPVFTDKVDISSQISSMNQSLQQSKDYIKEAQRLLDTV NPSLISMLSMIILYVLSIASLCIGLITFISFIIVEKKRNTYSRL EDRRVRPTSSGDLIYIGT | 80 |
| Nipah virus G protein | >sp\|Q9IH62\|GLYCP_NIPAV Glycoprotein G OS = Nipah virus GN = G PE = 1 SV = 1 MPAENKKVRFENTTSDKGKIPSKVIKSYYGTMDIKKINEGLLDS KILSAFNTVIALLGSIVIIVMNIMIIQNYTRSTDNQAVIKDALQ GIQQQIKGLADKIGTEIGPKVSLIDTSSTITIPANIGLLGSKIS QSTASINENVNEKCKFTLPPLKIHECNISCPNPLPFREYRPQTE GVSNLVGLPNNICLQKTSNQILKPKLISYTLPVVGQSGTCITDP LLAMDEGYFAYSHLERIGSCSRGVSKQRIIGVGEVLDRGDEVPS | 81 |

TABLE 3-continued

Non-Limiting List of Antigen Sequences

| Antigen | Amino Acid Sequence (UniPmot) | SEQ ID NO |
|---|---|---|
| | LFMTNVWTPPNPNTVYHCSAVYNNEFYYVLCAVSTVGDPILNST YWSGSLMMTRLAVKPKSNGGGYNQHQLALRSIEKGRYDKVMPYG PSGIKQGDTLYFPAVGFLVRTEFKYNDSNCPITKCQYSKPENCR LSMGIRPNSHYILPSGLLKYNLSDGENPKVVFIEISDQRLSIGS PSKIYDSLGQPVFYQASFSWDTMIKFGDVLTVNPLVVNWRNNTV ISRPGQSQCPRFNTCPEICWEGVYNDAFLIDRINWISAGVFLDS NQTAENPVFTVFKDNEILYRAQLASEDTNAQKTITNCFLLKNKI WCISLVEIYDTGDNVIRPKLFAVKIPEQCT | |
| Rotavirus VP4 protein | >sp\|P11193\|VP4_ROTHW Outer capsid protein VP4 OS = Rotavirus A (strain RVA/Human/United States/Wa/1974/G1P1A[8]) PE = 1 SV = 3 MASLIYRQLLTNSYSVDLHDEIEQIGSEKTQNVTINFSPFAQTR YAPVNWGHGEINDSTTVEPILDGPYQPTTFTPPNDYWILINSNT NGVVYESTNNSDFWTAVVAIEPHVNPVDRQYTIFGESKQFNVSN DSNKWKFLEMFRSSSQNEFYNRRTLTSDTRFVGILKYGGRVWTF HGETPRATTDSSSTANLNNISITIHSEFYIIPRSQESKCNEYIN NGLPPIQNTRNVVPLPLSSRSIQYKRAQVNEDIIVSKTSLWKEM QYNRDIIIRFKFGNSIVKMGGLGYKWSEISYKAANYQYNYLRDG EQVTAHTTCSVNGVNNFSYNGGSLPTDFGISRYEVIKENSYVYV DYWDDSKAFRNMVYVRSLAANLNSVKCTGGSYNFSIPVGAWPVM NGGAVSLHFAGVTLSTQFTDFVSLNSLRFRFSLTVDEPPFSILR TRTVNLYGLPAANPNNGNEYYEISGRFSLIYLVPTNDDYQTPIM NSVTVRQDLERQLTDLREEFNSLSQEIAMAQLIDLALLPLDMFS MFSGIKSTIDLTKSMATSVMKKFRKSKLATSISEMTNSLSDAAS SASRNVSIRSNLSAISNWTNVSNDVSNVTNSLNDISTQTSTISK KFRLKEMITQTEGMSFDDISAAVLKTKIDMSTQIGKNTLPDIVT EASFEKFPKRSYRILKDDEVMEINTEGKFFAYFINTFDEVPFDV NKFAELVTDSPVISAIIDFKTLKNLNDNYGITRTEALNLIKSNP NMLRNFINQNNPIIRNRIEQLILQCKL | 82 |
| Rotavirus VP8 protein | >Sp\|P11193\|1-230 MASLIYRQLLTNSYSVDLHDEIEQIGSEKTQNVTINFSPFAQTR YAPVNWGHGEINDSTTVEPILDGPYQPTTFTPPNDYWILINSNT NGVVYESTNNSDFWTAVVAIEPHVNPVDRQYTIFGESKQFNVSN DSNKWKFLEMFRSSSQNEFYNRRTLTSDTRFVGILKYGGRVWTF HGETPRATTDSSSTANLNNISITIHSEFYIIPRSQESKCNEYIN NGLPPIQNTR | 83 |
| Human metapneumovirus (hMPV) F protein | >sp\|Q6WB98\|FUS_HMPVC Fusion glycoprotein F0 OS = Human metapneumovirus (strain CAN97-83 GN = F PE = 1 SV = 1 MSWKVVIIFSLLITPQHGLKESYLEESCSTITEGYLSVLRTGWY TNVFTLEVGDVENLTCSDGPSLIKTELDLTKSALRELKTVSADQ LAREEQIENPRQSRFVLGAIALGVATAAAVTAGVAIAKTIRLES EVTAIKNALKTTNEAVSTLGNGVRVLATAVRELKDFVSKNLTRA INKNKCDIDDLKMAVSFSQFNRRFLNVVRQFSDNAGITPAISLD LMTDAELARAVSNMPTSAGQIKLMLENRAMVRRKGFGILIGVYG SSVIYMVQLPIFGVIDTPCWIVKAAPSCSGKKGNYACLLREDQG WYCQNAGSTVYYPNEKDCETRGDHVFCDTAAGINVAEQSKECNI NISTTNYPCKVSTGRHPISMVALSPLGALVACYKGVSCSIGSNR VGIIKQLNKGCSYITNQDADTVTIDNTVYQLSKVEGEQHVIKGR PVSSSFDPIKFPEDQFNVALDQVFENIENSQALVDQSNRILSSA EKGNTGFIIVIILIAVLGSSMILVSIFIIIKKTKKPTGAPPELS GVTNNGFIPHS | 84 |
| Human metapneumovirus (hMPV) G protein | >sp\|Q6WB94\|VGLG_HMPVC Major surface glycoprotein G OS = Human metapneumovirus (strain CAN97-83) GN = G PE = 1 SV = 1 MEVKVENIRAIDMLKARVKNRVARSKCFKNASLILIGITTLSIA LNIYLIINYTIQKTSSESEHHTSSPPTESNKEASTISTDNPDIN PNSQHPTQQSTENPTLNPAASVSPSETEPASTPDTTNRLSSVDR STAQPSESRTKTKPTVHTRNNPSTASSTQSPPRATTKAIRRATT FRMSSTGKRPTTTSVQSDSSTTTQNHEETGSANPQASVSTMQN | 85 |
| Human parainfluenza virus (PV) F protein | >sp\|P12605\|FUS_PI1HC Fusion glycoprotein F0 OS = HUMAN parainfluenza 1 virus (strain C39) GN = F PE = 2 SV = 1 MQKSEILFLIYSSLLLSSSLCQIPVDKLSNVGVIINEGKLLKIA GSYESRYIVLSLVPSIDLEDGCGTTQIIQYKNLLNRLLIPLKDA LDLQESLITITNDTTVTNDNPQSRFFGAVIGTIALGVATAAQIT AGIALAEAREARKDIALIKDSIIKTHNSVELIQRGIGEQIIALK TLQDFVNNEIRPAIGELRCETTALKLGIKLTQHYSELATAFSSN LGTIGEKSLTLQALSSLYSANITEILSTIKKDKSDIYDIIYTEQ | 86 |

TABLE 3-continued

Non-Limiting List of Antigen Sequences

| Antigen | Amino Acid Sequence (UniPmot) | SEQ ID NO |
|---|---|---|
| | VKGTVIDVDLEKYMVTLLVKIPILSEIPGVLIYRASSISYNIEG EEWHVAIPNYIINKASSLGGADVTNCIESRLAYICPRDPTQLIP DNQQKCILGDVSKCPVTKVINNLVPKFAFINGGVVANCIASTCT CGTNRIPVNQDRSRGVTFLTYTNCGLIGINGIELYANKRGRDTT WGNQIIKVGPAVSIRPVDISLNLASATNFLEESKIELMKAKAII SAVGGWHNTESTQIIIIIIVCILIIIICGILYYLYRVRRLLVMI NSTHNSPVNTYTLESRMRPYIGNNSN | |
| Human parainfluenza virus HN protein | >sp\|P25466\|HN_PI2HT Hemagglutinin-neuraminidase OS = Human parainfluenza 2 virus (strain Toshiba) GN = HN PE = 2 SV = 1 MEDYSNLSLKSIPKRTCRIIFRTATILGICTLIVLCSSILHEII HLDVSSGLMDSDDSQQGIIQPIIESLKSLIALANQILYNVAIII PLKIDSIETVIFSALKDMHTGSMSNTNCTPGNLLLHDAAYINGI NKFLVLKSYNGTPKYGPLLNIPSFIPSATSPNGCTRIPSFSLIK THWCYTHNVMLGDCLDFTTSNQYLAMGIIQQSAAAFPIFRTMKT IYLSDGINRKSCSVTAIPGGCVLYCYVATRSEKEDYATTDLAEL RLAFYYYNDTFIERVISLPNTTGQWATINPAVGSGIYHLGFILF PVYGGLISGTPSYNKQSSRYFIPKHPNITCAGNSSEQAAAARSS YVIRYHSNRLIQSAVLICPLSDMHTARCNLVMFNNSQVMMGAEG RLYVIDNNLYYYQRSSSWWSASLFYRINTDFSKGIPPIIEAQWV PSYQVPRPGVMPCNATSFCPANCITGVYADVWPLNDPEPTSQNA LNPNYRFAGAFLRNESNRTNPTFYTASASALLNTTGFNNTNHKA AYTSSTCFKNTGTQKIYCLIIIEMGSSLLGEFQIIPPLRELIP | 87 |
| Malaria Pfs25 surface antigen | >sp\|P13829\|OS25_PLAFO 25 kDa ookinete surface antigen OS = Plasmodium falciparum (isolate NF54) PE = 1 SV = 1 MNKLYSLFLFLFIQLSIKYNNAKVTVDTVCKRGFLIQMSGHLEC KCENDLVLVNEETCEEKVLKCDEKTVNKPCGDFSKCIKIDGNPV SYACKCNLGYDMVNNVCIPNECKNVTCGNGKCILDTSNPVKTGV CSCNIGKVPNVQDQNKCSKDGETKCSLKCLKENETCKAVDGIYK CDCKDGFIIDNESSICTAFSAYNILNLSIMFILFSVCFFIM | 88 |
| serogroup B Neisseria meningitidis (MenB) fHbp | >tr\|Q6QCC2\|Q6QCC2_NEIME Factor H-binding protein OS = Neisseria meningitidis OX = 487 GN = gna1870 PE = 1 SV = 1 MNPTAFCCLSLTTALILTACSSGGGGVAADIGAGLADALTAPLD HKDKGLQSLTLDQSVRKNEKLKLAAQGAEKTYGNGDSLNTGKLK NDKVSPFDFIRQIEVDGQLITLESGEFQVYKQSHSALTAFQTEQ IQDSEHSGKMVAKRQFRIGDIAGEHTSFDKLPEGGRATYRGTAF GSDDAGGKLTYTIDFAAKQGNGKIEHLKSPELNVDLAAADIKPD GKRHAVISGSVLYNQAEKGSYSLGIFGGKAQEVAGSAEVKTVNG IRHIGLAAKQ | 98 |
| serogroup B Neisseria meningitidis (MenB) NadA | >tr\|X5F9B9\|X5F9B9_NEIME Quinolinate synthase A OS = Neisseria meningitidis OS = 487 GN = nadA2 PE = 3 SV = 1 MQTAARRSFDYDMPLIQTPTSACQIRQAWAKVADTPDRETAGRL KDEIKALLKETNAVLVAHYYVDPLIQDLALETGGCVGDSLEMAR FGAEHEAGTLVVAGVRFMGESAKILCPEKTVLMPDLEAECSLDL GCPEEAFSAFCDQHPDRTVVVYANTSAAVKARADWVTSSVALE IVSYLKSRGEKLIWGPDRHLGDYIRRETGADMLLWQGSCIVHNE FKGQELAALKAEHPDAVVLVHPESPQSVIELGDVVGSTSKLLKA AVSRPEKKFIVATDLGILHEMQKQAPDKQFIAAPTAGNGGSCKS CAFCPWMAMNSLGGIKYALTSGHNEILLDRKLGEAAKLPLQRML DFAAGLKRGDVFNGMGPA | 99 |
| serogroup B Neisseria meningitidis (MenB) NHBA | >tr\|Q9JPH1\|Q9JPH1_NEIME Gna2132 OS = Neisseria meningitidis OX = 487 GN = gna2132 PE = 4 SV = 1 MFKRSVIAMACIFALSACGGGGGGSPDVKSADTLSKPAAPVVSE KETEAKEDAPQAGSQGQGAPSAQGGQDMAAVSEENTGNGGAAAT DKPKNEDEGAQNDMPQNAADTDSLTPNHTPASNMPAGNMENQAP DAGESEQPANQPDMANTADGMQGDDPSAGGENAGNTAAQGTNQA ENNQTAGSQNPASSTNPSATNSGGDFGRTNVGNSVVIDGPSQNI TLTHCKGDSCSGNNFLDEEVQLKSEFEKLSDADKISNYKKDGKN DGKNDKFVGLVADSVQMKGINQYIIFYKPKPTSFARFRRSARSR RSLPAEMPLIPVNQADTLIVDGEAYSLTGHSGNIFAREGNYRYL TYGAEKLPGGSYALRVQGEPSKGEMLAGTAVYNGEVLHFHTENG RPSPSRGRFAAKVDFGSKSVDGIIDSGDGLHMGTQKFKAAIDGN GFKGTWTENGGGDVSGKFYGPAGEEVAGKYSYRPTDAEKGGFGV FAGKKEQD | 100 |

4. Assembly Domains and Linkers

In an embodiment, the nanostructure comprises a trimeric assembly. The trimeric assembly comprises a protein-protein interface that induces three copies of the first polypeptides to self-associate to form trimeric building blocks. Each copy of the first polypeptides further comprises a surface-exposed interface that interacts with a complementary surface-exposed interface on a second assembly domain. As described in King et al. (Nature 510, 103-108, 2014), Bale et al. (Science 353, 389-394, 2016), and patent publications WO2014124301 A1 and US20160122392 A1, the complementary protein-protein interface between the trimeric assembly domain and second assembly domain drives the assembly of multiple copies of the trimeric assembly domain and second assembly domain to a target nanostructure. In some embodiments, each copy of the trimeric assembly domains of the nanostructure bears an antigenic proteins, or antigenic fragment thereof, as a genetic fusion; these nanostructures display the proteins at full valency. In other embodiments, the nanostructures of the invention comprise one or more copies of trimeric assembly domains bearing antigens proteins, or antigenic fragments thereof as genetic fusions as well as one or more trimeric assembly domains that do not bear antigenic proteins as genetic fusions; these nanostructures display the F proteins at partial valency. The trimeric assembly domain can be any polypeptide sequence that forms a trimer and interacts with a second assembly domain to drive assembly to a target nanostructure. In some embodiments, the nanostructure comprises first and second polypeptides selected from those disclosed in US 20130274441 A1, US 2015/0356240 A1, US 2016/0122392 A1, WO 2018/187325 A1, each of which is incorporated by reference herein in its entirety.

In the nanostructures of the present disclosure, the antigenic protein and the core of the nanostructure may be genetically fused such that they are both present in a single polypeptide. Preferably, the linkage between the protein and the core of the nanostructure allows the protein, or antigenic fragment thereof, to be displayed on the exterior of the nanostructure. As such, the point of connection to the core of the nanostructure should be on the exterior of the core of the nanostructure formed. As will be understood by those of skill in the art, a wide variety of polypeptide sequences can be used to link the proteins, or antigenic fragments thereof and the core of the nanostructure. These polypeptide sequences are referred to as linkers. Any suitable linker can be used; there is no amino acid sequence requirement to serve as an appropriate linker. There is no requirement that the linker impose a rigid relative orientation of the protein or antigenic fragment thereof to the core of the nanostructure beyond enabling the protein or antigenic fragment thereof to be displayed on the exterior of the nanostructure. In some embodiments, the linker includes additional trimerization domains (e.g., the foldon domain of T4 fibritin) that assist in stabilizing the trimeric form of the F protein.

```
>4 fibritin foldon domain (optional in the linker
regiion)
                                      (SEQ ID NO: 89)
GYIPEAPRDGQAYVRKDGEWVLLSTFL
```

In some embodiments, the linker may comprise a Gly-Ser linker (i.e. a linker consisting of glycine and serine residues) of any suitable length. In some embodiments, the Gly-Ser linker may be 3, 4, 5, 6, 7, 8, 9, 10, 11, 12, 13, 14, 15, 16, 17, 18, 19, 20, or more amino acids in length. In some embodiments, the Gly-Ser linker may comprise or consist of the amino acid sequence of GSGGSGSGSGGSGSG, GGSGGSGS or GSGGSGSG.

5. Assembly of Nanostructures

In some embodiments, one or more purified samples of pluralities of the polypeptides for use in forming a nanostructure are mixed in an approximately equimolar molar ratio in aqueous conditions. The polypeptides interact with one another to drive assembly of the target nanostructure. Successful assembly of the target nanostructure can be confirmed by analyzing the in vitro assembly reaction by common biochemical or biophysical methods used to assess the physical size of proteins or protein assemblies, including but not limited to size exclusion chromatography, native (non-denaturing) gel electrophoresis, dynamic light scattering, multi-angle light scattering, analytical ultracentrifugation, negative stain electron microscopy, cryo-electron microscopy, or X-ray crystallography. If necessary, the assembled nanostructure can be purified from other species or molecules present in the in vitro assembly reaction using preparative techniques commonly used to isolate proteins by their physical size, including but not limited to size exclusion chromatography, preparative ultracentrifugation, tangential flow filtration, or preparative gel electrophoresis. The presence of the antigenic protein in the nanostructure can be assessed by techniques commonly used to determine the identity of protein molecules in aqueous solutions, including but not limited to SDS-PAGE, mass spectrometry, protein sequencing, or amino acid analysis. The accessibility of the protein on the exterior of the particle, as well as its conformation or antigenicity, can be assessed by techniques commonly used to detect the presence and conformation of an antigen, including but not limited to binding by monoclonal antibodies, conformation-specific monoclonal antibodies, or anti-sera specific to the antigen.

In other embodiments, the nanostructures of the invention comprise two or more distinct first polypeptides bearing different antigenic proteins as genetic fusions; these nanostructures co-display multiple different proteins on the same nanostructure. These multi-antigen nanostructures are produced by performing in vitro assembly with mixtures of first polypeptides in which each first polypeptide bears one of two or more distinct proteins as a genetic fusion. The fraction of each first polypeptide in the mixture determines the average valency of each antigenic protein in the resulting nanostructures. The presence and average valency of each protein-bearing first polypeptides in a given sample can be assessed by quantitative analysis using the techniques described above for evaluating the presence of antigenic proteins in full-valency nanostructures.

In various embodiments, the nanostructures are between about 20 nanometers (nm) to about 40 nm in diameter, with interior lumens between about 15 nm to about 32 nm across and pore sizes in the protein shells between about 1 nm to about 14 nm in their longest dimensions.

In one embodiment, the nanostructure has icosahedral symmetry. In this embodiment, the nanostructure may comprise 60 copies of a first polypeptide and 60 copies of a second polypeptide. In one such embodiment, the number of identical first polypeptides in each first assembly is different than the number of identical second polypeptides in each second assembly. For example, in one embodiment, the nanostructure comprises twelve first assemblies and twenty second assemblies; in this embodiment, each first assembly may, for example, comprise five copies of the identical first polypeptide, and each second assembly may, for example, comprise three copies of the identical second polypeptide. In another embodiment, the nanostructure comprises twelve first assemblies and thirty second assemblies; in this embodiment, each first assembly may, for example, comprise five copies of the identical first polypeptide, and each second assembly may, for example, comprise two copies of the identical second polypeptide. In a further embodiment, the nanostructure comprises twenty first assemblies and thirty second assemblies; in this embodiment, each first assembly may, for example, comprise three copies of the identical first polypeptide, and each second assembly may, for example, comprise two copies of the identical second polypeptide. All of these embodiments are capable of forming synthetic nanomaterials with regular icosahedral symmetry.

In various further embodiments, oligomeric states of the first and second polypeptides are as follows:
I53-34A: trimer+I53-34B: pentamer;
I53-40A: pentamer+I53-40B: trimer;
I53-47A: trimer+I53-47B: pentamer;
I53-50A: trimer+I53-50B: pentamer;
I53-51A: trimer+I53-51B: pentamer;
I32-06A: dimer+I32-06B: trimer;
I32-19A: trimer+I32-19B: dimer;
I32-28A: trimer+I32-28B: dimer;
I52-03A: pentamer+I52-03B: dimer:
I52-32A: dimer+I52-32B: pentamer: and
I52-33A: pentamer+I52-33B: dimer 6. Nucleic Acids In another aspect, the present disclosure provides isolated nucleic acids encoding a fusion protein of the present disclosure. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the disclosure.

In a further aspect, the present disclosure provides recombinant expression vectors comprising the isolated nucleic acid of any embodiment or combination of embodiments of the disclosure operatively linked a suitable control sequence. "Recombinant expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray. The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the disclosure is intended to include other expression vectors that serve equivalent functions, such as viral vectors.

In another aspect, the present disclosure provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, N.Y.). A method of producing a polypeptide according to the disclosure is an additional part of the disclosure. The method comprises the steps of (a) culturing a host according to this aspect of the disclosure under conditions conducive to the expression of the polypeptide, and (b) optionally, recovering the expressed polypeptide.

7. Vaccines and Administration

The disclosure also provides vaccines comprising the nanostructures described herein. Such compositions can be used to raise antibodies in a mammal (e.g. a human). The vaccines compositions of the disclosure typically include a pharmaceutically acceptable carrier, and a thorough discussion of such carriers is available in Remington: The Science and Practice of Pharmacy.

The pH of the composition is usually between about 4.5 to about 11, such as between about 5 to about 11, between about 5.5 to about 11, between about 6 to about 11, between about 5 to about 10.5, between about 5.5 to about 10.5, between about 6 to about 10.5, between about 5 to about 10, between about 5.5 to about 10, between about 6 to about 10, between about 5 to about 9.5, between about 5.5 to about 9.5, between about 6 to about 9.5, between about 5 to about 9, between about 5.5 to about 9, between about 6 to about 9, between about 5 to about 8.5, between about 5.5 to about 8.5, between about 6 to about 8.5, between about 5 to about 8, between about 5.5 to about 8, between about 6 to about 8, about 4.5, about 5, about 6.5, about 6, about 6.5, about 7, about 7.5, about 8, about 8.5, about 9, about 9.5, about 10, about 10.5, about 11, etc. Stable pH may be maintained by the use of a buffer e.g. a Tris buffer, a citrate buffer, phosphate buffer, or a histidine buffer. Thus a composition will generally include a buffer.

A composition may be sterile and/or pyrogen free. Compositions may be isotonic with respect to humans.

A vaccine composition comprises an immunologically effective amount of its antigen(s). An "immunologically effective amount" is an amount which, when administered to a subject, is effective for eliciting an antibody response against the antigen. This amount can vary depending upon the health and physical condition of the individual to be treated, their age, the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the disclosure will generally be expressed in terms of the mass of protein per dose. A dose of 10-500 µg (e.g. 50 µg) per antigen can be useful.

Vaccine compositions may include an immunological adjuvant. Exemplary adjuvants include the following: 1. mineral-containing compositions; 2. oil emulsions: 3. saponin formulations; 4. virosomes and virus-like particles; 5. bacterial or microbial derivatives; 6. bioadhesives and mucoadhesives; 7. liposomes; 8. polyoxyethylene ether and polyoxyethylene ester formulations: 9. polyphosphazene (pcpp); 10. muramyl peptides; 11. imidazoquinolone compounds: 12. thiosemicarbazone compounds; 13. tryptanthrin compounds; 14. human immunomodulators; 15. lipopeptides; 16. benzonaphthyridines; 17. microparticles; 18. immunostimulatory polynucleotide (such as ma or dna; e.g., cpg-containing oligonucleotides).

For example, the composition may include an aluminum salt adjuvant, an oil in water emulsion (e.g. an oil-in-water emulsion comprising squalene, such as MF59 or AS3), a TLR7 agonist (such as imidazoquinoline or imiquimod), or a combination thereof. Suitable aluminum salts include hydroxides (e.g. oxyhydroxides), phosphates (e.g. hydroxyphosphates, orthophosphates), (e.g. see chapters 8 & 9 of Vaccine Design . . . (1995) eds. Powell & Newman. ISBN: 030644867X. Plenum), or mixtures thereof. The salts can take any suitable form (e.g. gel, crystalline, amorphous, etc.), with adsorption of antigen to the salt being an example. The concentration of $Al^{+++}$ in a composition for administration to a patient may be less than 5 mg/ml e.g. <4 mg/ml, <3 mg/ml, <2 mg/ml, <1 mg/ml, etc. A preferred range is between 0.3 and 1 mg/ml. A maximum of 0.85 mg/dose is preferred. Aluminum hydroxide and aluminium phosphate adjuvants are suitable for use with the disclosure.

Exemplary adjuvants include, but are not limited to, Adju-Phos, Adjumerlm, albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL™, MPL-SE, MTP-PE, MTP-PE Liposomes, Murametide, Murapalmitine, NAGO, nCT native Cholera Toxin, Non-Ionic Surfactant Vesicles, non-toxic mutant E1 12K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochlcates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. Selection of an adjuvant depends on the subject to be treated. Preferably. a pharmaceutically acceptable adjuvant is used.

One suitable immunological adjuvant comprises a compound of Formula (I) as defined in WO2011/027222, or a pharmaceutically acceptable salt thereof, adsorbed to an aluminum salt. Many further adjuvants can be used, including any of those disclosed in Powell & Newman (1995).

Compositions may include an antimicrobial, particularly when packaged in multiple dose format. Antimicrobials such as thiomersal and 2-phenoxyethanol are commonly found in vaccines, but sometimes it may be desirable to use either a mercury-free preservative or no preservative at all.

Compositions may comprise detergent e.g. a polysorbate, such as polysorbate 80. Detergents are generally present at low levels e.g. <0.01%.

Compositions may include sodium salts (e.g. sodium chloride) to give tonicity. A concentration of 10±2 mg/ml NaCl is typical e.g. about 9 mg/ml.

In some embodiments, the buffer in the vaccine composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the composition additionally includes a stabilizer, e.g., a molecule which substantially prevents or reduces chemical and/or physical instability of the nanostructure, in lyophilized or liquid form. Exemplary stabilizers include sucrose, sorbitol, glycine, inositol, sodium chloride, methionine, arginine, and arginine hydrochloride.

In another aspect, the disclosure provides a method of inducing an immune response against an infectious agent, comprising administering to a subject in need thereof an immunologically effective amount of the immunogenic composition described herein, which comprises the nanostructure as described herein.

In certain embodiments, the immune response comprises the production of neutralizing antibodies against an infectious agent. In certain embodiments, the neutralizing antibodies are complement-independent.

The immune response can comprise a humoral immune response, a cell-mediated immune response, or both. In some embodiments an immune response is induced against each delivered antigenic protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies. Neutralizing antibodies block viral infection of cells. Viruses infect epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a virus of a strain other than the strain used in the composition.

A useful measure of antibody potency in the art is "50% neutralization titer." To determine 50% neutralizing titer, serum from immunized animals is diluted to assess how dilute serum can be yet retain the ability to block entry of 50% of viruses into cells. For example, a titer of 700 means that serum retained the ability to neutralize 50% of virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500. about 6000, about 6500, or about 7000. The 50% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 25000. "About" means plus or minus 10% of the recited value.

Compositions of the disclosure will generally be administered directly to a subject. Direct delivery may be accomplished by parenteral injection (e.g. subcutaneously, intraperitoneally, intravenously, intramuscularly, or to the interstitial space of a tissue), or by any other suitable route. For example, intramuscular administration may be used e.g. to the thigh or the upper arm. Injection may be via a needle (e.g. a hypodermic needle), but needle-free injection may alternatively be used. A typical intramuscular dosage volume is 0.5 ml.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The subject may be an animal, preferably a vertebrate, more preferably a mammal. Exemplary subject includes, e.g., a human, a cow, a pig, a chicken, a cat or a dog, as the infectious agents covered herein may be problematic across a wide range of species. Where the vaccine is for prophylactic use, the human is preferably a child (e.g., a toddler or infant), a teenager, or an adult: where the vaccine is for therapeutic use, the human is preferably a teenager or an adult. A vaccine intended for children may also be administered to adults, e.g., to assess safety, dosage, immunogenicity, etc.

Vaccines of the disclosure may be prophylactic (i.e. to prevent disease) or therapeutic (i.e. to reduce or eliminate the symptoms of a disease). The term prophylactic may be considered as reducing the severity of or preventing the onset of a particular condition. For the avoidance of doubt, the term prophylactic vaccine may also refer to vaccines that ameliorate the effects of a future infection, for example by reducing the severity or duration of such an infection.

Isolated and/or purified nanostructures described herein can be administered alone or as either prime or boost in mixed-modality regimes, such as a RNA prime followed by a protein boost. Benefits of the RNA-prime/protein-boost strategy, as compared to a protein-prime/protein-boost strategy, include, for example, increased antibody titers, a more balanced IgG1:IgG2a subtype profile, induction of TH1-type CD4+ T cell-mediated immune response that was similar to that of viral particles, and reduced production of non-neutralizing antibodies. The RNA prime can increase the immunogenicity of compositions regardless of whether they contain or do not contain an adjuvant.

In the RNA-prime/protein boost-strategy, the RNA and the protein are directed to the same target antigen. Examples of suitable modes of delivering RNAs include virus-like replicon particles (VRPs), alphavirus RNA, replicons encapsulated in lipid nanoparticles (LNPs) or formulated RNAs, such as replicons formulated with cationic nanoemulsions (CNEs). Suitable cationic oil-in-water nanoemulsions are disclosed in WO2012/006380 e.g. comprising an oil core (e.g. comprising squalene) and a cationic lipid (e.g. DOTAP, DMTAP, DSTAP, DC-cholesterol, etc.).

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion, or combinations thereof.

Also provided herein are kits for administration of nucleic acid (e.g., RNA), purified proteins, and purified nanostructures described herein, and instructions for use. The disclosure also provides a delivery device pre-filled with a composition or a vaccine disclosed herein.

The pharmaceutical compositions described herein can be administered in combination with one or more additional therapeutic agents. The additional therapeutic agents may include, but are not limited to antibiotics or antibacterial agents, antiemetic agents, antifungal agents, anti-inflammatory agents, antiviral agents. immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferon, ribavirin, hormones, and other toll-like receptor modulators, immunoglobulins (Igs), and antibodies modulating Ig function (such as anti-IgE (omalizumab)).

In certain embodiments, the compositions disclosed herein may be used as a medicament, e.g., for use in inducing or enhancing an immune response in a subject in need thereof, such as a mammal.

In certain embodiments, the compositions disclosed herein may be used in the manufacture of a medicament for inducing or enhancing an immune response in a subject in need thereof, such as a mammal.

One way of checking efficacy of therapeutic treatment involves monitoring infection by an infectious agent after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

8. Terminology

All publications and patents mentioned herein are hereby incorporated by reference in their entirety as if each individual publication or patent was specifically and individually indicated to be incorporated by reference. In case of conflict. the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique.* $_{2nd}$ Ed (RI. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

The section headings used herein are for organizational purposes only and are not to be construed as limiting the subject matter described.

Unless specifically defined otherwise, the following terms and phrases, which are common to the various embodiments disclosed herein, are defined as follows:

As used herein, the term protein refers to a protein or a glycoprotein.

As used herein, the term immunogenic refers to the ability of a specific protein, or a specific region thereof, to elicit an immune response to the specific protein, or to proteins comprising an amino acid sequence having a high degree of identity with the specific protein. According to the present disclosure, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical.

As used herein, an immune response to a vaccine, or nanostructure, of the present disclosure is the development in a subject of a humoral and/or a cellular immune response to an antigenic protein present in the vaccine. For purposes of the present disclosure, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (NIHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a hemagglutinin protein present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

As used herein the term "antibody" includes intact molecules as well as functional fragments thereof, such as Fab, F(ab')2, Fv, scFv, dsFv, or single domain molecules such as VH and VL that are capable of specifically binding to an epitope of an antigen. The term "antibody" encompasses B-cell receptors. The term "antibody" further encompasses camelid antibodies.

As used herein in describing viruses, neutralizing antibodies are antibodies that prevent virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of viral proteins, fusion of the viral membrane with the endosomal membrane, release of viral ribonucleoproteins into the cytoplasm, formation of new viral particles and budding of viral particles from the host cell membrane.

As used herein, broadly neutralizing antibodies are antibodies that neutralize more than one type, subtype and/or strain of bacteria, virus, or parasite. For example, broadly neutralizing antibodies elicited against an influenza HA protein from a Type A influenza virus may neutralize a Type B or Type C virus. As a further example, broadly neutralizing antibodies elicited against an influenza HA protein from Group I influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15 or H16.

With regard to antigens, it is understood by those skilled in the art that antigen proteins from different strains may have different lengths due to mutations (insertions, deletions) in the protein. Thus, reference to a corresponding region refers to a region of another proteins that is identical, or nearly so (e.g., at least 95%, identical, at least 98% identical or at least 99% identical), in sequence. structure and/or function to the region being compared. For example, with regard to an epitope of a protein, the corresponding region in a corresponding protein from a different strain of the organism may not have the same residue numbers, but will have a similar or nearly identical sequence and will perform the same function. To better clarify sequences comparisons between strains, numbering systems are used by those in the field, which relate amino acid positions to a reference sequence. Thus, corresponding amino acid residues in antigen proteins from different strains may not have the same residue number with respect to their distance from the N-terminal amino acid of the protein. e use of such numbering systems is understood by those skilled in the art.

According to the present disclosure, a trimerization domain is a series of amino acids that when joined (also referred to as fused) to a protein or peptide, allow the fusion protein to interact with other fusion proteins containing the trimerization domain, such that a trimeric structure is formed. Any known trimerization domain can be used in the present disclosure. Examples of trimerization domains include, but are not limited to, the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain.

As used herein, a variant refers to a protein, or nucleic acid molecule, the sequence of which is similar, but not identical to, a reference sequence. wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57). or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present disclosure can contain amino acid substitutions relative to the nanostructure antigen proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe: F), praline (Pro; P), serine (Ser; S), threonine (Thr; T), tryptophan (Trp; W), tyrosine (Tyr; Y), and valine (Val; V). As used herein, "about" means+/−5% of the recited parameter.

Naturally occurring residues may be divided into classes based on common side chain properties: 1) hydrophobic: Met, Ala, Val, Leu, lie: 2) neutral hydrophilic: Cys, Ser, Thr; 3) acidic: Asp, Glu: 4) basic: Asn, Gln, His, Lys, Arg; 5) residues that influence chain orientation: Gly, Pro; and 6) aromatic: Trp, Tyr, Phe. For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9): alanine (+1.8): glycine (−0.4); threonine (−0.7); serine (−0.8): tryptophan (−0.9); tyrosine (−1.3); proline (−1.6); histidine (−3.2); glutamate (−3.5): glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those within +1 are particularly preferred, and those within +0.5 are even more particularly preferred.

It is also understood in the art that the substitution of like amino acids can be made effectively on the basis of hydrophilicity, particularly where the biologically functionally equivalent protein or peptide thereby created is intended for use in immunological disclosure, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3): asparagine (+0.2); glutamine (+0.2): glycine (0); threonine (−0.4): proline (−0.5±1); alanine (−0.5): histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 4.

TABLE 4

Amino Acid Substitutions

| Original Amino Acid | Exemplar/Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Len, Val, Met, Ala |
| Leu | Ile, Val, Met, Ala |
| Lys | Ara, Gln, Asn |
| Met | Leu, Phe, Ile |
| Phe | Leu, Val, Ile, Ala, Tyr |
| Pro | Ala |

TABLE 4-continued

Amino Acid Substitutions

| Original Amino Acid | Exemplar/Substitutions |
|---|---|
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein's activity" refers to a decrease in the activity of a protein by at least 10%, at least 20%, at least 30%, at least 40% or at least 50%. With regard to the present disclosure, such an activity may be measured, for example, as the ability of a protein to elicit neutralizing antibodies against a virus. Such activity may be measured by measuring the titer of such antibodies against virus, or by measuring the number of types, subtypes or strains neutralized by the elicited antibodies. Methods of determining antibody titers and methods of performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up a polypeptide, and the amino acid sequences of antigen proteins are not normally found joined together via a peptide bond.

The terms individual, subject, and patient are well-recognized in the art, and are herein used interchangeably to refer to any human or other animal susceptible to infection. Examples include, but are not limited to, humans and other primates, including non-human primates such as chimpanzees and other apes and monkey species; farm animals such as cattle, sheep, pigs, seals, goats and horses: domestic mammals such as dogs and cats; laboratory animals including rodents such as mice, rats and guinea pigs, birds, including domestic. wild and game birds such as chickens. turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present disclosure can be applied to any race, including, for example, Caucasian (white), African-American (black), Native American, Native Hawaiian, Hispanic, Latino, Asian, and European.

As used herein, a vaccinated subject is a subject that has been administered a vaccine that is intended to provide a protective effect against a bacteria, virus, or parasite.

As used herein, the terms exposed, exposure, and the like, indicate the subject has come in contact with a person of animal that is known to be infected with a bacteria, virus, or parasite.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed. In addition, all sub-combinations are also specifically embraced by the present disclosure and are disclosed herein just as if each and every such sub-combination was individually and explicitly disclosed herein.

The disclosure is further described in the following Examples, which do not limit the scope of the disclosure described in the claims.

9. Examples

9.1. Example 1: Respiratory Syncytial Virus (RSV)

9.1.1. Sequences

In embodiments of the present disclosure, RSV F protein is present as a fusion protein with the first polypeptide and a linker is used, the F protein-linker sequence may comprise the following:

```
>DS-Cav1-foldon
                                              (SEQ ID NO: 90)
(MELLILKANAITTILTAVTFCFASG)QNITEEFYQSTCSAVSKGYLSALR
TGWYTSVITIELSNIKENKCNGTDAKVKLIKQELDKYKNAVTELQLLMQST
PATNNRARRELPRFMNYTLNNAKKTNVTLSKKRKRRFLGFLLGVGSAIASG
VAVCKVHLHLEGEVNKIKSALLSTNKAVVSLSNGVSVLTFKVLDLKNYIDK
QLLPILNKQSCSISNIETVIEFQQKNNRLLEITREFSVNAGVTTPVSTYML
TNSELISLINDMPITNDQKKIMSNNVQIVRQQSYSIMCIIKEEVLAYVVQL
PINGVIDTPCWKLHTSPLCTTNTKEGSNICLTRTDRGWYCDNAGSVSFFPQ
AETCKVQSNRVFCDTMNSLTLPSEVNLCNVDIFNPKYDCKIMTSKTDVSSS
VITSLGAIVSCYGKTKCTASNKNRGIIKTFSNGCDYVSNKGVDTVSVGNTL
YYVNKQEGKSLYVKGEPIINFYDPLVFPSDEFDASISQVNEKINQSLAFIR
(KSDELL)GYIPEAPRDGQAYVRKDGEWVLLSTFL
```

In various further embodiments, the first polypeptides comprise or consist of first polypeptides having a sequence selected from the following (optional residues in parentheses):

```
>DS-Cav1-foldon-T33-31A
                                              (SEQ ID NO: 91)
(MELLILKANVIATILTAVTFCFASS)QNITEEFYQSTCSAVSKGYLSALRTGWYTSVITI
ELSNIKENKCNGTDAKVKLIKQELDKYKNAVTELQLLMQSTPATNNRARRELPRFM
NYTLNNAKKTNVTLSKKRKRRFLGFLLGVGSAIASGVAVCKVHLHLEGEVNKIKSALL
STNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIM
CIIKEEVLAYVVQLPLYGVIDTPCWKLHTSPLCTTNTKEGSNICLTRTDRGWYCDNA
GSVSFFPQAETCKVQSNRVFCDTMNSLTLPSEVNLCNVDIFNPKYDCKIMTSKTDVSS
SVITSLGAIVSCYGKTKCTASNKNRGIIKTFSNGCDYVSNKGVDTVSVGNTLYYVNK
QEGKSLYVKGEPIINFYDPLVFPSDEFDASISQVNEKINQSLAFIR(KSDELL)GYIPEAP
RDGQAYVRKDGEWVLLSTFLGGSMEEVVLITVPSALVAVKIAHALVEERLAACVNI
VPGLTSIYREEGSVVSDHELLLLVKTTTDAFPKLKERVKELHPYEVPEIVALPIAEGNR
EYLDWLRENTG >DS-Cav1-T33-31A
                                              (SEQ ID NO: 92)
(MELLILKANVIATILTAVTFCFASS)QNITEEFYQSTCSAVSKGYLSALRTGWYTSVITI
ELSNIKENKCNGTDAKVKLIKQELDKYKNAVTELQLLMQSTPATNNRARRELPRFM
NYTLNNAKKTNVTLSKKRKRRFLGFLLGVGSAIASGVAVCKVHLHLEGEVNKIKSALL
STNKAVVSLSNGVSVLTFKVLDLKNYIDKQLLPILNKQSCSISNIETVIEFQQKNNRLL
```

EITREFSVNAGVTTPVSTYMLTNSELLSLINDMPITNDQKKLMSNNVQIVRQQSYSIM
CIIKEEVLAYVVQLPLYGVIDTPCWKLHTSPLCTTNTKEGSNICLTRTDRGWYCDNA
GSVSFFPQAETCKVQSNRVFCDTMNSLTLPSEVNLCNVDIFNPKYDCKIMTSKTDVSS
SVITSLGAIVSCYGKTKCTASNKNRGIIKTFSNGCDYVSNKGVDTVSVGNTLYYVNK
QEGKSLYVKGEPIINFYDPLVFPPSDEFDASISQVNEKINQSLAFIR(KSDELL)GGSMEE
VVLITVPSALVAVKIAIIALVEERLAACVNIVPGLTSFYREEGSVVSDFIELLELNKTII
DAFPKLKERVKELHPYEVPEIVALPIAEGNREYLDWLRENTG

>DS-Cav1-foldon-T33-15B (SEQ ID NO: 93)
(MELLILKANVIATILTAVTFCFASS)QNITEEFYQSTCSAVSKGYLSALRTGWYTSVITI
ELSNIKENKCNGTDAKVKLIKQELDKYKNAVTELQLLMQSTPATNNRARRELPRFM
NYTENNAKKTNVTLSKKRKRRFLGFLLGVGSAIASGVAVCKVLHLEGEVNKIKSALL
STNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIM
CIIKEEVLAYVVQLPLYGVIDTPCWKLHTSPLCTTNTKEGSNICLTRTDRGWYCDNA
GSVSFFPQAETCKVQSNRVFCDTMNSLTLPSEVNLCNVDIFNPKYDCKIMTSKTDVSS
SVITSLGAIVSCYGKTKCTASNKNRGIIKTFSNGCDYVSNKGVDTVSVGNTLYYVNK
QEGKSLYVKGEPIINFYDPLVFPPSDEFDASISQVNEKINQSLAFIR(KSDELL)GYIPEAP
RDGQAYVRKDGEWYLLSTFLGGSMVRGIRGAITVNSDTPTSIIIATILLLEKMLEANGI
QSYEELAAVIFTVTEDLTSAFPAEAARQIGMHRVPLLSAREVPVPGSLPRVIRVLALW
NTDTPQDRVRHVYLSEAVRLRPDLESAQ >DS-Cav1-T33-15B (SEQ ID NO: 94)
(MELLILKANVIATILTAVTFCFASS)QNITEEFYQSTCSAVSKGYLSALRTGWYTSVITI
ELSNIKENKCNGTDAKVKLIKQELDKYKNAVTELQLLMQSTPATNNRARRELPRFM
NYTLNNAKKTNVTLSKKRKRRFLGFLLGVGSAIASGVAVCKVLHLEGEVNKIKSALL
STNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQPIRQQSYSIM
CIIKEEVLAYVVQLPLYGVIDTPCWKLHTSPLCTTNTKEGSNICLTRTDRGWYCDNA
GSVSFFPQAETCKVQSNRVFCDTMNSLTLPSEVNLCNVDIFNPKYDCKIMTSKTDVSS
SVITSLGAIVSCYGKTKCTASNKNRGIIKTFSNGCDYVSNKGVDTVSVGNTLYYVNK
QEGKSLYVKGEPIINFYDPLVFPPSDEFDASISQVNEKINQSLAFIR(KSDELL)GGSMVR
GIRGAITVNSDTPTSIIIATILLLEKMLEANGIQSYEELAAVIFTVTEDLTSAFPAEAARQ
IGMHRVPLLSAREVPVPGSLPRVIRVLALWNTDTPQDRVRHVYLSEAVRLRPDLESA
Q >DS-Cav1-foldon-I53-50A (SEQ ID NO: 95)
(MELLILKANAITTILTAVTFCFASG)QNITEEFYQSTCSAVSKGYLSALRIGWYTSVIT
IELSNIKENKCNGTDAKVKLIKQELDKYKNAVTELQLLMQSTPATNNRARRELPRFM
NYTLNNAKKTNVTLSKKRKRRFLGFLLGVGSAIASGVAVCKVLHLEGEVNKIKSALL
STNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIM
CIIKEEVLAYVVQLPLYGVIDTPCWKLHTSPLCTTNTKEGSNICLTRTDRGWYCDNA
GSVSFFPQAETCKVQSNRVFCDTMNSLTLPSEVNLCNVDIFNPKYDCKIMTSKTDVSS -continued

SVITSLGAIVSCYGKTKCTASNKNRGIIKTFSNGCDYVSNKGVDTVSVGNTLYYVNK

QEGKSLYVKGEPIINFYDPLVFPSDEFDASISQVNEKINQSLAFIRGYIPEAPRDGQAY

VRKDGEWVLLSTFLGSGSHHHHHHHGGSGGSGSEKAAKAEEAARKMEELFKKHK

IVAVLRANSVEEAIEKAVAVFAGGVHLIEITFTVPDADTVIKALSVLKEKGAIIGAGTV

TSVEQCRKAVESGAEFIVSPHLDEEISQFCKEKGVFYMPGVMTPTELVKAMKLGHTI

LKLFPGEVVGPQFVKAMKGPFPNVKFVPTGGVNLDNVCEWFKAGVLAVGVGSALV

KGTPDEVREKAKAFVEKIRGCTE

>DS-Cav1-I53-50A                                              (SEQ ID NO: 96)
(MELLILKANVIATILTAVTFCFASS)QNITEEFFYQSTCSAVSKGYLSALRTGWYTSVITI

ELSNIKENKCNGTDAKVKLIKQELDKYKNAVTELQLLMQSTPATNNRARRELPRFM

NYTLNNAKKTNVTLSKKRKRRFLGFLLGVGSAIASGVAVCKVLHLEGEVNKIKSALL

STNKAVVSLSNGIVSVLTFKVLDLKNYIDKQLLPILNKQSCSISNIETVIEFQQKNNRLL

EITREFSVNAGVTTPVSTYMLTNSELLSLINDMPITNDQKKLMSNNVQIVRQQSYSIM

CIIKEEVLAYVVQLPLYGVIDTPCWKLHTSPLCTTNTKEGSNICLTRTDRGWYCDNA

GSVSFFPQAETCKVQSNRVFCDTMNSLTLPSEVNLCNVDIFNPKYDCKIMTSKTDVSS

SVITSLGAIVSCYGKTKCTASNKNRGIIKTFSNGCDYVSNKGVDTVSVGNTLYYYNK

QEGKSLYVKGEPIINFYDPLVFPSDEFDASISQVNEKINQSLAFIRGGSGGSGSEKAAK

AEEAARKMEELFKKHKIVAVLRANSVEEAIEKAVAVFAGGVHLIEITFTVPDADTVIK

ALSVLKEKGAIIGAGTVTSVEQCRKAVESGAEFIVSPHLDEEISQFCKEKGVFYMPGV

MTPTELVKAMKLGHTILKLFPGEVVGPQFVKAMKGPFPNVKFVPTGGVNLDNVCE

WFKAGVLAVGVGSALVKGTPDEVREKAKAFVEKIRGCTE

>DS-Cav1-I32-28A                                              (SEQ ID NO: 97)
(MELLILKANAITTILTAVTFCFASG)QNITEEFYQSTCSAVSKGYLSALRTGWYTSVIT

IELSNIKENKCNGTDAKVKLIKQELDKYKNAVTELQLLMQSTPATNNRARRELPRFM

NYTLNNAKKTNVTLSKKRKRRFLGFLLGVGSAIASGVAVCKVLHLEGEVNKIKSALL

STNKAVVSLSNGVSVLTFKVLDLKNYIDKQLLPILNKQSCSISNIETVIEFQQKNNRLL

EITREFSVNAGVTTPVSTYMLTNSELLSLINDMPITNDQKKLMSNNVQIVRQQSYSIM

CIIKEEVLAYVVQLPLYGVIDTPCWKLHTSPLCTTNTKEGSNICLTRTDRGWYCDNA

GSVSFFPQAETCKVQSNRVFCDTMNSLTLPSEVNLCNVDIFNPKYDCKIMTSKTDVSS

SVITSLGAIVSCYGKTKCTASNKNRGIIKTFSNGCDYVSNKGVDTVSVIGNTLYYVNK

QEGKSLYVKGEKIINFYDPVFPSDEFDASISQVNEKINQSLAFIR(KSDELL)GGSGGS

GSDDARIAAIGDVDELNSQIGVLLAEPLPDDVRAALSAIQHDLFDLGGELCIPHAAIT

EDHLLRLALWLVHYNGQLPPLEEFILPGGARGAALAHVCRTVCRRAERSIKALGASE

PLNIAPAAYVNLLSDLLFVLARVLNRAAGGADVLWDRTRAH

>DS-Cav1-Tr-foldon-T33-31A                                   (SEQ ID NO: 101)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAXVVQLPLYGVIDTPC

```
WKLHTSPLCTTNTKEGSNICLTRTDRGWYCDNAGSVSFFPQAETCKVQSNRVFCDT

MNSLTLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPLVFPS

DEFDASISQVNEKINQSLAFIRGYIPEAPRDGQAYVRKDGEWLLSTFLGGSMEEVVL

ITVPSALVAVKIAHALVEERLAACVNIVPGLTSIYREEGSVVSDHELLLLVKTTTDAFP

KLKERVKELHPYEVPEIVALPIAEGNREYLDWLRENTG

>DS-Cav1-Tr-T33-31A
                                                    (SEQ ID NO: 102)
QNITEEFYQSTCSAVSKGYISALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSINKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLYGVIDTPC

WKLHTSPLCTTNTKEGSNICLTRTDRGWYCDNAGSVSFFPQAETCKVQSNRVFCDT

MNSLTLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPLVFPS

DEFDASISQVNEKINQSLAFIRGGSMEENVVLITVPSALVAVKIAHALVEERLAACVNIV

PGLTSIYREEGSVVSDHELLLLVKTTTDAFPKLKERVKMELHPYEAVPEIVALPIAEGNRE

YLDWLRENTG

>DS-Cav1-Tr-foldon-T33-15B
                                                    (SEQ ID NO: 103)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLYGVIDTPC

WKLETSPLCTTNTKEGSNICLTRTDRGWYCDNAGSVSFFPQAETCKVQSNRVFCDT

MNSLFLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPLVFPS

DEFDASISQVNEKINQSLAFIRGYIPEAPRDGQAYVRKDGEWVLLSTFLGGSMVRGIR

GAITVNSDTPTSIIIATILLLEKMLEANGIQSYEELAAVIFTVTEDLTSAFTAEAARQIG

MHRVPLLSAREVPVPGSLPRVIRVLALWNTDTPQDRVRHVYLSEAVRLRPDLESAQ

>DS-Cav1-Tr-T33-15B
                                                    (SEQ ID NO: 104)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLYGVIDTPC

WKLHTSPLCTTNTKEGSNICLTRTDRGWYCDNAGSVSFFPQAETCKVQSNRVECDT

MNSULTLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPLVFPS
```

-continued

```
DEFDASISQVNEKINQSLAFIRGGSMVRGIRGAITVNSDTPTSIIIATILLLEKMLEANGI

QSYEELAAVIFTVTEDLTSAFPAEAARQIGMHRVPLLSAREVPVPGSLPRVIRVLALW

NTDTPQDRVRHVYLSEAVRLRPDLESAQ

>DS-Cav1-Tr-foldon-I53-50A
                                                  (SEQ ID NO: 105)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVTRQQSYSIMCIIKEEVLAYVVQLPLYGVIDTPC

WKLHTSPLCTTNTKEGSNICLTRTDRGWYCDNAGSVSFFPQAETCKVQSNRVFCDT

MNSLTLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPLNFPS

DEFDASISQVNEKINQSLAFIRGYIPEAPRDGQAYVRKDGEWVLLSTFLGSGSHHHHH

HHHGGSGGSGSEKAAKAEEAARKMEELFKKHKIVAVIRANSVEEAIEKAVAVFAGG

VHLIEITFTVPDADTVIKALSVLKEKGAIIGAGTVTSVEQCRKAVESGAEFIVSPHLDE

EISQFCKEKGVFYMPGVMTPTELVKAMKLGHTILKLFPGEVVGPQFVKAMKGPFPN

VKFVPTGGVNLDNVCEWFKAGVLAVGVGSALVKGTPDEVREKAKAFVEKIRGCTE

>DS-Cav1-Tr-I53-50A
                                                  (SEQ ID NO: 106)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLYGVIDTPC

WKLHTSPLCTTNTKEGSNICLTRTDRGWYCDNAGSVSFFPQAETCKVQSNRVFCDT

MNSLTLPSEVNLCNVDIFNPKYDCKIMTSKTDVSSSNIVITSLGAIVSCYGKTKCTASNK

NRGIIKTFSNGCDYVSNKGVDTVSVGNTLYYVNKQEGKSLYVKGEPIINFYDPLVFPS

DEFDASISQVNEKINQSLAFIRGGSGGSGSEKAAKAEEAARKMEELFKKHKIVAVLR

ANSVEEAIEKAVAVFAGGVHLIEITFTVPDADTVIKALSVLKEKGAIIGAGTVTSVEQ

CRKAVESGAEFIVSPHLDEEISQFCKEKGVFYMGVMTPTELVKAMKLGHTILKLFP

GEVVGPQFVKAMKGPFPNVKFVPTGGVNLDNVCEWFKAGVLAVGVGSALVKGTP

DEVREKAKAFVEKIRGCTE

>DS-Cav1-Tr-I32-28A
                                                  (SEQ ID NO: 107)
QNITEEFYQSTCSAVSKGYLSALRTGWYTSVITIELSNIKENKCNGTDAKVKLIKQEL

DKYKNAVTELQLLMQSTPATNNRARRELPRFMNYTLNNAKKTNVTLSKKRKRRFL

GFLLGVGSAIASGVAVCKVLHLEGEVNKIKSALLSTNKAVVSLSNGVSVLTFKVLDL

KNYIDKQLLPILNKQSCSISNIETVIEFQQKNNRLLEITREFSVNAGVTTPVSTYMLTNS

ELLSLINDMPITNDQKKLMSNNVQIVRQQSYSIMCIIKEEVLAYVVQLPLYGVIDTPC

WKLHTSPLCTTNTKEGSNICLTRTDRGWYCDNAGSVSFFPQAETCKVQSNRVFCDT

MNSLTLPSEVNLCNVDIFNPKYDCKIMTSKTDVSSSVITSLGAIVSCYGKTKCTASNK

NRGIIKTFSNGCDYVSNKGVDTVSVGNTLYYVNKQEGKSLYVKGEPIINFYDPINFPS
```

-continued

```
DEFDASISQVNEKINQSLAFIRGGSGGSGSDDARIAAIGDVDELNSQIGVLLAEPLPDD

VRAALSAIQHDLFDLGGELCIPGHAAITEDHLLRLALWLVHYNGQLPPLEEFILPGGA

RGAALAHVCRTVCRRAERSIKALGASEPLNIAPAAYVNLLSDLLFVLARVLNRAAGG

ADVLWDRTRAH
```

9.1.2. Methods

Expression and Screening of Trimeric Building Blocks Comprising an F Protein and a Trimeric Assembly Domain.

Human codon-optimized sequences for trimeric building blocks including and lacking DS-Cav1 fusions were ordered from Genscript. Building blocks for single-component nanostructures (i.e., 13-01) were cloned into the pcDNA3.1 vector (ThermoFisher Scientific) containing one CMV promoter, while building blocks for two-component nanostructures (e.g., I53-50) were cloned into the pBudCE4.1 vector (ThermoFisher Scientific) containing both CMV and EF-1α promoters. Recombinant proteins were expressed by transient transfection of Expi293F cells (ThermoFisher Scientific) using polyethylenimine (PEI). Cell cultures were harvested five days post-transfection by centrifugation. Secreted proteins were analysed by ELISA, using either direct coating of the cell supernatants or by sandwich ELISA. Briefly, 96-well MaxiSorp plates (Nunc) were coated with cell supernatant for direct ELISA or murine anti-His tag monoclonal antibody (ThermoFisher Scientific) for sandwich ELISA. Secreted proteins were detected using the human Palivizumab, MPE8, RSD5, and D25 monoclonal antibodies. Transfected Expi293F cells were fixed and permeabilized with BD cytofix/cytoperm (BD Biosciences), incubated with human Palivizumab. MPE8, and D25 monoclonal antibodies, and stained with Alexa Fluor 647-conjugated anti-human IgG antibody (Jackson ImmunoResearch). Stained cells were counted with a FACS Fortessa flow cytometer (BD Biosciences). Analysis was performed with FlowJo software. Cell lines were routinely tested for *Mycoplasma* contamination.

Expression and Purification of DS-Cav1-I53-50A

Lentivirus was produced by transient transfection of 293T (ATCC) cells using linear 25-kDa polyethyleneimine (PEI; Polysciences). Briefly, $4\times10^6$ cells were plated onto 10 cm tissue culture plates. After 24 h, 3 μg of psPAX2, 1.5 μg of pMD2G (Addgene plasmid #12260 and #12259, respectively) and 6 μg of lentiviral vector plasmid were mixed in 500 pi diluent (5 mM HEPES, 150 mM NaCl, pH=7.05) and 42 μl of PEI (1 mg/ml) and incubated for 15 min. The DNA/PEI complex was then added to the plate drop-wise. Lentivirus was harvested 48 h post-transfection and concentrated 100-fold by low-speed centrifugation at 8000 g for 18 h. Transduction of the target cell line was carried out in 125 mL shake flasks containing $10\times10^6$ cells in 10 mL of growth media. 100 uL of 100× lentivirus was added to the flask and the cells were incubated with shaking (225 rpm) at 37° C., in 8% $CO_2$ for 4-6 h. 20 mL of growth media was added to the shake flask after 4-6 h.

Transduced cells were expanded every other day to a density of $1\times10^6$ cells/ml until a final culture size of 4 L was reached. The media was harvested after 17 days of total incubation after measuring final cell concentration (~$5\times10^6$ cells/mL) and viability (~90% viable). Culture supernatant was harvested by low-speed centrifugation to remove cells from the supernatant. NaCl and $NaN_3$ were added to final concentrations of 250 mM and 0.02%, respectively. The supernatant was loaded over one 5 mL HisTrap FF Crude column (GE Healthsciences) at 5 ml/min by an AKTA Pure (GE Healthsciences). The nickel elution was applied to a HiLoad 16/600 Superdex 200 μg column (GE Healthsciences) to further purify the target protein by size-exclusion chromatography. The size-exclusion purified target protein was snap frozen in liquid nitrogen and stored at −80° C.

In Vitro Assembly of DS-Cav1-Bearing Nanostructures

100% valency particles (20 DS-Cav1 trimers per icosahedral nanostructure) were prepared by mixing DS-Cav1-foldon-I53-50A trimers and I53-50B.4PT1 pentamers at 50 μM each and incubating with rocking overnight at 4° C. In some cases, assembled nanostructures were purified from excess components remaining in the in vitro assembly reaction using a GE Sephacryl S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin 20 30 kDa MWCO centrifugal filter, and quantified using an Agilent 8454 spectrophotometer.

66% valency particles (~14 DS-Cav1 trimers per icosahedral nanostructure) were prepared by mixing DS-Cav1-foldon-I53-50A trimers, I53-50A trimers, and I53-50B.4PosT1 pentamers at 50, 25, and 75 μM, respectively. 33% valency particles (−7 DS-Cav1 trimers per icosahedral nanostructure) were prepared by mixing DS-Cav1-foldon-I53-50A trimers, I53-50A trimers, and I53-50B.4PosT1 pentamers at 25, 50, and 75 M, respectively. The in vitro assembly reactions were allowed to incubate with rocking overnight at 4° C. In some cases, assembled nanostructures were purified from excess components remaining in the in vitro assembly reaction using a GE Sephacryl S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin 20 30 kDa MWCO centrifugal filter, and quantified using an Agilent 8454 spectrophotometer after centrifuging at ~21,000 g for 10 minutes at 4° C. Samples were then transferred to cryogenic tubes in 1 mL aliquots at 1.1 mg/mL for the 33% valency particles and 0.6 mg/mL for the 66% valency particles, flash frozen in liquid nitrogen, and stored at −80° C.

Electron Microscopy of DS-Cav1-Bearing Nanostructures

Samples were prepared for negative stain EM by diluting to 0.01 mg/mL using 25 mM Tris pH 8, 250 mM NaCl, 5% glycerol and 3.5 μL was incubated on a glow-discharged, copper, carbon-coated grid for 20 seconds before blotting away the liquid with a piece of Whatman No. 1 filter paper. Within seconds of blotting away the sample, a 3.5 μL droplet of stain (2% w/v uranyl formate) was deposited and blotted away immediately, and then a second cycle of staining/blotting was performed.

Circular Dichroism (CD) Spectropolarimetry

CD spectra from F proteins (0.5 mg $ml^{-1}$) were recorded on a Chirascan spectropolarimeter (Applied Photophysics)

over the wavelength range of 195 to 260 nm at a bandwidth of 1 nm, step size of 0.5 nm, and 1 s per step. The spectra in the far-ultraviolet region required an average of three scans and were subtracted from blank spectra performed with buffer. Thermal denaturation was monitored by performing scans at intervals of 1° C., after equilibration for 1 min at each temperature. Data were fitted to a simple first order curve. The values of ΔA222 are represented on the y axis as the percentage of the values recorded at 20° C.

Enzyme-Linked Immunosorbent Assay (ELISA)

To test specific binding of antibody or sera, 96-well MaxiSorp plates (Nunc) were coated with serial dilutions of tissue culture supernatants from cells expressing trimeric building blocks comprising F proteins and a trimeric assembly domain or 2 μg ml$^{-1}$ of the following purified proteins: Ds-Cav1 with foldon, Ds-Cav1 fused to a trimeric first polypeptide or DS-Cav1-displaying nanostructures. Plates were blocked with 1% bovine serum albumin (BSA) and incubated with titrated antibodies (D25, MPE8, Palivizumab, RSD5) or murine sera followed by AP-conjugated goat anti-human IgG (Southern Biotech, 2040-04) or goat anti-mouse IgG (Southern Biotech, 1030-04). Plates were then washed with PBS buffer (Gibco, Invitrogen), 0.05% Tween-20 and substrate (p-NPP, Sigma) was added and plates were read at 405 nm.

Surface Plasmon Resonance (SPR)

The experiments were carried out at 25° C. on a ProteON XPR-36 instrument (Bio-Rad Laboratories) in a PBS buffer (Gibco, Invitrogen), 0.05% Tween-20. The D25 mAb was immobilized on a GLM sensor chip surface through amine coupling at 1000 response units (RU) and a blank surface with no protein was created under identical coupling conditions for use as a reference. Monoclonal antibodies (D25, MPE8, Palivizumab and 131-2a) were injected at a flow rate of 100 μl/min, at concentrations of 50 nM in different sensor channels. The data were processed using Proteon software and double referenced by subtraction of the blank surface and buffer only injection before local fitting of the data.

Vaccination and Serological Analysis

Female BALB/c mice 6-9 wk of age were obtained from Harlan Laboratories Inc. All procedures were performed in accordance with guidelines of the Swiss Federal Veterinary Office and after obtaining local ethical approval. Mice were immunized i.p. with 100 μL of immunogen formulation on day 0, 14, and 28. Priming infection at day 0 was performed with the Murine TLR9 ligand agonist (ODN 1668, Invivo-Gen). Mice were bled on day 10, 20 and 40, and antigen- and site-specific IgG titers were measured in the serum by ELISA. Neutralizing titers were also determined on HEp-2 cell as described below.

Virus Neutralization Assay and Microscopy Analysis

Confluent layers of HEp-2 cells in 96-well flat-bottom plates were infected with a fixed amount of Human Respiratory Syncytial Virus with Green Fluorescent Protein (RSV strain A2, Vira Tree #R121) at MOI of 1. 48 hours postinfection the cells were stained with Hoechst (Sigma #H6024) and images were acquired on BD Pathway bioimaging system. Percentage of the infected cells was automatically calculated by BD AttoVision software. The number of infected cells was plotted as dose response curves by plotting the relative infected cells against the antibodies dilutions.

Stability of DS-Cav1-Bearing Nanostructures

Physical stability of the prefusion conformation of designed DS-Cav1-foldon-I53-50 was assessed by incubating protein at various concentrations in a PCR cycler with heated lid at 80° C. for 1 h. Residual prefusion conformation was evaluated by direct coating of the protein and ELISA with the prefusion-specific antibody D25.

Statistical Analysis

No statistical methods were used to predetermine sample size. Data were analyzed with Prism 6 (GraphPad Software) using the two-tailed non-parametric Mann-Whitney U test for two groups' comparison, or Kruskall-Wallis test (and Dunn's posttest) when three or more groups were compared.

9.1.3. Results

Trimeric Building Blocks Comprising an F Protein and a Trimeric Assembly Domain

Several trimeric building blocks, each comprising an F protein genetically fused to a trimeric assembly domain, were found to be secreted from HEK293F cells with their F proteins in a well-folded, prefusion conformation as judged by prefusion-specific monoclonal antibody binding in ELISA assays. FIG. 2 shows an example of ELISA data analyzing the supernatant of HEK293F cells expressing DS-Cav1-foldon, DS-Cav1-foldon-T33-31A, and DS-Cav1-T33-31A. Several other trimeric building blocks yielded detectable secretion of well-folded, prefusion F proteins.

Expression and Purification of DS-Cav1-Foldon-I53-50A

Figure 3:
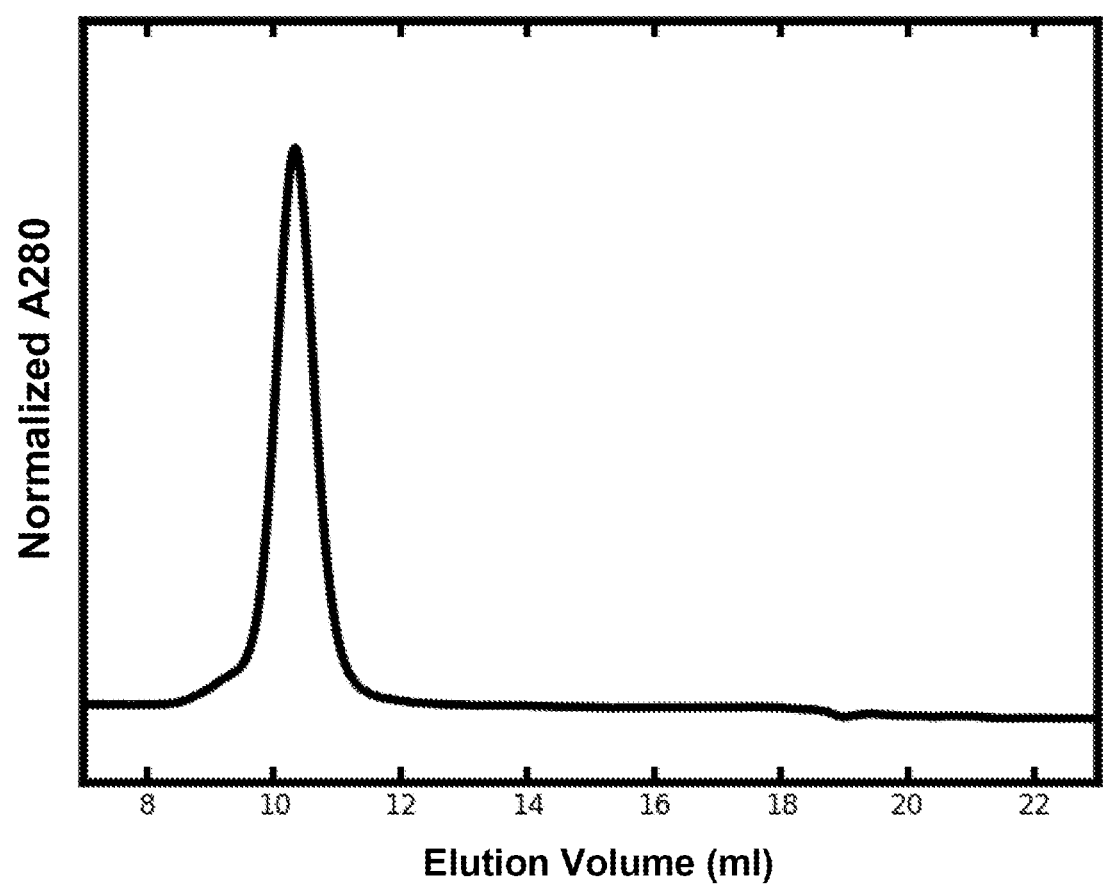
FIG. 3 shows size-exclusion chromatography of DS-Cav1-I53-50A. Protein purified from tissue culture supernatants by immobilized metal affinity chromatography was applied to a Superose 6 10/300 GL size exclusion column. The protein eluted as a single, monodisperse species.

A lentiviral vector encoding DS-Cav1-foldon-I53-50A was used to transduce HEK293F cells for large-scale expression. The secreted protein was purified from tissue culture supernatants by immobilized metal affinity chromatography and size exclusion chromatography. Size exclusion chromatograms (FIG. 3) indicated that the purified protein formed a single, monodisperse species.

Expression and Purification of I53-50B.4PT1

I53-50B.4PT, a pentameric protein comprising a second assembly domain that interacts with the trimeric assembly domain in I53-50A or DS-Cav1-foldon-I53-50A to drive assembly of icosahedral I53-50-based nanostructures, was expressed and purified as described in Bale et al. and patent publication US20160122392 A1.

In Vitro Assembly and Characterization of DS-Cav1-Bearing I53-50 Nanostructures

Figure 4:
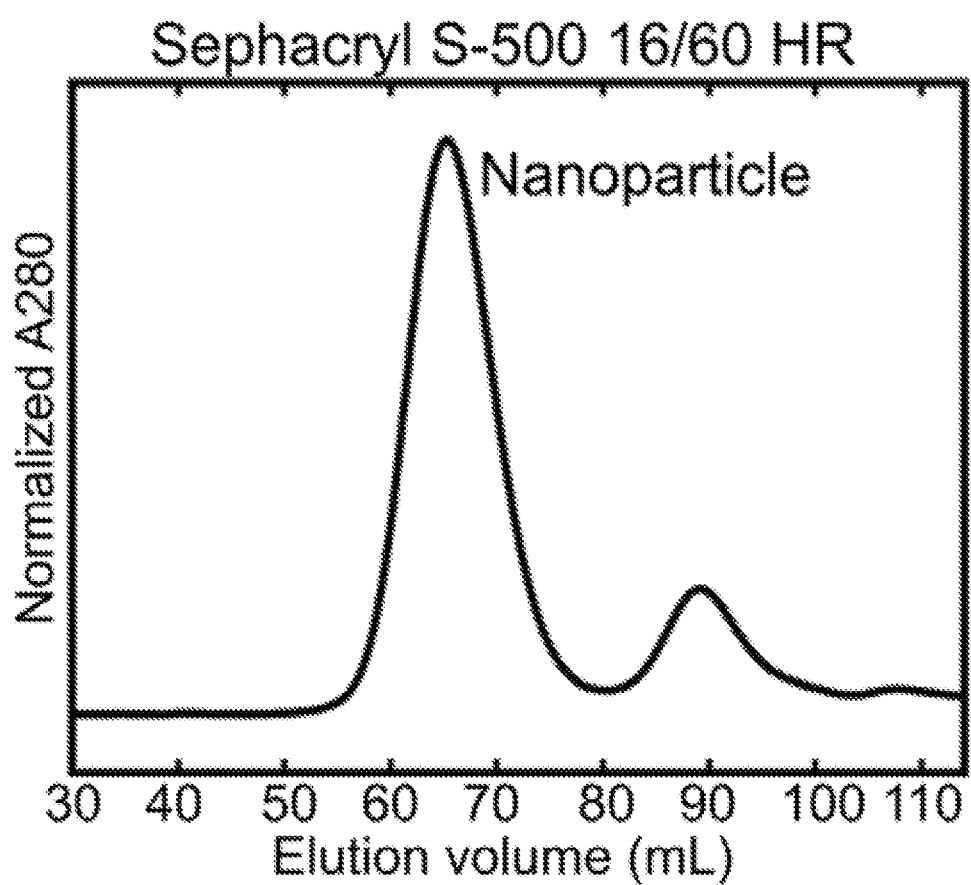
FIG. 4 shows size exclusion chromatography of in vitro-assembled DS-Cav1-I53-50 nanostructures. Purified DS-Cav1-I53-50A and I53-50B.4PT1 proteins were mixed at an approximately 1:1 molar ratio, incubated overnight at 4° C., and then applied to a Sephacryl S-500 16/60 HR size exclusion column. The assembled nanostructure eluted as a single, monodisperse peak around 65 mL, while excess DS-Cav1-I53-50A trimeric component eluted around 90 mL.
Figure 5:
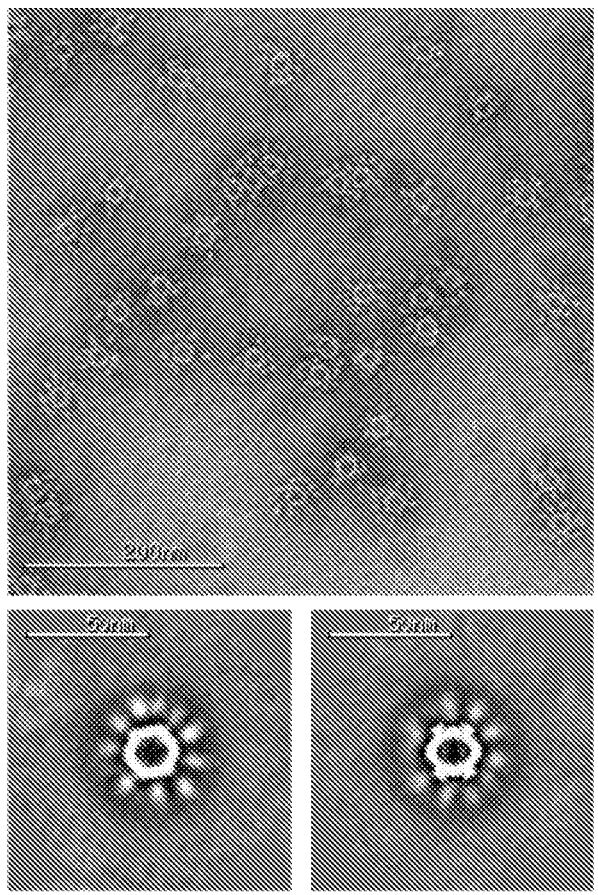
FIG. 5 shows a negative stain electron micrograph and two-dimensional class averages of in vitro-assembled DS-Cav-I53-50 nanostructures. In vitro-assembled DS-Cav1-I53-50 nanostructures, purified by size exclusion chromatography, were imaged by negative stain electron microscopy (top). Averaging many nanostructures yielded two-dimensional class averages (bottom) that indicate that the I53-50 portion of the nanostructures is highly ordered and consistent, while the precise three-dimensional position of the displayed antigen varies slightly due to the flexible nature of the linker between the DS-Cav1 and I53-50A domains of the DS-Cav1-I53-50A fusion protein.

I53-50 is a 120-subunit two-component nanostructure with icosahedral symmetry comprising 20 trimeric (I53-50A) and 12 pentameric (I53-50B) building blocks, as recently described by Bale et al. The N terminus of I53-50A is exposed on the exterior of the I53-50 nanostructure, which enables the display of antigens on the nanostructure exterior through genetic fusion to the I53-530A N terminus. Purified DS-Cav1-foldon-I53-50A and I53-50B.4PT were assembled in vitro to form 120-subunit icosahedral nanostructures displaying various amounts of DS-Cav1 on the nanostructure exteriors by mixing the two purified proteins in various molar ratios. In separate preparations, nanostructures displaying DS-Cav1 at valencies of 100% (20 trimers), 66% (~14 trimers), and 33% (~7 trimers) were prepared as described above. The species present in the in vitro assembly reactions after overnight incubation were assessed by several techniques, including size exclusion chromatography-multi-angle light scattering (SEC-MALS), dynamic light scattering, and UV/vis spectroscopy. Assembled, 120-subunit nanostructures were purified from the in vitro assembly reactions using size exclusion chromatography (an example chromatogram obtained using the 100% valency nanostructures is presented in FIG. 4). The purified nanostructures were characterized by negative stain electron microscopy, which revealed fields of monodiperse particles in which DS-Cav1 was clearly visible as spikes projecting outward from the core icosahedral I53-50 assembly (an example micrograph obtained using the 100% valency particles is presented in FIG. 5). ELSA assays using monoclonal antibodies specific to the prefusion conformation confirmed that the DS-Cav1 thus displayed on the nanostructure exteriors was well-folded and antigenically intact (FIG. 6). Surface plasmon resonance experiments evaluating the kinetics of monoclonal antibody binding revealed that antibody dissociation from the 100% valency DS-Cav-foldon-I53-50 nanostructures was slower than from DS-Cav1-foldon trimers, likely due to avidity effects deriving from the multivalent presentation of DS-Cav1 on the nanostructure exterior (FIG. 6). Together, these experiments confirmed that the DS-Cavfoldon-I53-50 nanostructures formed monodisperse, icosahedral nanostructures that display well-folded, antigenically intact DS-Cav1 trimers on their exteriors. These findings motivated experiments to evaluate the utility of the DS-Cavfoldon-I53-50 nanostructures as immunogens for inducing humoral immune responses against DS-Cav1 in animals.

Immunogenicity of DS-Cav1-Foldon-I53-50 Nanostructures

Figure 7:
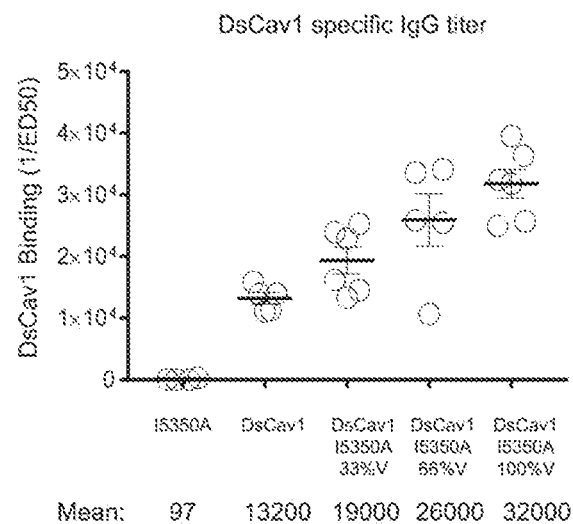
FIG. 7 is a graph depicting DS-Cav-specific serum antibody titers from mice immunized with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. DS-Cav1-specific serum antibody titers were measured by ELISA on plates coated with DS-Cav1. Serum antibody titers for each mouse are plotted as circles, with the geometric mean within each group plotted as a horizontal line and reported numerically at bottom.

The DS-Cav1-foldon-I53-50 nanostructures displaying DS-Cav1 at 33%, 66%, and 100% valency were injected into mice using a prime-boost strategy as described above. Additional groups of mice were injected with trimeric DS-Cav1-foldon as a benchmark for the humoral immune response induced against DS-Cav1 by the nanostructures or I53-50 nanostructures lacking displayed DS-Cav1 as negative controls for a DS-Cav1 specific response. ELISA assays of serum extracted from the mice at defined timepoints after the injections were used to measure DS-Cav1 specific antibody titers present in the sera of the injected animals (FIG. 7). As expected, sera from animals injected with the I53-50 nanostructures lacking displayed DS-Cav1 did not contain antibodies specific to DS-Cav1. Trimeric DS-Cav1-foldon induced DS-Cav1-specific antibodies, in accordance with previous results (McClellan et al.). The 33%, 66%, and 100% valency DS-Cav1 nanostructures all induced higher DS-Cav1-specific antibody titers than trimeric DS-Cav1-foldon, with the antibody titers increasing with increasing DS-Cav1 valency. DS-Cav1-specific titers were roughly 2.5-fold higher on average in mice injected with 100% valency DS-Cav1-foldon-I53-50 nanostructures compared to DS-Cav1. These results demonstrate that immunogens in which paramyxovirus F proteins are multivalently displayed on self-assembling protein nanostructures can induce higher humoral immune responses when injected into animals.

Figure 8:
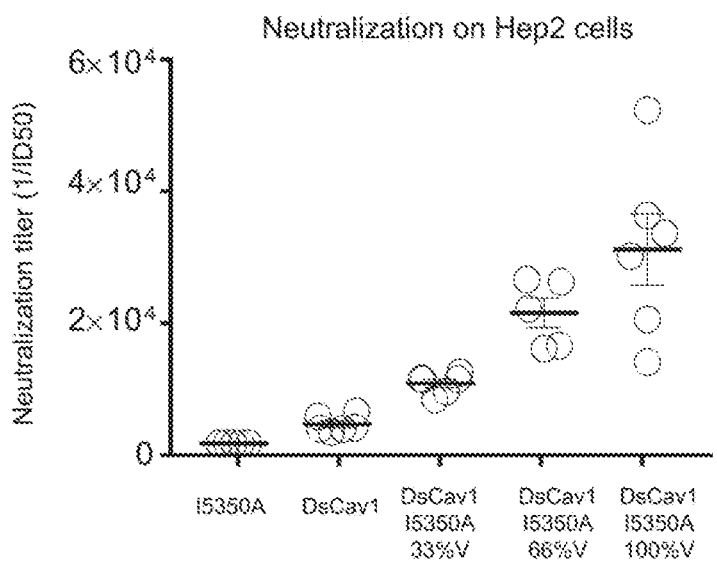
FIG. 8 is a graph depicting serum neutralization activity elicited by immunization with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. Neutralization titers for each mouse are plotted as circles, with the geometric mean within each group plotted as a horizontal line.
Figure 9A:
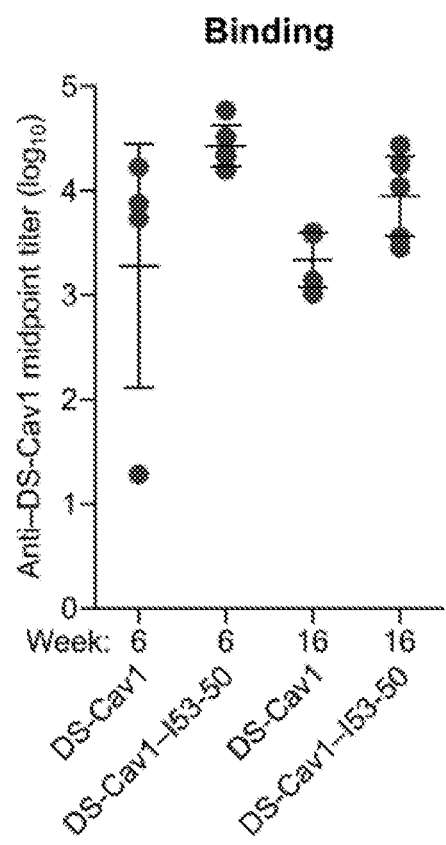
FIGS. 9A-9B are graphs depicting immunogenicity in a primate immune system elicited by immunization with DS-Cav1-foldon I53-50 nanostructures. Rhesus macaques were injected with DS-Cav1-foldon-I53-50 nanostructures intramuscularly at weeks 0 and 4 with either free DS-Cav1 trimer or DS-Cav1-foldon-I53-50 nanostructures displaying DS-Cav1 at 100% valency. In both cases, the dose of DS-Cav1 antigen was 50 µg, and the immunogens were formulated with the MF59-like, squalene-based oil-in-water emulsion adjuvant SWE. Sera obtained from the animals at weeks 6 and 16 were evaluated for anti-DS-Cav1 antibody titers (FIG. 9A) and RSV-neutralizing antibody titers (FIG. 9A).
Figure 9B:
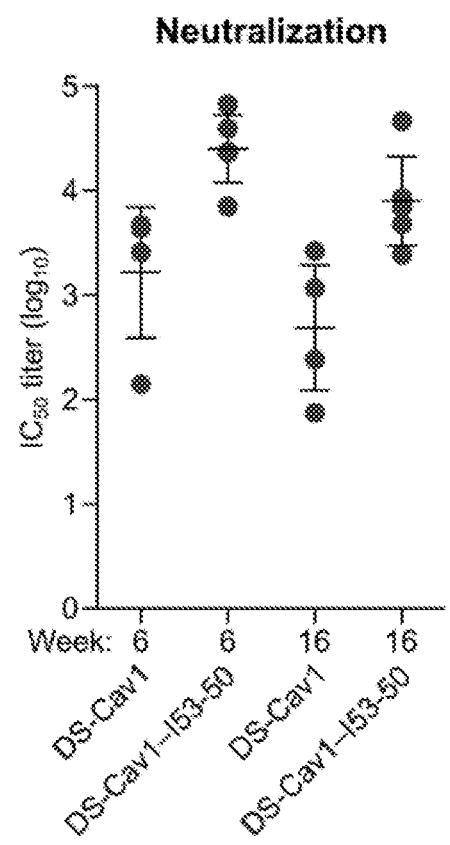

The sera from the mice injected with the series of immunogens described above was also evaluated for the presence of neutralizing antibody titers using the standard neutralization assay in HEp-2 cells (FIG. 8). The trend in serum neutralizing antibody titers correlated highly with the trend observed in DS-Cav1-specific binding antibody titers. Sera from animals injected with the I53-50 nanostructures lacking displayed DS-Cav1 did not neutralize virus, consistent with the lack of DS-Cav1-specific antibodies in these sera. The sera from animals injected with trimeric DS-Cav-1-foldon neutralized virus with an average titer ($1/ID_{50}$) of 3,030. The 33%, 66%, and 100% valency DS-Cav1-I53-50 nanostructures induced higher neutralizing antibody titers than trimeric DS-Cav1-foldon, with average titers of 9,400, 20,000, and 30,500, respectively. These results demonstrate that the higher response induced by immunogens in which paramyxovirus F proteins are multivalently displayed on self-assembling protein nanostructures result in more effective virus neutralization.

Physical Stabilization of DS-Cav1 by Fusion to I53-50A

Figure 10:
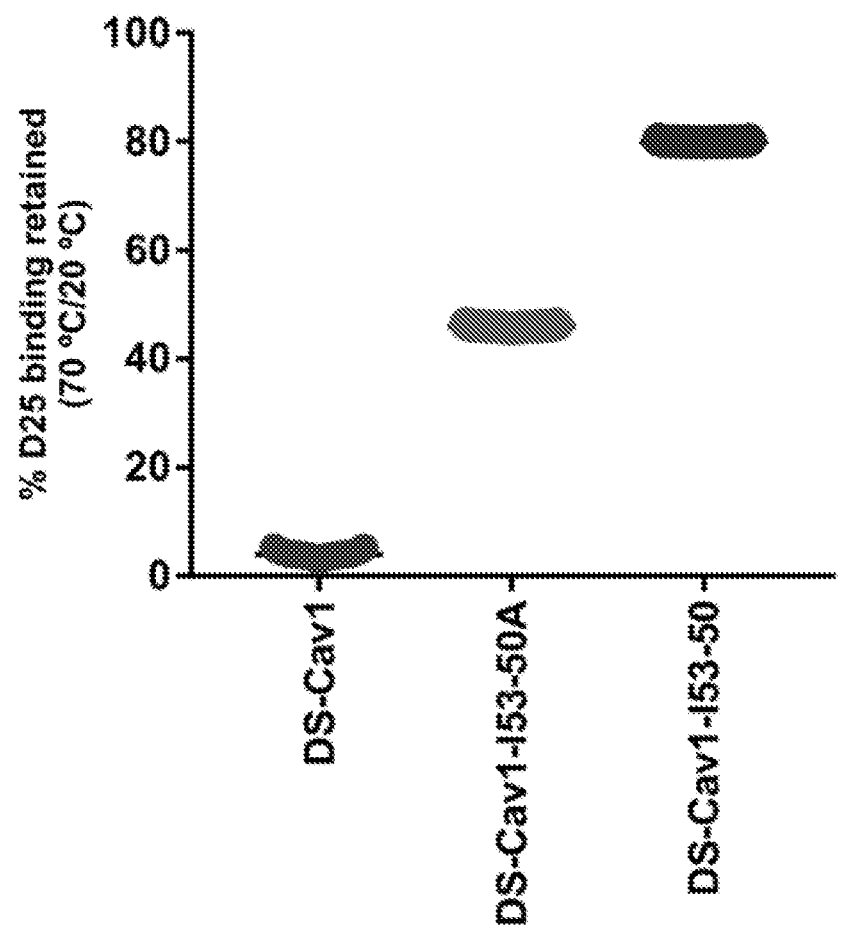
FIG. 10 is a graph depicting the physical stability of DS-Cav1 when fused to I53-50A and/or when further assembled into the icosahedral nanostructure. Samples of trimeric DS-Cav1, trimeric DS-Cav1-foldon-I53-50A, and DS-Cav1-foldon-I53-50 nanostructures containing equivalent concentrations (50 nM) of DS-Cav1 were split into four aliquots and incubated at 20, 50, 70 or 80° C. for 1 hour. After cooling to room temperature, D25 binding was assayed by surface plasmon resonance (SPR).

Given the key antigenic properties of prefusion F. we used two orthogonal approaches to measure the physical stability of DS-Cav1 when fused to I53-50A and/or when further assembled into the icosahedral nanostructure. The first assay measured the retention of binding by a prefusion-specific mAb (D25) after thermal stress, an approach that has been used previously to characterize prefusion F stability (McLellan et al. 2013; Joyce et al. 2016; Krarup et al. 2015). Samples of trimeric DS-Cav1, trimeric DS-Cav1-I53-50A. and DS-Cav1-I53-50 nanostructures containing equivalent concentrations (50 nM) of DS-Cav1 were split into four aliquots and incubated at 20, 50, 70 or 80° C. for 1 hour. After cooling to room temperature, D25 binding was assayed by surface plasmon resonance (SPR). We found that all samples bound D25 equivalently at 20 and 50° C., but lost most of their reactivity to D25 after 1 hour at 80° C. as previously reported for DS-Cav1 (McLellan et al. 2013; Joyce et al. 2016) (FIG. 10). Interestingly, while D25 was also unable to bind trimeric DS-Cav1 incubated at 70° C. for 1 hour, trimeric DS-Cav153-50A and the DS-Cav1-I53-50 nanostructures retained 50 and 80% of their respective binding signals (FIG. 10). While the multivalent nature of the DS-Cav1-I53-50 nanostructures complicates direct quantitative comparisons to trimeric DS-Cav1, these results indicate that genetic fusion to the I53-50A trimer further stabilizes the prefusion conformation of DS-Cav1, and suggest that this increased stability is maintained in the context of the assembled nanostructure immunogen.

We used chemical denaturation in guanidine hydrochloride (GdnHCl), monitored by intrinsic tryptophan fluorescence, as a second, antibody-independent technique to evaluate physical stability. Analyzing fluorescence emission from DS-Cav1 incubated in 0-6.5 M GdnHCl revealed that the protein undergoes two subtly distinct transitions, one between 0.25 and 2.25 M GdnHCl and another between 2.25 and 5.75 M (FIGS. 11A-11J). In contrast, only a single transition is apparent for trimeric DS-Cav1-I53-50A. occurring between 2.25 and 6.25 M GdnHCl (FIGS. 11A-11J). It is unclear at present whether the transition at lower [GdnHCl] observed for DS-Cav1 is absent from trimeric DS-Cav1-I53-50A or simply shifted to higher [GdnHCl]. However, it is clear that the native conformation of DS-Cav1 is stabilized by genetic fusion to trimeric I53-50A, mirroring the results obtained by measuring D25 binding after thermal stress. Comparing the data for the DS-Cav1-I53-50 nanostructure and the I53-50 nanostructure alone (lacking fused DS-Cav1) indicated that the stabilization is maintained upon assembly to the icosahedral nanostructure (FIGS. 11A-11J). The source of this effect is likely the extreme stability of the I53-50A trimer. I53-50A is derived from the KDPG aldolase of the hyperthermophilic bacterium *T. maritima* and only began to exhibit changes in fluorescence at very high (5.75 M) GdnHCl concentrations (FIGS. 11A-11J).

We made addition constructs to assess the number of GS repeats and the need for a stabilization domain such as the Foldon moiety.

Sequence Information

| IPD Name | MS (Da) | Construct information |
| --- | --- | --- |
| RSV_F-10 | 74005.38 | DS-Cav1-8GS-HclExt-50A (SEQ ID NO: 108) |
| RSV_F-11 | 74293.64 | DS-Cav1-12GS-HelExt-50A (SEQ ID NO: 109) |

-continued

| IPD Name | MS (Da) | Construct information |
|---|---|---|
| RSV_F-12 | 74551.87 | DS-Cav1-16GS-HelExt-50A (SEQ ID NO: 110) |
| RSV_F-13 | 77212.97 | DS-Cav1-foldon-10GS-HelExt-50A (SEQ ID NO: 111) |
| RSV_F-14 | 77558.28 | DS-Cav1-foldon-15GS-HelExt-50A (SEQ NO: 112) |
| RSV_F-15 | 77933.62 | DS-Cav1-foldon-20GS-HelExt-50A (SEQ ID NO: 113) |

```
>RSV_F-10
                                                  (SEQ ID NO: 108)
QNITEEFYQSTCSAVSKGYLSALRIGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGIVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFTQAETCKVQSNRVFCDTMNSLTLPSEVNLCNVDIFNPKYDCKIMTSK

TDVSSSVITSLGAIVSCYGKTKCTASNKNRGIIKTFSNGCDYVSNKGVDTVSVGNTLY

YVNKQEGKSLYVKGEPIINFYDPLVFPSDEFDASISQVNEKINQSLAFIRGSGGSGSGE

KAAKAEEAARKMEELFKKHKIVAVLRANSVEEAIEKAVAVFAGGVHLIEITFTVPDA

DTVIKALSVLKEKGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLD

NVCEWFKAGVLAVGVGSALVKGTPDEVREKAKAFVEKIRGCTE

>RSV_F-11
                                                  (SEQ ID NO: 109)
QNITEEFQSTCSAVSKGYLSALRTGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSK

TDVSSSVITSLGAIVSCYGKTKCTASNKNRGIIKTFSNGCDYVSNKGVDTVSVGNTLY

YVNKQEGKSLYVKGEPIINFYDPLVFPSDEFDASISQVNEKINQSLAFIRGSGGSGSGS

GGSEKAAKAEEAARKMEELFKKHKIVAVIJRANSVEEAIEKAVAVFAGGVHLIEITFT

VPDADTVIKALSVLKEKGAIIGAGTVTSVEQCRKAVESGAEFIVSPHLDEEISQFCKEK

GVFYMPGVMTPTELVKAMKLGHTILKLFPGEVVGPQFVKAMKGPFPNVKFVPTGG

VNLDNVCEWFKAGVLAVGVGSALVKGTPDEVREKAKAFVEKIRGCTE

>RSV_F-12
                                                  (SEQ ID NO: 110)
QNITEEFYQSTCSAVSKGYLSALRTGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSK

TDVSSSVITSLGAIVSCYGKTKCTASNKNRGIIKITSNGCDYVSNKGVDTVSVGNTLY

YVNKQEGKSLYVKGEPIINFYDPLVFPSDEFDASISQVNEKINQSLAFIRGSGGSGSGS
```

-continued

GGSGSGGEKAAKAEEAARKMEELFKKHKIVAVLRANSVEEAIEKAVAVFAGGVHLI

EITFTVPDADTVIKALSVLKEKGAIIGAGTVTSVEQCRKAVESGAEFIVSPHLDEEISQF

CKEKGVFYMPGVMTPTELVKAMKLGHTILKLFPGEVVGPQFVKAMKGPFPNVKFVP

TGGVNLDNVCEWFKAGVLAVGVGSALVKGTPDEVREKAKAFVEKIRGCTE

>RSV_F-13
(SEQ ID NO: 111)
QNITEEFYQSTCSAVSKGYLSALRTGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSK

TDVSSSVITSLGAIVSCYGKTKCTASNKNRGIIKTFSNGCDYVSNKGVDTVSVGNTLY

YVNKQEGKSLYVKGEPIINFYDPLVFPSDEFDASISQVNEKINQSLAFIRGSGGSGSGS

GEKAAKAEEAARKMEELFKKHKIVAVLRANSVEEAIEKAVAVFAGGVHLIEITFTNP

DADTVIKALSVLKEKGAIIGAGTVTSVEQCRKAVESGAEFIVSPHLDEEISQFCKEKG

VFYMPGVMTPTELVKAMKLGHTILKLFPGEVVGPQFVKAMKGPFPNVKFVPTGGV

NLDNVCEWFKAGVLAVGVGSALVKGTPDEVREKAKAFVEKIRGCTE

>RSV_F-14
(SEQ ID NO: 112)
QNITEEFYQSTCSAVSKGYLSALRTGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSK

TDVSSSVITSLGAIVSCYGKTKCTASNKNRGIIKTFSNGCDYVSNKGVDTVSVGNTLY

YVNKQEGKSLYVKGEPIINFYDPLVFPSDEFDASISQVNEKINQSLAFIRGYIPEAPRD

GQAYVRKDGEWVLLSTFLGSGGSGSGSGGSGSGEKAAKAEEAARKMEELFKKHKIV

AVLRANSVEEAIEKAVAVFAGGVHLIEITFTVPDADTVIKALSVLKEKGAIIGAGTVT

SVEQCRKAVESGAEFIVSPHLDEEISQFCKEKGVFYMPGVMTPTELVKAMKLGHTIL

KLFPGEVVGPQFVKAMKGPFPNVKFVPTGGVNLDNVCEWFKAGVLAVGVGSALVK

GTPDEVREKAKAFVEKIRGCTE

>RSV_F-15
(SEQ ID NO: 113)
QNITEEFYQSTCSAVSKGYLSALRTGWYTSVITIELSNIKENKCNGTDAKVKLIKQEL

DKYKNAVTELQLLMQSTPATNNRARRFLGFLLGVGSAIASGVAVCKVLHLEGEVNK

IKSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQAETCKVQSNRVFCDTMNSLTLPSEVNLCNVDIFNPKYDCKIMTSK

TDVSSSVITSLGAIVSCYGKTKCTASNKNRGIIKTFSNGCDYVSNKGVDTVSVGNTLY

YVNKQEGKSLYVKGEPIINFYDPLVFPSDEFDASISQVNEKINQSLAFIRGYIPEAPRD

-continued

```
GQAYVRKDGEWVLLSTFLGSGGSGSGSGGSGSGGSSGSEKAAKAEEAARKMEELFK

KHKIVAVLRANSVEEAIEKAVAVFAGGVHLIEITFTVPDADTVIKALSVLKEKGAIIG

AGTVTSVEQCRKAVESGAEFIVSPHLDEEISQFCKEKGVFYMPGVMTPTELVKAMKL

GHTILKLFPGEVVGPQFVKAMKGPFPNVKVPTGGVNLDNVCEWFKAGVLAVGVG

SALVKGTPDEVREKAKAFVEKIRGCTE
```

Studies were based on expression yield in a small-scale transient transfection. Plasmids capable of expressing the relevant constructs were transformed into NEB 5a *E. coli* cells and selected on LB+carbenicillin agar plates. 1 mL cultures were prepared by inoculating TB media with a bacterial colony and again selecting with 50 ug/mL carbenicillin. A Qiagen Mini Prep kit was used to purify plasmid from the *E. coli* cultures in accordance with their protocol. Expi293F™ Cells (ThermoFisher) were cultured in Expi293™ Expression Medium (ThermoFisher) supplemented with penicillin (100 u/mL) and streptomycin (100 μg/mL) at 8% $CO_2$, 37° C., and 125 rpm shaking.

On the day prior to transfection, cells were seeded at a concentration of 2E6 cells/mL. On the day of transfection, cells were counted by a Countess II (ThermoFisher) with trypan blue to determine cell viability. Cell concentration was adjusted to 2.5E6 cells/mL, and cells where plated into untreated 12-well plates (Corning) in 1 mL volumes. 1 μg of DNA plasmid were transfected per each well using Expifectamine™ (ThermoFisher), following the manufacturer's directions. Enhancers, components of ThermoFisher's Expifectamine™ Transfection Kit, were added 18 hours after transfection. The 1 mL cultures were harvested 5 days post-transfection, and the cells were pelleted from the supernatant by centrifugation at 1,500×g for 5 minutes at 4° C. Supernatants were filtered through a 0.45 μM filter with a PVDF membrane.

Filtered supernatants containing DS-Cav1-I53-50A constructs were denatured and boiled for 10 minutes at 95° C. for 10 minutes in 2× Laemmli buffer with 2-mercaptoethanol. SDS-PAGE separated the sample fractions, which were then transferred to a nitrocellulose membrane and probed with palivizumab, followed with a secondary antibody, anti-human conjugated to HRP. Blot was imaged using Clarity Western ECL Blotting Substrate (Bio-Rad).

Filtered supernatants containing DS-Cav1-I53-50A constructs were bound to Nunc MaxiSorp 96-well plates in a two-fold dilution series. The pre-fusion conformation-specific antibody D25 was used to detect DS-Cav1-I53-50A. followed by a secondary anti-human antibody conjugated to HRP. Protein yield was determined colorimetrically via the substrate TMB and absorbances were collected at 450 nm.

The expression yields and binding of the prefusion-specific mAb D25 (data not shown) indicate that all constructs express well and are in the prefusion conformation. As is known to those of skill in the art, a heterologous trimerization domain (e.g., the foldon) is typically required for proper expression and folding of prefusion F constructs. Our results indicate that the I53-50A nanostructure component can support the expression and proper folding of DS-Cav1 without the use of a trimerization domain like the foldon. Binding of D25 to these constructs suggests that they are antigenically intact and would be expected to induce potent immune responses, including neutralizing antibodies, similarly to nanostructures comprising the DS-Cav1-foldon-I53-50 fusion polypeptide.

9.2. Example 2: Cytomegalovirus (CMV)

Protein-based vaccines for CMV are described, for example, in U.S. Patent Pub. Nos. US 2016/0159864 A1 and US 2017/0369532 A1; International Patent Pub No. WO 2016/092460 A3; and Kirchmeier al. Enveloped virus-like particle expression of human cytomegalovirus glycoprotein B antigen induces antibodies with potent and broad neutralizing activity. Clin Vaccine Immunol. 2014; 21(2):174-80. The homotrimer complex of gB, the trimeric gH/gL/gO complex, or the pentameric gH/gL/pUL128/pUL130/pUL131A complex are considered the three major targets for CMV vaccination.

The first of these targets, gB, forms a trimeric structure which comprises several hydrophobic surfaces. The C terminus of the extracellular domain of gB is proximal to the transmembrane region and lies near the 3-fold axis of the molecule. See Chandramouli et al. Structure of HCMV glycoprotein B in the postfusion conformation bound to a neutralizing human antibody. Nat Commun. 2015 Sep. 14; 6:8176. By substitution of the transmembrane region of gB for a linker, the gB protein of CMV is N-terminally linked to a nanostructure having a free N terminus at or near the 3-fold axis of the nanostructure. The resulting nanostructure has displays 20 copies of the gB trimer on its surface and effectively elicits a immune response to CMV gB. Mutations to the gB protein as described in International Patent Pub No. WO 2016/092460 A3, improve the solubility and immunogenicity of the nanostructure-based vaccine.

The second of these targets, the trimeric gH/gL/gO complex, and the third of these targets, the pentameric gH/gL/pUL128/pUL130/pUL131A. form by mutually exclusive interactions of the envelope glycoproteins gH/gL with either gO or pUL128/pUL130/pUL131A. See Ciferri et al. Structural and biochemical studies of HCMV gHgL/gO and Pentamer reveal mutually exclusive cell entry complexes. Proc. Natl. Acad. Sci. U.S.A. 112, 1767-1772 (2015). The gH component is targeted by antibodies neutralizing infection of both fibroblasts and endothelial/epithelial cells. The UL region contains the binding sites for potently neutralizing antibodies of epithelial and endothelial cells infection.

The gH component is expressed as a gene fusion to a nanostructure polypeptide and either gL/gO or gL/pUL128/pUL130/pUL131A are co-expressed. The expressed proteins self-assemble into either gH/gL/gO or gH/gL/pUL128/pUL130/pUL131A nanostructure-based vaccines, respectively. Expression and correct folding of the nanostructure is assessed by binding of the MSL-109 antibody of an Fab fragment thereof to the nanostructure. Correct folding and antigenicity of the pentameric complex is assessed using antibodies and Fab fragments described in Chandramouli et al. Structural basis for potent antibody-mediated neutralization of human cytomegalovirus Sci. Immunol. 2, eaan1457 (2017).

9.3. Example 3: Epstein-Barr Virus (EBV)

Epstein-Barr virus (EBV) represents a major global health problem. Though it is associated with infectious mononucleosis and ~200,000 cancers annually worldwide. a vaccine is not available. The major target of immunity is EBV glycoprotein 350/220 (gp350) that mediates attachment to B cells through complement receptor 2 (CR2/CD21). See Kanekiyo et al. Rational Design of an Epstein-Barr Virus Vaccine Targeting the Receptor-Binding Site. Cell 162(5): 1090-1100 (2015). The gp350 ectodomain or the $D_{123}$ fragment of gp350 is expressed as a gene fusion to a nanostructure polypeptides as either an N-terminal or C-terminal fusion. The resulting gene fusions are expressed, assembled, and formulated into nanostructure-based vaccines. Antigenicity is determined using the monoclonal antibodies 72A1 and 2L10.

What is claimed:

1. A self-assembling icosahedral protein nanostructure, comprising:

20 trimeric assemblies having 3-fold symmetry, each trimeric assembly comprising 3 trimer proteins, each trimer protein comprising a polypeptide consisting of, in N- to C-terminal order, an extracellular domain of influenza HA, a polypeptide linker, and a trimer subunit comprising a polypeptide comprising an amino acid sequence that is at least 95% identical to the amino acid sequence selected from SEQ ID NO: 7 or 29-31; and 12 pentameric assemblies having 5-fold symmetry, each pentameric assembly comprising 5 pentamer subunits, wherein each pentamer subunit comprises a polypeptide comprising an amino acid sequence that is at least 95% identical to the amino acid sequence selected from SEQ ID NO: 8 or 32-34;

wherein the trimeric assemblies and the pentameric assemblies form an icosahedron.

2. A vaccine comprising a nanostructure of claim 1, wherein the vaccine is capable of eliciting a neutralizing antibody response to influenza.

3. A pharmaceutical composition comprising the vaccine of claim 2.

4. A method of generating immunity to influenza in a subject, comprising an effective amount of the nanostructure of claim 1.

5. The nanostructure of claim 1, wherein the influenza HA extracellular domains and the trimer subunits each independently homotrimerize to form the trimeric assemblies.

6. The nanostructure of claim 1, wherein the influenza HA extracellular domains are displayed on the surface of the icosahedron as trimers.

7. The nanostructure of claim 1, wherein each trimer subunit comprises interface residues at amino acid positions 25, 29, 33, 54, and 57 of a trimer reference sequence selected from SEQ ID NO: 7 or 29-31, wherein each trimer subunit is identical at least at 1, 2, 3, 4, or 5 interface positions to the polypeptide sequence of the trimer reference sequence, wherein each pentamer subunit comprises interface residues at amino acid positions 24, 28, 36, 124, 125, 127, 128, 129, 131, 132, 133, 135, and 139 of a pentamer reference sequence selected from SEQ ID NO: 8 or 32-34, and wherein each pentamer subunit is identical at least at 1, 2, 3, 4, 5, 6, 7, 8, 9, 10, 11, 12, or 13 interface positions to the polypeptide sequence of the pentamer reference sequence.

8. The nanostructure of claim 1, wherein the polypeptide linker comprises a polypeptide sequence selected from GSGGSGSGSGGSGSG (SEQ ID NO:114), GGSGGSGS (SEQ ID NO:115), and GSGGSGSG (SEQ ID NO:116).

9. The nanostructure of claim 1, wherein each trimer subunit comprises an amino acid sequence that is at least 95% identical to the amino acid sequence of SEQ ID NO: 7.

10. The nanostructure of claim 1, wherein each pentamer subunit comprises an amino acid sequence that is at least 95% identical to the amino acid sequence of SEQ ID NO: 34.

11. The nanostructure of claim 1, wherein the influenza HA extracellular domain comprises an amino acid sequence that is at least 85% identical to the amino acid sequence of SEQ ID NO: 57.

12. The nanostructure of claim 1, wherein the influenza HA extracellular domain comprises an amino acid sequence that is at least 90% identical to the amino acid sequence of SEQ ID NO: 57.

13. The nanostructure of claim 1, wherein the influenza HA extracellular domain comprises an amino acid sequence that is at least 85% identical to the amino acid sequence of SEQ ID NO: 58.

14. The nanostructure of claim 1, wherein the influenza HA extracellular domain comprises an amino acid sequence that is at least 90% identical to the amino acid sequence of SEQ ID NO: 58.

15. The nanostructure of claim 1, wherein each trimer subunit comprises an amino acid sequence that is at least 95% identical to the amino acid sequence of SEQ ID NO: 7, and wherein each pentamer subunit comprises an amino acid sequence that is at least 95% identical to the amino acid sequence of SEQ ID NO: 34.

16. The nanostructure of claim 1, wherein each trimer subunit comprises an amino acid sequence that is at least 95% identical to the amino acid sequence of SEQ ID NO: 7, wherein each pentamer subunit comprises an amino acid sequence that is at least 95% identical to the amino acid sequence of SEQ ID NO: 34, and wherein the influenza HA extracellular domain comprises an amino acid sequence that is at least 85% identical to the amino acid sequence of SEQ ID NO: 57.

17. The nanostructure of claim 1, wherein each trimer subunit comprises an amino acid sequence that is at least 95% identical to the amino acid sequence of SEQ ID NO: 7, wherein each pentamer subunit comprises an amino acid sequence that is at least 95% identical to the amino acid sequence of SEQ ID NO: 34, and wherein the influenza HA extracellular domain comprises an amino acid sequence that is at least 85% identical to the amino acid sequence of SEQ ID NO: 58.

18. The nanostructure of claim 1, wherein each trimer subunit comprises an amino acid sequence that is at least 99% identical to the amino acid sequence of SEQ ID NO: 7, wherein each pentamer subunit comprises an amino acid sequence that is at least 99% identical to the amino acid sequence of SEQ ID NO: 34, and wherein the influenza HA extracellular domain comprises an amino acid sequence that is at least 95% identical to the amino acid sequence of SEQ ID NO: 57.

19. The nanostructure of claim 1, wherein each trimer subunit comprises the amino acid sequence according to SEQ ID NO: 7, wherein each pentamer subunit comprises the amino acid sequence according to SEQ ID NO: 34, and wherein the influenza HA extracellular domain comprises an amino acid sequence that is at least 85% identical to the amino acid sequence of SEQ ID NO: 57.

20. The nanostructure of claim 1, wherein each trimer subunit comprises the amino acid sequence according to SEQ ID NO: 7, wherein each pentamer subunit comprises the amino acid sequence according to SEQ ID NO: 34, and wherein the influenza HA extracellular domain comprises an amino acid sequence that is at least 85% identical to the amino acid sequence of SEQ ID NO: 58.

* * * * *

SEQUENCE LISTING

```
<160> NUMBER OF SEQ ID NOS: 116

<210> SEQ ID NO 1
<211> LENGTH: 207
<212> TYPE: PRT
<213> ORGANISM: Artificial Sequence
<220> FEATURE:
<223> OTHER INFORMATION: synthetically constructed nanostructure
      polypeptide

<400> SEQUENCE: 1

Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
            20                  25                  30

Val Leu Glu Leu Met Gly Val Gly Ala Leu Glu Ile Thr Leu Arg Thr
        35                  40                  45

Glu Lys Gly Leu Glu Ala Leu Lys Ala Leu Arg Lys Ser Gly Leu Leu
    50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
            100                 105                 110

Thr Pro Thr Glu Val Glu Arg Ala Leu Ala Leu Gly Leu Ser Ala Leu
        115                 120                 125

Lys Phe Phe Pro Ala Glu Pro Phe Gln Gly Val Arg Val Leu Arg Ala
130                 135                 140

Tyr Ala Glu Val Phe Pro Glu Val Arg Phe Leu Pro Thr Gly Gly Ile
145                 150                 155                 160

Lys Glu Glu His Leu Pro His Tyr Ala Ala Leu Pro Asn Leu Leu Ala
                165                 170                 175

Val Gly Gly Ser Trp Leu Leu Gln Gly Asp Leu Ala Ala Val Met Lys
            180                 185                 190

Lys Val Lys Ala Ala Lys Ala Leu Leu Ser Pro Gln Ala Pro Gly
        195                 200                 205

<210> SEQ ID NO 2
<211> LENGTH: 156
<212> TYPE: PRT
<213> ORGANISM: Artificial Sequence
<220> FEATURE:
<223> OTHER INFORMATION: synthetically constructed nanostructure
      polypeptide

<400> SEQUENCE: 2

Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
            20                  25                  30

Lys Ile Ile Arg Lys Thr Val Pro Gly Ile Lys Asp Leu Pro Val Ala
```

```
                   35                  40                  45

Cys Lys Lys Leu Leu Glu Glu Glu Gly Cys Asp Ile Val Met Ala Leu
 50                  55                  60

Gly Met Pro Gly Lys Ala Glu Lys Asp Lys Val Cys Ala His Glu Ala
 65                  70                  75                  80

Ser Leu Gly Leu Met Leu Ala Gln Leu Met Thr Asn Lys His Ile Ile
                 85                  90                  95

Glu Val Phe Val His Glu Asp Glu Ala Lys Asp Asp Glu Leu Asp
                100                 105                 110

Ile Leu Ala Leu Val Arg Ala Ile Glu His Ala Ala Asn Val Tyr Tyr
                115                 120                 125

Leu Leu Phe Lys Pro Glu Tyr Leu Thr Arg Met Ala Gly Lys Gly Leu
                130                 135                 140

Arg Gln Gly Arg Glu Asp Ala Gly Pro Ala Arg Glu
145                 150                 155

<210> SEQ ID NO 3
<211> LENGTH: 156
<212> TYPE: PRT
<213> ORGANISM: Artificial Sequence
<220> FEATURE:
<223> OTHER INFORMATION: synthetically constructed nanostructure
      polypeptide

<400> SEQUENCE: 3

Met Thr Lys Lys Val Gly Ile Val Asp Thr Thr Phe Ala Arg Val Asp
 1               5                  10                  15

Met Ala Ser Ala Ala Ile Leu Thr Leu Lys Met Glu Ser Pro Asn Ile
                 20                  25                  30

Lys Ile Ile Arg Lys Thr Val Pro Gly Ile Lys Asp Leu Pro Val Ala
                 35                  40                  45

Cys Lys Lys Leu Leu Glu Glu Glu Gly Cys Asp Ile Val Met Ala Leu
 50                  55                  60

Gly Met Pro Gly Lys Ala Glu Lys Asp Lys Val Cys Ala His Glu Ala
 65                  70                  75                  80

Ser Leu Gly Leu Met Leu Ala Gln Leu Met Thr Asn Lys His Ile Ile
                 85                  90                  95

Glu Val Phe Val His Glu Asp Glu Ala Lys Asp Asp Ala Glu Leu Lys
                100                 105                 110

Ile Leu Ala Ala Arg Arg Ala Ile Glu His Ala Leu Asn Val Tyr Tyr
                115                 120                 125

Leu Leu Phe Lys Pro Glu Tyr Leu Thr Arg Met Ala Gly Lys Gly Leu
                130                 135                 140

Arg Gln Gly Phe Glu Asp Ala Gly Pro Ala Arg Glu
145                 150                 155

<210> SEQ ID NO 4
<211> LENGTH: 209
<212> TYPE: PRT
<213> ORGANISM: Artificial Sequence
<220> FEATURE:
<223> OTHER INFORMATION: synthetically constructed nanostructure
      polypeptide

<400> SEQUENCE: 4

Met Ser Thr Ile Asn Asn Gln Leu Lys Ala Leu Lys Val Ile Pro Val
 1               5                  10                  15

Ile Ala Ile Asp Asn Ala Glu Asp Ile Ile Pro Leu Gly Lys Val Leu
```

```
                    20                  25                  30

Ala Glu Asn Gly Leu Pro Ala Ala Glu Ile Thr Phe Arg Ser Ser Ala
             35                  40                  45

Ala Val Lys Ala Ile Met Leu Leu Arg Ser Ala Gln Pro Glu Met Leu
 50                  55                  60

Ile Gly Ala Gly Thr Ile Leu Asn Gly Val Gln Ala Leu Ala Ala Lys
 65                  70                  75                  80

Glu Ala Gly Ala Thr Phe Val Val Ser Pro Gly Phe Asn Pro Asn Thr
                 85                  90                  95

Val Arg Ala Cys Gln Ile Ile Gly Ile Asp Ile Val Pro Gly Val Asn
                100                 105                 110

Asn Pro Ser Thr Val Glu Ala Ala Leu Glu Met Gly Leu Thr Thr Leu
            115                 120                 125

Lys Phe Phe Pro Ala Glu Ala Ser Gly Gly Ile Ser Met Val Lys Ser
        130                 135                 140

Leu Val Gly Pro Tyr Gly Asp Ile Arg Leu Met Pro Thr Gly Gly Ile
145                 150                 155                 160

Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
            180                 185                 190

Trp Asp Glu Ile Ala Arg Leu Thr Arg Glu Ile Val Glu Gln Val Asn
        195                 200                 205

Pro

<210> SEQ ID NO 5
<211> LENGTH: 114
<212> TYPE: PRT
<213> ORGANISM: Artificial Sequence
<220> FEATURE:
<223> OTHER INFORMATION: synthetically constructed nanostructure
      polypeptide

<400> SEQUENCE: 5

Met Pro Ile Phe Thr Leu Asn Thr Asn Ile Lys Ala Thr Asp Val Pro
 1               5                  10                  15

Ser Asp Phe Leu Ser Leu Thr Ser Arg Leu Val Gly Leu Ile Leu Ser
                20                  25                  30

Lys Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Ser Lys Asn Arg Asp His Ser Ala Val Leu
 65                  70                  75                  80

Phe Asp His Leu Asn Ala Met Leu Gly Ile Pro Lys Asn Arg Met Tyr
                 85                  90                  95

Ile His Phe Val Asn Leu Asn Gly Asp Asp Val Gly Trp Asn Gly Thr
            100                 105                 110

Thr Phe

<210> SEQ ID NO 6
<211> LENGTH: 157
<212> TYPE: PRT
<213> ORGANISM: Artificial Sequence
<220> FEATURE:
<223> OTHER INFORMATION: synthetically constructed nanostructure
      polypeptide
```

<400> SEQUENCE: 6

```
Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Ala Glu His His Arg
        115                 120                 125

Phe Phe Ala Ala His Phe Ala Val Lys Gly Val Glu Ala Ala Arg Ala
    130                 135                 140

Cys Ile Glu Ile Leu Ala Ala Arg Glu Lys Ile Ala Ala
145                 150                 155
```

<210> SEQ ID NO 7
<211> LENGTH: 205
<212> TYPE: PRT
<213> ORGANISM: Artificial Sequence
<220> FEATURE:
<223> OTHER INFORMATION: synthetically constructed nanostructure polypeptide

<400> SEQUENCE: 7

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190
```

```
Ala Lys Ala Phe Val Glu Lys Ile Arg Gly Cys Thr Glu
        195                 200                 205

<210> SEQ ID NO 8
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 8

Met Asn Gln His Ser His Lys Asp Tyr Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Ala Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 9
<211> LENGTH: 177
<212> TYPE: PRT
<213> ORGANISM: Artificial Sequence
<220> FEATURE:
<223> OTHER INFORMATION: synthetically constructed nanostructure
      polypeptide

<400> SEQUENCE: 9

Met Phe Thr Lys Ser Gly Asp Asp Gly Asn Thr Asn Val Ile Asn Lys
1               5                   10                  15

Arg Val Gly Lys Asp Ser Pro Leu Val Asn Phe Leu Gly Asp Leu Asp
            20                  25                  30

Glu Leu Asn Ser Phe Ile Gly Phe Ala Ile Ser Lys Ile Pro Trp Glu
        35                  40                  45

Asp Met Lys Lys Asp Leu Glu Arg Val Gln Val Glu Leu Phe Glu Ile
    50                  55                  60

Gly Glu Asp Leu Ser Thr Gln Ser Ser Lys Lys Lys Ile Asp Glu Ser
65                  70                  75                  80

Tyr Val Leu Trp Leu Leu Ala Ala Thr Ala Ile Tyr Arg Ile Glu Ser
                85                  90                  95

Gly Pro Val Lys Leu Phe Val Ile Pro Gly Gly Ser Glu Glu Ala Ser
            100                 105                 110

Val Leu His Val Thr Arg Ser Val Ala Arg Arg Val Glu Arg Asn Ala
        115                 120                 125
```

```
Val Lys Tyr Thr Lys Glu Leu Pro Glu Ile Asn Arg Met Ile Ile Val
            130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 10
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 10

Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
                20                  25                  30

Phe Glu Glu Ala Met Ala Asp Ala Gly Gly Asp Arg Phe Ala Val Asp
            35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Ser Ser Arg Glu His His Glu
        115                 120                 125

Phe Phe Arg Glu His Phe Met Val Lys Gly Val Glu Ala Ala Ala Ala
    130                 135                 140

Cys Ile Thr Ile Leu Ala Ala Arg Glu Lys Ile Ala Ala
145                 150                 155

<210> SEQ ID NO 11
<211> LENGTH: 201
<212> TYPE: PRT
<213> ORGANISM: Artificial Sequence
<220> FEATURE:
<223> OTHER INFORMATION: synthetically constructed nanostructure
      polypeptide

<400> SEQUENCE: 11

Met Gly His Thr Lys Gly Pro Thr Pro Gln Gln His Asp Gly Ser Ala
1               5                   10                  15

Leu Arg Ile Gly Ile Val His Ala Arg Trp Asn Lys Thr Ile Ile Met
                20                  25                  30

Pro Leu Leu Ile Gly Thr Ile Ala Lys Leu Leu Glu Cys Gly Val Lys
            35                  40                  45

Ala Ser Asn Ile Val Val Gln Ser Val Pro Gly Ser Trp Glu Leu Pro
    50                  55                  60

Ile Ala Val Gln Arg Leu Tyr Ser Ala Ser Gln Leu Gln Thr Pro Ser
65                  70                  75                  80
```

```
Ser Gly Pro Ser Leu Ser Ala Gly Asp Leu Gly Ser Ser Thr Thr
                85                  90                  95

Asp Leu Thr Ala Leu Pro Thr Thr Ala Ser Ser Thr Gly Pro Phe
               100                 105                 110

Asp Ala Leu Ile Ala Ile Gly Val Leu Ile Lys Gly Glu Thr Met His
               115                 120                 125

Phe Glu Tyr Ile Ala Asp Ser Val Ser His Gly Leu Met Arg Val Gln
           130                 135                 140

Leu Asp Thr Gly Val Pro Val Ile Phe Gly Val Leu Thr Val Leu Thr
145                 150                 155                 160

Asp Asp Gln Ala Lys Ala Arg Ala Gly Val Ile Glu Gly Ser His Asn
                165                 170                 175

His Gly Glu Asp Trp Gly Leu Ala Ala Val Glu Met Gly Val Arg Arg
            180                 185                 190

Arg Asp Trp Ala Ala Gly Lys Thr Glu
                195                 200

<210> SEQ ID NO 12
<211> LENGTH: 237
<212> TYPE: PRT
<213> ORGANISM: Artificial Sequence
<220> FEATURE:
<223> OTHER INFORMATION: synthetically constructed nanostructure
      polypeptide

<400> SEQUENCE: 12

Met Tyr Glu Val Asp His Ala Asp Val Tyr Asp Leu Phe Tyr Leu Gly
1               5                   10                  15

Arg Gly Lys Asp Tyr Ala Ala Glu Ala Ser Asp Ile Ala Asp Leu Val
                20                  25                  30

Arg Ser Arg Thr Pro Glu Ala Ser Ser Leu Leu Asp Val Ala Cys Gly
            35                  40                  45

Thr Gly Thr His Leu Glu His Phe Thr Lys Glu Phe Gly Asp Thr Ala
        50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Gln Leu Gly
                85                  90                  95

Arg Lys Phe Ser Ala Val Val Ser Met Phe Ser Ser Val Gly Tyr Leu
               100                 105                 110

Lys Thr Val Ala Glu Leu Gly Ala Ala Val Ala Ser Phe Ala Glu His
           115                 120                 125

Leu Glu Pro Gly Gly Val Val Val Glu Pro Trp Trp Phe Pro Glu
           130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Arg Glu Tyr
            195                 200                 205

Glu Ala Ala Phe Met Ala Ala Gly Leu Arg Val Glu Tyr Leu Glu Gly
        210                 215                 220

Gly Pro Ser Gly Arg Gly Leu Phe Val Gly Val Pro Ala
225                 230                 235
```

```
<210> SEQ ID NO 13
<211> LENGTH: 138
<212> TYPE: PRT
<213> ORGANISM: Artificial Sequence
<220> FEATURE:
<223> OTHER INFORMATION: synthetically constructed nanostructure
      polypeptide

<400> SEQUENCE: 13

Met Gly Met Lys Glu Lys Phe Val Leu Ile Ile Thr His Gly Asp Phe
1               5                   10                  15

Gly Lys Gly Leu Leu Ser Gly Ala Glu Val Ile Ile Gly Lys Gln Glu
            20                  25                  30

Asn Val His Thr Val Gly Leu Asn Leu Gly Asp Asn Ile Glu Lys Val
        35                  40                  45

Ala Lys Glu Val Met Arg Ile Ile Ala Lys Leu Ala Glu Asp Lys
    50                  55                  60

Glu Ile Ile Ile Val Val Asp Leu Phe Gly Gly Ser Pro Phe Asn Ile
65                  70                  75                  80

Ala Leu Glu Met Met Lys Thr Phe Asp Val Lys Val Ile Thr Gly Ile
                85                  90                  95

Asn Met Pro Met Leu Val Glu Leu Leu Thr Ser Ile Asn Val Tyr Asp
            100                 105                 110

Thr Thr Glu Leu Leu Glu Asn Ile Ser Lys Ile Gly Lys Asp Gly Ile
        115                 120                 125

Lys Val Ile Glu Lys Ser Ser Leu Lys Met
    130                 135

<210> SEQ ID NO 14
<211> LENGTH: 154
<212> TYPE: PRT
<213> ORGANISM: Artificial Sequence
<220> FEATURE:
<223> OTHER INFORMATION: synthetically constructed nanostructure
      polypeptide

<400> SEQUENCE: 14

Met Lys Tyr Asp Gly Ser Lys Leu Arg Ile Gly Ile Leu His Ala Arg
1               5                   10                  15

Trp Asn Leu Glu Ile Ile Ala Ala Leu Val Ala Gly Ala Ile Lys Arg
            20                  25                  30

Leu Gln Glu Phe Gly Val Lys Ala Glu Asn Ile Ile Glu Thr Val
        35                  40                  45

Pro Gly Ser Phe Glu Leu Pro Tyr Gly Ser Lys Leu Phe Val Glu Lys
    50                  55                  60

Gln Lys Arg Leu Gly Lys Pro Leu Asp Ala Ile Pro Ile Gly Val
65                  70                  75                  80

Leu Ile Lys Gly Ser Thr Met His Phe Glu Tyr Ile Cys Asp Ser Thr
                85                  90                  95

Thr His Gln Leu Met Lys Leu Asn Phe Glu Leu Gly Ile Pro Val Ile
            100                 105                 110

Phe Gly Val Leu Thr Cys Leu Thr Asp Glu Gln Ala Glu Ala Arg Ala
        115                 120                 125

Gly Leu Ile Glu Gly Lys Met His Asn His Gly Glu Asp Trp Gly Ala
    130                 135                 140

Ala Ala Val Glu Met Ala Thr Lys Phe Asn
145                 150
```

```
<210> SEQ ID NO 15
<211> LENGTH: 164
<212> TYPE: PRT
<213> ORGANISM: Artificial Sequence
<220> FEATURE:
<223> OTHER INFORMATION: synthetically constructed nanostructure
      polypeptide

<400> SEQUENCE: 15

Met Ala Val Lys Gly Leu Gly Glu Val Asp Gln Lys Tyr Asp Gly Ser
1               5                   10                  15

Lys Leu Arg Ile Gly Ile Leu His Ala Arg Trp Asn Arg Lys Ile Ile
            20                  25                  30

Leu Ala Leu Val Ala Gly Ala Val Leu Arg Leu Leu Glu Phe Gly Val
        35                  40                  45

Lys Ala Glu Asn Ile Ile Ile Glu Thr Val Pro Gly Ser Phe Glu Leu
    50                  55                  60

Pro Tyr Gly Ser Lys Leu Phe Val Glu Lys Gln Lys Arg Leu Gly Lys
65                  70                  75                  80

Pro Leu Asp Ala Ile Ile Pro Ile Gly Val Leu Ile Lys Gly Ser Thr
                85                  90                  95

Met His Phe Glu Tyr Ile Cys Asp Ser Thr Thr His Gln Leu Met Lys
            100                 105                 110

Leu Asn Phe Glu Leu Gly Ile Pro Val Ile Phe Gly Val Leu Thr Cys
        115                 120                 125

Leu Thr Asp Glu Gln Ala Glu Ala Arg Ala Gly Leu Ile Glu Gly Lys
    130                 135                 140

Met His Asn His Gly Glu Asp Trp Gly Ala Ala Ala Val Glu Met Ala
145                 150                 155                 160

Thr Lys Phe Asn

<210> SEQ ID NO 16
<211> LENGTH: 175
<212> TYPE: PRT
<213> ORGANISM: Artificial Sequence
<220> FEATURE:
<223> OTHER INFORMATION: synthetically constructed nanostructure
      polypeptide

<400> SEQUENCE: 16

Met Gly Ala Asn Trp Tyr Leu Asp Asn Glu Ser Ser Arg Leu Ser Phe
1               5                   10                  15

Thr Ser Thr Lys Asn Ala Asp Ile Ala Glu Val His Arg Phe Leu Val
            20                  25                  30

Leu His Gly Lys Val Asp Pro Lys Gly Leu Ala Glu Val Glu Val Glu
        35                  40                  45

Thr Glu Ser Ile Ser Thr Gly Ile Pro Leu Arg Asp Met Leu Leu Arg
    50                  55                  60

Val Leu Val Phe Gln Val Ser Lys Phe Pro Val Ala Gln Ile Asn Ala
65                  70                  75                  80

Gln Leu Asp Met Arg Pro Ile Asn Asn Leu Ala Pro Gly Ala Gln Leu
                85                  90                  95

Glu Leu Arg Leu Pro Leu Thr Val Ser Leu Arg Gly Lys Ser His Ser
            100                 105                 110

Tyr Asn Ala Glu Leu Leu Ala Thr Arg Leu Asp Glu Arg Arg Phe Gln
        115                 120                 125
```

Val Val Thr Leu Glu Pro Leu Val Ile His Ala Gln Asp Phe Asp Met
130                 135                 140

Val Arg Ala Phe Asn Ala Leu Arg Leu Val Ala Gly Leu Ser Ala Val
145                 150                 155                 160

Ser Leu Ser Val Pro Val Gly Ala Val Leu Ile Phe Thr Ala Arg
                165                 170                 175

<210> SEQ ID NO 17
<211> LENGTH: 208
<212> TYPE: PRT
<213> ORGANISM: Artificial Sequence
<220> FEATURE:
<223> OTHER INFORMATION: synthetically constructed nanostructure
      polypeptide

<400> SEQUENCE: 17

Met Thr Asp Tyr Ile Arg Asp Gly Ser Ala Ile Lys Ala Leu Ser Phe
1               5                   10                  15

Ala Ile Ile Leu Ala Glu Ala Asp Leu Arg His Ile Pro Gln Asp Leu
                20                  25                  30

Gln Arg Leu Ala Val Arg Val Ile His Ala Cys Gly Met Val Asp Val
            35                  40                  45

Ala Asn Asp Leu Ala Phe Ser Glu Gly Ala Gly Lys Ala Gly Arg Asn
50                  55                  60

Ala Leu Leu Ala Gly Ala Pro Ile Leu Cys Asp Ala Arg Met Val Ala
65                  70                  75                  80

Glu Gly Ile Thr Arg Ser Arg Leu Pro Ala Asp Asn Arg Val Ile Tyr
                85                  90                  95

Thr Leu Ser Asp Pro Ser Val Pro Glu Leu Ala Lys Lys Ile Gly Asn
                100                 105                 110

Thr Arg Ser Ala Ala Ala Leu Asp Leu Trp Leu Pro His Ile Glu Gly
            115                 120                 125

Ser Ile Val Ala Ile Gly Asn Ala Pro Thr Ala Leu Phe Arg Leu Phe
130                 135                 140

Glu Leu Leu Asp Ala Gly Ala Pro Lys Pro Ala Leu Ile Ile Gly Met
145                 150                 155                 160

Pro Val Gly Phe Val Gly Ala Ala Glu Ser Lys Asp Glu Leu Ala Ala
                165                 170                 175

Asn Ser Arg Gly Val Pro Tyr Val Ile Val Arg Gly Arg Gly Gly
            180                 185                 190

Ser Ala Met Thr Ala Ala Val Asn Ala Leu Ala Ser Glu Arg Glu
            195                 200                 205

<210> SEQ ID NO 18
<211> LENGTH: 128
<212> TYPE: PRT
<213> ORGANISM: Artificial Sequence
<220> FEATURE:
<223> OTHER INFORMATION: synthetically constructed nanostructure
      polypeptide

<400> SEQUENCE: 18

Met Ile Thr Val Phe Gly Leu Lys Ser Lys Leu Ala Pro Arg Arg Glu
1               5                   10                  15

Lys Leu Ala Glu Val Ile Tyr Ser Ser Leu His Leu Gly Leu Asp Ile
                20                  25                  30

Pro Lys Gly Lys His Ala Ile Arg Phe Leu Cys Leu Glu Lys Glu Asp
            35                  40                  45

```
Phe Tyr Tyr Pro Phe Asp Arg Ser Asp Asp Tyr Thr Val Ile Glu Ile
 50                  55                  60

Asn Leu Met Ala Gly Arg Ser Glu Glu Thr Lys Met Leu Leu Ile Phe
 65                  70                  75                  80

Leu Leu Phe Ile Ala Leu Glu Arg Lys Leu Gly Ile Arg Ala His Asp
                 85                  90                  95

Val Glu Ile Thr Ile Lys Glu Gln Pro Ala His Cys Trp Gly Phe Arg
                100                 105                 110

Gly Arg Thr Gly Asp Ser Ala Arg Asp Leu Asp Tyr Asp Ile Tyr Val
                115                 120                 125
```

<210> SEQ ID NO 19
<211> LENGTH: 235
<212> TYPE: PRT
<213> ORGANISM: Artificial Sequence
<220> FEATURE:
<223> OTHER INFORMATION: synthetically constructed nanostructure
     polypeptide

<400> SEQUENCE: 19

```
Met Gly Ser Asp Leu Gln Lys Leu Gln Arg Phe Ser Thr Cys Asp Ile
 1               5                  10                  15

Ser Asp Gly Leu Leu Asn Val Tyr Asn Ile Pro Thr Gly Gly Tyr Phe
                 20                  25                  30

Pro Asn Leu Thr Ala Ile Ser Pro Gln Asn Ser Ser Ile Val Gly
                 35                  40                  45

Thr Ala Tyr Thr Val Leu Phe Ala Pro Ile Asp Pro Arg Pro Ala
 50                  55                  60

Val Asn Tyr Ile Asp Ser Val Pro Pro Asn Ser Ile Leu Val Leu Ala
 65                  70                  75                  80

Leu Glu Pro His Leu Gln Ser Gln Phe His Pro Phe Ile Lys Ile Thr
                 85                  90                  95

Gln Ala Met Tyr Gly Gly Leu Met Ser Thr Arg Ala Gln Tyr Leu Lys
                100                 105                 110

Ser Asn Gly Thr Val Val Phe Gly Arg Ile Arg Asp Val Asp Glu His
                115                 120                 125

Arg Thr Leu Asn His Pro Val Phe Ala Tyr Gly Val Gly Ser Cys Ala
                130                 135                 140

Pro Lys Ala Val Val Lys Ala Val Gly Thr Asn Val Gln Leu Lys Ile
145                 150                 155                 160

Leu Thr Ser Asp Gly Val Thr Gln Thr Ile Cys Pro Gly Asp Tyr Ile
                165                 170                 175

Ala Gly Asp Asn Asn Gly Ile Val Arg Ile Pro Val Gln Glu Thr Asp
                180                 185                 190

Ile Ser Lys Leu Val Thr Tyr Ile Glu Lys Ser Ile Glu Val Asp Arg
                195                 200                 205

Leu Val Ser Glu Ala Ile Lys Asn Gly Leu Pro Ala Lys Ala Ala Gln
                210                 215                 220

Thr Ala Arg Arg Met Val Leu Lys Asp Tyr Ile
225                 230                 235
```

<210> SEQ ID NO 20
<211> LENGTH: 162
<212> TYPE: PRT
<213> ORGANISM: Artificial Sequence
<220> FEATURE:
<223> OTHER INFORMATION: synthetically constructed nanostructure
     polypeptide -continued

<400> SEQUENCE: 20

Met Ser Gly Met Arg Val Tyr Leu Gly Ala Asp His Ala Gly Tyr Glu
1               5                   10                  15

Leu Lys Gln Ala Ile Ile Ala Phe Leu Lys Met Thr Gly His Glu Pro
            20                  25                  30

Ile Asp Cys Gly Ala Leu Arg Tyr Asp Ala Asp Asp Tyr Pro Ala
        35                  40                  45

Phe Cys Ile Ala Ala Ala Thr Arg Thr Val Ala Asp Pro Gly Ser Leu
    50                  55                  60

Gly Ile Val Leu Gly Gly Ser Gly Asn Gly Glu Gln Ile Ala Ala Asn
65                  70                  75                  80

Lys Val Pro Gly Ala Arg Cys Ala Leu Ala Trp Ser Val Gln Thr Ala
                85                  90                  95

Ala Leu Ala Arg Glu His Asn Asn Ala Gln Leu Ile Gly Ile Gly Gly
            100                 105                 110

Arg Met His Thr Leu Glu Glu Ala Leu Arg Ile Val Lys Ala Phe Val
        115                 120                 125

Thr Thr Pro Trp Ser Lys Ala Gln Arg His Gln Arg Arg Ile Asp Ile
130                 135                 140

Leu Ala Glu Tyr Glu Arg Thr His Glu Ala Pro Pro Val Pro Gly Ala
145                 150                 155                 160

Pro Ala

<210> SEQ ID NO 21
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 21

Met Gly Asp Asp Ala Arg Ile Ala Ala Ile Gly Asp Val Asp Glu Leu
1               5                   10                  15

Asn Ser Gln Ile Gly Val Leu Leu Ala Glu Pro Leu Pro Asp Asp Val
            20                  25                  30

Arg Ala Ala Leu Ser Ala Ile Gln His Asp Leu Phe Asp Leu Gly Gly
        35                  40                  45

Glu Leu Cys Ile Pro Gly His Ala Ala Ile Thr Glu Asp His Leu Leu
    50                  55                  60

Arg Leu Ala Leu Trp Leu Val His Tyr Asn Gly Gln Leu Pro Pro Leu
65                  70                  75                  80

Glu Glu Phe Ile Leu Pro Gly Gly Ala Arg Gly Ala Ala Leu Ala His
                85                  90                  95

Val Cys Arg Thr Val Cys Arg Arg Ala Glu Arg Ser Ile Lys Ala Leu
            100                 105                 110

Gly Ala Ser Glu Pro Leu Asn Ile Ala Pro Ala Ala Tyr Val Asn Leu
        115                 120                 125

Leu Ser Asp Leu Leu Phe Val Leu Ala Arg Val Leu Asn Arg Ala Ala
    130                 135                 140

Gly Gly Ala Asp Val Leu Trp Asp Arg Thr Arg Ala His
145                 150                 155

<210> SEQ ID NO 22
<211> LENGTH: 157

```
<212> TYPE: PRT
<213> ORGANISM: Artificial Sequence
<220> FEATURE:
<223> OTHER INFORMATION: synthetically constructed nanostructure
      polypeptide

<400> SEQUENCE: 22

Met Ile Leu Ser Ala Glu Gln Ser Phe Thr Leu Arg His Pro His Gly
1               5                   10                  15

Gln Ala Ala Leu Ala Phe Val Arg Glu Pro Ala Ala Ala Leu Ala
            20                  25                  30

Gly Val Gln Arg Leu Arg Gly Leu Asp Ser Asp Gly Glu Gln Val Trp
        35                  40                  45

Gly Glu Leu Leu Val Arg Val Pro Leu Leu Gly Glu Val Asp Leu Pro
    50                  55                  60

Phe Arg Ser Glu Ile Val Arg Thr Pro Gln Gly Ala Glu Leu Arg Pro
65                  70                  75                  80

Leu Thr Leu Thr Gly Glu Arg Ala Trp Val Ala Val Ser Gly Gln Ala
                85                  90                  95

Thr Ala Ala Glu Gly Gly Glu Met Ala Phe Ala Phe Gln Phe Gln Ala
            100                 105                 110

His Leu Ala Thr Pro Glu Ala Glu Gly Glu Gly Gly Ala Ala Phe Glu
        115                 120                 125

Val Met Val Gln Ala Ala Ala Gly Val Thr Leu Leu Leu Val Ala Met
    130                 135                 140

Ala Leu Pro Gln Gly Leu Ala Ala Gly Leu Pro Pro Ala
145                 150                 155

<210> SEQ ID NO 23
<211> LENGTH: 156
<212> TYPE: PRT
<213> ORGANISM: Artificial Sequence
<220> FEATURE:
<223> OTHER INFORMATION: synthetically constructed nanostructure
      polypeptide

<400> SEQUENCE: 23

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Glu Gly Cys Asp Ile Val Met Ala Leu
    50                  55                  60

Gly Met Pro Gly Lys Lys Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155
```

<210> SEQ ID NO 24
<211> LENGTH: 209
<212> TYPE: PRT
<213> ORGANISM: Artificial Sequence
<220> FEATURE:
<223> OTHER INFORMATION: synthetically constructed nanostructure polypeptide

<400> SEQUENCE: 24

Met Asp Asp Ile Asn Asn Gln Leu Lys Arg Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
50                  55                  60

Ile Gly Ala Gly Thr Ile Leu Asn Gly Val Gln Ala Leu Ala Ala Lys
65                  70                  75                  80

Glu Ala Gly Ala Asp Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Gln Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Asp Asn Ile Asp Asn Tyr Leu Ala Ile Pro Gln Val Leu Ala
                165                 170                 175

Cys Gly Gly Thr Trp Met Val Asp Lys Lys Leu Val Arg Asn Gly Glu
            180                 185                 190

Trp Asp Glu Ile Ala Arg Leu Thr Arg Glu Ile Val Glu Gln Val Asn
        195                 200                 205

Pro

<210> SEQ ID NO 25
<211> LENGTH: 114
<212> TYPE: PRT
<213> ORGANISM: Artificial Sequence
<220> FEATURE:
<223> OTHER INFORMATION: synthetically constructed nanostructure polypeptide

<400> SEQUENCE: 25

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Asp Lys Asn Arg Asp His Ser Ala Val Leu
65                  70                  75                  80

Phe Asp His Leu Asn Ala Met Leu Gly Ile Pro Lys Asn Arg Met Tyr

```
                    85                  90                  95

Ile His Phe Val Asn Leu Asn Gly Asp Asp Val Gly Trp Asn Gly Thr
                100                 105                 110

Thr Phe

<210> SEQ ID NO 26
<211> LENGTH: 114
<212> TYPE: PRT
<213> ORGANISM: Artificial Sequence
<220> FEATURE:
<223> OTHER INFORMATION: synthetically constructed nanostructure
      polypeptide

<400> SEQUENCE: 26

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
                20                  25                  30

Glu Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Asp Lys Asn Glu Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asp Leu Asp Gly Asp Asp Val Gly Trp Asn Gly Thr
                100                 105                 110

Thr Phe

<210> SEQ ID NO 27
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 27

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
            35                  40                  45

Val Phe Asp Val Pro Gly Ala Tyr Glu Ile Pro Leu His Ala Arg Thr
        50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
                100                 105                 110

Ala Val Leu Thr Pro His Arg Tyr Arg Asp Ser Asp Glu His His Arg
            115                 120                 125

Phe Phe Ala Ala His Phe Ala Val Lys Gly Val Glu Ala Ala Arg Ala
        130                 135                 140
```

Cys Ile Glu Ile Leu Asn Ala Arg Glu Lys Ile Ala Ala
145                 150                 155

<210> SEQ ID NO 28
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 28

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
                35                  40                  45

Val Phe Asp Val Pro Gly Ala Tyr Glu Ile Pro Leu His Ala Arg Thr
            50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                    85                  90                  95

Asp Gly Met Met Asn Val Gln Leu Asp Thr Gly Val Pro Val Leu Ser
                100                 105                 110

Ala Val Leu Thr Pro His Glu Tyr Glu Asp Ser Asp Glu Asp His Glu
                115                 120                 125

Phe Phe Ala Ala His Phe Ala Val Lys Gly Val Glu Ala Ala Arg Ala
130                 135                 140

Cys Ile Glu Ile Leu Asn Ala Arg Glu Lys Ile Ala Ala
145                 150                 155

<210> SEQ ID NO 29
<211> LENGTH: 205
<212> TYPE: PRT
<213> ORGANISM: Artificial Sequence
<220> FEATURE:
<223> OTHER INFORMATION: synthetically constructed nanostructure
      polypeptide

<400> SEQUENCE: 29

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
                35                  40                  45

Asp Thr Val Ile Lys Ala Leu Ser Val Leu Lys Glu Lys Gly Ala Ile
            50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                    85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Asp Ile Leu
                115                 120                 125

```
Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Val Arg Glu Lys
                180                 185                 190

Ala Lys Lys Phe Val Glu Lys Ile Arg Gly Cys Thr Glu
        195                 200                 205

<210> SEQ ID NO 30
<211> LENGTH: 205
<212> TYPE: PRT
<213> ORGANISM: Artificial Sequence
<220> FEATURE:
<223> OTHER INFORMATION: synthetically constructed nanostructure
      polypeptide

<400> SEQUENCE: 30

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Asp Ile Leu
            115                 120                 125

Lys Leu Phe Pro Gly Glu Val Val Gly Pro Glu Phe Val Glu Ala Met
        130                 135                 140

Lys Gly Pro Phe Pro Asn Val Lys Phe Val Pro Thr Gly Gly Val Asp
145                 150                 155                 160

Leu Asp Asp Val Cys Glu Trp Phe Asp Ala Gly Val Leu Ala Val Gly
                165                 170                 175

Val Gly Asp Ala Leu Val Glu Gly Asp Pro Asp Glu Val Arg Glu Asp
                180                 185                 190

Ala Lys Glu Phe Val Glu Glu Ile Arg Gly Cys Thr Glu
        195                 200                 205

<210> SEQ ID NO 31
<211> LENGTH: 205
<212> TYPE: PRT
<213> ORGANISM: Artificial Sequence
<220> FEATURE:
<223> OTHER INFORMATION: synthetically constructed nanostructure
      polypeptide

<400> SEQUENCE: 31

Met Lys Met Glu Glu Leu Phe Lys Lys His Lys Ile Val Ala Val Leu
1               5                   10                  15
```

```
Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Lys Trp Phe Lys Ala Gly Val Leu Ala Val Gly
                165                 170                 175

Val Gly Lys Ala Leu Val Lys Gly Lys Pro Asp Glu Val Arg Glu Lys
            180                 185                 190

Ala Lys Lys Phe Val Lys Lys Ile Arg Gly Cys Thr Glu
        195                 200                 205

<210> SEQ ID NO 32
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 32

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 33
```

-continued

```
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 33

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Ala Asp Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 34
<211> LENGTH: 157
<212> TYPE: PRT
<213> ORGANISM: Artificial Sequence
<220> FEATURE:
<223> OTHER INFORMATION: synthetically constructed nanostructure
      polypeptide

<400> SEQUENCE: 34

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155
```

<210> SEQ ID NO 35
<211> LENGTH: 156
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (70)..(70)
<223> OTHER INFORMATION: Xaa is Ala or Lys

<400> SEQUENCE: 35

```
Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Glu Gly Cys Asp Ile Val Met Ala Leu
    50                  55                  60

Gly Met Pro Gly Lys Xaa Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155
```

<210> SEQ ID NO 36
<211> LENGTH: 209
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (2)..(2)
<223> OTHER INFORMATION: Xaa is Ser or Asp
<220> FEATURE:
<221> NAME/KEY: misc_feature
<222> LOCATION: (3)..(3)
<223> OTHER INFORMATION: Xaa is Thr or Asp
<220> FEATURE:
<221> NAME/KEY: misc_feature
<222> LOCATION: (10)..(10)
<223> OTHER INFORMATION: Xaa is Ala or Arg
<220> FEATURE:
<221> NAME/KEY: misc_feature
<222> LOCATION: (85)..(85)
<223> OTHER INFORMATION: Xaa is Thr or Asp
<220> FEATURE:
<221> NAME/KEY: misc_feature
<222> LOCATION: (119)..(119)
<223> OTHER INFORMATION: Xaa is Ala or Gln
<220> FEATURE:
<221> NAME/KEY: misc_feature
<222> LOCATION: (163)..(163)
<223> OTHER INFORMATION: Xaa is Ser or Asp
<220> FEATURE:

<221> NAME/KEY: misc_feature
<222> LOCATION: (189)..(189)
<223> OTHER INFORMATION: Xaa is Thr or Arg

<400> SEQUENCE: 36

```
Met Xaa Xaa Ile Asn Asn Gln Leu Lys Xaa Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Xaa Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Xaa Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Xaa Asn Ile Asp Asn Tyr Leu Ala Ile Pro Gln Val Leu Ala
                165                 170                 175

Cys Gly Gly Thr Trp Met Val Asp Lys Lys Leu Val Xaa Asn Gly Glu
            180                 185                 190

Trp Asp Glu Ile Ala Arg Leu Thr Arg Glu Ile Val Glu Gln Val Asn
        195                 200                 205

Pro
```

<210> SEQ ID NO 37
<211> LENGTH: 114
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (13)..(13)
<223> OTHER INFORMATION: Xaa is Thr or Asp
<220> FEATURE:
<221> NAME/KEY: misc_feature
<222> LOCATION: (33)..(33)
<223> OTHER INFORMATION: Xaa is Lys or Glu
<220> FEATURE:
<221> NAME/KEY: misc_feature
<222> LOCATION: (71)..(71)
<223> OTHER INFORMATION: Xaa is Ser or Asp
<220> FEATURE:
<221> NAME/KEY: misc_feature
<222> LOCATION: (74)..(74)
<223> OTHER INFORMATION: Xaa is Arg or Glu
<220> FEATURE:
<221> NAME/KEY: misc_feature
<222> LOCATION: (101)..(101)
<223> OTHER INFORMATION: Xaa is Asn or Asp
<220> FEATURE:
<221> NAME/KEY: misc_feature
<222> LOCATION: (103)..(103)
<223> OTHER INFORMATION: Xaa is Asn or Asp

<400> SEQUENCE: 37

Met Pro Ile Phe Thr Leu Asn Thr Asn Ile Lys Ala Xaa Asp Val Pro
1               5                   10                  15

Ser Asp Phe Leu Ser Leu Thr Ser Arg Leu Val Gly Leu Ile Leu Ser
            20                  25                  30

Xaa Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Xaa Lys Asn Xaa Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Xaa Leu Xaa Gly Asp Asp Val Gly Trp Asn Gly Thr
                100                 105                 110

Thr Phe

<210> SEQ ID NO 38
<211> LENGTH: 157
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (9)..(9)
<223> OTHER INFORMATION: Xaa is Tyr or His
<220> FEATURE:
<221> NAME/KEY: misc_feature
<222> LOCATION: (82)..(82)
<223> OTHER INFORMATION: Xaa is Asn or Asp
<220> FEATURE:
<221> NAME/KEY: misc_feature
<222> LOCATION: (87)..(87)
<223> OTHER INFORMATION: Xaa is Arg or Asp
<220> FEATURE:
<221> NAME/KEY: misc_feature
<222> LOCATION: (105)..(105)
<223> OTHER INFORMATION: Xaa is Ser or Asp
<220> FEATURE:
<221> NAME/KEY: misc_feature
<222> LOCATION: (119)..(119)
<223> OTHER INFORMATION: Xaa is Arg or Glu
<220> FEATURE:
<221> NAME/KEY: misc_feature
<222> LOCATION: (121)..(121)
<223> OTHER INFORMATION: Xaa is Arg or Glu
<220> FEATURE:
<221> NAME/KEY: misc_feature
<222> LOCATION: (124)..(124)
<223> OTHER INFORMATION: Xaa is Ala or Asp
<220> FEATURE:
<221> NAME/KEY: misc_feature
<222> LOCATION: (126)..(126)
<223> OTHER INFORMATION: Xaa is His or Asp
<220> FEATURE:
<221> NAME/KEY: misc_feature
<222> LOCATION: (128)..(128)
<223> OTHER INFORMATION: Xaa is Arg or Glu
<220> FEATURE:
<221> NAME/KEY: misc_feature
<222> LOCATION: (150)..(150)
<223> OTHER INFORMATION: Xaa is Ala or Asn

<400> SEQUENCE: 38

Met Asn Gln His Ser His Lys Asp Xaa Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Asp Gly Met Met Asn Val Gln Leu Xaa Thr Gly Val Pro Val Leu Ser
            100                 105                 110

Ala Val Leu Thr Pro His Xaa Tyr Xaa Asp Ser Xaa Glu Xaa His Xaa
        115                 120                 125

Phe Phe Ala Ala His Phe Ala Val Lys Gly Val Glu Ala Ala Arg Ala
    130                 135                 140

Cys Ile Glu Ile Leu Xaa Ala Arg Glu Lys Ile Ala Ala
145                 150                 155

```
<210> SEQ ID NO 39
<211> LENGTH: 205
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (126)..(126)
<223> OTHER INFORMATION: Xaa is Thr or Asp
<220> FEATURE:
<221> NAME/KEY: misc_feature
<222> LOCATION: (139)..(139)
<223> OTHER INFORMATION: Xaa is Gln or Glu
<220> FEATURE:
<221> NAME/KEY: misc_feature
<222> LOCATION: (142)..(142)
<223> OTHER INFORMATION: Xaa is Lys or Glu
<220> FEATURE:
<221> NAME/KEY: misc_feature
<222> LOCATION: (160)..(160)
<223> OTHER INFORMATION: Xaa is Asn or Asp
<220> FEATURE:
<221> NAME/KEY: misc_feature
<222> LOCATION: (163)..(163)
<223> OTHER INFORMATION: Xaa is Asn or Asp
<220> FEATURE:
<221> NAME/KEY: misc_feature
<222> LOCATION: (166)..(166)
<223> OTHER INFORMATION: Xaa is Glu or Lys
<220> FEATURE:
<221> NAME/KEY: misc_feature
<222> LOCATION: (169)..(169)
<223> OTHER INFORMATION: Xaa is Lys or Asp
<220> FEATURE:
<221> NAME/KEY: misc_feature
<222> LOCATION: (179)..(179)
<223> OTHER INFORMATION: Xaa is Ser, Lys or Asp
<220> FEATURE:
<221> NAME/KEY: misc_feature
<222> LOCATION: (183)..(183)
<223> OTHER INFORMATION: Xaa is Lys or Glu
<220> FEATURE:
<221> NAME/KEY: misc_feature
<222> LOCATION: (185)..(185)
<223> OTHER INFORMATION: Xaa is Thr, Asp or Lys
<220> FEATURE:
<221> NAME/KEY: misc_feature
<222> LOCATION: (192)..(192)
```

```
<223> OTHER INFORMATION: Xaa is Lys or Asp
<220> FEATURE:
<221> NAME/KEY: misc_feature
<222> LOCATION: (195)..(195)
<223> OTHER INFORMATION: Xaa is Ala, Glu or Lys
<220> FEATURE:
<221> NAME/KEY: misc_feature
<222> LOCATION: (198)..(198)
<223> OTHER INFORMATION: Xaa is Glu or Lys
<220> FEATURE:
<221> NAME/KEY: misc_feature
<222> LOCATION: (199)..(199)
<223> OTHER INFORMATION: Xaa is Lys or Glu

<400> SEQUENCE: 39

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Xaa Ile Leu
        115                 120                 125

Lys Leu Phe Pro Gly Glu Val Val Gly Pro Xaa Phe Val Xaa Ala Met
    130                 135                 140

Lys Gly Pro Phe Pro Asn Val Lys Phe Val Pro Thr Gly Gly Val Xaa
145                 150                 155                 160

Leu Asp Xaa Val Cys Xaa Trp Phe Xaa Ala Gly Val Leu Ala Val Gly
                165                 170                 175

Val Gly Xaa Ala Leu Val Xaa Gly Xaa Pro Asp Glu Val Arg Glu Xaa
            180                 185                 190

Ala Lys Xaa Phe Val Xaa Xaa Ile Arg Gly Cys Thr Glu
        195                 200                 205

<210> SEQ ID NO 40
<211> LENGTH: 157
<212> TYPE: PRT
<213> ORGANISM: Artificial Sequence
<220> FEATURE:
<223> OTHER INFORMATION: synthetically constructed nanostructure
      polypeptide
<220> FEATURE:
<221> NAME/KEY: misc_feature
<222> LOCATION: (9)..(9)
<223> OTHER INFORMATION: Xaa is Tyr or His
<220> FEATURE:
<221> NAME/KEY: misc_feature
<222> LOCATION: (38)..(38)
<223> OTHER INFORMATION: Xaa is Ala or Arg
<220> FEATURE:
<221> NAME/KEY: misc_feature
<222> LOCATION: (82)..(82)
<223> OTHER INFORMATION: Xaa is Asn or Asp
<220> FEATURE:
<221> NAME/KEY: misc_feature
<222> LOCATION: (87)..(87)
<223> OTHER INFORMATION: Xaa is Arg or Asp
```

```
<220> FEATURE:
<221> NAME/KEY: misc_feature
<222> LOCATION: (97)..(97)
<223> OTHER INFORMATION: Xaa is Asp or Asn
<220> FEATURE:
<221> NAME/KEY: misc_feature
<222> LOCATION: (105)..(105)
<223> OTHER INFORMATION: Xaa is Ser, Asp or Asn
<220> FEATURE:
<221> NAME/KEY: misc_feature
<222> LOCATION: (119)..(119)
<223> OTHER INFORMATION: Xaa is Arg, Glu or Asn
<220> FEATURE:
<221> NAME/KEY: misc_feature
<222> LOCATION: (121)..(121)
<223> OTHER INFORMATION: Xaa is Arg, Asp or Glu
<220> FEATURE:
<221> NAME/KEY: misc_feature
<222> LOCATION: (122)..(122)
<223> OTHER INFORMATION: Xaa is Asp or Lys
<220> FEATURE:
<221> NAME/KEY: misc_feature
<222> LOCATION: (124)..(124)
<223> OTHER INFORMATION: Xaa is Asp or Lys
<220> FEATURE:
<221> NAME/KEY: misc_feature
<222> LOCATION: (126)..(126)
<223> OTHER INFORMATION: Xaa is His or Asp

<400> SEQUENCE: 40

Met Asn Gln His Ser His Lys Asp Xaa Glu Thr Val Arg Ile Ala Val
1               5                   10                  15

Val Arg Ala Arg Trp His Ala Glu Ile Val Asp Ala Cys Val Ser Ala
                20                  25                  30

Phe Glu Ala Ala Met Xaa Asp Ile Gly Gly Asp Arg Phe Ala Val Asp
            35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Xaa Gly Met Met Asn Val Gln Leu Xaa Thr Gly Val Pro Val Leu Ser
            100                 105                 110

Ala Val Leu Thr Pro His Xaa Tyr Xaa Xaa Ser Xaa Ala Xaa Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 41
<211> LENGTH: 159
<212> TYPE: PRT
<213> ORGANISM: Artificial Sequence
<220> FEATURE:
<223> OTHER INFORMATION: synthetically constructed nanostructure
      polypeptide

<400> SEQUENCE: 41

Met Gly Glu Val Pro Ile Gly Asp Pro Lys Glu Leu Asn Gly Met Glu
1               5                   10                  15

Ile Ala Ala Val Tyr Leu Gln Pro Ile Glu Met Glu Pro Arg Gly Ile
                20                  25                  30

Asp Leu Ala Ala Ser Leu Ala Asp Ile His Leu Glu Ala Asp Ile His
```

```
                    35                  40                  45
Ala Leu Lys Asn Asn Pro Asn Gly Phe Pro Glu Gly Phe Trp Met Pro
 50                  55                  60

Tyr Leu Thr Ile Ala Tyr Ala Leu Ala Asn Ala Asp Thr Gly Ala Ile
 65                  70                  75                  80

Lys Thr Gly Thr Leu Met Pro Met Val Ala Asp Asp Gly Pro His Tyr
                 85                  90                  95

Gly Ala Asn Ile Ala Met Glu Lys Asp Lys Lys Gly Gly Phe Gly Val
                100                 105                 110

Gly Thr Tyr Ala Leu Thr Phe Leu Ile Ser Asn Pro Glu Lys Gln Gly
                115                 120                 125

Phe Gly Arg His Val Asp Glu Glu Thr Gly Val Gly Lys Trp Phe Glu
130                 135                 140

Pro Phe Val Val Thr Tyr Phe Phe Lys Tyr Thr Gly Thr Pro Lys
145                 150                 155
```

<210> SEQ ID NO 42
<211> LENGTH: 184
<212> TYPE: PRT
<213> ORGANISM: Artificial Sequence
<220> FEATURE:
<223> OTHER INFORMATION: synthetically constructed nanostructure
      polypeptide

<400> SEQUENCE: 42

```
Met Ser Gln Ala Ile Gly Ile Leu Glu Leu Thr Ser Ile Ala Lys Gly
 1               5                  10                  15

Met Glu Leu Gly Asp Ala Met Leu Lys Ser Ala Asn Val Asp Leu Leu
                 20                  25                  30

Val Ser Lys Thr Ile Ser Pro Gly Lys Phe Leu Leu Met Leu Gly Gly
                 35                  40                  45

Asp Ile Gly Ala Ile Gln Gln Ala Ile Glu Thr Gly Thr Ser Gln Ala
 50                  55                  60

Gly Glu Met Leu Val Asp Ser Leu Val Leu Ala Asn Ile His Pro Ser
 65                  70                  75                  80

Val Leu Pro Ala Ile Ser Gly Leu Asn Ser Val Asp Lys Arg Gln Ala
                 85                  90                  95

Val Gly Ile Val Glu Thr Trp Ser Val Ala Ala Cys Ile Ser Ala Ala
                100                 105                 110

Asp Leu Ala Val Lys Gly Ser Asn Val Thr Leu Val Arg Val His Met
                115                 120                 125

Ala Phe Gly Ile Gly Gly Lys Cys Tyr Met Val Val Ala Gly Asp Val
                130                 135                 140

Leu Asp Val Ala Ala Ala Val Ala Thr Ala Ser Leu Ala Ala Gly Ala
145                 150                 155                 160

Lys Gly Leu Leu Val Tyr Ala Ser Ile Ile Pro Arg Pro His Glu Ala
                165                 170                 175

Met Trp Arg Gln Met Val Glu Gly
                180
```

<210> SEQ ID NO 43
<211> LENGTH: 103
<212> TYPE: PRT
<213> ORGANISM: Artificial Sequence
<220> FEATURE:
<223> OTHER INFORMATION: synthetically constructed nanostructure
      polypeptide -continued

<400> SEQUENCE: 43

Met Glu Glu Val Val Leu Ile Thr Val Pro Ser Ala Leu Val Ala Val
1               5                   10                  15

Lys Ile Ala His Ala Leu Val Glu Glu Arg Leu Ala Ala Cys Val Asn
            20                  25                  30

Ile Val Pro Gly Leu Thr Ser Ile Tyr Arg Trp Gln Gly Ser Val Val
        35                  40                  45

Ser Asp His Glu Leu Leu Leu Val Lys Thr Thr Thr His Ala Phe
    50                  55                  60

Pro Lys Leu Lys Glu Arg Val Lys Ala Leu His Pro Tyr Thr Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly
            100

<210> SEQ ID NO 44
<211> LENGTH: 122
<212> TYPE: PRT
<213> ORGANISM: Artificial Sequence
<220> FEATURE:
<223> OTHER INFORMATION: synthetically constructed nanostructure
      polypeptide

<400> SEQUENCE: 44

Met Val Arg Gly Ile Arg Gly Ala Ile Thr Val Glu Glu Asp Thr Pro
1               5                   10                  15

Ala Ala Ile Leu Ala Ala Thr Ile Glu Leu Leu Leu Lys Met Leu Glu
            20                  25                  30

Ala Asn Gly Ile Gln Ser Tyr Glu Glu Leu Ala Ala Val Ile Phe Thr
        35                  40                  45

Val Thr Glu Asp Leu Thr Ser Ala Phe Pro Ala Glu Ala Ala Arg Leu
    50                  55                  60

Ile Gly Met His Arg Val Pro Leu Leu Ser Ala Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Asn Glu Ala Val
            100                 105                 110

Arg Leu Arg Pro Asp Leu Glu Ser Ala Gln
        115                 120

<210> SEQ ID NO 45
<211> LENGTH: 177
<212> TYPE: PRT
<213> ORGANISM: Artificial Sequence
<220> FEATURE:
<223> OTHER INFORMATION: synthetically constructed nanostructure
      polypeptide

<400> SEQUENCE: 45

Met Ser Lys Ala Lys Ile Gly Ile Val Thr Val Ser Asp Arg Ala Ser
1               5                   10                  15

Ala Gly Ile Thr Ala Asp Ile Ser Gly Lys Ala Ile Ile Leu Ala Leu
            20                  25                  30

Asn Leu Tyr Leu Thr Ser Glu Trp Glu Pro Ile Tyr Gln Val Ile Pro
        35                  40                  45

Asp Glu Gln Asp Val Ile Glu Thr Thr Leu Ile Lys Met Ala Asp Glu

```
                    50                  55                  60

Gln Asp Cys Cys Leu Ile Val Thr Thr Gly Gly Thr Gly Pro Ala Lys
65                  70                  75                  80

Arg Asp Val Thr Pro Glu Ala Thr Glu Ala Val Cys Asp Arg Met Met
                85                  90                  95

Pro Gly Phe Gly Glu Leu Met Arg Ala Glu Ser Leu Lys Glu Val Pro
            100                 105                 110

Thr Ala Ile Leu Ser Arg Gln Thr Ala Gly Leu Arg Gly Asp Ser Leu
        115                 120                 125

Ile Val Asn Leu Pro Gly Asp Pro Ala Ser Ile Ser Asp Cys Leu Leu
    130                 135                 140

Ala Val Phe Pro Ala Ile Pro Tyr Cys Ile Asp Leu Met Glu Gly Pro
145                 150                 155                 160

Tyr Leu Glu Cys Asn Glu Ala Met Ile Lys Pro Phe Arg Pro Lys Ala
                165                 170                 175

Lys

<210> SEQ ID NO 46
<211> LENGTH: 122
<212> TYPE: PRT
<213> ORGANISM: Artificial Sequence
<220> FEATURE:
<223> OTHER INFORMATION: synthetically constructed nanostructure
      polypeptide

<400> SEQUENCE: 46

Met Val Arg Gly Ile Arg Gly Ala Ile Thr Val Asn Ser Asp Thr Pro
1               5                   10                  15

Thr Ser Ile Ile Ile Ala Thr Ile Leu Leu Leu Glu Lys Met Leu Glu
            20                  25                  30

Ala Asn Gly Ile Gln Ser Tyr Glu Glu Leu Ala Ala Val Ile Phe Thr
        35                  40                  45

Val Thr Glu Asp Leu Thr Ser Ala Phe Pro Ala Glu Ala Ala Arg Gln
    50                  55                  60

Ile Gly Met His Arg Val Pro Leu Leu Ser Ala Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Ser Glu Ala Val
            100                 105                 110

Arg Leu Arg Pro Asp Leu Glu Ser Ala Gln
        115                 120

<210> SEQ ID NO 47
<211> LENGTH: 172
<212> TYPE: PRT
<213> ORGANISM: Artificial Sequence
<220> FEATURE:
<223> OTHER INFORMATION: synthetically constructed nanostructure
      polypeptide

<400> SEQUENCE: 47

Met Arg Ile Thr Thr Lys Val Gly Asp Lys Gly Ser Thr Arg Leu Phe
1               5                   10                  15

Gly Gly Glu Glu Val Trp Lys Asp Ser Pro Ile Ile Glu Ala Asn Gly
            20                  25                  30

Thr Leu Asp Glu Leu Thr Ser Phe Ile Gly Glu Ala Lys His Tyr Val
        35                  40                  45
```

```
Asp Glu Glu Met Lys Gly Ile Leu Glu Glu Ile Gln Asn Asp Ile Tyr
            50                  55                  60

Lys Ile Met Gly Glu Ile Gly Ser Lys Gly Lys Ile Glu Gly Ile Ser
 65                  70                  75                  80

Glu Glu Arg Ile Ala Trp Leu Leu Lys Leu Ile Leu Arg Tyr Met Glu
                85                  90                  95

Met Val Asn Leu Lys Ser Phe Val Leu Pro Gly Gly Thr Leu Glu Ser
            100                 105                 110

Ala Lys Leu Asp Val Cys Arg Thr Ile Ala Arg Arg Ala Leu Arg Lys
        115                 120                 125

Val Leu Thr Val Thr Arg Glu Phe Gly Ile Gly Ala Glu Ala Ala Ala
    130                 135                 140

Tyr Leu Ala Leu Ser Asp Leu Leu Phe Leu Ala Arg Val Ile
145                 150                 155                 160

Glu Ile Glu Lys Asn Lys Leu Lys Glu Val Arg Ser
                165                 170

<210> SEQ ID NO 48
<211> LENGTH: 123
<212> TYPE: PRT
<213> ORGANISM: Artificial Sequence
<220> FEATURE:
<223> OTHER INFORMATION: synthetically constructed nanostructure
      polypeptide

<400> SEQUENCE: 48

Met Pro His Leu Val Ile Glu Ala Thr Ala Asn Leu Arg Leu Glu Thr
 1               5                  10                  15

Ser Pro Gly Glu Leu Leu Glu Gln Ala Asn Lys Ala Leu Phe Ala Ser
                20                  25                  30

Gly Gln Phe Gly Glu Ala Asp Ile Lys Ser Arg Phe Val Thr Leu Glu
            35                  40                  45

Ala Tyr Arg Gln Gly Thr Ala Ala Val Glu Arg Ala Tyr Leu His Ala
        50                  55                  60

Cys Leu Ser Ile Leu Asp Gly Arg Asp Ile Ala Thr Arg Thr Leu Leu
 65                  70                  75                  80

Gly Ala Ser Leu Cys Ala Val Leu Ala Glu Ala Val Ala Gly Gly Gly
                85                  90                  95

Glu Glu Gly Val Gln Val Ser Val Glu Val Arg Glu Met Glu Arg Leu
            100                 105                 110

Ser Tyr Ala Lys Arg Val Val Ala Arg Gln Arg
        115                 120

<210> SEQ ID NO 49
<211> LENGTH: 158
<212> TYPE: PRT
<213> ORGANISM: Artificial Sequence
<220> FEATURE:
<223> OTHER INFORMATION: synthetically constructed nanostructure
      polypeptide

<400> SEQUENCE: 49

Met Glu Ser Val Asn Thr Ser Phe Leu Ser Pro Ser Leu Val Thr Ile
 1               5                  10                  15

Arg Asp Phe Asp Asn Gly Gln Phe Ala Val Leu Arg Ile Gly Arg Thr
                20                  25                  30

Gly Phe Pro Ala Asp Lys Gly Asp Ile Asp Leu Cys Leu Asp Lys Met
            35                  40                  45
```

```
Ile Gly Val Arg Ala Ala Gln Ile Phe Leu Gly Asp Asp Thr Glu Asp
        50                  55                  60

Gly Phe Lys Gly Pro His Ile Arg Ile Arg Cys Val Asp Ile Asp Asp
65                  70                  75                  80

Lys His Thr Tyr Asn Ala Met Val Tyr Val Asp Leu Ile Val Gly Thr
                85                  90                  95

Gly Ala Ser Glu Val Glu Arg Glu Thr Ala Glu Glu Ala Lys Leu
            100                 105                 110

Ala Leu Arg Val Ala Leu Gln Val Asp Ile Ala Asp Glu His Ser Cys
        115                 120                 125

Val Thr Gln Phe Glu Met Lys Leu Arg Glu Glu Leu Leu Ser Ser Asp
    130                 135                 140

Ser Phe His Pro Asp Lys Asp Glu Tyr Tyr Lys Asp Phe Leu
145                 150                 155

<210> SEQ ID NO 50
<211> LENGTH: 113
<212> TYPE: PRT
<213> ORGANISM: Artificial Sequence
<220> FEATURE:
<223> OTHER INFORMATION: synthetically constructed nanostructure
      polypeptide

<400> SEQUENCE: 50

Met Pro Val Ile Gln Thr Phe Val Ser Thr Pro Leu Asp His His Lys
1               5                   10                  15

Arg Leu Leu Leu Ala Ile Ile Tyr Arg Ile Val Thr Arg Val Val Leu
            20                  25                  30

Gly Lys Pro Glu Asp Leu Val Met Met Thr Phe His Asp Ser Thr Pro
        35                  40                  45

Met His Phe Phe Gly Ser Thr Asp Pro Val Ala Cys Val Arg Val Glu
    50                  55                  60

Ala Leu Gly Gly Tyr Gly Pro Ser Glu Pro Lys Val Thr Ser Ile
65                  70                  75                  80

Val Thr Ala Ala Ile Thr Ala Val Cys Gly Ile Val Ala Asp Arg Ile
                85                  90                  95

Phe Val Leu Tyr Phe Ser Pro Leu His Cys Gly Trp Asn Gly Thr Asn
            100                 105                 110

Phe

<210> SEQ ID NO 51
<211> LENGTH: 103
<212> TYPE: PRT
<213> ORGANISM: Artificial Sequence
<220> FEATURE:
<223> OTHER INFORMATION: synthetically constructed nanostructure
      polypeptide

<400> SEQUENCE: 51

Met Glu Glu Val Val Leu Ile Thr Val Pro Ser Ala Leu Val Ala Val
1               5                   10                  15

Lys Ile Ala His Ala Leu Val Glu Glu Arg Leu Ala Ala Cys Val Asn
            20                  25                  30

Ile Val Pro Gly Leu Thr Ser Ile Tyr Arg Glu Glu Gly Ser Val Val
        35                  40                  45

Ser Asp His Glu Leu Leu Leu Leu Val Lys Thr Thr Thr Asp Ala Phe
    50                  55                  60
```

```
Pro Lys Leu Lys Glu Arg Val Lys Glu Leu His Pro Tyr Glu Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly
            100

<210> SEQ ID NO 52
<211> LENGTH: 869
<212> TYPE: PRT
<213> ORGANISM: Human immunodeficiency virus 1

<400> SEQUENCE: 52

Met Arg Val Lys Gly Ile Lys Lys Asn Tyr Gln His Trp Trp Arg Gly
1               5                   10                  15

Gly Ile Met Leu Leu Gly Met Leu Met Ile Cys Ser Ser Ala Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Gln Asn Pro Glu Met
    50                  55                  60

His Asn Ile Trp Ala Thr His Ala Cys Val Pro Thr Asp Pro Asn Pro
65                  70                  75                  80

Gln Glu Val Ile Leu Lys Asn Leu Thr Glu Glu Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Glu Ser Leu Asn Cys Thr Ala Thr Asn Gly Thr
    130                 135                 140

Asn Asn Cys Ser Ala Ser Thr Lys Pro Met Glu Glu Met Lys Asn Cys
145                 150                 155                 160

Ser Phe Asn Ile Thr Thr Ser Val Gln Asp Lys Lys Gln Gln Glu Tyr
                165                 170                 175

Ala Leu Phe Tyr Lys Leu Asp Ile Ile Pro Ile Asp Asn Asn Glu Asn
            180                 185                 190

Asp Leu Asn Asn Thr Asn Tyr Thr Ser Tyr Arg Leu Ile Ser Cys Asn
        195                 200                 205

Thr Ser Val Ile Thr Gln Ala Cys Pro Lys Ile Thr Phe Glu Pro Ile
    210                 215                 220

Pro Ile His Tyr Cys Ala Pro Ala Gly Phe Ala Ile Leu Lys Cys Lys
225                 230                 235                 240

Asp Lys Arg Phe Asn Gly Thr Gly Pro Cys Lys Asn Val Ser Thr Val
                245                 250                 255

Gln Cys Thr His Gly Ile Arg Pro Val Val Ser Thr Gln Leu Leu Leu
            260                 265                 270

Asn Gly Ser Leu Ala Glu Glu Gly Val Val Leu Arg Ser Glu Asn Phe
        275                 280                 285

Thr Asp Asn Ala Lys Asn Ile Ile Val Gln Leu Lys Asp Pro Val Asn
    290                 295                 300

Ile Thr Cys Thr Arg Pro Asn Asn Asn Thr Arg Lys Ser Ile Thr Ile
305                 310                 315                 320

Gly Pro Gly Arg Ala Phe Tyr Ala Thr Gly Gln Val Ile Gly Asp Ile
                325                 330                 335
```

```
Arg Lys Ala His Cys Asp Leu Asn Gly Thr Glu Trp Asp Asn Ala Leu
            340                 345                 350

Lys Gln Ile Val Glu Glu Leu Arg Lys Gln Tyr Gly Asn Asn Ile Thr
            355                 360                 365

Ile Phe Asn Ser Ser Ser Gly Gly Asp Pro Glu Ile Val Met His Ser
            370                 375                 380

Phe Asn Cys Gly Gly Glu Phe Phe Tyr Cys Asn Thr Ala Gln Leu Phe
385                 390                 395                 400

Asn Ser Thr Trp Leu Phe Asn Ser Thr Trp Asn Ser Thr Glu Arg Leu
                405                 410                 415

Gly Asn Asp Thr Glu Arg Thr Asn Asp Thr Ile Thr Leu Pro Cys Lys
            420                 425                 430

Ile Lys Gln Val Ile Asn Met Trp Gln Thr Val Gly Lys Ala Met Tyr
            435                 440                 445

Ala Pro Pro Ile Arg Gly Leu Ile Arg Cys Ser Ser Asn Ile Thr Gly
            450                 455                 460

Leu Ile Leu Thr Arg Asp Gly Ser Gly Asn Thr Thr Gly Asn Glu Thr
465                 470                 475                 480

Phe Arg Pro Gly Gly Gly Asn Met Lys Asp Asn Trp Arg Ser Glu Leu
                485                 490                 495

Tyr Lys Tyr Lys Val Val Lys Ile Glu Pro Leu Gly Val Ala Pro Thr
            500                 505                 510

Arg Ala Lys Arg Arg Val Val Gln Arg Glu Lys Arg Ala Ala Gly Leu
            515                 520                 525

Gly Ala Leu Phe Leu Gly Phe Leu Gly Met Ala Gly Ser Thr Met Gly
            530                 535                 540

Ala Ala Ser Leu Thr Leu Thr Val Gln Ala Arg Gln Leu Leu Ser Gly
545                 550                 555                 560

Ile Val Gln Gln Gln Asn Asn Leu Leu Arg Ala Ile Glu Ala Gln Gln
                565                 570                 575

His Leu Leu Gln Leu Thr Val Trp Gly Ile Lys Gln Leu Gln Ala Arg
            580                 585                 590

Val Leu Ala Val Glu Arg Tyr Leu Arg Asp Gln Gln Leu Leu Gly Ile
            595                 600                 605

Trp Gly Cys Ser Gly Lys Leu Ile Cys Thr Thr Thr Val Pro Trp Asn
            610                 615                 620

Ala Ser Trp Ser Asn Lys Ser Leu Asp Asn Ile Trp Glu Asn Met Thr
625                 630                 635                 640

Trp Met Gln Trp Glu Lys Glu Ile Asp Asn Tyr Thr Asp Val Ile Tyr
                645                 650                 655

Lys Leu Leu Glu Glu Ser Gln Asn Gln Gln Glu Lys Asn Glu Gln Glu
            660                 665                 670

Leu Leu Glu Leu Asp Lys Trp Ala Ser Leu Trp Asn Trp Phe Asp Ile
            675                 680                 685

Thr Arg Trp Leu Trp Tyr Ile Lys Ile Phe Ile Met Ile Val Gly Gly
            690                 695                 700

Leu Val Gly Leu Arg Ile Val Phe Ala Val Leu Ser Ile Val Asn Arg
705                 710                 715                 720

Val Arg Gln Gly Tyr Ser Pro Leu Ser Phe Gln Thr Leu Phe Pro Ala
                725                 730                 735

Pro Arg Gly Pro Asp Arg Pro Glu Gly Thr Glu Glu Gly Gly Gly Glu
            740                 745                 750
```

-continued

```
Arg Gly Arg Asp Ser Ser Asp Arg Ser Ala His Gly Phe Leu Ala Leu
            755                 760                 765

Ile Trp Gly Asp Leu Trp Ser Leu Cys Leu Phe Ser Tyr Arg Arg Leu
    770                 775                 780

Arg Asp Leu Leu Leu Ile Ala Ala Arg Ile Val Glu Leu Leu Gly Arg
785                 790                 795                 800

Arg Gly Trp Glu Val Leu Lys Tyr Trp Trp Ser Leu Leu Gln Tyr Trp
                805                 810                 815

Ser Gln Glu Leu Lys Lys Ser Ala Val Ser Leu Leu Asn Ala Thr Ala
                820                 825                 830

Ile Ala Val Ala Glu Gly Thr Asp Arg Ile Ile Glu Ile Val Gln Arg
            835                 840                 845

Ala Gly Arg Ala Ile Ile His Ile Pro Arg Arg Ile Arg Gln Gly Ala
    850                 855                 860

Glu Arg Ala Leu Leu
865

<210> SEQ ID NO 53
<211> LENGTH: 492
<212> TYPE: PRT
<213> ORGANISM: Human immunodeficiency virus 1

<400> SEQUENCE: 53

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Gln Asn Pro Glu Met
                20                  25                  30

His Asn Ile Trp Ala Thr His Ala Cys Val Pro Thr Asp Pro Asn Pro
            35                  40                  45

Gln Glu Val Ile Leu Lys Asn Leu Thr Glu Glu Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asn Ala Glu Ser Leu Asn Cys Thr Ala Thr Asn Gly Thr
            100                 105                 110

Asn Asn Cys Ser Ala Ser Thr Lys Pro Met Glu Glu Met Lys Asn Cys
    115                 120                 125

Ser Phe Asn Ile Thr Thr Ser Val Gln Asp Lys Lys Gln Gln Glu Tyr
130                 135                 140

Ala Leu Phe Tyr Lys Leu Asp Ile Ile Pro Ile Asp Asn Asn Glu Asn
145                 150                 155                 160

Asp Leu Asn Asn Thr Asn Tyr Thr Ser Tyr Arg Leu Ile Ser Cys Asn
                165                 170                 175

Thr Ser Val Ile Thr Gln Ala Cys Pro Lys Ile Thr Phe Glu Pro Ile
            180                 185                 190

Pro Ile His Tyr Cys Ala Pro Ala Gly Phe Ala Ile Leu Lys Cys Lys
    195                 200                 205

Asp Lys Arg Phe Asn Gly Thr Gly Pro Cys Lys Asn Val Ser Thr Val
210                 215                 220

Gln Cys Thr His Gly Ile Arg Pro Val Val Ser Thr Gln Leu Leu Leu
225                 230                 235                 240

Asn Gly Ser Leu Ala Glu Glu Gly Val Val Leu Arg Ser Glu Asn Phe
                245                 250                 255
```

```
Thr Asp Asn Ala Lys Asn Ile Ile Val Gln Leu Lys Asp Pro Val Asn
                260                 265                 270

Ile Thr Cys Thr Arg Pro Asn Asn Asn Thr Arg Lys Ser Ile Thr Ile
            275                 280                 285

Gly Pro Gly Arg Ala Phe Tyr Ala Thr Gly Gln Val Ile Gly Asp Ile
        290                 295                 300

Arg Lys Ala His Cys Asp Leu Asn Gly Thr Glu Trp Asp Asn Ala Leu
305                 310                 315                 320

Lys Gln Ile Val Glu Glu Leu Arg Lys Gln Tyr Gly Asn Asn Ile Thr
                325                 330                 335

Ile Phe Asn Ser Ser Gly Gly Asp Pro Glu Ile Val Met His Ser
            340                 345                 350

Phe Asn Cys Gly Gly Glu Phe Phe Tyr Cys Asn Thr Ala Gln Leu Phe
            355                 360                 365

Asn Ser Thr Trp Leu Phe Asn Ser Thr Trp Asn Ser Thr Glu Arg Leu
        370                 375                 380

Gly Asn Asp Thr Glu Arg Thr Asn Asp Thr Ile Thr Leu Pro Cys Lys
385                 390                 395                 400

Ile Lys Gln Val Ile Asn Met Trp Gln Thr Val Gly Lys Ala Met Tyr
                405                 410                 415

Ala Pro Pro Ile Arg Gly Leu Ile Arg Cys Ser Ser Asn Ile Thr Gly
            420                 425                 430

Leu Ile Leu Thr Arg Asp Gly Ser Gly Asn Thr Thr Gly Asn Glu Thr
        435                 440                 445

Phe Arg Pro Gly Gly Asn Met Lys Asp Asn Trp Arg Ser Glu Leu
450                 455                 460

Tyr Lys Tyr Lys Val Val Lys Ile Glu Pro Leu Gly Val Ala Pro Thr
465                 470                 475                 480

Arg Ala Lys Arg Arg Val Val Gln Arg Glu Lys Arg
                485                 490

<210> SEQ ID NO 54
<211> LENGTH: 191
<212> TYPE: PRT
<213> ORGANISM: Human immunodeficiency virus 1

<400> SEQUENCE: 54

Met Gly Ala Ala Ser Leu Thr Leu Thr Val Gln Ala Arg Gln Leu Leu
1               5                   10                  15

Ser Gly Ile Val Gln Gln Gln Asn Asn Leu Leu Arg Ala Ile Glu Ala
                20                  25                  30

Gln Gln His Leu Leu Gln Leu Thr Val Trp Gly Ile Lys Gln Leu Gln
            35                  40                  45

Ala Arg Val Leu Ala Val Glu Arg Tyr Leu Arg Asp Gln Gln Leu Leu
        50                  55                  60

Gly Ile Trp Gly Cys Ser Gly Lys Leu Ile Cys Thr Thr Thr Val Pro
65                  70                  75                  80

Trp Asn Ala Ser Trp Ser Asn Lys Ser Leu Asp Asn Ile Trp Glu Asn
                85                  90                  95

Met Thr Trp Met Gln Trp Glu Lys Glu Ile Asp Asn Tyr Thr Asp Val
                100                 105                 110

Ile Tyr Lys Leu Leu Glu Glu Ser Gln Asn Gln Gln Glu Lys Asn Glu
            115                 120                 125

Gln Glu Leu Leu Glu Leu Asp Lys Trp Ala Ser Leu Trp Asn Trp Phe
```

```
    130                 135                 140

Asp Ile Thr Arg Trp Leu Trp Tyr Ile Lys Ile Phe Ile Met Ile Val
145                 150                 155                 160

Gly Gly Leu Val Gly Leu Arg Ile Val Phe Ala Val Leu Ser Ile Val
                165                 170                 175

Asn Arg Val Arg Gln Gly Tyr Ser Pro Leu Ser Phe Gln Thr Leu
            180                 185                 190

<210> SEQ ID NO 55
<211> LENGTH: 22
<212> TYPE: PRT
<213> ORGANISM: Human immunodeficiency virus 1

<400> SEQUENCE: 55

Glu Leu Asp Lys Trp Ala Ser Leu Trp Asn Trp Phe Asp Ile Thr Arg
1               5                   10                  15

Trp Leu Trp Tyr Ile Lys
            20

<210> SEQ ID NO 56
<211> LENGTH: 574
<212> TYPE: PRT
<213> ORGANISM: Respiratory syncytial virus type A

<400> SEQUENCE: 56

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

```
                    245                 250                 255
Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Ile
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
            515                 520                 525

Thr Ile Ile Ile Val Ile Ile Val Ile Leu Leu Leu Ile Ala Val
        530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 57
<211> LENGTH: 566
<212> TYPE: PRT
<213> ORGANISM: Influenza A virus

<400> SEQUENCE: 57

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

-continued

```
Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
            210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
```

```
              465                 470                 475                 480
          Cys Phe Glu Phe Tyr His Lys Cys Asp Asn Thr Cys Met Glu Ser Val
                          485                 490                 495

Lys Asn Gly Thr Tyr Asp Tyr Pro Lys Tyr Ser Glu Glu Ala Lys Leu
                          500                 505                 510

Asn Arg Glu Glu Ile Asp Gly Val Lys Leu Glu Ser Thr Arg Ile Tyr
                          515                 520                 525

Gln Ile Leu Ala Ile Tyr Ser Thr Val Ala Ser Ser Leu Val Leu Val
                          530                 535                 540

Val Ser Leu Gly Ala Ile Ser Phe Trp Met Cys Ser Asn Gly Ser Leu
          545                 550                 555                 560

Gln Cys Arg Ile Cys Ile
                          565

<210> SEQ ID NO 58
<211> LENGTH: 584
<212> TYPE: PRT
<213> ORGANISM: Influenza B virus

<400> SEQUENCE: 58

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Lys Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Ala Asn Leu Leu Arg Gly
            115                 120                 125

Tyr Glu Asn Ile Arg Leu Ser Thr Gln Asn Val Ile Asp Ala Glu Lys
        130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
                180                 185                 190

Tyr Ile Cys Ala Glu Gly Glu Asp Gln Ile Thr Val Trp Gly Phe His
            195                 200                 205

Ser Asp Asn Lys Thr Gln Met Lys Asn Leu Tyr Gly Asp Ser Asn Pro
        210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
                260                 265                 270
```

```
Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
        290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 59
<211> LENGTH: 907
<212> TYPE: PRT
<213> ORGANISM: Epstein-Barr virus

<400> SEQUENCE: 59

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60
```

```
Phe Gly Gln Leu Thr Pro His Thr Lys Ala Val Tyr Gln Pro Arg Gly
 65                  70                  75                  80

Ala Phe Gly Gly Ser Glu Asn Ala Thr Asn Leu Phe Leu Leu Glu Leu
                 85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
450                 455                 460

Gly Pro Thr Val Ser Thr Ala Asp Val Thr Ser Pro Thr Pro Ala Gly
465                 470                 475                 480
```

```
Thr Thr Ser Gly Ala Ser Pro Val Thr Pro Ser Pro Trp Asp
            485             490             495
Asn Gly Thr Glu Ser Lys Ala Pro Asp Met Thr Ser Ser Thr Ser Pro
        500             505             510
Val Thr Thr Pro Thr Pro Asn Ala Thr Ser Pro Thr Pro Ala Val Thr
        515             520             525
Thr Pro Thr Pro Asn Ala Thr Ser Pro Thr Pro Ala Val Thr Thr Pro
    530             535             540
Thr Pro Asn Ala Thr Ser Pro Thr Leu Gly Lys Thr Ser Pro Thr Ser
545             550             555             560
Ala Val Thr Thr Pro Thr Pro Asn Ala Thr Ser Pro Thr Leu Gly Lys
            565             570             575
Thr Ser Pro Thr Ser Ala Val Thr Thr Pro Thr Pro Asn Ala Thr Ser
        580             585             590
Pro Thr Leu Gly Lys Thr Ser Pro Thr Ser Ala Val Thr Thr Pro Thr
        595             600             605
Pro Asn Ala Thr Gly Pro Thr Val Gly Glu Thr Ser Pro Gln Ala Asn
    610             615             620
Ala Thr Asn His Thr Leu Gly Gly Thr Ser Pro Thr Pro Val Val Thr
625             630             635             640
Ser Gln Pro Lys Asn Ala Thr Ser Ala Val Thr Thr Gly Gln His Asn
            645             650             655
Ile Thr Ser Ser Ser Thr Ser Ser Met Ser Leu Arg Pro Ser Ser Asn
        660             665             670
Pro Glu Thr Leu Ser Pro Ser Thr Ser Asp Asn Ser Thr Ser His Met
        675             680             685
Pro Leu Leu Thr Ser Ala His Pro Thr Gly Gly Glu Asn Ile Thr Gln
    690             695             700
Val Thr Pro Ala Ser Ile Ser Thr His His Val Ser Thr Ser Ser Pro
705             710             715             720
Ala Pro Arg Pro Gly Thr Thr Ser Gln Ala Ser Gly Pro Gly Asn Ser
            725             730             735
Ser Thr Ser Thr Lys Pro Gly Glu Val Asn Val Thr Lys Gly Thr Pro
        740             745             750
Pro Gln Asn Ala Thr Ser Pro Gln Ala Pro Ser Gly Gln Lys Thr Ala
        755             760             765
Val Pro Thr Val Thr Ser Thr Gly Gly Lys Ala Asn Ser Thr Thr Gly
    770             775             780
Gly Lys His Thr Thr Gly His Gly Ala Arg Thr Ser Thr Glu Pro Thr
785             790             795             800
Thr Asp Tyr Gly Gly Asp Ser Thr Thr Pro Arg Pro Arg Tyr Asn Ala
            805             810             815
Thr Thr Tyr Leu Pro Pro Ser Thr Ser Ser Lys Leu Arg Pro Arg Trp
        820             825             830
Thr Phe Thr Ser Pro Pro Val Thr Thr Ala Gln Ala Thr Val Pro Val
        835             840             845
Pro Pro Thr Ser Gln Pro Arg Phe Ser Asn Leu Ser Met Leu Val Leu
    850             855             860
Gln Trp Ala Ser Leu Ala Val Leu Thr Leu Leu Leu Leu Val Met Ala
865             870             875             880
Ala Asp Cys Ala Phe Arg Arg Asn Leu Ser Thr Ser His Thr Tyr Thr
            885             890             895
Thr Pro Pro Tyr Asp Asp Ala Glu Thr Tyr Val
```

-continued

```
              900           905
```

<210> SEQ ID NO 60
<211> LENGTH: 906
<212> TYPE: PRT
<213> ORGANISM: Human cytomegalovirus

<400> SEQUENCE: 60

```
Met Glu Ser Arg Ile Trp Cys Leu Val Cys Val Asn Leu Cys Ile
1               5                   10                  15

Val Cys Leu Gly Ala Ala Val Ser Ser Ser Thr Ser His Ala Thr
                20                  25                  30

Ser Ser Thr His Asn Gly Ser His Thr Ser Arg Thr Thr Ser Ala Gln
                35                  40                  45

Thr Arg Ser Val Tyr Ser Gln His Val Thr Ser Ser Glu Ala Val Ser
50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
                115                 120                 125

Tyr Lys Arg Asn Ile Val Ala His Thr Phe Lys Val Arg Val Tyr Gln
                130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
                180                 185                 190

Ile Gly Gly Thr Val Phe Val Ala Tyr His Arg Asp Ser Tyr Glu Asn
                195                 200                 205

Lys Thr Met Gln Leu Ile Pro Asp Asp Tyr Ser Asn Thr His Ser Thr
                210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
                260                 265                 270

Val Val Tyr Ile Ser Pro Phe Tyr Asn Gly Thr Asn Arg Asn Ala Ser
                275                 280                 285

Tyr Phe Gly Glu Asn Ala Asp Lys Phe Phe Ile Phe Pro Asn Tyr Thr
                290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
                355                 360                 365
```

```
Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
```

```
                    785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Ser Ser Asp Ala
                820                 825                 830

Ser Thr Ala Ala Pro Pro Tyr Thr Asn Glu Gln Ala Tyr Gln Met Leu
                835                 840                 845

Leu Ala Leu Ala Arg Leu Asp Ala Glu Gln Arg Ala Gln Gln Asn Gly
                850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
                900                 905

<210> SEQ ID NO 61
<211> LENGTH: 171
<212> TYPE: PRT
<213> ORGANISM: Human cytomegalovirus

<400> SEQUENCE: 61

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
                35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65              70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
                100                 105                 110

Lys Val Asn Asp Lys Ala Gln Tyr Leu Leu Gly Ala Ala Gly Ser Val
                115                 120                 125

Pro Tyr Arg Trp Ile Asn Leu Glu Tyr Asp Lys Ile Thr Arg Ile Val
                130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 62
<211> LENGTH: 214
<212> TYPE: PRT
<213> ORGANISM: Human cytomegalovirus

<400> SEQUENCE: 62

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
```

```
                    35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Tyr Asn Arg Glu Gly
                    85                  90                  95

Gln Thr Leu Val Glu Arg Ser Ser Thr Trp Val Lys Val Ile Trp
                100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
        210

<210> SEQ ID NO 63
<211> LENGTH: 129
<212> TYPE: PRT
<213> ORGANISM: Human cytomegalovirus

<400> SEQUENCE: 63

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 64
<211> LENGTH: 743
<212> TYPE: PRT
<213> ORGANISM: Human cytomegalovirus

<400> SEQUENCE: 64

Met Arg Pro Gly Leu Pro Pro Tyr Leu Thr Val Phe Thr Val Tyr Leu
1               5                   10                  15
```

```
Leu Ser His Leu Pro Ser Gln Arg Tyr Gly Asp Ala Ala Ser Glu
            20                  25                  30

Ala Leu Asp Pro His Ala Phe His Leu Leu Asn Thr Tyr Gly Arg
            35                  40                  45

Pro Ile Arg Phe Leu Arg Glu Asn Thr Thr Gln Cys Thr Tyr Asn Ser
50                      55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
                100                 105                 110

Thr Glu Thr Leu Glu Arg Tyr Gln Gln Arg Leu Asn Thr Tyr Ala Leu
                115                 120                 125

Val Ser Lys Asp Leu Ala Ser Tyr Arg Ser Phe Ser Gln Gln Leu Lys
    130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Asp Trp Lys Gly Ser His Thr Thr Ser Gly Leu His Arg Pro His Phe
                180                 185                 190

Asn Gln Thr Cys Ile Leu Phe Asp Gly His Asp Leu Leu Phe Ser Thr
                195                 200                 205

Val Thr Pro Cys Leu His Gln Gly Phe Tyr Leu Met Asp Glu Leu Arg
                210                 215                 220

Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
                260                 265                 270

Thr Glu Lys His Glu Leu Leu Val Leu Val Lys Lys Ala Gln Leu Asn
                275                 280                 285

Arg His Ser Tyr Leu Lys Asp Ser Asp Phe Leu Asp Ala Ala Leu Asp
    290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335

Arg Thr Val Glu Met Ala Phe Ala Tyr Ala Leu Ala Leu Phe Ala Ala
                340                 345                 350

Ala Arg Gln Glu Glu Ala Gly Thr Glu Ile Ser Ile Pro Arg Ala Leu
    355                 360                 365

Asp Arg Gln Ala Ala Leu Leu Gln Ile Gln Glu Phe Met Ile Thr Cys
    370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asp Gln Ile Thr Asp
                405                 410                 415

Ile Thr Ser Leu Val Arg Leu Val Tyr Ile Leu Ser Lys Gln Asn Gln
                420                 425                 430
```

Gln His Leu Ile Pro Gln Trp Ala Leu Arg Gln Ile Ala Asp Phe Ala
            435                 440                 445

Leu Gln Leu His Lys Thr His Leu Ala Ser Phe Leu Ser Ala Phe Ala
450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
            515                 520                 525

Arg Asp His Ser Leu Glu Arg Leu Thr Arg Leu Phe Pro Asp Ala Thr
530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
            595                 600                 605

Val Val Gly Gln Ser Leu Ile Ile Thr Gln Thr Asp Ser Gln Thr Lys
            610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
            675                 680                 685

Ser Ser Pro Arg Thr His Tyr Leu Met Leu Leu Lys Asn Gly Thr Val
690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740

<210> SEQ ID NO 65
<211> LENGTH: 278
<212> TYPE: PRT
<213> ORGANISM: Human cytomegalovirus

<400> SEQUENCE: 65

Met Cys Arg Arg Pro Asp Cys Gly Phe Ser Phe Ser Pro Gly Pro Val
1               5                   10                  15

Val Leu Leu Trp Cys Cys Leu Leu Pro Ile Val Ser Ser Val Ala
                20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Gln Gly Asp Lys
50                  55                  60

```
Tyr Glu Ser Trp Leu Arg Pro Leu Val Asn Val Thr Arg Arg Asp Gly
 65                  70                  75                  80

Pro Leu Ser Gln Leu Ile Arg Tyr Arg Pro Val Thr Pro Glu Ala Ala
                 85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Ala Pro Glu Gly Ile Thr Leu Phe Tyr Gly
            210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
            275

<210> SEQ ID NO 66
<211> LENGTH: 272
<212> TYPE: PRT
<213> ORGANISM: Borreliella burgdorferi

<400> SEQUENCE: 66

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Val Pro Gly Gly Met Lys Val Leu Val Ser Lys Glu Lys Asn Lys
             35                  40                  45

Asp Gly Lys Tyr Asp Leu Met Ala Thr Val Asp Asn Val Asp Leu Lys
         50                  55                  60

Gly Thr Ser Asp Lys Asn Asn Gly Ser Gly Ile Leu Glu Gly Val Lys
 65                  70                  75                  80

Ala Asp Lys Ser Lys Val Lys Leu Thr Val Ala Asp Asp Leu Ser Lys
                 85                  90                  95

Thr Thr Leu Glu Val Leu Lys Glu Asp Gly Thr Val Val Ser Arg Lys
            100                 105                 110

Val Thr Ser Lys Asp Lys Ser Thr Thr Glu Ala Lys Phe Asn Glu Lys
            115                 120                 125

Gly Glu Leu Ser Glu Lys Thr Met Thr Arg Ala Asn Gly Thr Thr Leu
130                 135                 140

Glu Tyr Ser Gln Met Thr Asn Glu Asp Asn Ala Ala Lys Ala Val Glu
```

```
                145                 150                 155                 160
        Thr Leu Lys Asn Gly Ile Lys Phe Glu Gly Asn Leu Ala Ser Gly Lys
                        165                 170                 175

Thr Ala Val Glu Ile Lys Glu Gly Thr Val Thr Leu Lys Arg Glu Ile
                        180                 185                 190

Asp Lys Asn Gly Lys Val Thr Val Ser Leu Asn Asp Thr Ala Ser Gly
                        195                 200                 205

Ser Lys Lys Thr Ala Ser Trp Gln Ser Thr Ser Thr Leu Thr Ile
                        210                 215                 220

Ser Ala Asn Ser Lys Lys Thr Lys Asp Leu Val Phe Leu Thr Asn Gly
        225                 230                 235                 240

Thr Ile Thr Val Gln Asn Tyr Asp Ser Ala Gly Thr Lys Leu Glu Gly
                        245                 250                 255

Ser Ala Ala Glu Ile Lys Lys Leu Asp Glu Leu Lys Asn Ala Leu Arg
                        260                 265                 270

<210> SEQ ID NO 67
<211> LENGTH: 269
<212> TYPE: PRT
<213> ORGANISM: Bordetella pertussis

<400> SEQUENCE: 67

Met Arg Cys Thr Arg Ala Ile Arg Gln Thr Ala Arg Thr Gly Trp Leu
        1               5                   10                  15

Thr Trp Leu Ala Ile Leu Ala Val Thr Ala Pro Val Thr Ser Pro Ala
                        20                  25                  30

Trp Ala Asp Asp Pro Pro Ala Thr Val Tyr Arg Tyr Asp Ser Arg Pro
                        35                  40                  45

Pro Glu Asp Val Phe Gln Asn Gly Phe Thr Ala Trp Gly Asn Asn Asp
                        50                  55                  60

Asn Val Leu Asp His Leu Thr Gly Arg Ser Cys Gln Val Gly Ser Ser
        65                  70                  75                  80

Asn Ser Ala Phe Val Ser Thr Ser Ser Arg Arg Tyr Thr Glu Val
                        85                  90                  95

Tyr Leu Glu His Arg Met Gln Glu Ala Val Glu Ala Glu Arg Ala Gly
                        100                 105                 110

Arg Gly Thr Gly His Phe Ile Gly Tyr Ile Tyr Glu Val Arg Ala Asp
                        115                 120                 125

Asn Asn Phe Tyr Gly Ala Ala Ser Ser Tyr Phe Glu Tyr Val Asp Thr
                        130                 135                 140

Tyr Gly Asp Asn Ala Gly Arg Ile Leu Ala Gly Ala Leu Ala Thr Tyr
        145                 150                 155                 160

Gln Ser Glu Tyr Leu Ala His Arg Arg Ile Pro Pro Glu Asn Ile Arg
                        165                 170                 175

Arg Val Thr Arg Val Tyr His Asn Gly Ile Thr Gly Glu Thr Thr Thr
                        180                 185                 190

Thr Glu Tyr Ser Asn Ala Arg Tyr Val Ser Gln Gln Thr Arg Ala Asn
                        195                 200                 205

Pro Asn Pro Tyr Thr Ser Arg Arg Ser Val Ala Ser Ile Val Gly Thr
                        210                 215                 220

Leu Val Arg Met Ala Pro Val Ile Gly Ala Cys Met Ala Arg Gln Ala
        225                 230                 235                 240

Glu Ser Ser Glu Ala Met Ala Ala Trp Ser Glu Arg Ala Gly Glu Ala
                        245                 250                 255
```

Met Val Leu Val Tyr Tyr Glu Ser Ile Ala Tyr Ser Phe
            260                 265

<210> SEQ ID NO 68
<211> LENGTH: 495
<212> TYPE: PRT
<213> ORGANISM: Dengue virus

<400> SEQUENCE: 68

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Glu Lys Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

```
Ala Glu Pro Pro Phe Gly Glu Ser Tyr Ile Val Val Gly Ala Gly Glu
        370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
                435                 440                 445

Ser Gly Val Ser Trp Thr Met Lys Ile Gly Ile Gly Ile Leu Leu Thr
        450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 69
<211> LENGTH: 1255
<212> TYPE: PRT
<213> ORGANISM: Human SARS coronavirus

<400> SEQUENCE: 69

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                100                 105                 110

Ser Val Ile Ile Ile Asn Asn Ser Thr Asn Val Val Ile Arg Ala Cys
            115                 120                 125

Asn Phe Glu Leu Cys Asp Asn Pro Phe Phe Ala Val Ser Lys Pro Met
        130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
        210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
```

```
                    245                 250                 255
Leu Lys Pro Thr Thr Phe Met Leu Lys Tyr Asp Glu Asn Gly Thr Ile
            260                 265                 270
Thr Asp Ala Val Asp Cys Ser Gln Asn Pro Leu Ala Glu Leu Lys Cys
            275                 280                 285
Ser Val Lys Ser Phe Glu Ile Asp Lys Gly Ile Tyr Gln Thr Ser Asn
            290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
            325                 330                 335
Val Tyr Ala Trp Glu Arg Lys Lys Ile Ser Asn Cys Val Ala Asp Tyr
            340                 345                 350
Ser Val Leu Tyr Asn Ser Thr Phe Phe Ser Thr Phe Lys Cys Tyr Gly
            355                 360                 365
Val Ser Ala Thr Lys Leu Asn Asp Leu Cys Phe Ser Asn Val Tyr Ala
            370                 375                 380
Asp Ser Phe Val Val Lys Gly Asp Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
            420                 425                 430
Thr Gly Asn Tyr Asn Tyr Lys Tyr Arg Tyr Leu Arg His Gly Lys Leu
            435                 440                 445
Arg Pro Phe Glu Arg Asp Ile Ser Asn Val Pro Phe Ser Pro Asp Gly
    450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Thr Gly Ile Gly Tyr Gln Pro Tyr Arg Val
                485                 490                 495
Val Val Leu Ser Phe Glu Leu Leu Asn Ala Pro Ala Thr Val Cys Gly
            500                 505                 510
Pro Lys Leu Ser Thr Asp Leu Ile Lys Asn Gln Cys Val Asn Phe Asn
    515                 520                 525
Phe Asn Gly Leu Thr Gly Thr Gly Val Leu Thr Pro Ser Ser Lys Arg
    530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
                565                 570                 575
Ser Phe Gly Gly Val Ser Val Ile Thr Pro Gly Thr Asn Ala Ser Ser
            580                 585                 590
Glu Val Ala Val Leu Tyr Gln Asp Val Asn Cys Thr Asp Val Ser Thr
            595                 600                 605
Ala Ile His Ala Asp Gln Leu Thr Pro Ala Trp Arg Ile Tyr Ser Thr
            610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
                645                 650                 655
Cys Ala Ser Tyr His Thr Val Ser Leu Leu Arg Ser Thr Ser Gln Lys
            660                 665                 670
```

```
Ser Ile Val Ala Tyr Thr Met Ser Leu Gly Ala Asp Ser Ile Ala
        675                 680                 685

Tyr Ser Asn Asn Thr Ile Ala Ile Pro Thr Asn Phe Ser Ile Ser Ile
690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080
```

```
Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 70
<211> LENGTH: 1353
<212> TYPE: PRT
<213> ORGANISM: Middle East respiratory syndrome-related coronavirus

<400> SEQUENCE: 70

Met Ile His Ser Val Phe Leu Leu Met Phe Leu Leu Thr Pro Thr Glu
1               5                   10                  15

Ser Tyr Val Asp Val Gly Pro Asp Ser Ile Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190
```

-continued

```
Asn His Cys Pro Ala Gly Asn Ser Tyr Thr Ser Phe Ala Thr Tyr His
        195                 200                 205
Thr Pro Ala Thr Asp Cys Ser Asp Gly Asn Tyr Asn Arg Asn Ala Ser
    210                 215                 220
Leu Asn Ser Phe Lys Glu Tyr Phe Asn Leu Arg Asn Cys Thr Phe Met
225                 230                 235                 240
Tyr Thr Tyr Asn Ile Thr Glu Asp Glu Ile Leu Glu Trp Phe Gly Ile
                245                 250                 255
Thr Gln Thr Ala Gln Gly Val His Leu Phe Ser Ser Arg Tyr Val Asp
            260                 265                 270
Leu Tyr Gly Gly Asn Met Phe Gln Phe Ala Thr Leu Pro Val Tyr Asp
        275                 280                 285
Thr Ile Lys Tyr Tyr Ser Ile Ile Pro His Ser Ile Arg Ser Ile Gln
    290                 295                 300
Ser Asp Arg Lys Ala Trp Ala Ala Phe Tyr Val Tyr Lys Leu Gln Pro
305                 310                 315                 320
Leu Thr Phe Leu Leu Asp Phe Ser Val Asp Gly Tyr Ile Arg Arg Ala
                325                 330                 335
Ile Asp Cys Gly Phe Asn Asp Leu Ser Gln Leu His Cys Ser Tyr Glu
            340                 345                 350
Ser Phe Asp Val Glu Ser Gly Val Tyr Ser Val Ser Ser Phe Glu Ala
        355                 360                 365
Lys Pro Ser Gly Ser Val Val Glu Gln Ala Glu Gly Val Glu Cys Asp
    370                 375                 380
Phe Ser Pro Leu Leu Ser Gly Thr Pro Pro Gln Val Tyr Asn Phe Lys
385                 390                 395                 400
Arg Leu Val Phe Thr Asn Cys Asn Tyr Asn Leu Thr Lys Leu Leu Ser
                405                 410                 415
Leu Phe Ser Val Asn Asp Phe Thr Cys Ser Gln Ile Ser Pro Ala Ala
            420                 425                 430
Ile Ala Ser Asn Cys Tyr Ser Ser Leu Ile Leu Asp Tyr Phe Ser Tyr
        435                 440                 445
Pro Leu Ser Met Lys Ser Asp Leu Ser Val Ser Ser Ala Gly Pro Ile
    450                 455                 460
Ser Gln Phe Asn Tyr Lys Gln Ser Phe Ser Asn Pro Thr Cys Leu Ile
465                 470                 475                 480
Leu Ala Thr Val Pro His Asn Leu Thr Thr Ile Thr Lys Pro Leu Lys
                485                 490                 495
Tyr Ser Tyr Ile Asn Lys Cys Ser Arg Leu Leu Ser Asp Asp Arg Thr
            500                 505                 510
Glu Val Pro Gln Leu Val Asn Ala Asn Gln Tyr Ser Pro Cys Val Ser
        515                 520                 525
Ile Val Pro Ser Thr Val Trp Glu Asp Gly Asp Tyr Tyr Arg Lys Gln
    530                 535                 540
Leu Ser Pro Leu Glu Gly Gly Gly Trp Leu Val Ala Ser Gly Ser Thr
545                 550                 555                 560
Val Ala Met Thr Glu Gln Leu Gln Met Gly Phe Gly Ile Thr Val Gln
                565                 570                 575
Tyr Gly Thr Asp Thr Asn Ser Val Cys Pro Lys Leu Glu Phe Ala Asn
            580                 585                 590
Asp Thr Lys Ile Ala Ser Gln Leu Gly Asn Cys Val Glu Tyr Ser Leu
        595                 600                 605
```

```
Tyr Gly Val Ser Gly Arg Gly Val Phe Gln Asn Cys Thr Ala Val Gly
    610             615                 620

Val Arg Gln Gln Arg Phe Val Tyr Asp Ala Tyr Gln Asn Leu Val Gly
625             630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Asp Ser Thr Tyr
    690                 695                 700

Gly Pro Leu Gln Thr Pro Val Gly Cys Val Leu Gly Leu Val Asn Ser
705             710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
770             775                 780

Asn Phe Ser Phe Gly Val Thr Gln Glu Tyr Ile Gln Thr Thr Ile Gln
785             790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe His Lys Val Gln
        1010                1015                1020

Asp Ala Val Asn Asn Asn Ala Gln Ala Leu Ser Lys Leu Ala Ser
```

1025                1030                1035

Glu Leu Ser Asn Thr Phe Gly Ala Ile Ser Ala Ser Ile Gly Asp
                1040                1045                1050

Ile Ile Gln Arg Leu Asp Val Leu Glu Gln Asp Ala Gln Ile Asp
        1055                1060                1065

Arg Leu Ile Asn Gly Arg Leu Thr Thr Leu Asn Ala Phe Val Ala
        1070                1075                1080

Gln Gln Leu Val Arg Ser Glu Ser Ala Ala Leu Ser Ala Gln Leu
        1085                1090                1095

Ala Lys Asp Lys Val Asn Glu Cys Val Lys Ala Gln Ser Lys Arg
        1100                1105                1110

Ser Gly Phe Cys Gly Gln Gly Thr His Ile Val Ser Phe Val Val
        1115                1120                1125

Asn Ala Pro Asn Gly Leu Tyr Phe Met His Val Gly Tyr Tyr Pro
        1130                1135                1140

Ser Asn His Ile Glu Val Val Ser Ala Tyr Gly Leu Cys Asp Ala
        1145                1150                1155

Ala Asn Pro Thr Asn Cys Ile Ala Pro Val Asn Gly Tyr Phe Ile
        1160                1165                1170

Lys Thr Asn Asn Thr Arg Ile Val Asp Glu Trp Ser Tyr Thr Gly
        1175                1180                1185

Ser Ser Phe Tyr Ala Pro Glu Pro Ile Thr Ser Leu Asn Thr Lys
        1190                1195                1200

Tyr Val Ala Pro Gln Val Thr Tyr Gln Asn Ile Ser Thr Asn Leu
        1205                1210                1215

Pro Pro Pro Leu Leu Gly Asn Ser Thr Gly Ile Asp Phe Gln Asp
        1220                1225                1230

Glu Leu Asp Glu Phe Phe Lys Asn Val Ser Thr Ser Ile Pro Asn
        1235                1240                1245

Phe Gly Ser Leu Thr Gln Ile Asn Thr Thr Leu Leu Asp Leu Thr
        1250                1255                1260

Tyr Glu Met Leu Ser Leu Gln Gln Val Val Lys Ala Leu Asn Glu
        1265                1270                1275

Ser Tyr Ile Asp Leu Lys Glu Leu Gly Asn Tyr Thr Tyr Tyr Asn
        1280                1285                1290

Lys Trp Pro Trp Tyr Ile Trp Leu Gly Phe Ile Ala Gly Leu Val
        1295                1300                1305

Ala Leu Ala Leu Cys Val Phe Phe Ile Leu Cys Cys Thr Gly Cys
        1310                1315                1320

Gly Thr Asn Cys Met Gly Lys Leu Lys Cys Asn Arg Cys Cys Asp
        1325                1330                1335

Arg Tyr Glu Glu Tyr Asp Leu Glu Pro His Lys Val His Val His
        1340                1345                1350

<210> SEQ ID NO 71
<211> LENGTH: 676
<212> TYPE: PRT
<213> ORGANISM: Zaire ebolavirus

<400> SEQUENCE: 71

Met Gly Val Thr Gly Ile Leu Gln Leu Pro Arg Asp Arg Phe Lys Arg
1               5                   10                  15

Thr Ser Phe Phe Leu Trp Val Ile Leu Phe Gln Arg Thr Phe Ser
            20                  25                  30

```
Ile Pro Leu Gly Val Ile His Asn Ser Thr Leu Gln Val Ser Asp Val
         35                  40                  45

Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Lys Val
                 85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
        290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
        370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
```

```
                450             455             460
His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 72
<211> LENGTH: 681
<212> TYPE: PRT
<213> ORGANISM: Lake Victoria marburgvirus

<400> SEQUENCE: 72

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
                20                  25                  30

Val Asp Ser Val Cys Ser Gly Thr Leu Gln Lys Thr Glu Asp Val His
            35                  40                  45

Leu Met Gly Phe Thr Leu Ser Gly Gln Lys Val Ala Asp Ser Pro Leu
        50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140
```

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
            165                 170                 175

Met Ile Phe Ser Arg Gln Gly Gln Gly Tyr Arg His Met Asn Leu Thr
        180                 185                 190

Ser Thr Asn Lys Tyr Trp Thr Ser Ser Asn Gly Thr Gln Thr Asn Asp
    195                 200                 205

Thr Gly Cys Phe Gly Ala Leu Gln Glu Tyr Asn Ser Thr Lys Asn Gln
        210                 215                 220

Thr Cys Ala Pro Ser Lys Ile Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
            340                 345                 350

Thr Leu Ser Ala Pro Leu Gln Asn Thr Thr Asn Asp Asn Thr Gln Ser
        355                 360                 365

Thr Ile Thr Glu Asn Glu Gln Thr Ser Ala Pro Ser Ile Thr Thr Leu
    370                 375                 380

Pro Pro Thr Gly Asn Pro Thr Thr Ala Lys Ser Thr Ser Ser Lys Lys
385                 390                 395                 400

Gly Pro Ala Thr Ala Pro Asn Thr Thr Asn Glu His Phe Thr Ser
                405                 410                 415

Pro Pro Pro Thr Pro Ser Ser Thr Ala Gln His Leu Val Tyr Phe Arg
        420                 425                 430

Arg Lys Arg Ser Ile Leu Trp Arg Glu Gly Asp Met Phe Pro Phe Leu
    435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
            485                 490                 495

Asn Ile Asn Glu Asn Thr Ala Tyr Ser Gly Glu Asn Glu Asn Asp Cys
        500                 505                 510

Asp Ala Glu Leu Arg Ile Trp Ser Val Gln Glu Asp Asp Leu Ala Ala
    515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val

```
                         565                 570                 575

Thr Thr Glu Glu Arg Thr Phe Ser Leu Ile Asn Arg His Ala Ile Asp
                 580                 585                 590

Phe Leu Leu Thr Arg Trp Gly Gly Thr Cys Lys Val Leu Gly Pro Asp
                 595                 600                 605

Cys Cys Ile Gly Ile Glu Asp Leu Ser Lys Asn Ile Ser Glu Gln Ile
            610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                 645                 650                 655

Ile Leu Leu Leu Leu Ser Ile Ala Val Leu Ile Ala Leu Ser Cys Ile
                 660                 665                 670

Cys Arg Ile Phe Thr Lys Tyr Ile Gly
            675                 680

<210> SEQ ID NO 73
<211> LENGTH: 630
<212> TYPE: PRT
<213> ORGANISM: Hanta virus

<400> SEQUENCE: 73

Leu Arg Asn Val Tyr Asp Met Lys Ile Glu Cys Pro His Thr Val Ser
1               5                   10                  15

Phe Gly Glu Asn Ser Val Ile Gly Tyr Val Glu Leu Pro Pro Val Pro
                20                  25                  30

Leu Ala Asp Thr Ala Gln Met Val Pro Glu Ser Ser Cys Asn Met Asp
            35                  40                  45

Asn His Gln Ser Leu Asn Thr Ile Thr Lys Tyr Thr Gln Val Ser Trp
        50                  55                  60

Arg Gly Lys Ala Asp Gln Ser Gln Ser Ser Gln Asn Ser Phe Glu Thr
65                  70                  75                  80

Val Ser Thr Glu Val Asp Leu Lys Gly Thr Cys Val Leu Lys His Lys
                85                  90                  95

Met Val Glu Ser Tyr Arg Ser Arg Lys Ser Val Thr Cys Tyr Asp
                100                 105                 110

Leu Ser Cys Asn Ser Thr Tyr Cys Lys Pro Thr Leu Tyr Met Ile Val
            115                 120                 125

Pro Ile His Ala Cys Asn Met Met Lys Ser Cys Leu Ile Ala Leu Gly
130                 135                 140

Pro Tyr Arg Val Gln Val Val Tyr Glu Arg Ser Tyr Cys Met Thr Gly
145                 150                 155                 160

Val Leu Ile Glu Gly Lys Cys Phe Val Pro Asp Gln Ser Val Val Ser
                165                 170                 175

Ile Ile Lys His Gly Ile Phe Asp Ile Ala Ser Val His Ile Val Cys
            180                 185                 190

Phe Phe Val Ala Val Lys Gly Asn Thr Tyr Lys Ile Phe Glu Gln Val
        195                 200                 205

Lys Lys Ser Phe Glu Ser Thr Cys Asn Asp Thr Glu Asn Lys Val Gln
210                 215                 220

Gly Tyr Tyr Ile Cys Ile Val Gly Gly Asn Ser Ala Pro Ile Tyr Val
225                 230                 235                 240

Pro Thr Leu Asp Asp Phe Arg Ser Met Glu Ala Phe Thr Gly Ile Phe
                245                 250                 255
```

Arg Ser Pro His Gly Glu Asp His Asp Leu Ala Gly Glu Ile Ala
            260                 265                 270

Ser Tyr Ser Ile Val Gly Pro Ala Asn Ala Lys Val Pro His Ser Ala
        275                 280                 285

Ser Ser Asp Thr Leu Ser Leu Ile Ala Tyr Ser Gly Ile Pro Ser Tyr
290                 295                 300

Ser Ser Leu Ser Ile Leu Thr Ser Ser Thr Glu Ala Lys His Val Phe
305                 310                 315                 320

Ser Pro Gly Leu Phe Pro Lys Leu Asn His Thr Asn Cys Asp Lys Ser
                325                 330                 335

Ala Ile Pro Leu Ile Trp Thr Gly Met Ile Asp Leu Pro Gly Tyr Tyr
            340                 345                 350

Glu Ala Val His Pro Cys Thr Val Phe Cys Val Leu Ser Gly Pro Gly
            355                 360                 365

Ala Ser Cys Glu Ala Phe Ser Glu Gly Gly Ile Phe Asn Ile Thr Ser
370                 375                 380

Pro Met Cys Leu Val Ser Lys Gln Asn Arg Phe Arg Leu Thr Glu Gln
385                 390                 395                 400

Gln Val Asn Phe Val Cys Gln Arg Val Asp Met Asp Ile Val Val Tyr
                405                 410                 415

Cys Asn Gly Gln Arg Lys Val Ile Leu Thr Lys Thr Leu Val Ile Gly
            420                 425                 430

Gln Cys Ile Tyr Thr Ile Thr Ser Leu Phe Ser Leu Leu Pro Gly Val
            435                 440                 445

Ala His Ser Ile Ala Val Glu Leu Cys Val Pro Gly Phe His Gly Trp
450                 455                 460

Ala Thr Ala Ala Leu Leu Val Thr Phe Cys Phe Gly Trp Val Leu Ile
465                 470                 475                 480

Pro Ala Ile Thr Phe Ile Ile Leu Thr Val Leu Lys Phe Ile Ala Asn
                485                 490                 495

Ile Phe His Thr Ser Asn Gln Glu Asn Arg Leu Lys Ser Val Leu Arg
            500                 505                 510

Lys Ile Lys Glu Glu Phe Glu Lys Thr Lys Gly Ser Met Val Cys Asp
            515                 520                 525

Val Cys Lys Tyr Glu Cys Glu Thr Tyr Lys Glu Leu Lys Ala His Gly
530                 535                 540

Val Ser Cys Pro Gln Ser Gln Cys Pro Tyr Cys Phe Thr His Cys Glu
545                 550                 555                 560

Pro Thr Glu Ala Ala Phe Gln Ala His Tyr Lys Val Cys Gln Val Thr
                565                 570                 575

His Arg Phe Arg Asp Asp Leu Lys Lys Thr Val Thr Pro Gln Asn Phe
            580                 585                 590

Thr Pro Gly Cys Tyr Arg Thr Leu Asn Leu Phe Arg Tyr Lys Ser Arg
            595                 600                 605

Cys Tyr Ile Phe Thr Met Trp Ile Phe Leu Leu Val Leu Glu Ser Ile
610                 615                 620

Leu Trp Ala Ala Ser Ala
625                 630

<210> SEQ ID NO 74
<211> LENGTH: 487
<212> TYPE: PRT
<213> ORGANISM: Hanta virus

<400> SEQUENCE: 74

```
Ser Glu Thr Pro Leu Thr Pro Val Trp Asn Asp Asn Ala His Gly Val
1               5                   10                  15

Gly Ser Val Pro Met His Thr Asp Leu Glu Leu Asp Phe Ser Leu Thr
                20                  25                  30

Ser Ser Ser Lys Tyr Thr Tyr Arg Arg Lys Leu Thr Asn Pro Leu Glu
            35                  40                  45

Glu Ala Gln Ser Ile Asp Leu His Ile Glu Ile Glu Glu Gln Thr Ile
        50                  55                  60

Gly Val Asp Val His Ala Leu Gly His Trp Phe Asp Gly Arg Leu Asn
65                  70                  75                  80

Leu Lys Thr Ser Phe His Cys Tyr Gly Ala Cys Thr Lys Tyr Glu Tyr
                85                  90                  95

Pro Trp His Thr Ala Lys Cys His Tyr Glu Arg Asp Tyr Gln Tyr Glu
                100                 105                 110

Thr Ser Trp Gly Cys Asn Pro Ser Asp Cys Pro Gly Val Gly Thr Gly
            115                 120                 125

Cys Thr Ala Cys Gly Leu Tyr Leu Asp Gln Leu Lys Pro Val Gly Ser
        130                 135                 140

Ala Tyr Lys Ile Ile Thr Ile Arg Tyr Ser Arg Arg Val Cys Val Gln
145                 150                 155                 160

Phe Gly Glu Glu Asn Leu Cys Lys Ile Ile Asp Met Asn Asp Cys Phe
                165                 170                 175

Val Ser Arg His Val Lys Val Cys Ile Ile Gly Thr Val Ser Lys Phe
                180                 185                 190

Ser Gln Gly Asp Thr Leu Leu Phe Phe Gly Pro Leu Glu Gly Gly Gly
            195                 200                 205

Leu Ile Phe Lys His Trp Cys Thr Ser Thr Cys Gln Phe Gly Asp Pro
        210                 215                 220

Gly Asp Ile Met Ser Pro Arg Asp Lys Gly Phe Leu Cys Pro Glu Phe
225                 230                 235                 240

Pro Gly Ser Phe Arg Lys Lys Cys Asn Phe Ala Thr Thr Pro Ile Cys
                245                 250                 255

Glu Tyr Asp Gly Asn Met Val Ser Gly Tyr Lys Lys Val Met Ala Thr
                260                 265                 270

Ile Asp Ser Phe Gln Ser Phe Asn Thr Ser Thr Met His Phe Thr Asp
            275                 280                 285

Glu Arg Ile Glu Trp Lys Asp Pro Asp Gly Met Leu Arg Asp His Ile
        290                 295                 300

Asn Ile Leu Val Thr Lys Asp Ile Asp Phe Asp Asn Leu Gly Glu Asn
305                 310                 315                 320

Pro Cys Lys Ile Gly Leu Gln Thr Ser Ser Ile Glu Gly Ala Trp Gly
                325                 330                 335

Ser Gly Val Gly Phe Thr Leu Thr Cys Leu Val Ser Leu Thr Glu Cys
            340                 345                 350

Pro Thr Phe Leu Thr Ser Ile Lys Ala Cys Asp Lys Ala Ile Cys Tyr
        355                 360                 365

Gly Ala Glu Ser Val Thr Leu Thr Arg Gly Gln Asn Thr Val Lys Val
        370                 375                 380

Ser Gly Lys Gly Gly His Ser Gly Ser Thr Phe Arg Cys Cys His Gly
385                 390                 395                 400

Glu Asp Cys Ser Gln Ile Gly Leu His Ala Ala Pro His Leu Asp
                405                 410                 415
```

-continued

```
Lys Val Asn Gly Ile Ser Glu Ile Glu Asn Ser Lys Val Tyr Asp Asp
            420                 425                 430

Gly Ala Pro Gln Cys Gly Ile Lys Cys Trp Phe Val Lys Ser Gly Glu
        435                 440                 445

Trp Ile Ser Gly Ile Phe Ser Gly Asn Trp Ile Val Leu Ile Val Leu
    450                 455                 460

Cys Val Phe Leu Leu Phe Ser Leu Val Leu Leu Ser Ile Leu Cys Pro
465                 470                 475                 480

Val Arg Lys His Lys Lys Ser
                485

<210> SEQ ID NO 75
<211> LENGTH: 226
<212> TYPE: PRT
<213> ORGANISM: Hepatitis B

<400> SEQUENCE: 75

Met Glu Asn Ile Thr Ser Gly Phe Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asn Ser Trp Trp Thr Ser Leu Ser Phe Leu Gly Gly Asn Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Lys Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Ile
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 76
<211> LENGTH: 617
<212> TYPE: PRT
<213> ORGANISM: Measles virus

<400> SEQUENCE: 76

Met Ser Pro Gln Arg Asp Arg Ile Asn Ala Phe Tyr Lys Asp Asn Pro
1               5                   10                  15
```

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His

-continued

```
        435                 440                 445

Asn Asn Val Tyr Trp Leu Thr Ile Pro Pro Met Lys Asn Leu Ala Leu
    450                 455                 460
Gly Val Ile Asn Thr Leu Glu Trp Ile Pro Arg Phe Lys Val Ser Pro
465                 470                 475                 480
Tyr Leu Phe Asn Val Pro Ile Lys Glu Ala Gly Glu Asp Cys His Ala
                485                 490                 495
Pro Thr Tyr Leu Pro Ala Glu Val Asp Gly Asp Val Lys Leu Ser Ser
            500                 505                 510
Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540
Pro Ser Arg Ser Phe Ser Tyr Phe Tyr Pro Phe Arg Leu Pro Ile Lys
545                 550                 555                 560
Gly Val Pro Ile Glu Leu Gln Val Glu Cys Phe Thr Trp Asp Gln Lys
                565                 570                 575
Leu Trp Cys Arg His Phe Cys Val Leu Ala Asp Ser Glu Ser Gly Gly
            580                 585                 590
His Ile Thr His Ser Gly Met Glu Gly Met Gly Val Ser Cys Thr Val
        595                 600                 605

Thr Arg Glu Asp Gly Thr Asn Arg Arg
    610                 615

<210> SEQ ID NO 77
<211> LENGTH: 550
<212> TYPE: PRT
<213> ORGANISM: Measles virus
<400> SEQUENCE: 77

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Asn Leu Ser Lys
            20                  25                  30

Ile Gly Val Val Gly Ile Gly Ser Ala Ser Tyr Lys Val Met Thr Arg
        35                  40                  45

Ser Ser His Gln Ser Leu Val Ile Lys Leu Met Pro Asn Ile Thr Leu
    50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190
```

```
Leu Ser Cys Asp Leu Ile Gly Gln Lys Leu Gly Lys Leu Leu Arg
        195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
            275                 280                 285

Ser Glu Ile Lys Gly Val Ile Val His Arg Leu Glu Gly Val Ser Tyr
290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
            355                 360                 365

Thr Leu Val Ser Gly Ser Phe Gly Asn Arg Phe Ile Leu Ser Gln Gly
            370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
            435                 440                 445

Gly Pro Pro Ile Ser Leu Glu Arg Leu Asp Val Gly Thr Asn Leu Gly
450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
            515                 520                 525

Gly Met Ser Arg Pro Gly Leu Lys Pro Asp Leu Thr Gly Thr Ser Lys
530                 535                 540

Ser Tyr Val Arg Ser Leu
545                 550

<210> SEQ ID NO 78
<211> LENGTH: 500
<212> TYPE: PRT
<213> ORGANISM: Zika virus

<400> SEQUENCE: 78

Ile Arg Cys Ile Gly Val Ser Asn Arg Asp Phe Val Glu Gly Met Ser
1               5                   10                  15
```

```
Gly Gly Thr Trp Val Asp Val Leu Glu His Gly Gly Cys Val Thr
            20              25              30
Val Met Ala Gln Asp Lys Pro Thr Val Asp Ile Glu Leu Val Thr Thr
        35              40              45
Thr Val Ser Asn Met Ala Glu Val Arg Ser Tyr Cys Tyr Glu Ala Ser
    50              55              60
Ile Ser Asp Met Ala Ser Asp Ser Arg Cys Pro Thr Gln Gly Glu Ala
65              70              75              80
Tyr Leu Asp Lys Gln Ser Asp Thr Gln Tyr Val Cys Lys Arg Thr Leu
            85              90              95
Val Asp Arg Gly Trp Gly Asn Gly Cys Gly Leu Phe Gly Lys Gly Ser
            100             105             110
Leu Val Thr Cys Ala Lys Phe Thr Cys Ser Lys Lys Met Thr Gly Lys
            115             120             125
Ser Ile Gln Pro Glu Asn Leu Glu Tyr Arg Ile Met Leu Ser Val His
            130             135             140
Gly Ser Gln His Ser Gly Met Ile Gly Tyr Glu Thr Asp Glu Asp Arg
145             150             155             160
Ala Lys Val Glu Val Thr Pro Asn Ser Pro Arg Ala Glu Ala Thr Leu
            165             170             175
Gly Gly Phe Gly Ser Leu Gly Leu Asp Cys Glu Pro Arg Thr Gly Leu
            180             185             190
Asp Phe Ser Asp Leu Tyr Tyr Leu Thr Met Asn Asn Lys His Trp Leu
            195             200             205
Val His Lys Glu Trp Phe His Asp Ile Pro Leu Pro Trp His Ala Gly
            210             215             220
Ala Asp Thr Gly Thr Pro His Trp Asn Asn Lys Glu Ala Leu Val Glu
225             230             235             240
Phe Lys Asp Ala His Ala Lys Arg Gln Thr Val Val Val Leu Gly Ser
            245             250             255
Gln Glu Gly Ala Val His Thr Ala Leu Ala Gly Ala Leu Glu Ala Glu
            260             265             270
Met Asp Gly Ala Lys Gly Arg Leu Phe Ser Gly His Leu Lys Cys Arg
            275             280             285
Leu Lys Met Asp Lys Leu Arg Leu Lys Gly Val Ser Tyr Ser Leu Cys
            290             295             300
Thr Ala Ala Phe Thr Phe Thr Lys Val Pro Ala Glu Thr Leu His Gly
305             310             315             320
Thr Val Thr Val Glu Val Gln Tyr Ala Gly Thr Asp Gly Pro Cys Lys
            325             330             335
Ile Pro Val Gln Met Ala Val Asp Met Gln Thr Leu Thr Pro Val Gly
            340             345             350
Arg Leu Ile Thr Ala Asn Pro Val Ile Thr Glu Ser Thr Glu Asn Ser
            355             360             365
Lys Met Met Leu Glu Leu Asp Pro Pro Phe Gly Asp Ser Tyr Ile Val
            370             375             380
Ile Gly Val Gly Asp Lys Lys Ile Thr His His Trp His Arg Ser Gly
385             390             395             400
Ser Thr Ile Gly Lys Ala Phe Glu Ala Thr Val Arg Gly Ala Lys Arg
            405             410             415
Met Ala Val Leu Gly Asp Thr Ala Trp Asp Phe Gly Ser Val Gly Gly
            420             425             430
```

```
Val Phe Asn Ser Leu Gly Lys Gly Ile His Gln Ile Phe Gly Ala Ala
            435                 440                 445

Phe Lys Ser Leu Phe Gly Gly Met Ser Trp Phe Ser Gln Ile Leu Ile
450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500

<210> SEQ ID NO 79
<211> LENGTH: 378
<212> TYPE: PRT
<213> ORGANISM: Plasmodium vivax

<400> SEQUENCE: 79

Met Lys Asn Phe Ile Leu Leu Ala Val Ser Ile Leu Leu Val Asp
1               5                   10                  15

Leu Phe Pro Thr His Cys Gly His Asn Val Asp Leu Ser Lys Ala Ile
                20                  25                  30

Asn Leu Asn Gly Val Asn Phe Asn Asn Val Asp Ala Ser Ser Leu Gly
            35                  40                  45

Ala Ala His Val Gly Gln Ser Ala Ser Arg Gly Arg Gly Leu Gly Glu
        50                  55                  60

Asn Pro Asp Asp Glu Glu Gly Asp Ala Lys Lys Lys Asp Gly Lys
65                  70                  75                  80

Lys Ala Glu Pro Lys Asn Pro Arg Glu Asn Lys Leu Lys Gln Pro Gly
                85                  90                  95

Asp Arg Ala Asp Gly Gln Pro Ala Gly Asp Arg Ala Asp Gly Gln Pro
            100                 105                 110

Ala Gly Asp Arg Ala Asp Gly Gln Pro Ala Gly Asp Arg Ala Ala Gly
        115                 120                 125

Gln Pro Ala Gly Asp Arg Ala Asp Gly Gln Pro Ala Gly Asp Arg Ala
    130                 135                 140

Asp Gly Gln Pro Ala Gly Asp Arg Ala Asp Gly Gln Pro Ala Gly Asp
145                 150                 155                 160

Arg Ala Asp Gly Gln Pro Ala Gly Asp Arg Ala Ala Gly Gln Pro Ala
                165                 170                 175

Gly Asp Arg Ala Ala Gly Gln Pro Ala Gly Asp Arg Ala Asp Gly Gln
            180                 185                 190

Pro Ala Gly Asp Arg Ala Ala Gly Gln Pro Ala Gly Asp Arg Ala Asp
        195                 200                 205

Gly Gln Pro Ala Gly Asp Arg Ala Ala Gly Gln Pro Ala Gly Asp Arg
    210                 215                 220

Ala Asp Gly Gln Pro Ala Gly Asp Arg Ala Ala Gly Gln Pro Ala Gly
225                 230                 235                 240

Asp Arg Ala Ala Gly Gln Pro Ala Gly Asp Arg Ala Ala Gly Gln Pro
                245                 250                 255

Ala Gly Asp Arg Ala Ala Gly Gln Pro Ala Gly Asn Gly Ala Gly Gly
            260                 265                 270

Gln Ala Ala Gly Gly Asn Ala Gly Gly Gln Gly Gln Asn Asn Glu
        275                 280                 285

Gly Ala Asn Ala Pro Asn Glu Lys Ser Val Lys Glu Tyr Leu Asp Lys
    290                 295                 300
```

Val Arg Ala Thr Val Gly Thr Glu Trp Thr Pro Cys Ser Val Thr Cys
305                 310                 315                 320

Gly Val Gly Val Arg Val Arg Arg Val Asn Ala Ala Asn Lys Lys
            325                 330                 335

Pro Glu Asp Leu Thr Leu Asn Asp Leu Glu Thr Asp Val Cys Thr Met
            340                 345                 350

Asp Lys Cys Ala Gly Ile Phe Asn Val Val Ser Asn Ser Leu Gly Leu
            355                 360                 365

Val Ile Leu Leu Val Leu Ala Leu Phe Asn
370                 375

<210> SEQ ID NO 80
<211> LENGTH: 546
<212> TYPE: PRT
<213> ORGANISM: Nipah virus

<400> SEQUENCE: 80

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp

```
            290                 295                 300
Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
    530                 535                 540

Gly Thr
545

<210> SEQ ID NO 81
<211> LENGTH: 602
<212> TYPE: PRT
<213> ORGANISM: Nipah virus

<400> SEQUENCE: 81

Met Pro Ala Glu Asn Lys Lys Val Arg Phe Glu Asn Thr Thr Ser Asp
1               5                   10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Ile Lys Gly
            85                  90                  95

Leu Ala Asp Lys Ile Gly Thr Glu Ile Gly Pro Lys Val Ser Leu Ile
            100                 105                 110
```

```
Asp Thr Ser Ser Thr Ile Thr Ile Pro Ala Asn Ile Gly Leu Leu Gly
            115                 120                 125

Ser Lys Ile Ser Gln Ser Thr Ala Ser Ile Asn Glu Asn Val Asn Glu
        130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
```

```
            530                 535                 540
Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
                580                 585                 590

Phe Ala Val Lys Ile Pro Glu Gln Cys Thr
                595                 600
```

<210> SEQ ID NO 82
<211> LENGTH: 775
<212> TYPE: PRT
<213> ORGANISM: Rotavirus A

<400> SEQUENCE: 82

```
Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
                20                  25                  30

Val Thr Ile Asn Pro Ser Pro Phe Ala Gln Thr Arg Tyr Ala Pro Val
            35                  40                  45

Asn Trp Gly His Gly Glu Ile Asn Asp Ser Thr Thr Val Glu Pro Ile
        50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
                100                 105                 110

Asn Pro Val Asp Arg Gln Tyr Thr Ile Phe Gly Glu Ser Lys Gln Phe
            115                 120                 125

Asn Val Ser Asn Asp Ser Asn Lys Trp Lys Phe Leu Glu Met Phe Arg
        130                 135                 140

Ser Ser Ser Gln Asn Glu Phe Tyr Asn Arg Arg Thr Leu Thr Ser Asp
145                 150                 155                 160

Thr Arg Phe Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
                180                 185                 190

Leu Asn Asn Ile Ser Ile Thr Ile His Ser Glu Phe Tyr Ile Ile Pro
            195                 200                 205

Arg Ser Gln Glu Ser Lys Cys Asn Glu Tyr Ile Asn Asn Gly Leu Pro
        210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asn Glu Asp Ile Ile Val Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Ile Val Lys Met Gly Gly Leu Gly Tyr
            275                 280                 285

Lys Trp Ser Glu Ile Ser Tyr Lys Ala Ala Asn Tyr Gln Tyr Asn Tyr
        290                 295                 300
```

```
Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Gly Ile Ser Arg Tyr Glu Val Ile Lys Glu Asn Ser Tyr Val Tyr Val
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Thr Gly Gly Ser Tyr
370                 375                 380

Asn Phe Ser Ile Pro Val Gly Ala Trp Pro Val Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Pro Phe Ser Ile Leu Arg Thr Arg Thr Val Asn Leu Tyr Gly
        435                 440                 445

Leu Pro Ala Ala Asn Pro Asn Asn Gly Asn Glu Tyr Tyr Glu Ile Ser
450                 455                 460

Gly Arg Phe Ser Leu Ile Tyr Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
            500                 505                 510

Met Ala Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Asn Val Ser Ile Arg Ser Asn Leu Ser Ala Ile Ser Asn Trp Thr Asn
            580                 585                 590

Val Ser Asn Asp Val Ser Asn Val Thr Asn Ser Leu Asn Asp Ile Ser
        595                 600                 605

Thr Gln Thr Ser Thr Ile Ser Lys Lys Phe Arg Leu Lys Glu Met Ile
610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Phe Phe Ala Tyr Lys Ile Asn Thr Phe Asp Glu Val Pro Phe Asp Val
690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
```

```
                725                 730                 735

Arg Thr Glu Ala Leu Asn Leu Ile Lys Ser Asn Pro Asn Met Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775

<210> SEQ ID NO 83
<211> LENGTH: 230
<212> TYPE: PRT
<213> ORGANISM: Rotavirus A

<400> SEQUENCE: 83

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Ile Asn Pro Ser Pro Phe Ala Gln Thr Arg Tyr Ala Pro Val
        35                  40                  45

Asn Trp Gly His Gly Glu Ile Asn Asp Ser Thr Thr Val Glu Pro Ile
    50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
            100                 105                 110

Asn Pro Val Asp Arg Gln Tyr Thr Ile Phe Gly Glu Ser Lys Gln Phe
        115                 120                 125

Asn Val Ser Asn Asp Ser Asn Lys Trp Lys Phe Leu Glu Met Phe Arg
    130                 135                 140

Ser Ser Ser Gln Asn Glu Phe Tyr Asn Arg Arg Thr Leu Thr Ser Asp
145                 150                 155                 160

Thr Arg Phe Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
            180                 185                 190

Leu Asn Asn Ile Ser Ile Thr Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg
225                 230

<210> SEQ ID NO 84
<211> LENGTH: 539
<212> TYPE: PRT
<213> ORGANISM: Human metapneumovirus

<400> SEQUENCE: 84

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
```

```
            35                  40                  45
Thr Leu Glu Val Gly Asp Val Glu Asn Leu Thr Cys Ser Asp Gly Pro
 50                  55                  60

Ser Leu Ile Lys Thr Glu Leu Asp Leu Thr Lys Ser Ala Leu Arg Glu
 65                  70                  75                  80

Leu Lys Thr Val Ser Ala Asp Gln Leu Ala Arg Glu Glu Gln Ile Glu
                 85                  90                  95

Asn Pro Arg Gln Ser Arg Phe Val Leu Gly Ala Ile Ala Leu Gly Val
                100                 105                 110

Ala Thr Ala Ala Ala Val Thr Ala Gly Val Ala Ile Ala Lys Thr Ile
            115                 120                 125

Arg Leu Glu Ser Glu Val Thr Ala Ile Lys Asn Ala Leu Lys Thr Thr
            130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
                180                 185                 190

Phe Ser Gln Phe Asn Arg Arg Phe Leu Asn Val Val Arg Gln Phe Ser
            195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
            275                 280                 285

Ala Pro Ser Cys Ser Gly Lys Lys Gly Asn Tyr Ala Cys Leu Leu Arg
            290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
            355                 360                 365

Pro Ile Ser Met Val Ala Leu Ser Pro Leu Gly Ala Leu Val Ala Cys
            370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
            435                 440                 445

Ile Lys Phe Pro Glu Asp Gln Phe Asn Val Ala Leu Asp Gln Val Phe
            450                 455                 460
```

```
Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
        530                 535

<210> SEQ ID NO 85
<211> LENGTH: 219
<212> TYPE: PRT
<213> ORGANISM: Human metapneumovirus

<400> SEQUENCE: 85

Met Glu Val Lys Val Glu Asn Ile Arg Ala Ile Asp Met Leu Lys Ala
1               5                   10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Ser Ser Glu Ser Glu His
    50                  55                  60

His Thr Ser Ser Pro Pro Thr Glu Ser Asn Lys Glu Ala Ser Thr Ile
65                  70                  75                  80

Ser Thr Asp Asn Pro Asp Ile Asn Pro Asn Ser Gln His Pro Thr Gln
                85                  90                  95

Gln Ser Thr Glu Asn Pro Thr Leu Asn Pro Ala Ala Ser Val Ser Pro
            100                 105                 110

Ser Glu Thr Glu Pro Ala Ser Thr Pro Asp Thr Thr Asn Arg Leu Ser
        115                 120                 125

Ser Val Asp Arg Ser Thr Ala Gln Pro Ser Glu Ser Arg Thr Lys Thr
    130                 135                 140

Lys Pro Thr Val His Thr Arg Asn Asn Pro Ser Thr Ala Ser Ser Thr
145                 150                 155                 160

Gln Ser Pro Pro Arg Ala Thr Thr Lys Ala Ile Arg Arg Ala Thr Thr
                165                 170                 175

Phe Arg Met Ser Ser Thr Gly Lys Arg Pro Thr Thr Thr Ser Val Gln
            180                 185                 190

Ser Asp Ser Ser Thr Thr Thr Gln Asn His Glu Glu Thr Gly Ser Ala
        195                 200                 205

Asn Pro Gln Ala Ser Val Ser Thr Met Gln Asn
    210                 215

<210> SEQ ID NO 86
<211> LENGTH: 555
<212> TYPE: PRT
<213> ORGANISM: Human parainfluenza virus

<400> SEQUENCE: 86

Met Gln Lys Ser Glu Ile Leu Phe Leu Ile Tyr Ser Ser Leu Leu Leu
1               5                   10                  15

Ser Ser Ser Leu Cys Gln Ile Pro Val Asp Lys Leu Ser Asn Val Gly
            20                  25                  30
```

```
Val Ile Ile Asn Glu Gly Lys Leu Leu Lys Ile Ala Gly Ser Tyr Glu
            35                  40                  45

Ser Arg Tyr Ile Val Leu Ser Leu Val Pro Ser Ile Asp Leu Glu Asp
        50                  55                  60

Gly Cys Gly Thr Thr Gln Ile Ile Gln Tyr Lys Asn Leu Leu Asn Arg
65                  70                  75                  80

Leu Leu Ile Pro Leu Lys Asp Ala Leu Asp Leu Gln Glu Ser Leu Ile
                85                  90                  95

Thr Ile Thr Asn Asp Thr Thr Val Thr Asn Asp Asn Pro Gln Ser Arg
                    100                 105                 110

Phe Phe Gly Ala Val Ile Gly Thr Ile Ala Leu Gly Val Ala Thr Ala
                115                 120                 125

Ala Gln Ile Thr Ala Gly Ile Ala Leu Ala Glu Ala Arg Glu Ala Arg
            130                 135                 140

Lys Asp Ile Ala Leu Ile Lys Asp Ser Ile Ile Lys Thr His Asn Ser
145                 150                 155                 160

Val Glu Leu Ile Gln Arg Gly Ile Gly Glu Gln Ile Ile Ala Leu Lys
                    165                 170                 175

Thr Leu Gln Asp Phe Val Asn Asn Glu Ile Arg Pro Ala Ile Gly Glu
                180                 185                 190

Leu Arg Cys Glu Thr Thr Ala Leu Lys Leu Gly Ile Lys Leu Thr Gln
            195                 200                 205

His Tyr Ser Glu Leu Ala Thr Ala Phe Ser Ser Asn Leu Gly Thr Ile
            210                 215                 220

Gly Glu Lys Ser Leu Thr Leu Gln Ala Leu Ser Ser Leu Tyr Ser Ala
225                 230                 235                 240

Asn Ile Thr Glu Ile Leu Ser Thr Ile Lys Lys Asp Lys Ser Asp Ile
                    245                 250                 255

Tyr Asp Ile Ile Tyr Thr Glu Gln Val Lys Gly Thr Val Ile Asp Val
                260                 265                 270

Asp Leu Glu Lys Tyr Met Val Thr Leu Leu Val Lys Ile Pro Ile Leu
            275                 280                 285

Ser Glu Ile Pro Gly Val Leu Ile Tyr Arg Ala Ser Ser Ile Ser Tyr
            290                 295                 300

Asn Ile Glu Gly Glu Glu Trp His Val Ala Ile Pro Asn Tyr Ile Ile
305                 310                 315                 320

Asn Lys Ala Ser Ser Leu Gly Gly Ala Asp Val Thr Asn Cys Ile Glu
                    325                 330                 335

Ser Arg Leu Ala Tyr Ile Cys Pro Arg Asp Pro Thr Gln Leu Ile Pro
                340                 345                 350

Asp Asn Gln Gln Lys Cys Ile Leu Gly Asp Val Ser Lys Cys Pro Val
            355                 360                 365

Thr Lys Val Ile Asn Asn Leu Val Pro Lys Phe Ala Phe Ile Asn Gly
        370                 375                 380

Gly Val Val Ala Asn Cys Ile Ala Ser Thr Cys Thr Cys Gly Thr Asn
385                 390                 395                 400

Arg Ile Pro Val Asn Gln Asp Arg Ser Arg Gly Val Thr Phe Leu Thr
                    405                 410                 415

Tyr Thr Asn Cys Gly Leu Ile Gly Ile Asn Gly Ile Glu Leu Tyr Ala
                420                 425                 430

Asn Lys Arg Gly Arg Asp Thr Thr Trp Gly Asn Gln Ile Ile Lys Val
            435                 440                 445
```

Gly Pro Ala Val Ser Ile Arg Pro Val Asp Ile Ser Leu Asn Leu Ala
450                 455                 460

Ser Ala Thr Asn Phe Leu Glu Glu Ser Lys Ile Glu Leu Met Lys Ala
465                 470                 475                 480

Lys Ala Ile Ile Ser Ala Val Gly Gly Trp His Asn Thr Glu Ser Thr
                485                 490                 495

Gln Ile Ile Ile Ile Ile Val Cys Ile Leu Ile Ile Ile Ile Ile Cys
                500                 505                 510

Gly Ile Leu Tyr Tyr Leu Tyr Arg Val Arg Arg Leu Leu Val Met Ile
                515                 520                 525

Asn Ser Thr His Asn Ser Pro Val Asn Thr Tyr Thr Leu Glu Ser Arg
530                 535                 540

Met Arg Asn Pro Tyr Ile Gly Asn Asn Ser Asn
545                 550                 555

<210> SEQ ID NO 87
<211> LENGTH: 571
<212> TYPE: PRT
<213> ORGANISM: Human parainfluenza virus

<400> SEQUENCE: 87

Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
                20                  25                  30

Ile Val Leu Cys Ser Ser Ile Leu His Glu Ile Ile His Leu Asp Val
            35                  40                  45

Ser Ser Gly Leu Met Asp Ser Asp Ser Gln Gln Gly Ile Ile Gln
50                  55                  60

Pro Ile Ile Glu Ser Leu Lys Ser Leu Ile Ala Leu Ala Asn Gln Ile
65                  70                  75                  80

Leu Tyr Asn Val Ala Ile Ile Ile Pro Leu Lys Ile Asp Ser Ile Glu
                85                  90                  95

Thr Val Ile Phe Ser Ala Leu Lys Asp Met His Thr Gly Ser Met Ser
                100                 105                 110

Asn Thr Asn Cys Thr Pro Gly Asn Leu Leu Leu His Asp Ala Ala Tyr
            115                 120                 125

Ile Asn Gly Ile Asn Lys Phe Leu Val Leu Lys Ser Tyr Asn Gly Thr
130                 135                 140

Pro Lys Tyr Gly Pro Leu Leu Asn Ile Pro Ser Phe Ile Pro Ser Ala
145                 150                 155                 160

Thr Ser Pro Asn Gly Cys Thr Arg Ile Pro Ser Phe Ser Leu Ile Lys
                165                 170                 175

Thr His Trp Cys Tyr Thr His Asn Val Met Leu Gly Asp Cys Leu Asp
                180                 185                 190

Phe Thr Thr Ser Asn Gln Tyr Leu Ala Met Gly Ile Ile Gln Gln Ser
            195                 200                 205

Ala Ala Ala Phe Pro Ile Phe Arg Thr Met Lys Thr Ile Tyr Leu Ser
210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
                260                 265                 270

Asp Thr Phe Ile Glu Arg Val Ile Ser Leu Pro Asn Thr Thr Gly Gln
            275                 280                 285

Trp Ala Thr Ile Asn Pro Ala Val Gly Ser Gly Ile Tyr His Leu Gly
        290                 295                 300

Phe Ile Leu Phe Pro Val Tyr Gly Gly Leu Ile Ser Gly Thr Pro Ser
305                 310                 315                 320

Tyr Asn Lys Gln Ser Ser Arg Tyr Phe Ile Pro Lys His Pro Asn Ile
                325                 330                 335

Thr Cys Ala Gly Asn Ser Ser Glu Gln Ala Ala Ala Arg Ser Ser
                340                 345                 350

Tyr Val Ile Arg Tyr His Ser Asn Arg Leu Ile Gln Ser Ala Val Leu
                355                 360                 365

Ile Cys Pro Leu Ser Asp Met His Thr Ala Arg Cys Asn Leu Val Met
370                 375                 380

Phe Asn Ser Gln Val Met Met Gly Ala Glu Gly Arg Leu Tyr Val
385                 390                 395                 400

Ile Asp Asn Asn Leu Tyr Tyr Gln Arg Ser Ser Ser Trp Trp Ser
                405                 410                 415

Ala Ser Leu Phe Tyr Arg Ile Asn Thr Asp Phe Ser Lys Gly Ile Pro
            420                 425                 430

Pro Ile Ile Glu Ala Gln Trp Val Pro Ser Tyr Gln Val Pro Arg Pro
            435                 440                 445

Gly Val Met Pro Cys Asn Ala Thr Ser Phe Cys Pro Ala Asn Cys Ile
        450                 455                 460

Thr Gly Val Tyr Ala Asp Val Trp Pro Leu Asn Asp Pro Glu Pro Thr
465                 470                 475                 480

Ser Gln Asn Ala Leu Asn Pro Asn Tyr Arg Phe Ala Gly Ala Phe Leu
                485                 490                 495

Arg Asn Glu Ser Asn Arg Thr Asn Pro Thr Phe Tyr Thr Ala Ser Ala
            500                 505                 510

Ser Ala Leu Leu Asn Thr Thr Gly Phe Asn Asn Thr Asn His Lys Ala
        515                 520                 525

Ala Tyr Thr Ser Ser Thr Cys Phe Lys Asn Thr Gly Thr Gln Lys Ile
        530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Ile Pro
                565                 570

<210> SEQ ID NO 88
<211> LENGTH: 217
<212> TYPE: PRT
<213> ORGANISM: Plasmodium falciparum

<400> SEQUENCE: 88

Met Asn Lys Leu Tyr Ser Leu Phe Leu Phe Leu Phe Ile Gln Leu Ser
1               5                   10                  15

Ile Lys Tyr Asn Asn Ala Lys Val Thr Val Asp Thr Val Cys Lys Arg
            20                  25                  30

Gly Phe Leu Ile Gln Met Ser Gly His Leu Glu Cys Lys Cys Glu Asn
        35                  40                  45

Asp Leu Val Leu Val Asn Glu Glu Thr Cys Glu Glu Lys Val Leu Lys
    50                  55                  60

Cys Asp Glu Lys Thr Val Asn Lys Pro Cys Gly Asp Phe Ser Lys Cys

```
                    65                  70                  75                  80
Ile Lys Ile Asp Gly Asn Pro Val Ser Tyr Ala Cys Lys Cys Asn Leu
                    85                  90                  95

Gly Tyr Asp Met Val Asn Asn Val Cys Ile Pro Asn Glu Cys Lys Asn
                    100                 105                 110

Val Thr Cys Gly Asn Gly Lys Cys Ile Leu Asp Thr Ser Asn Pro Val
                    115                 120                 125

Lys Thr Gly Val Cys Ser Cys Asn Ile Gly Lys Val Pro Asn Val Gln
                    130                 135                 140

Asp Gln Asn Lys Cys Ser Lys Asp Gly Glu Thr Lys Cys Ser Leu Lys
145                 150                 155                 160

Cys Leu Lys Glu Asn Glu Thr Cys Lys Ala Val Asp Gly Ile Tyr Lys
                    165                 170                 175

Cys Asp Cys Lys Asp Gly Phe Ile Ile Asp Asn Glu Ser Ser Ile Cys
                    180                 185                 190

Thr Ala Phe Ser Ala Tyr Asn Ile Leu Asn Leu Ser Ile Met Phe Ile
                    195                 200                 205

Leu Phe Ser Val Cys Phe Phe Ile Met
                    210                 215

<210> SEQ ID NO 89
<211> LENGTH: 27
<212> TYPE: PRT
<213> ORGANISM: Artificial Sequence
<220> FEATURE:
<223> OTHER INFORMATION: T4 fibritin foldon domain

<400> SEQUENCE: 89

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
                20                  25

<210> SEQ ID NO 90
<211> LENGTH: 540
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 90

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly

```
Leu Ser Lys Lys Arg Lys Arg Arg Phe Leu Gly Phe Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
                180                 185                 190

Leu Asp Leu Lys Asn Tyr Ile Asp Lys Gln Leu Leu Pro Ile Leu Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Gly Tyr Ile Pro Glu Ala Pro Arg Asp Gly Gln Ala Tyr Val Arg
        515                 520                 525

Lys Asp Gly Glu Trp Val Leu Leu Ser Thr Phe Leu
530                 535                 540
```

-continued

```
<210> SEQ ID NO 91
<211> LENGTH: 646
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 91

Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

```
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu Gly Tyr Ile Pro Glu Ala Pro Arg Asp Gly Gln Ala Tyr Val Arg
        515                 520                 525
Lys Asp Gly Glu Trp Val Leu Leu Ser Thr Phe Leu Gly Gly Ser Met
    530                 535                 540
Glu Glu Val Val Leu Ile Thr Val Pro Ser Ala Leu Val Ala Val Lys
545                 550                 555                 560
Ile Ala His Ala Leu Val Glu Glu Arg Leu Ala Ala Cys Val Asn Ile
                565                 570                 575
Val Pro Gly Leu Thr Ser Ile Tyr Arg Glu Glu Gly Ser Val Val Ser
            580                 585                 590
Asp His Glu Leu Leu Leu Val Lys Thr Thr Thr Asp Ala Phe Pro
        595                 600                 605
Lys Leu Lys Glu Arg Val Lys Glu Leu His Pro Tyr Glu Val Pro Glu
    610                 615                 620
Ile Val Ala Leu Pro Ile Ala Glu Gly Asn Arg Glu Tyr Leu Asp Trp
625                 630                 635                 640
Leu Arg Glu Asn Thr Gly
            645

<210> SEQ ID NO 92
<211> LENGTH: 619
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 92

Met Glu Leu Leu Ile Leu Lys Ala Asn Val Ile Ala Thr Ile Leu Thr
1               5                   10                  15
Ala Val Thr Phe Cys Phe Ala Ser Ser Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Asn Lys Cys Asn Gly Thr Asp Ala Lys Val Lys Leu Ile Lys
```

```
                65                  70                  75                  80
Gln Glu Leu Asp Lys Tyr Lys Asn Ala Val Thr Glu Leu Gln Leu Leu
                    85                  90                  95
Met Gln Ser Thr Pro Ala Thr Asn Asn Arg Ala Arg Arg Glu Leu Pro
                100                 105                 110
Arg Phe Met Asn Tyr Thr Leu Asn Asn Ala Lys Lys Thr Asn Val Thr
                115                 120                 125
Leu Ser Lys Lys Arg Lys Arg Arg Phe Leu Gly Phe Leu Leu Gly Val
            130                 135                 140
Gly Ser Ala Ile Ala Ser Gly Val Ala Val Cys Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
                180                 185                 190
Leu Asp Leu Lys Asn Tyr Ile Asp Lys Gln Leu Leu Pro Ile Leu Asn
            195                 200                 205
Lys Gln Ser Cys Ser Ile Ser Asn Ile Glu Thr Val Ile Glu Phe Gln
            210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
            275                 280                 285
Met Cys Ile Ile Lys Glu Glu Val Leu Ala Tyr Val Val Gln Leu Pro
            290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
```

```
Glu Lys Ile Asn Gln Ser Leu Ala Phe Ile Arg Lys Ser Asp Glu Leu
            500                 505                 510

Leu Gly Gly Ser Met Glu Val Val Leu Ile Thr Val Pro Ser Ala
        515                 520                 525

Leu Val Ala Val Lys Ile Ala His Ala Leu Val Glu Glu Arg Leu Ala
530                 535                 540

Ala Cys Val Asn Ile Val Pro Gly Leu Thr Ser Ile Tyr Arg Glu Glu
545                 550                 555                 560

Gly Ser Val Val Ser Asp His Glu Leu Leu Leu Val Lys Thr Thr
                565                 570                 575

Thr Asp Ala Phe Pro Lys Leu Lys Glu Arg Val Lys Glu Leu His Pro
            580                 585                 590

Tyr Glu Val Pro Glu Ile Val Ala Leu Pro Ile Ala Glu Gly Asn Arg
                595                 600                 605

Glu Tyr Leu Asp Trp Leu Arg Glu Asn Thr Gly
            610                 615

<210> SEQ ID NO 93
<211> LENGTH: 665
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 93

Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
```

```
            225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Ser Tyr Ser Ile
                275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Gly Tyr Ile Pro Glu Ala Pro Arg Asp Gly Gln Ala Tyr Val Arg
                515                 520                 525

Lys Asp Gly Glu Trp Val Leu Leu Ser Thr Phe Leu Gly Gly Ser Met
530                 535                 540

Val Arg Gly Ile Arg Gly Ala Ile Thr Val Asn Ser Asp Thr Pro Thr
545                 550                 555                 560

Ser Ile Ile Ile Ala Thr Ile Leu Leu Leu Glu Lys Met Leu Glu Ala
                565                 570                 575

Asn Gly Ile Gln Ser Tyr Glu Glu Leu Ala Ala Val Ile Phe Thr Val
                580                 585                 590

Thr Glu Asp Leu Thr Ser Ala Phe Pro Ala Glu Ala Ala Arg Gln Ile
                595                 600                 605

Gly Met His Arg Val Pro Leu Leu Ser Ala Arg Glu Val Pro Val Pro
                610                 615                 620

Gly Ser Leu Pro Arg Val Ile Arg Val Leu Ala Leu Trp Asn Thr Asp
625                 630                 635                 640

Thr Pro Gln Asp Arg Val Arg His Val Tyr Leu Ser Glu Ala Val Arg
                645                 650                 655
```

Leu Arg Pro Asp Leu Glu Ser Ala Gln
            660                 665

<210> SEQ ID NO 94
<211> LENGTH: 638
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 94

Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe

```
                340             345             350
Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Gly Gly Ser Met Val Arg Gly Ile Arg Gly Ala Ile Thr Val Asn
            515                 520                 525

Ser Asp Thr Pro Thr Ser Ile Ile Ile Ala Thr Ile Leu Leu Leu Glu
        530                 535                 540

Lys Met Leu Glu Ala Asn Gly Ile Gln Ser Tyr Glu Glu Leu Ala Ala
545                 550                 555                 560

Val Ile Phe Thr Val Thr Glu Asp Leu Thr Ser Ala Phe Pro Ala Glu
                565                 570                 575

Ala Ala Arg Gln Ile Gly Met His Arg Val Pro Leu Leu Ser Ala Arg
            580                 585                 590

Glu Val Pro Val Pro Gly Ser Leu Pro Arg Val Ile Arg Val Leu Ala
        595                 600                 605

Leu Trp Asn Thr Asp Thr Pro Gln Asp Arg Val Arg His Val Tyr Leu
610                 615                 620

Ser Glu Ala Val Arg Leu Arg Pro Asp Leu Glu Ser Ala Gln
                630                 635
625

<210> SEQ ID NO 95
<211> LENGTH: 769
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 95

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
```

```
                485                 490                 495
Glu Lys Ile Asn Gln Ser Leu Ala Phe Ile Arg Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Ser His His His His His His
    530                 535                 540

His His Gly Gly Ser Gly Gly Ser Gly Ser Glu Lys Ala Ala Lys Ala
545                 550                 555                 560

Glu Glu Ala Ala Arg Lys Met Glu Glu Leu Phe Lys Lys His Lys Ile
                565                 570                 575

Val Ala Val Leu Arg Ala Asn Ser Val Glu Glu Ala Ile Glu Lys Ala
            580                 585                 590

Val Ala Val Phe Ala Gly Gly Val His Leu Ile Glu Ile Thr Phe Thr
        595                 600                 605

Val Pro Asp Ala Asp Thr Val Ile Lys Ala Leu Ser Val Leu Lys Glu
    610                 615                 620

Lys Gly Ala Ile Ile Gly Ala Gly Thr Val Thr Ser Val Glu Gln Cys
625                 630                 635                 640

Arg Lys Ala Val Glu Ser Gly Ala Glu Phe Ile Val Ser Pro His Leu
                645                 650                 655

Asp Glu Glu Ile Ser Gln Phe Cys Lys Glu Lys Gly Val Phe Tyr Met
            660                 665                 670

Pro Gly Val Met Thr Pro Thr Glu Leu Val Lys Ala Met Lys Leu Gly
        675                 680                 685

His Thr Ile Leu Lys Leu Phe Pro Gly Glu Val Val Gly Pro Gln Phe
    690                 695                 700

Val Lys Ala Met Lys Gly Pro Phe Pro Asn Val Lys Phe Val Pro Thr
705                 710                 715                 720

Gly Gly Val Asn Leu Asp Asn Val Cys Glu Trp Phe Lys Ala Gly Val
                725                 730                 735

Leu Ala Val Gly Val Gly Ser Ala Leu Val Lys Gly Thr Pro Asp Glu
            740                 745                 750

Val Arg Glu Lys Ala Lys Ala Phe Val Glu Lys Ile Arg Gly Cys Thr
        755                 760                 765

Glu

<210> SEQ ID NO 96
<211> LENGTH: 730
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 96

Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
```

```
                65                  70                  75                  80
Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
                180                 185                 190

Leu Asp Leu Lys Asn Tyr Ile Asp Lys Gln Leu Leu Pro Ile Leu Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Cys Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495
```

```
Glu Lys Ile Asn Gln Ser Leu Ala Phe Ile Arg Gly Ser Gly Gly
                500                 505                 510

Ser Gly Ser Glu Lys Ala Ala Lys Ala Glu Ala Ala Arg Lys Met
        515                 520                 525

Glu Glu Leu Phe Lys Lys His Lys Ile Val Ala Val Leu Arg Ala Asn
530                 535                 540

Ser Val Glu Glu Ala Ile Glu Lys Ala Val Ala Phe Ala Gly Gly
545                 550                 555                 560

Val His Leu Ile Glu Ile Thr Phe Thr Val Pro Asp Ala Asp Thr Val
                565                 570                 575

Ile Lys Ala Leu Ser Val Leu Lys Glu Lys Gly Ala Ile Ile Gly Ala
                580                 585                 590

Gly Thr Val Thr Ser Val Glu Gln Cys Arg Lys Ala Val Glu Ser Gly
            595                 600                 605

Ala Glu Phe Ile Val Ser Pro His Leu Asp Glu Glu Ile Ser Gln Phe
            610                 615                 620

Cys Lys Glu Lys Gly Val Phe Tyr Met Pro Gly Val Met Thr Pro Thr
625                 630                 635                 640

Glu Leu Val Lys Ala Met Lys Leu Gly His Thr Ile Leu Lys Leu Phe
                645                 650                 655

Pro Gly Glu Val Val Gly Pro Gln Phe Val Lys Ala Met Lys Gly Pro
                660                 665                 670

Phe Pro Asn Val Lys Phe Val Pro Thr Gly Gly Val Asn Leu Asp Asn
            675                 680                 685

Val Cys Glu Trp Phe Lys Ala Gly Val Leu Ala Val Gly Val Gly Ser
            690                 695                 700

Ala Leu Val Lys Gly Thr Pro Asp Glu Val Arg Glu Lys Ala Lys Ala
705                 710                 715                 720

Phe Val Glu Lys Ile Arg Gly Cys Thr Glu
                725                 730

<210> SEQ ID NO 97
<211> LENGTH: 676
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 97

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
```

```
            115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Cys Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
            245                 250                 255
Leu Leu Ser Leu Ile Asn Asp Met Pro Ile Thr Asn Asp Gln Lys Lys
        260                 265                 270
Leu Met Ser Asn Asn Val Gln Ile Val Arg Gln Gln Ser Tyr Ser Ile
        275                 280                 285
Met Cys Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu Gly Gly Ser Gly Gly Ser Gly Ser Asp Asp Ala Arg Ile Ala Ala
        515                 520                 525
Ile Gly Asp Val Asp Glu Leu Asn Ser Gln Ile Gly Val Leu Leu Ala
        530                 535                 540
```

Glu Pro Leu Pro Asp Asp Val Arg Ala Ala Leu Ser Ala Ile Gln His
545                 550                 555                 560

Asp Leu Phe Asp Leu Gly Gly Glu Leu Cys Ile Pro Gly His Ala Ala
            565                 570                 575

Ile Thr Glu Asp His Leu Leu Arg Leu Ala Leu Trp Leu Val His Tyr
        580                 585                 590

Asn Gly Gln Leu Pro Pro Leu Glu Glu Phe Ile Leu Pro Gly Gly Ala
    595                 600                 605

Arg Gly Ala Ala Leu Ala His Val Cys Arg Thr Val Cys Arg Arg Ala
610                 615                 620

Glu Arg Ser Ile Lys Ala Leu Gly Ala Ser Glu Pro Leu Asn Ile Ala
625                 630                 635                 640

Pro Ala Ala Tyr Val Asn Leu Leu Ser Asp Leu Leu Phe Val Leu Ala
                645                 650                 655

Arg Val Leu Asn Arg Ala Ala Gly Gly Ala Asp Val Leu Trp Asp Arg
            660                 665                 670

Thr Arg Ala His
        675

<210> SEQ ID NO 98
<211> LENGTH: 274
<212> TYPE: PRT
<213> ORGANISM: Neisseria meningitidis

<400> SEQUENCE: 98

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser

```
                225                 230                 235                 240
Tyr Ser Leu Gly Ile Phe Gly Lys Ala Gln Glu Val Ala Gly Ser
                    245                 250                 255

Ala Glu Val Lys Thr Val Asn Gly Ile Arg His Ile Gly Leu Ala Ala
                    260                 265                 270

Lys Gln

<210> SEQ ID NO 99
<211> LENGTH: 370
<212> TYPE: PRT
<213> ORGANISM: Neisseria meningitidis

<400> SEQUENCE: 99

Met Gln Thr Ala Ala Arg Arg Ser Phe Asp Tyr Asp Met Pro Leu Ile
1               5                   10                  15

Gln Thr Pro Thr Ser Ala Cys Gln Ile Arg Gln Ala Trp Ala Lys Val
                20                  25                  30

Ala Asp Thr Pro Asp Arg Glu Thr Ala Gly Arg Leu Lys Asp Glu Ile
            35                  40                  45

Lys Ala Leu Leu Lys Glu Thr Asn Ala Val Leu Ala His Tyr Tyr
50                  55                  60

Val Asp Pro Leu Ile Gln Asp Leu Ala Leu Glu Thr Gly Gly Cys Val
65                  70                  75                  80

Gly Asp Ser Leu Glu Met Ala Arg Phe Gly Ala Glu His Glu Ala Gly
                85                  90                  95

Thr Leu Val Val Ala Gly Val Arg Phe Met Gly Glu Ser Ala Lys Ile
            100                 105                 110

Leu Cys Pro Glu Lys Thr Val Leu Met Pro Asp Leu Glu Ala Glu Cys
        115                 120                 125

Ser Leu Asp Leu Gly Cys Pro Glu Glu Ala Phe Ser Ala Phe Cys Asp
130                 135                 140

Gln His Pro Asp Arg Thr Val Val Val Tyr Ala Asn Thr Ser Ala Ala
145                 150                 155                 160

Val Lys Ala Arg Ala Asp Trp Val Val Thr Ser Ser Val Ala Leu Glu
                165                 170                 175

Ile Val Ser Tyr Leu Lys Ser Arg Gly Glu Lys Leu Ile Trp Gly Pro
            180                 185                 190

Asp Arg His Leu Gly Asp Tyr Ile Arg Arg Glu Thr Gly Ala Asp Met
        195                 200                 205

Leu Leu Trp Gln Gly Ser Cys Ile Val His Asn Glu Phe Lys Gly Gln
210                 215                 220

Glu Leu Ala Ala Leu Lys Ala Glu His Pro Asp Ala Val Val Leu Val
225                 230                 235                 240

His Pro Glu Ser Pro Gln Ser Val Ile Glu Leu Gly Asp Val Val Gly
                245                 250                 255

Ser Thr Ser Lys Leu Leu Lys Ala Ala Val Ser Arg Pro Glu Lys Lys
            260                 265                 270

Phe Ile Val Ala Thr Asp Leu Gly Ile Leu His Glu Met Gln Lys Gln
        275                 280                 285

Ala Pro Asp Lys Gln Phe Ile Ala Pro Thr Ala Gly Asn Gly Gly
290                 295                 300

Ser Cys Lys Ser Cys Ala Phe Cys Pro Trp Met Ala Met Asn Ser Leu
305                 310                 315                 320

Gly Gly Ile Lys Tyr Ala Leu Thr Ser Gly His Asn Glu Ile Leu Leu
```

```
                     325                 330                 335
Asp Arg Lys Leu Gly Glu Ala Ala Lys Leu Pro Leu Gln Arg Met Leu
            340                 345                 350

Asp Phe Ala Ala Gly Leu Lys Arg Gly Asp Val Phe Asn Gly Met Gly
        355                 360                 365

Pro Ala
    370

<210> SEQ ID NO 100
<211> LENGTH: 492
<212> TYPE: PRT
<213> ORGANISM: Neisseria meningitidis

<400> SEQUENCE: 100

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Gly Gln Asp Met Ala Ala Val Ser Glu Glu Asn Thr
65                  70                  75                  80

Gly Asn Gly Gly Ala Ala Ala Thr Asp Lys Pro Lys Asn Glu Asp Glu
                85                  90                  95

Gly Ala Gln Asn Asp Met Pro Gln Asn Ala Ala Asp Thr Asp Ser Leu
            100                 105                 110

Thr Pro Asn His Thr Pro Ala Ser Asn Met Pro Ala Gly Asn Met Glu
        115                 120                 125

Asn Gln Ala Pro Asp Ala Gly Glu Ser Glu Gln Pro Ala Asn Gln Pro
    130                 135                 140

Asp Met Ala Asn Thr Ala Asp Gly Met Gln Gly Asp Asp Pro Ser Ala
145                 150                 155                 160

Gly Gly Glu Asn Ala Gly Asn Thr Ala Ala Gln Gly Thr Asn Gln Ala
                165                 170                 175

Glu Asn Asn Gln Thr Ala Gly Ser Gln Asn Pro Ala Ser Ser Thr Asn
            180                 185                 190

Pro Ser Ala Thr Asn Ser Gly Gly Asp Phe Gly Arg Thr Asn Val Gly
        195                 200                 205

Asn Ser Val Val Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Gly Lys Asn Asp Lys Phe Val
            260                 265                 270

Gly Leu Val Ala Asp Ser Val Gln Met Lys Gly Ile Asn Gln Tyr Ile
        275                 280                 285

Ile Phe Tyr Lys Pro Lys Pro Thr Ser Phe Ala Arg Phe Arg Arg Ser
    290                 295                 300

Ala Arg Ser Arg Arg Ser Leu Pro Ala Glu Met Pro Leu Ile Pro Val
305                 310                 315                 320
```

-continued

```
Asn Gln Ala Asp Thr Leu Ile Val Asp Gly Glu Ala Val Ser Leu Thr
            325                 330                 335

Gly His Ser Gly Asn Ile Phe Ala Pro Glu Gly Asn Tyr Arg Tyr Leu
        340                 345                 350

Thr Tyr Gly Ala Glu Lys Leu Pro Gly Gly Ser Tyr Ala Leu Arg Val
    355                 360                 365

Gln Gly Glu Pro Ser Lys Gly Glu Met Leu Ala Gly Thr Ala Val Tyr
370                 375                 380

Asn Gly Glu Val Leu His Phe His Thr Glu Asn Gly Arg Pro Ser Pro
385                 390                 395                 400

Ser Arg Gly Arg Phe Ala Ala Lys Val Asp Phe Gly Ser Lys Ser Val
                405                 410                 415

Asp Gly Ile Ile Asp Ser Gly Asp Gly Leu His Met Gly Thr Gln Lys
            420                 425                 430

Phe Lys Ala Ala Ile Asp Gly Asn Gly Phe Lys Gly Thr Trp Thr Glu
        435                 440                 445

Asn Gly Gly Gly Asp Val Ser Gly Lys Phe Tyr Gly Pro Ala Gly Glu
    450                 455                 460

Glu Val Ala Gly Lys Tyr Ser Tyr Arg Pro Thr Asp Ala Glu Lys Gly
465                 470                 475                 480

Gly Phe Gly Val Phe Ala Gly Lys Lys Glu Gln Asp
                485                 490

<210> SEQ ID NO 101
<211> LENGTH: 615
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 101

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
        115                 120                 125

Val Cys Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190
```

-continued

```
Glu Thr Val Ile Glu Phe Gln Gln Lys Asn Asn Arg Leu Leu Glu Ile
            195                 200                 205
Thr Arg Glu Phe Ser Val Asn Ala Gly Val Thr Thr Pro Val Ser Thr
    210                 215                 220
Tyr Met Leu Thr Asn Ser Glu Leu Leu Ser Leu Ile Asn Asp Met Pro
225                 230                 235                 240
Ile Thr Asn Asp Gln Lys Lys Leu Met Ser Asn Asn Val Gln Ile Val
                245                 250                 255
Arg Gln Gln Ser Tyr Ser Ile Met Cys Ile Ile Lys Glu Glu Val Leu
            260                 265                 270
Ala Tyr Val Val Gln Leu Pro Leu Tyr Gly Val Ile Asp Thr Pro Cys
        275                 280                 285
Trp Lys Leu His Thr Ser Pro Leu Cys Thr Thr Asn Thr Lys Glu Gly
    290                 295                 300
Ser Asn Ile Cys Leu Thr Arg Thr Asp Arg Gly Trp Tyr Cys Asp Asn
305                 310                 315                 320
Ala Gly Ser Val Ser Phe Phe Pro Gln Ala Glu Thr Cys Lys Val Gln
                325                 330                 335
Ser Asn Arg Val Phe Cys Asp Thr Met Asn Ser Leu Thr Leu Pro Ser
            340                 345                 350
Glu Val Asn Leu Cys Asn Val Asp Ile Phe Asn Pro Lys Tyr Asp Cys
        355                 360                 365
Lys Ile Met Thr Ser Lys Thr Asp Val Ser Ser Ser Val Ile Thr Ser
    370                 375                 380
Leu Gly Ala Ile Val Ser Cys Tyr Gly Lys Thr Lys Cys Thr Ala Ser
385                 390                 395                 400
Asn Lys Asn Arg Gly Ile Ile Lys Thr Phe Ser Asn Gly Cys Asp Tyr
                405                 410                 415
Val Ser Asn Lys Gly Val Asp Thr Val Ser Val Gly Asn Thr Leu Tyr
            420                 425                 430
Tyr Val Asn Lys Gln Glu Gly Lys Ser Leu Tyr Val Lys Gly Glu Pro
        435                 440                 445
Ile Ile Asn Phe Tyr Asp Pro Leu Val Phe Pro Ser Asp Glu Phe Asp
    450                 455                 460
Ala Ser Ile Ser Gln Val Asn Glu Lys Ile Asn Gln Ser Leu Ala Phe
465                 470                 475                 480
Ile Arg Gly Tyr Ile Pro Glu Ala Pro Arg Asp Gly Gln Ala Tyr Val
                485                 490                 495
Arg Lys Asp Gly Glu Trp Val Leu Leu Ser Thr Phe Leu Gly Gly Ser
            500                 505                 510
Met Glu Glu Val Val Leu Ile Thr Val Pro Ser Ala Leu Val Ala Val
        515                 520                 525
Lys Ile Ala His Ala Leu Val Glu Glu Arg Leu Ala Ala Cys Val Asn
    530                 535                 540
Ile Val Pro Gly Leu Thr Ser Ile Tyr Arg Glu Gly Ser Val Val
545                 550                 555                 560
Ser Asp His Glu Leu Leu Leu Leu Val Lys Thr Thr Asp Ala Phe
                565                 570                 575
Pro Lys Leu Lys Glu Arg Val Lys Glu Leu His Pro Tyr Glu Val Pro
            580                 585                 590
Glu Ile Val Ala Leu Pro Ile Ala Glu Gly Asn Arg Glu Tyr Leu Asp
        595                 600                 605
```

```
Trp Leu Arg Glu Asn Thr Gly
    610                 615

<210> SEQ ID NO 102
<211> LENGTH: 588
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 102

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
        115                 120                 125

Val Cys Lys Val Leu His Leu Glu Gly Glu Val Asn Lys Ile Lys Ser
130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Cys Ile Ile Lys Glu Glu Val Leu
            260                 265                 270

Ala Tyr Val Val Gln Leu Pro Leu Tyr Gly Val Ile Asp Thr Pro Cys
        275                 280                 285

Trp Lys Leu His Thr Ser Pro Leu Cys Thr Thr Asn Thr Lys Glu Gly
290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350
```

```
Glu Val Asn Leu Cys Asn Val Asp Ile Phe Asn Pro Lys Tyr Asp Cys
            355                 360                 365

Lys Ile Met Thr Ser Lys Thr Asp Val Ser Ser Val Ile Thr Ser
        370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
            435                 440                 445

Ile Ile Asn Phe Tyr Asp Pro Leu Val Phe Pro Ser Asp Glu Phe Asp
            450                 455                 460

Ala Ser Ile Ser Gln Val Asn Glu Lys Ile Asn Gln Ser Leu Ala Phe
465                 470                 475                 480

Ile Arg Gly Gly Ser Met Glu Glu Val Leu Ile Thr Val Pro Ser
                485                 490                 495

Ala Leu Val Ala Val Lys Ile Ala His Ala Leu Val Glu Glu Arg Leu
            500                 505                 510

Ala Ala Cys Val Asn Ile Val Pro Gly Leu Thr Ser Ile Tyr Arg Glu
            515                 520                 525

Glu Gly Ser Val Val Ser Asp His Glu Leu Leu Leu Leu Val Lys Thr
            530                 535                 540

Thr Thr Asp Ala Phe Pro Lys Leu Lys Glu Arg Val Lys Glu Leu His
545                 550                 555                 560

Pro Tyr Glu Val Pro Glu Ile Val Ala Leu Pro Ile Ala Glu Gly Asn
                565                 570                 575

Arg Glu Tyr Leu Asp Trp Leu Arg Glu Asn Thr Gly
            580                 585

<210> SEQ ID NO 103
<211> LENGTH: 634
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 103

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
```

```
              115                 120                 125
Val Cys Lys Val Leu His Leu Glu Gly Glu Val Asn Lys Ile Lys Ser
130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                    165                 170                 175

Gln Leu Leu Pro Ile Leu Asn Lys Gln Ser Cys Ser Ile Ser Asn Ile
                180                 185                 190

Glu Thr Val Ile Glu Phe Gln Gln Lys Asn Asn Arg Leu Leu Glu Ile
            195                 200                 205

Thr Arg Glu Phe Ser Val Asn Ala Gly Val Thr Thr Pro Val Ser Thr
        210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                    245                 250                 255

Arg Gln Gln Ser Tyr Ser Ile Met Cys Ile Ile Lys Glu Glu Val Leu
                260                 265                 270

Ala Tyr Val Val Gln Leu Pro Leu Tyr Gly Val Ile Asp Thr Pro Cys
            275                 280                 285

Trp Lys Leu His Thr Ser Pro Leu Cys Thr Thr Asn Thr Lys Glu Gly
        290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                    325                 330                 335

Ser Asn Arg Val Phe Cys Asp Thr Met Asn Ser Leu Thr Leu Pro Ser
                340                 345                 350

Glu Val Asn Leu Cys Asn Val Asp Ile Phe Asn Pro Lys Tyr Asp Cys
            355                 360                 365

Lys Ile Met Thr Ser Lys Thr Asp Val Ser Ser Ser Val Ile Thr Ser
        370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                    405                 410                 415

Val Ser Asn Lys Gly Val Asp Thr Val Ser Val Gly Asn Thr Leu Tyr
                420                 425                 430

Tyr Val Asn Lys Gln Glu Gly Lys Ser Leu Tyr Val Lys Gly Glu Pro
            435                 440                 445

Ile Ile Asn Phe Tyr Asp Pro Leu Val Phe Pro Ser Asp Glu Phe Asp
        450                 455                 460

Ala Ser Ile Ser Gln Val Asn Glu Lys Ile Asn Gln Ser Leu Ala Phe
465                 470                 475                 480

Ile Arg Gly Tyr Ile Pro Glu Ala Pro Arg Asp Gly Gln Ala Tyr Val
                    485                 490                 495

Arg Lys Asp Gly Glu Trp Val Leu Leu Ser Thr Phe Leu Gly Gly Ser
                500                 505                 510

Met Val Arg Gly Ile Arg Gly Ala Ile Thr Val Asn Ser Asp Thr Pro
            515                 520                 525

Thr Ser Ile Ile Ile Ala Thr Ile Leu Leu Leu Glu Lys Met Leu Glu
        530                 535                 540
```

Ala Asn Gly Ile Gln Ser Tyr Glu Glu Leu Ala Ala Val Ile Phe Thr
545                 550                 555                 560

Val Thr Glu Asp Leu Thr Ser Ala Phe Pro Ala Glu Ala Ala Arg Gln
            565                 570                 575

Ile Gly Met His Arg Val Pro Leu Leu Ser Ala Arg Glu Val Pro Val
        580                 585                 590

Pro Gly Ser Leu Pro Arg Val Ile Arg Val Leu Ala Leu Trp Asn Thr
    595                 600                 605

Asp Thr Pro Gln Asp Arg Val Arg His Val Tyr Leu Ser Glu Ala Val
610                 615                 620

Arg Leu Arg Pro Asp Leu Glu Ser Ala Gln
625                 630

<210> SEQ ID NO 104
<211> LENGTH: 607
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 104

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
        115                 120                 125

Val Cys Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
    210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Cys Ile Ile Lys Glu Glu Val Leu

Ala Tyr Val Val Gln Leu Pro Leu Tyr Gly Val Ile Asp Thr Pro Cys
          260                 265                 270

Trp Lys Leu His Thr Ser Pro Leu Cys Thr Thr Asn Thr Lys Glu Gly
     275                 280                 285

Ser Asn Ile Cys Leu Thr Arg Thr Asp Arg Gly Trp Tyr Cys Asp Asn
290                 295                 300

Ala Gly Ser Val Ser Phe Phe Pro Gln Ala Glu Thr Cys Lys Val Gln
305                 310                 315                 320

Ser Asn Arg Val Phe Cys Asp Thr Met Asn Ser Leu Thr Leu Pro Ser
         325                 330                 335

Glu Val Asn Leu Cys Asn Val Asp Ile Phe Asn Pro Lys Tyr Asp Cys
             340                 345                 350

Lys Ile Met Thr Ser Lys Thr Asp Val Ser Ser Ser Val Ile Thr Ser
                 355                 360                 365

Leu Gly Ala Ile Val Ser Cys Tyr Gly Lys Thr Lys Cys Thr Ala Ser
370                 375                 380

Asn Lys Asn Arg Gly Ile Ile Lys Thr Phe Ser Asn Gly Cys Asp Tyr
385                 390                 395                 400

Val Ser Asn Lys Gly Val Asp Thr Val Ser Val Gly Asn Thr Leu Tyr
         405                 410                 415

Tyr Val Asn Lys Gln Glu Gly Lys Ser Leu Tyr Val Lys Gly Glu Pro
             420                 425                 430

Ile Ile Asn Phe Tyr Asp Pro Leu Val Phe Pro Ser Asp Glu Phe Asp
                 435                 440                 445

Ala Ser Ile Ser Gln Val Asn Glu Lys Ile Asn Gln Ser Leu Ala Phe
450                 455                 460

Ile Arg Gly Gly Ser Met Val Arg Gly Ile Arg Gly Ala Ile Thr Val
465                 470                 475                 480

Asn Ser Asp Thr Pro Thr Ser Ile Ile Ile Ala Thr Ile Leu Leu Leu
         485                 490                 495

Glu Lys Met Leu Glu Ala Asn Gly Ile Gln Ser Tyr Glu Glu Leu Ala
             500                 505                 510

Ala Val Ile Phe Thr Val Thr Glu Asp Leu Thr Ser Ala Phe Pro Ala
                 515                 520                 525

Glu Ala Ala Arg Gln Ile Gly Met His Arg Val Pro Leu Leu Ser Ala
530                 535                 540

Arg Glu Val Pro Val Pro Gly Ser Leu Pro Arg Val Ile Arg Val Leu
545                 550                 555                 560

Ala Leu Trp Asn Thr Asp Thr Pro Gln Asp Arg Val Arg His Val Tyr
         565                 570                 575

Leu Ser Glu Ala Val Arg Leu Arg Pro Asp Leu Glu Ser Ala Gln
             580                 585                 590

<210> SEQ ID NO 105
<211> LENGTH: 744
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 105

Gln Asn Ile Thr Glu Glu Phe Tyr Gln Ser Thr Cys Ser Ala Val Ser
1               5                   10                  15

```
Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
            115                 120                 125

Val Cys Lys Val Leu His Leu Glu Gly Glu Val Asn Lys Ile Lys Ser
130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190

Glu Thr Val Ile Glu Phe Gln Gln Lys Asn Asn Arg Leu Leu Glu Ile
            195                 200                 205

Thr Arg Glu Phe Ser Val Asn Ala Gly Val Thr Thr Pro Val Ser Thr
210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Cys Ile Ile Lys Glu Glu Val Leu
            260                 265                 270

Ala Tyr Val Val Gln Leu Pro Leu Tyr Gly Val Ile Asp Thr Pro Cys
            275                 280                 285

Trp Lys Leu His Thr Ser Pro Leu Cys Thr Thr Asn Thr Lys Glu Gly
290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Val Asp Ile Phe Asn Pro Lys Tyr Asp Cys
            355                 360                 365

Lys Ile Met Thr Ser Lys Thr Asp Val Ser Ser Ser Val Ile Thr Ser
            370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
```

```
                435                 440                 445
Ile Ile Asn Phe Tyr Asp Pro Leu Val Phe Pro Ser Asp Glu Phe Asp
450                 455                 460

Ala Ser Ile Ser Gln Val Asn Glu Lys Ile Asn Gln Ser Leu Ala Phe
465                 470                 475                 480

Ile Arg Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Ser Gly
            500                 505                 510

Ser His His His His His His Gly Gly Ser Gly Gly Ser Gly
        515                 520                 525

Ser Glu Lys Ala Ala Lys Ala Glu Ala Ala Arg Lys Met Glu Glu
530                 535                 540

Leu Phe Lys Lys His Lys Ile Val Ala Val Leu Arg Ala Asn Ser Val
545                 550                 555                 560

Glu Glu Ala Ile Glu Lys Ala Val Ala Val Phe Ala Gly Gly Val His
                565                 570                 575

Leu Ile Glu Ile Thr Phe Thr Val Pro Asp Ala Asp Thr Val Ile Lys
            580                 585                 590

Ala Leu Ser Val Leu Lys Glu Lys Gly Ala Ile Ile Gly Ala Gly Thr
        595                 600                 605

Val Thr Ser Val Glu Gln Cys Arg Lys Ala Val Glu Ser Gly Ala Glu
610                 615                 620

Phe Ile Val Ser Pro His Leu Asp Glu Glu Ile Ser Gln Phe Cys Lys
625                 630                 635                 640

Glu Lys Gly Val Phe Tyr Met Pro Gly Val Met Thr Pro Thr Glu Leu
                645                 650                 655

Val Lys Ala Met Lys Leu Gly His Thr Ile Leu Lys Leu Phe Pro Gly
            660                 665                 670

Glu Val Val Gly Pro Gln Phe Val Lys Ala Met Lys Gly Pro Phe Pro
        675                 680                 685

Asn Val Lys Phe Val Pro Thr Gly Gly Val Asn Leu Asp Asn Val Cys
690                 695                 700

Glu Trp Phe Lys Ala Gly Val Leu Ala Val Gly Val Gly Ser Ala Leu
705                 710                 715                 720

Val Lys Gly Thr Pro Asp Glu Val Arg Glu Lys Ala Lys Ala Phe Val
                725                 730                 735

Glu Lys Ile Arg Gly Cys Thr Glu
            740

<210> SEQ ID NO 106
<211> LENGTH: 705
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 106

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45
```

-continued

```
Ala Lys Val Lys Leu Ile Lys Gln Glu Leu Asp Lys Tyr Lys Asn Ala
    50                  55                  60
Val Thr Glu Leu Gln Leu Leu Met Gln Ser Thr Pro Ala Thr Asn Asn
65                  70                  75                  80
Arg Ala Arg Arg Glu Leu Pro Arg Phe Met Asn Tyr Thr Leu Asn Asn
                85                  90                  95
Ala Lys Lys Thr Asn Val Thr Leu Ser Lys Arg Lys Arg Arg Phe
            100                 105                 110
Leu Gly Phe Leu Leu Gly Val Gly Ser Ala Ile Ala Ser Gly Val Ala
            115                 120                 125
Val Cys Lys Val Leu His Leu Glu Gly Glu Val Asn Lys Ile Lys Ser
    130                 135                 140
Ala Leu Leu Ser Thr Asn Lys Ala Val Val Ser Leu Ser Asn Gly Val
145                 150                 155                 160
Ser Val Leu Thr Phe Lys Val Leu Asp Leu Lys Asn Tyr Ile Asp Lys
                165                 170                 175
Gln Leu Leu Pro Ile Leu Asn Lys Gln Ser Cys Ser Ile Ser Asn Ile
            180                 185                 190
Glu Thr Val Ile Glu Phe Gln Gln Lys Asn Asn Arg Leu Leu Glu Ile
    195                 200                 205
Thr Arg Glu Phe Ser Val Asn Ala Gly Val Thr Thr Pro Val Ser Thr
210                 215                 220
Tyr Met Leu Thr Asn Ser Glu Leu Leu Ser Leu Ile Asn Asp Met Pro
225                 230                 235                 240
Ile Thr Asn Asp Gln Lys Lys Leu Met Ser Asn Asn Val Gln Ile Val
                245                 250                 255
Arg Gln Gln Ser Tyr Ser Ile Met Cys Ile Ile Lys Glu Glu Val Leu
            260                 265                 270
Ala Tyr Val Val Gln Leu Pro Leu Tyr Gly Val Ile Asp Thr Pro Cys
    275                 280                 285
Trp Lys Leu His Thr Ser Pro Leu Cys Thr Thr Asn Thr Lys Glu Gly
    290                 295                 300
Ser Asn Ile Cys Leu Thr Arg Thr Asp Arg Gly Trp Tyr Cys Asp Asn
305                 310                 315                 320
Ala Gly Ser Val Ser Phe Phe Pro Gln Ala Glu Thr Cys Lys Val Gln
                325                 330                 335
Ser Asn Arg Val Phe Cys Asp Thr Met Asn Ser Leu Thr Leu Pro Ser
            340                 345                 350
Glu Val Asn Leu Cys Asn Val Asp Ile Phe Asn Pro Lys Tyr Asp Cys
    355                 360                 365
Lys Ile Met Thr Ser Lys Thr Asp Val Ser Ser Val Ile Thr Ser
    370                 375                 380
Leu Gly Ala Ile Val Ser Cys Tyr Gly Lys Thr Lys Cys Thr Ala Ser
385                 390                 395                 400
Asn Lys Asn Arg Gly Ile Ile Lys Thr Phe Ser Asn Gly Cys Asp Tyr
                405                 410                 415
Val Ser Asn Lys Gly Val Asp Thr Val Ser Val Gly Asn Thr Leu Tyr
            420                 425                 430
Tyr Val Asn Lys Gln Glu Gly Lys Ser Leu Tyr Val Lys Gly Glu Pro
    435                 440                 445
Ile Ile Asn Phe Tyr Asp Pro Leu Val Phe Pro Ser Asp Glu Phe Asp
450                 455                 460
Ala Ser Ile Ser Gln Val Asn Glu Lys Ile Asn Gln Ser Leu Ala Phe
```

```
                465                 470                 475                 480
        Ile Arg Gly Gly Ser Gly Gly Ser Gly Ser Glu Lys Ala Ala Lys Ala
                            485                 490                 495

Glu Glu Ala Ala Arg Lys Met Glu Glu Leu Phe Lys Lys His Lys Ile
                        500                 505                 510

Val Ala Val Leu Arg Ala Asn Ser Val Glu Ala Ile Glu Lys Ala
                        515                 520                 525

Val Ala Val Phe Ala Gly Gly Val His Leu Ile Glu Ile Thr Phe Thr
                        530                 535                 540

Val Pro Asp Ala Asp Thr Val Ile Lys Ala Leu Ser Val Leu Lys Glu
        545                 550                 555                 560

Lys Gly Ala Ile Ile Gly Ala Gly Thr Val Thr Ser Val Glu Gln Cys
                            565                 570                 575

Arg Lys Ala Val Glu Ser Gly Ala Glu Phe Ile Val Ser Pro His Leu
                        580                 585                 590

Asp Glu Glu Ile Ser Gln Phe Cys Lys Glu Lys Gly Val Phe Tyr Met
                        595                 600                 605

Pro Gly Val Met Thr Pro Thr Glu Leu Val Lys Ala Met Lys Leu Gly
                    610                 615                 620

His Thr Ile Leu Lys Leu Phe Pro Gly Glu Val Val Gly Pro Gln Phe
        625                 630                 635                 640

Val Lys Ala Met Lys Gly Pro Phe Pro Asn Val Lys Phe Val Pro Thr
                            645                 650                 655

Gly Gly Val Asn Leu Asp Asn Val Cys Glu Trp Phe Lys Ala Gly Val
                        660                 665                 670

Leu Ala Val Gly Val Gly Ser Ala Leu Val Lys Gly Thr Pro Asp Glu
                    675                 680                 685

Val Arg Glu Lys Ala Lys Ala Phe Val Glu Lys Ile Arg Gly Cys Thr
                        690                 695                 700

Glu
        705

<210> SEQ ID NO 107
<211> LENGTH: 645
<212> TYPE: PRT
<213> ORGANISM: Artificial Sequence
<220> FEATURE:
<223> OTHER INFORMATION: synthetically constructed Respiratory Synticial
      Virus antigen

<400> SEQUENCE: 107

Gln Asn Ile Thr Glu Glu Phe Tyr Gln Ser Thr Cys Ser Ala Val Ser
        1               5                   10                  15

Lys Gly Tyr Leu Ser Ala Leu Arg Thr Gly Trp Tyr Thr Ser Val Ile
                        20                  25                  30

Thr Ile Glu Leu Ser Asn Ile Lys Glu Asn Lys Cys Asn Gly Thr Asp
                    35                  40                  45

Ala Lys Val Lys Leu Ile Lys Gln Glu Leu Asp Lys Tyr Lys Asn Ala
                50                  55                  60

Val Thr Glu Leu Gln Leu Leu Met Gln Ser Thr Pro Ala Thr Asn Asn
        65                  70                  75                  80

Arg Ala Arg Arg Glu Leu Pro Arg Phe Met Asn Tyr Thr Leu Asn Asn
                        85                  90                  95

Ala Lys Lys Thr Asn Val Thr Leu Ser Lys Lys Arg Lys Arg Arg Phe
                        100                 105                 110
```

```
Leu Gly Phe Leu Leu Gly Val Gly Ser Ala Ile Ala Ser Gly Val Ala
            115                 120                 125

Val Cys Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Phe Lys Val Leu Asp Leu Lys Asn Tyr Ile Asp Lys
                165                 170                 175

Gln Leu Leu Pro Ile Leu Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
    210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Cys Ile Ile Lys Glu Glu Val Leu
            260                 265                 270

Ala Tyr Val Val Gln Leu Pro Leu Tyr Gly Val Ile Asp Thr Pro Cys
        275                 280                 285

Trp Lys Leu His Thr Ser Pro Leu Cys Thr Thr Asn Thr Lys Glu Gly
    290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Val Asp Ile Phe Asn Pro Lys Tyr Asp Cys
        355                 360                 365

Lys Ile Met Thr Ser Lys Thr Asp Val Ser Ser Ser Val Ile Thr Ser
    370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
        435                 440                 445

Ile Ile Asn Phe Tyr Asp Pro Leu Val Phe Pro Ser Asp Glu Phe Asp
    450                 455                 460

Ala Ser Ile Ser Gln Val Asn Glu Lys Ile Asn Gln Ser Leu Ala Phe
465                 470                 475                 480

Ile Arg Gly Gly Ser Gly Gly Ser Asp Asp Ala Arg Ile Ala
                485                 490                 495

Ala Ile Gly Asp Val Asp Glu Leu Asn Ser Gln Ile Gly Val Leu Leu
            500                 505                 510

Ala Glu Pro Leu Pro Asp Asp Val Arg Ala Ala Leu Ser Ala Ile Gln
        515                 520                 525

His Asp Leu Phe Asp Leu Gly Gly Glu Leu Cys Ile Pro Gly His Ala
```

```
                530                 535                 540
Ala Ile Thr Glu Asp His Leu Leu Arg Leu Ala Leu Trp Leu Val His
545                 550                 555                 560

Tyr Asn Gly Gln Leu Pro Pro Leu Glu Glu Phe Ile Leu Pro Gly Gly
                565                 570                 575

Ala Arg Gly Ala Ala Leu Ala His Val Cys Arg Thr Val Cys Arg Arg
                580                 585                 590

Ala Glu Arg Ser Ile Lys Ala Leu Gly Ala Ser Glu Pro Leu Asn Ile
                595                 600                 605

Ala Pro Ala Ala Tyr Val Asn Leu Leu Ser Asp Leu Leu Phe Val Leu
                610                 615                 620

Ala Arg Val Leu Asn Arg Ala Ala Gly Gly Ala Asp Val Leu Trp Asp
625                 630                 635                 640

Arg Thr Arg Ala His
                645

<210> SEQ ID NO 108
<211> LENGTH: 678
<212> TYPE: PRT
<213> ORGANISM: Artificial Sequence
<220> FEATURE:
<223> OTHER INFORMATION: RSV F-10 DS-Cav1-8GS-HelExt-50A

<400> SEQUENCE: 108

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
                20                  25                  30

Thr Ile Glu Leu Ser Asn Ile Lys Glu Asn Lys Cys Asn Gly Thr Asp
                35                  40                  45

Ala Lys Val Lys Leu Ile Lys Gln Glu Leu Asp Lys Tyr Lys Asn Ala
                50                  55                  60

Val Thr Glu Leu Gln Leu Leu Met Gln Ser Thr Pro Ala Thr Asn Asn
65                  70                  75                  80

Arg Ala Arg Arg Phe Leu Gly Phe Leu Leu Gly Val Gly Ser Ala Ile
                85                  90                  95

Ala Ser Gly Val Ala Val Cys Lys Val Leu His Leu Glu Gly Glu Val
                100                 105                 110

Asn Lys Ile Lys Ser Ala Leu Leu Ser Thr Asn Lys Ala Val Val Ser
                115                 120                 125

Leu Ser Asn Gly Val Ser Val Leu Thr Phe Lys Val Leu Asp Leu Lys
                130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
                180                 185                 190

Thr Pro Val Ser Thr Tyr Met Leu Thr Asn Ser Glu Leu Leu Ser Leu
                195                 200                 205

Ile Asn Asp Met Pro Ile Thr Asn Asp Gln Lys Lys Leu Met Ser Asn
                210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
```

```
                    245                 250                 255
Ile Asp Thr Pro Cys Trp Lys Leu His Thr Ser Pro Leu Cys Thr Thr
                260                 265                 270

Asn Thr Lys Glu Gly Ser Asn Ile Cys Leu Thr Arg Thr Asp Arg Gly
            275                 280                 285

Trp Tyr Cys Asp Asn Ala Gly Ser Val Ser Phe Phe Pro Gln Ala Glu
        290                 295                 300

Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
                340                 345                 350

Ser Val Ile Thr Ser Leu Gly Ala Ile Val Ser Cys Tyr Gly Lys Thr
                355                 360                 365

Lys Cys Thr Ala Ser Asn Lys Asn Arg Gly Ile Ile Lys Thr Phe Ser
            370                 375                 380

Asn Gly Cys Asp Tyr Val Ser Asn Lys Gly Val Asp Thr Val Ser Val
385                 390                 395                 400

Gly Asn Thr Leu Tyr Tyr Val Asn Lys Gln Glu Gly Lys Ser Leu Tyr
                405                 410                 415

Val Lys Gly Glu Pro Ile Ile Asn Phe Tyr Asp Pro Leu Val Phe Pro
                420                 425                 430

Ser Asp Glu Phe Asp Ala Ser Ile Ser Gln Val Asn Glu Lys Ile Asn
            435                 440                 445

Gln Ser Leu Ala Phe Ile Arg Gly Ser Gly Gly Ser Gly Ser Gly Glu
        450                 455                 460

Lys Ala Ala Lys Ala Glu Glu Ala Ala Arg Lys Met Glu Glu Leu Phe
465                 470                 475                 480

Lys Lys His Lys Ile Val Ala Val Leu Arg Ala Asn Ser Val Glu Glu
                485                 490                 495

Ala Ile Glu Lys Ala Val Ala Val Phe Ala Gly Gly Val His Leu Ile
                500                 505                 510

Glu Ile Thr Phe Thr Val Pro Asp Ala Asp Thr Val Ile Lys Ala Leu
            515                 520                 525

Ser Val Leu Lys Glu Lys Gly Ala Ile Ile Gly Ala Gly Thr Val Thr
        530                 535                 540

Ser Val Glu Gln Cys Arg Lys Ala Val Glu Ser Gly Ala Glu Phe Ile
545                 550                 555                 560

Val Ser Pro His Leu Asp Glu Glu Ile Ser Gln Phe Cys Lys Glu Lys
                565                 570                 575

Gly Val Phe Tyr Met Pro Gly Val Met Thr Pro Thr Glu Leu Val Lys
                580                 585                 590

Ala Met Lys Leu Gly His Thr Ile Leu Lys Leu Phe Pro Gly Glu Val
            595                 600                 605

Val Gly Pro Gln Phe Val Lys Ala Met Lys Gly Pro Phe Pro Asn Val
        610                 615                 620

Lys Phe Val Pro Thr Gly Gly Val Asn Leu Asp Asn Val Cys Glu Trp
625                 630                 635                 640

Phe Lys Ala Gly Val Leu Ala Val Gly Val Gly Ser Ala Leu Val Lys
                645                 650                 655

Gly Thr Pro Asp Glu Val Arg Glu Lys Ala Lys Ala Phe Val Glu Lys
                660                 665                 670
```

Ile Arg Gly Cys Thr Glu
        675

<210> SEQ ID NO 109
<211> LENGTH: 682
<212> TYPE: PRT
<213> ORGANISM: Artificial Sequence
<220> FEATURE:
<223> OTHER INFORMATION: RSV F-11 DS-Cav1-12GS-HelExt-50A

<400> SEQUENCE: 109

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Phe Leu Gly Phe Leu Leu Gly Val Gly Ser Ala Ile
                85                  90                  95

Ala Ser Gly Val Ala Val Cys Lys Val Leu His Leu Glu Gly Glu Val
            100                 105                 110

Asn Lys Ile Lys Ser Ala Leu Leu Ser Thr Asn Lys Ala Val Val Ser
        115                 120                 125

Leu Ser Asn Gly Val Ser Val Leu Thr Phe Lys Val Leu Asp Leu Lys
    130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
            180                 185                 190

Thr Pro Val Ser Thr Tyr Met Leu Thr Asn Ser Glu Leu Leu Ser Leu
        195                 200                 205

Ile Asn Asp Met Pro Ile Thr Asn Asp Gln Lys Lys Leu Met Ser Asn
    210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
                245                 250                 255

Ile Asp Thr Pro Cys Trp Lys Leu His Thr Ser Pro Leu Cys Thr Thr
            260                 265                 270

Asn Thr Lys Glu Gly Ser Asn Ile Cys Leu Thr Arg Thr Asp Arg Gly
        275                 280                 285

Trp Tyr Cys Asp Asn Ala Gly Ser Val Ser Phe Phe Pro Gln Ala Glu
    290                 295                 300

Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
            340                 345                 350

Ser Val Ile Thr Ser Leu Gly Ala Ile Val Ser Cys Tyr Gly Lys Thr
                355                 360                 365

Lys Cys Thr Ala Ser Asn Lys Asn Arg Gly Ile Ile Lys Thr Phe Ser
370 375 380

Asn Gly Cys Asp Tyr Val Ser Asn Lys Gly Val Asp Thr Val Ser Val
385 390 395 400

Gly Asn Thr Leu Tyr Tyr Val Asn Lys Gln Glu Gly Lys Ser Leu Tyr
405 410 415

Val Lys Gly Glu Pro Ile Ile Asn Phe Tyr Asp Pro Leu Val Phe Pro
420 425 430

Ser Asp Glu Phe Asp Ala Ser Ile Ser Gln Val Asn Glu Lys Ile Asn
435 440 445

Gln Ser Leu Ala Phe Ile Arg Gly Ser Gly Gly Ser Gly Ser Gly Ser
450 455 460

Gly Gly Ser Glu Lys Ala Ala Lys Ala Glu Glu Ala Ala Arg Lys Met
465 470 475 480

Glu Glu Leu Phe Lys Lys His Lys Ile Val Ala Val Leu Arg Ala Asn
485 490 495

Ser Val Glu Glu Ala Ile Glu Lys Ala Val Ala Val Phe Ala Gly Gly
500 505 510

Val His Leu Ile Glu Ile Thr Phe Thr Val Pro Asp Ala Asp Thr Val
515 520 525

Ile Lys Ala Leu Ser Val Leu Lys Glu Lys Gly Ala Ile Ile Gly Ala
530 535 540

Gly Thr Val Thr Ser Val Glu Gln Cys Arg Lys Ala Val Glu Ser Gly
545 550 555 560

Ala Glu Phe Ile Val Ser Pro His Leu Asp Glu Glu Ile Ser Gln Phe
565 570 575

Cys Lys Glu Lys Gly Val Phe Tyr Met Pro Gly Val Met Thr Pro Thr
580 585 590

Glu Leu Val Lys Ala Met Lys Leu Gly His Thr Ile Leu Lys Leu Phe
595 600 605

Pro Gly Glu Val Val Gly Pro Gln Phe Val Lys Ala Met Lys Gly Pro
610 615 620

Phe Pro Asn Val Lys Phe Val Pro Thr Gly Gly Val Asn Leu Asp Asn
625 630 635 640

Val Cys Glu Trp Phe Lys Ala Gly Val Leu Ala Val Gly Val Gly Ser
645 650 655

Ala Leu Val Lys Gly Thr Pro Asp Glu Val Arg Glu Lys Ala Lys Ala
660 665 670

Phe Val Glu Lys Ile Arg Gly Cys Thr Glu
675 680

<210> SEQ ID NO 110
<211> LENGTH: 686
<212> TYPE: PRT
<213> ORGANISM: Artificial Sequence
<220> FEATURE:
<223> OTHER INFORMATION: RSV F-12 DS-Cav1-16GS-HelExt-50A

<400> SEQUENCE: 110

Gln Asn Ile Thr Glu Glu Phe Tyr Gln Ser Thr Cys Ser Ala Val Ser
1 5 10 15

Lys Gly Tyr Leu Ser Ala Leu Arg Thr Gly Trp Tyr Thr Ser Val Ile
20 25 30

```
Thr Ile Glu Leu Ser Asn Ile Lys Glu Asn Lys Cys Asn Gly Thr Asp
         35                  40                  45

Ala Lys Val Lys Leu Ile Lys Gln Glu Leu Asp Lys Tyr Lys Asn Ala
 50                  55                  60

Val Thr Glu Leu Gln Leu Leu Met Gln Ser Thr Pro Ala Thr Asn Asn
 65                  70                  75                  80

Arg Ala Arg Arg Phe Leu Gly Phe Leu Leu Gly Val Gly Ser Ala Ile
                 85                  90                  95

Ala Ser Gly Val Ala Val Cys Lys Val Leu His Leu Glu Gly Glu Val
            100                 105                 110

Asn Lys Ile Lys Ser Ala Leu Leu Ser Thr Asn Lys Ala Val Val Ser
        115                 120                 125

Leu Ser Asn Gly Val Ser Val Leu Thr Phe Lys Val Leu Asp Leu Lys
130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
            180                 185                 190

Thr Pro Val Ser Thr Tyr Met Leu Thr Asn Ser Glu Leu Leu Ser Leu
        195                 200                 205

Ile Asn Asp Met Pro Ile Thr Asn Asp Gln Lys Lys Leu Met Ser Asn
210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
                245                 250                 255

Ile Asp Thr Pro Cys Trp Lys Leu His Thr Ser Pro Leu Cys Thr Thr
            260                 265                 270

Asn Thr Lys Glu Gly Ser Asn Ile Cys Leu Thr Arg Thr Asp Arg Gly
        275                 280                 285

Trp Tyr Cys Asp Asn Ala Gly Ser Val Ser Phe Phe Pro Gln Ala Glu
290                 295                 300

Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
            340                 345                 350

Ser Val Ile Thr Ser Leu Gly Ala Ile Val Ser Cys Tyr Gly Lys Thr
        355                 360                 365

Lys Cys Thr Ala Ser Asn Lys Asn Arg Gly Ile Ile Lys Thr Phe Ser
370                 375                 380

Asn Gly Cys Asp Tyr Val Ser Asn Lys Gly Val Asp Thr Val Ser Val
385                 390                 395                 400

Gly Asn Thr Leu Tyr Tyr Val Asn Lys Gln Glu Gly Lys Ser Leu Tyr
                405                 410                 415

Val Lys Gly Glu Pro Ile Ile Asn Phe Tyr Asp Pro Leu Val Phe Pro
            420                 425                 430

Ser Asp Glu Phe Asp Ala Ser Ile Ser Gln Val Asn Glu Lys Ile Asn
        435                 440                 445
```

Gln Ser Leu Ala Phe Ile Arg Gly Ser Gly Ser Gly Ser
            450             455             460

Gly Gly Ser Gly Ser Gly Gly Glu Lys Ala Ala Lys Ala Glu Ala
465             470             475             480

Ala Arg Lys Met Glu Glu Leu Phe Lys Lys His Lys Ile Val Ala Val
            485             490             495

Leu Arg Ala Asn Ser Val Glu Ala Ile Glu Lys Ala Val Ala Val
            500             505             510

Phe Ala Gly Gly Val His Leu Ile Glu Ile Thr Phe Thr Val Pro Asp
            515             520             525

Ala Asp Thr Val Ile Lys Ala Leu Ser Val Leu Lys Glu Lys Gly Ala
            530             535             540

Ile Ile Gly Ala Gly Thr Val Thr Ser Val Glu Gln Cys Arg Lys Ala
545             550             555             560

Val Glu Ser Gly Ala Glu Phe Ile Val Ser Pro His Leu Asp Glu Glu
            565             570             575

Ile Ser Gln Phe Cys Lys Glu Lys Gly Val Phe Tyr Met Pro Gly Val
            580             585             590

Met Thr Pro Thr Glu Leu Val Lys Ala Met Lys Leu Gly His Thr Ile
            595             600             605

Leu Lys Leu Phe Pro Gly Glu Val Val Gly Pro Gln Phe Val Lys Ala
            610             615             620

Met Lys Gly Pro Phe Pro Asn Val Lys Phe Val Pro Thr Gly Gly Val
625             630             635             640

Asn Leu Asp Asn Val Cys Glu Trp Phe Lys Ala Gly Val Leu Ala Val
            645             650             655

Gly Val Gly Ser Ala Leu Val Lys Gly Thr Pro Asp Glu Val Arg Glu
            660             665             670

Lys Ala Lys Ala Phe Val Glu Lys Ile Arg Gly Cys Thr Glu
            675             680             685

<210> SEQ ID NO 111
<211> LENGTH: 680
<212> TYPE: PRT
<213> ORGANISM: Artificial Sequence
<220> FEATURE:
<223> OTHER INFORMATION: RSV F-13 DS-Cav1-foldon-10GS-HelExt-50A

<400> SEQUENCE: 111

Gln Asn Ile Thr Glu Glu Phe Tyr Gln Ser Thr Cys Ser Ala Val Ser
1               5               10              15

Lys Gly Tyr Leu Ser Ala Leu Arg Thr Gly Trp Tyr Thr Ser Val Ile
            20              25              30

Thr Ile Glu Leu Ser Asn Ile Lys Glu Asn Lys Cys Asn Gly Thr Asp
            35              40              45

Ala Lys Val Lys Leu Ile Lys Gln Glu Leu Asp Lys Tyr Lys Asn Ala
        50              55              60

Val Thr Glu Leu Gln Leu Leu Met Gln Ser Thr Pro Ala Thr Asn Asn
65              70              75              80

Arg Ala Arg Arg Phe Leu Gly Phe Leu Leu Gly Val Gly Ser Ala Ile
            85              90              95

Ala Ser Gly Val Ala Val Cys Lys Val Leu His Leu Glu Gly Glu Val
            100             105             110

Asn Lys Ile Lys Ser Ala Leu Leu Ser Thr Asn Lys Ala Val Val Ser
            115             120             125

```
Leu Ser Asn Gly Val Ser Val Leu Thr Phe Lys Val Leu Asp Leu Lys
130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
            180                 185                 190

Thr Pro Val Ser Thr Tyr Met Leu Thr Asn Ser Glu Leu Leu Ser Leu
        195                 200                 205

Ile Asn Asp Met Pro Ile Thr Asn Asp Gln Lys Lys Leu Met Ser Asn
210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
                245                 250                 255

Ile Asp Thr Pro Cys Trp Lys Leu His Thr Ser Pro Leu Cys Thr Thr
                260                 265                 270

Asn Thr Lys Glu Gly Ser Asn Ile Cys Leu Thr Arg Thr Asp Arg Gly
            275                 280                 285

Trp Tyr Cys Asp Asn Ala Gly Ser Val Ser Phe Phe Pro Gln Ala Glu
        290                 295                 300

Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
                340                 345                 350

Ser Val Ile Thr Ser Leu Gly Ala Ile Val Ser Cys Tyr Gly Lys Thr
            355                 360                 365

Lys Cys Thr Ala Ser Asn Lys Asn Arg Gly Ile Ile Lys Thr Phe Ser
        370                 375                 380

Asn Gly Cys Asp Tyr Val Ser Asn Lys Gly Val Asp Thr Val Ser Val
385                 390                 395                 400

Gly Asn Thr Leu Tyr Tyr Val Asn Lys Gln Glu Gly Lys Ser Leu Tyr
                405                 410                 415

Val Lys Gly Glu Pro Ile Ile Asn Phe Tyr Asp Pro Leu Val Phe Pro
            420                 425                 430

Ser Asp Glu Phe Asp Ala Ser Ile Ser Gln Val Asn Glu Lys Ile Asn
        435                 440                 445

Gln Ser Leu Ala Phe Ile Arg Gly Ser Gly Ser Gly Ser Gly Ser Ser
450                 455                 460

Gly Glu Lys Ala Ala Lys Ala Glu Glu Ala Ala Arg Lys Met Glu Glu
465                 470                 475                 480

Leu Phe Lys Lys His Lys Ile Val Ala Val Leu Arg Ala Asn Ser Val
                485                 490                 495

Glu Glu Ala Ile Glu Lys Ala Val Ala Val Phe Ala Gly Gly Val His
            500                 505                 510

Leu Ile Glu Ile Thr Phe Thr Val Pro Asp Ala Asp Thr Val Ile Lys
        515                 520                 525

Ala Leu Ser Val Leu Lys Glu Lys Gly Ala Ile Ile Gly Ala Gly Thr
530                 535                 540

Val Thr Ser Val Glu Gln Cys Arg Lys Ala Val Glu Ser Gly Ala Glu
```

```
                    545                 550                 555                 560
    Phe Ile Val Ser Pro His Leu Asp Glu Glu Ile Ser Gln Phe Cys Lys
                        565                 570                 575

Glu Lys Gly Val Phe Tyr Met Pro Gly Val Met Thr Pro Thr Glu Leu
                        580                 585                 590

Val Lys Ala Met Lys Leu Gly His Thr Ile Leu Lys Leu Phe Pro Gly
                        595                 600                 605

Glu Val Val Gly Pro Gln Phe Val Lys Ala Met Lys Gly Pro Phe Pro
                610                 615                 620

Asn Val Lys Phe Val Pro Thr Gly Val Asn Leu Asp Asn Val Cys
    625                 630                 635                 640

Glu Trp Phe Lys Ala Gly Val Leu Ala Val Gly Val Gly Ser Ala Leu
                        645                 650                 655

Val Lys Gly Thr Pro Asp Glu Val Arg Glu Lys Ala Lys Ala Phe Val
                        660                 665                 670

Glu Lys Ile Arg Gly Cys Thr Glu
                        675                 680

<210> SEQ ID NO 112
<211> LENGTH: 712
<212> TYPE: PRT
<213> ORGANISM: Artificial Sequence
<220> FEATURE:
<223> OTHER INFORMATION: RSV_F-14 DS-Cav1-foldon-15GS-HelExt-50A

<400> SEQUENCE: 112

Gln Asn Ile Thr Glu Glu Phe Tyr Gln Ser Thr Cys Ser Ala Val Ser
    1               5                   10                  15

Lys Gly Tyr Leu Ser Ala Leu Arg Thr Gly Trp Tyr Thr Ser Val Ile
                    20                  25                  30

Thr Ile Glu Leu Ser Asn Ile Lys Glu Asn Lys Cys Asn Gly Thr Asp
                    35                  40                  45

Ala Lys Val Lys Leu Ile Lys Gln Glu Leu Asp Lys Tyr Lys Asn Ala
                    50                  55                  60

Val Thr Glu Leu Gln Leu Leu Met Gln Ser Thr Pro Ala Thr Asn Asn
    65                  70                  75                  80

Arg Ala Arg Arg Phe Leu Gly Phe Leu Leu Gly Val Gly Ser Ala Ile
                    85                  90                  95

Ala Ser Gly Val Ala Val Cys Lys Val Leu His Leu Glu Gly Glu Val
                    100                 105                 110

Asn Lys Ile Lys Ser Ala Leu Leu Ser Thr Asn Lys Ala Val Val Ser
                    115                 120                 125

Leu Ser Asn Gly Val Ser Val Leu Thr Phe Lys Val Leu Asp Leu Lys
                    130                 135                 140

Asn Tyr Ile Asp Lys Gln Leu Leu Pro Ile Leu Asn Lys Gln Ser Cys
    145                 150                 155                 160

Ser Ile Ser Asn Ile Glu Thr Val Ile Glu Phe Gln Gln Lys Asn Asn
                    165                 170                 175

Arg Leu Leu Glu Ile Thr Arg Glu Phe Ser Val Asn Ala Gly Val Thr
                    180                 185                 190

Thr Pro Val Ser Thr Tyr Met Leu Thr Asn Ser Glu Leu Leu Ser Leu
                    195                 200                 205

Ile Asn Asp Met Pro Ile Thr Asn Asp Gln Lys Lys Leu Met Ser Asn
    210                 215                 220

Asn Val Gln Ile Val Arg Gln Gln Ser Tyr Ser Ile Met Cys Ile Ile
```

-continued

```
            225                 230                 235                 240
        Lys Glu Glu Val Leu Ala Tyr Val Val Gln Leu Pro Leu Tyr Gly Val
                            245                 250                 255

Ile Asp Thr Pro Cys Trp Lys Leu His Thr Ser Pro Leu Cys Thr Thr
                            260                 265                 270

Asn Thr Lys Glu Gly Ser Asn Ile Cys Leu Thr Arg Thr Asp Arg Gly
                            275                 280                 285

Trp Tyr Cys Asp Asn Ala Gly Ser Val Ser Phe Phe Pro Gln Ala Glu
                            290                 295                 300

Thr Cys Lys Val Gln Ser Asn Arg Val Phe Cys Asp Thr Met Asn Ser
        305                 310                 315                 320

Leu Thr Leu Pro Ser Glu Val Asn Leu Cys Asn Val Asp Ile Phe Asn
                            325                 330                 335

Pro Lys Tyr Asp Cys Lys Ile Met Thr Ser Lys Thr Asp Val Ser Ser
                            340                 345                 350

Ser Val Ile Thr Ser Leu Gly Ala Ile Val Ser Cys Tyr Gly Lys Thr
                            355                 360                 365

Lys Cys Thr Ala Ser Asn Lys Asn Arg Gly Ile Ile Lys Thr Phe Ser
                            370                 375                 380

Asn Gly Cys Asp Tyr Val Ser Asn Lys Gly Val Asp Thr Val Ser Val
        385                 390                 395                 400

Gly Asn Thr Leu Tyr Tyr Val Asn Lys Gln Glu Gly Lys Ser Leu Tyr
                            405                 410                 415

Val Lys Gly Glu Pro Ile Ile Asn Phe Tyr Asp Pro Leu Val Phe Pro
                            420                 425                 430

Ser Asp Glu Phe Asp Ala Ser Ile Ser Gln Val Asn Glu Lys Ile Asn
                            435                 440                 445

Gln Ser Leu Ala Phe Ile Arg Gly Tyr Ile Pro Glu Ala Pro Arg Asp
                            450                 455                 460

Gly Gln Ala Tyr Val Arg Lys Asp Gly Glu Trp Val Leu Leu Ser Thr
        465                 470                 475                 480

Phe Leu Gly Ser Gly Gly Ser Gly Ser Gly Gly Ser Gly Ser Gly Ser
                            485                 490                 495

Gly Glu Lys Ala Ala Lys Ala Glu Glu Ala Ala Arg Lys Met Glu Glu
                            500                 505                 510

Leu Phe Lys Lys His Lys Ile Val Ala Val Leu Arg Ala Asn Ser Val
                            515                 520                 525

Glu Glu Ala Ile Glu Lys Ala Val Ala Val Phe Ala Gly Gly Val His
                            530                 535                 540

Leu Ile Glu Ile Thr Phe Thr Val Pro Asp Ala Asp Thr Val Ile Lys
        545                 550                 555                 560

Ala Leu Ser Val Leu Lys Glu Lys Gly Ala Ile Ile Gly Ala Gly Thr
                            565                 570                 575

Val Thr Ser Val Glu Gln Cys Arg Lys Ala Val Glu Ser Gly Ala Glu
                            580                 585                 590

Phe Ile Val Ser Pro His Leu Asp Glu Glu Ile Ser Gln Phe Cys Lys
                            595                 600                 605

Glu Lys Gly Val Phe Tyr Met Pro Gly Val Met Thr Pro Thr Glu Leu
                            610                 615                 620

Val Lys Ala Met Lys Leu Gly His Thr Ile Leu Lys Leu Phe Pro Gly
        625                 630                 635                 640

Glu Val Val Gly Pro Gln Phe Val Lys Ala Met Lys Gly Pro Phe Pro
                            645                 650                 655
```

```
Asn Val Lys Phe Val Pro Thr Gly Gly Val Asn Leu Asp Asn Val Cys
            660                 665                 670

Glu Trp Phe Lys Ala Gly Val Leu Ala Val Gly Val Gly Ser Ala Leu
        675                 680                 685

Val Lys Gly Thr Pro Asp Glu Val Arg Glu Lys Ala Lys Ala Phe Val
    690                 695                 700

Glu Lys Ile Arg Gly Cys Thr Glu
705                 710

<210> SEQ ID NO 113
<211> LENGTH: 717
<212> TYPE: PRT
<213> ORGANISM: Artificial Sequence
<220> FEATURE:
<223> OTHER INFORMATION: RSV F-15 DS-Cav1-foldon-20GS-HelExt-50A

<400> SEQUENCE: 113

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Phe Leu Gly Phe Leu Leu Gly Val Gly Ser Ala Ile
                85                  90                  95

Ala Ser Gly Val Ala Val Cys Lys Val Leu His Leu Glu Gly Glu Val
            100                 105                 110

Asn Lys Ile Lys Ser Ala Leu Leu Ser Thr Asn Lys Ala Val Val Ser
        115                 120                 125

Leu Ser Asn Gly Val Ser Val Leu Thr Phe Lys Val Leu Asp Leu Lys
    130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
            180                 185                 190

Thr Pro Val Ser Thr Tyr Met Leu Thr Asn Ser Glu Leu Leu Ser Leu
        195                 200                 205

Ile Asn Asp Met Pro Ile Thr Asn Asp Gln Lys Lys Leu Met Ser Asn
    210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
                245                 250                 255

Ile Asp Thr Pro Cys Trp Lys Leu His Thr Ser Pro Leu Cys Thr Thr
            260                 265                 270

Asn Thr Lys Glu Gly Ser Asn Ile Cys Leu Thr Arg Thr Asp Arg Gly
        275                 280                 285

Trp Tyr Cys Asp Asn Ala Gly Ser Val Ser Phe Phe Pro Gln Ala Glu
    290                 295                 300
```

```
Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
            340                 345                 350

Ser Val Ile Thr Ser Leu Gly Ala Ile Val Ser Cys Tyr Gly Lys Thr
                355                 360                 365

Lys Cys Thr Ala Ser Asn Lys Asn Arg Gly Ile Ile Lys Thr Phe Ser
        370                 375                 380

Asn Gly Cys Asp Tyr Val Ser Asn Lys Gly Val Asp Thr Val Ser Val
385                 390                 395                 400

Gly Asn Thr Leu Tyr Tyr Val Asn Lys Gln Glu Gly Lys Ser Leu Tyr
                405                 410                 415

Val Lys Gly Glu Pro Ile Ile Asn Phe Tyr Asp Pro Leu Val Phe Pro
            420                 425                 430

Ser Asp Glu Phe Asp Ala Ser Ile Ser Gln Val Asn Glu Lys Ile Asn
        435                 440                 445

Gln Ser Leu Ala Phe Ile Arg Gly Tyr Ile Pro Glu Ala Pro Arg Asp
450                 455                 460

Gly Gln Ala Tyr Val Arg Lys Asp Gly Glu Trp Val Leu Leu Ser Thr
465                 470                 475                 480

Phe Leu Gly Ser Gly Ser Gly Ser Gly Ser Gly Ser Gly Ser Gly Ser
                485                 490                 495

Gly Gly Ser Ser Gly Ser Glu Lys Ala Ala Lys Ala Glu Glu Ala Ala
                500                 505                 510

Arg Lys Met Glu Glu Leu Phe Lys Lys His Lys Ile Val Ala Val Leu
        515                 520                 525

Arg Ala Asn Ser Val Glu Glu Ala Ile Glu Lys Ala Val Ala Val Phe
        530                 535                 540

Ala Gly Gly Val His Leu Ile Glu Ile Thr Phe Thr Val Pro Asp Ala
545                 550                 555                 560

Asp Thr Val Ile Lys Ala Leu Ser Val Leu Lys Glu Lys Gly Ala Ile
                565                 570                 575

Ile Gly Ala Gly Thr Val Thr Ser Val Glu Gln Cys Arg Lys Ala Val
            580                 585                 590

Glu Ser Gly Ala Glu Phe Ile Val Ser Pro His Leu Asp Glu Glu Ile
        595                 600                 605

Ser Gln Phe Cys Lys Glu Lys Gly Val Phe Tyr Met Pro Gly Val Met
        610                 615                 620

Thr Pro Thr Glu Leu Val Lys Ala Met Lys Leu Gly His Thr Ile Leu
625                 630                 635                 640

Lys Leu Phe Pro Gly Glu Val Val Gly Pro Gln Phe Val Lys Ala Met
                645                 650                 655

Lys Gly Pro Phe Pro Asn Val Lys Phe Val Pro Thr Gly Gly Val Asn
            660                 665                 670

Leu Asp Asn Val Cys Glu Trp Phe Lys Ala Gly Val Leu Ala Val Gly
        675                 680                 685

Val Gly Ser Ala Leu Val Lys Gly Thr Pro Asp Glu Val Arg Glu Lys
        690                 695                 700

Ala Lys Ala Phe Val Glu Lys Ile Arg Gly Cys Thr Glu
705                 710                 715
```

```
<210> SEQ ID NO 114
<211> LENGTH: 15
<212> TYPE: PRT
<213> ORGANISM: Artificial Sequence
<220> FEATURE:
<223> OTHER INFORMATION: synthetic

<400> SEQUENCE: 114

Gly Ser Gly Gly Ser Gly Ser Gly Ser Gly Gly Ser Gly Ser Gly
1               5                   10                  15

<210> SEQ ID NO 115
<211> LENGTH: 8
<212> TYPE: PRT
<213> ORGANISM: Artificial Sequence
<220> FEATURE:
<223> OTHER INFORMATION: synthetic

<400> SEQUENCE: 115

Gly Gly Ser Gly Gly Ser Gly Ser
1               5

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Ser Gly Gly Ser Gly Ser Gly
1               5
```